US007002020B1

(12) United States Patent
Gordeev et al.

(10) Patent No.: US 7,002,020 B1
(45) Date of Patent: Feb. 21, 2006

(54) OXAZOLIDINONE COMBINATORIAL LIBRARIES, COMPOSITIONS AND METHODS OF PREPARATION

(75) Inventors: Mikhail F. Gordeev, San Leandro, CA (US); Gary W. Luehr, Fremont, CA (US); Dinesh V. Patel, Fremont, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 677 days.

(21) Appl. No.: 09/641,396

(22) Filed: Aug. 17, 2000

Related U.S. Application Data

(60) Division of application No. 09/235,771, filed on Jan. 22, 1999, now Pat. No. 6,239,152, which is a continuation-in-part of application No. 09/086,702, filed on May 28, 1998, now abandoned, which is a continuation-in-part of application No. 09/012,535, filed on Jan. 23, 1998, now abandoned.

(51) Int. Cl.
   *C07D 263/04* (2006.01)

(52) U.S. Cl. ................... 548/231; 548/229; 548/232; 435/6

(58) Field of Classification Search .......... 435/DIG. 34, 435/DIG. 49, 6; 544/322; 546/162, 275; 548/139, 141, 163, 192, 195, 231, 232, 142, 548/175
See application file for complete search history.

(56) References Cited

U.S. PATENT DOCUMENTS

| 6,441,005 | B1 | * | 8/2002 | Gordeev et al. | ............ | 514/340 |
| 2002/0169191 | A1 | * | 11/2002 | Gordeev et al. | ............ | 514/376 |

FOREIGN PATENT DOCUMENTS

| DE | 196 49 095 | 8/1997 |
| EP | 0 050 827 | 5/1982 |
| EP | 0 184 170 A2 | 6/1986 |
| EP | 0 281 289 A1 | 9/1988 |
| EP | 0 312 000 | 4/1989 |
| EP | 0 316 594 A1 | 5/1989 |
| EP | 0 352 781 | 1/1990 |
| EP | 0 359 172 A1 | 3/1990 |
| EP | 0 359 418 A1 | 3/1990 |
| EP | 0 693 491 A1 | 1/1996 |
| EP | 0 694 543 A1 | 1/1996 |
| EP | 0 694 544 A1 | 1/1996 |
| EP | 0 738 726 A1 | 10/1996 |
| EP | 0 785 201 A1 | 7/1997 |
| EP | 0 789 026 A1 | 8/1997 |
| JP | 04-327580 A2 | 11/1992 |
| WO | WO 86/00991 | 2/1986 |
| WO | WO 91/07409 | 5/1991 |
| WO | WO 93/09103 | 5/1993 |
| WO | WO 93/23384 | 11/1993 |
| WO | WO 95/07271 | 3/1995 |
| WO | WO 95/14684 | 6/1995 |
| WO | WO 96/13502 | 5/1996 |
| WO | WO 97/09328 | 3/1997 |
| WO | WO 97/10223 | 3/1997 |
| WO | WO 97/19039 | 5/1997 |
| WO | WO 97/19089 | 5/1997 |
| WO | WO 97/21708 | 6/1997 |
| WO | WO 97/27188 | 7/1997 |
| WO | WO 97/30981 | 8/1997 |
| WO | WO 97/30995 | 8/1997 |
| WO | WO 97/31917 | 9/1997 |
| WO | WO 98/01446 | 1/1998 |
| WO | WO 98/01447 | 1/1998 |

OTHER PUBLICATIONS

Balkenhohl et al., (1996) "Combinatorial Synthesis of Small Organic Molecules," *Angewandte Chemie.* International Edition, vol. 35, No. 20, pp. 2288–2237.
Buchstaller, H. (Apr. 2, 1998) "Solid Phase Synthesis of Oxazolidinones via a Novel Cyclisation/Cleavage Reations," *Tetrahedron* vol. 54, No. 14, pp. 3465–3470.
Holte, P. et al., (Oct. 1, 1998). Solid–Phase Synthesis of 3,5–Disubstituted 1,3–Oxazolidin–2–ones by an Activation/Cyclo–elimination Process, *Tetrahedron Letters*, vol. 39, No. 40, pp. 7407–7410.
Alasandro, M., "Separation of diastereoisomers of DuP 105, a novel oxazolidinone antibacterial agent, by supercritical fluid chromatography on a Chiralcel OD column" (1996) *J. Pharm. Biomed.* 14:807–814.
Albert et al., "Comparison of in vitro trichomonacidal properties of some nitrofurans employed in therapeutics" (1973) *Ann. Pharm. Fr.* 31:57–62. (English translation abstract).
Augé et al., "Lithium trifluoromethanesulfonate–catalysed aminolysis of oxiranes" (1996) *Tetrahedron Letters* 37:7715–7716.
Barbachyn et al., "Potent Water Soluble Prodrugs of the Oxazolidine Antibacterial Agent Eperezolid", Poster F–23, 37th *Interscience Conference on Antimicrobial Agents and Chemotherepy*, Toronto, Canada, Sep. 28 to Oct. 1, 1997.
Barbachyn et al., "Synthesis and structure activity relationships of new tropone–substituted oxazolidinone antibacterial agents" (1995) *Abstracts of the 35th ICAAC Session 130. Poster Oxazolidinones.* p. 149. (Abstract F206).

(Continued)

*Primary Examiner*—Robert Gerstl
*Assistant Examiner*—Jon D. Epperson
(74) *Attorney, Agent, or Firm*—Jonathan P. O'Brien; Lucy X. Yang

(57) ABSTRACT

Oxazolidinones and methods for their synthesis are provided. Also provided are combinatorial libraries comprising oxazolidinones, and methods to prepare the libraries. Further provided are methods of making biologically active oxazolidinones as well as pharmaceutically acceptable compositions comprising the oxazolidinones. The methods of library preparation include the attachment of oxazolidinones to a solid support. The methods of compound preparation in one embodiment involve the reaction of an iminophosphorane with a carbonyl containing polymeric support.

7 Claims, 57 Drawing Sheets

OTHER PUBLICATIONS

Barbachyn et al., "Identification of new oxazolidinone antibacterial agents with potent in vivo antimycobacterial activity" (1995) *Abstracts of the 35th ICAAC Session 130. Poster Oxazolidinones.* p. 152. (Abstract F227).

Barbachyn et al., "Identification of a novel oxazolidinone (U–100480) with potent antimycobacterial activity" (1996) *J. Med. Chem.* 39:680–685.

Barry et al., "In vitro evaluation of DuP 105 and DuP 721, two new oxazolidinone antimicrobial agents" (1988) *Antimicrob. Agents Chemother.* 32:150–152.

Bartel et al., "Synthesis and Antibacterial Activity of Novel Hteroaryl Oxazolidinone I: Pyridyl Oxazolidinones", Poster F–017, 37th *Interscience Conference on Antimicrobial Agents and Chemotherepy,* Toronto, Canada, Sep. 28 to Oct. 1, 1997.

Bartel et al., "Synthesis and Antibacterial Activity of Novel Heteroaryl Oxazolidinones II: Pyridyl Oxazolidinones", Poster F–018, 37th *Interscience Conference on Antimicrobial Agents and Chemotherepy,* Toronto, Canada, Sep. 28 to Oct. 1, 1997.

Bartel et al., "Synthesis and Antibacterial Activity of Novel Heteroaryl Oxazolidinones III: Pyridyl Oxazolidinones", Poster F–019, 37th *Interscience Conference on Antimicrobial Agents and Chemotherepy,* Toronto, Canada, Sep. 28 to Oct. 1, 1997.

Batts et al., "U–100592, phase I, multiple–dose, randomized placebo–controlled, safety, tolerance and pharmacokinetics in healthy volunteers for 14.25 days using bulk drug in capsules" (1995) *Abstracts of the 35th ICAAC Session 130. Poster. Oxazolidinones.* p. 152. (Abstract F226).

Bostic et al., "Comparative in vitro and bactericidal activity of oxazolidinone antibiotics against multi–drug resistant enterococci" (1995) *Abstracts of the 35th ICAAC Session 130. Poster. Oxazolidinones.* p. 151. (abstract F219).

Brickner et al., "Synthesis of U–100592 and U–100766, two new oxazolidinone antibacterial agents in clinical trials for treatment of multiply resistant gram positive infections" (1995) *Abstracts of the 35th ICAAC Session 130. Poster. Oxazolidinones.* p. 149. (abstract F208).

Brickner et al., Synthesis and antibacterial activity of U–100592 and U–100766, two oxazolidinone antibacterial agents for the potential treatment of multidrug–resistant gram–positive bacterial infections (1996) *J. Med. Chem.* 39:673–679.

Brickner et al., "Oxazolidinone antibacterial agents" (1996) *Curr. Pharm. Des.* 2:175–194.

Brumfitt et al., "In–vitro microbiological activities of DuP 105 and DuP 721, novel synthetic oxazolidinones" (1988) *J. Antimicrob. Chemother.* 21:711–720.

Brumfitt et al., "Antibacterial oxazolidinones: In vitro activity of a new analogue, E3709" (1992) *Diagn. Microbiol. Infect. Dis.* 15:621–625.

Bush et al., "Kinetic interactitons of tazobactam with β–lactamases from all major structural classes" (1993) *Antimicrobial Agents and Chemotherapy* 37:851–858.

Canonne et al.. "Synthesis of Chiral 3–Substituted 2,4(1H, 3H)–Quinazolinediones" (1993), *Heterocycles,* 36:1305–1314.

Daly et al., "Activity and mechanism of action of DuP 105 and DuP 721, new oxazolidinone compounds" (1988) *J. Antimicrob. Chemother.* 21:721–730.

Daub et al., "Isolation, cloning, and sequencing of the *salmonella typhimurium ddlA* gene with purification and characterization of its product, D–alanine:D–alanine ligase (ADP forming)" (1989) *Biochemisry* 27:3701–3708.

Dellaria et al., "Optimization and in vivo evaluations of a series of small, potent, and specific renin inhibitors containing a novel Leu–Val replacement" (1987) *J. Med. Chem.* 30:2137–2144.

Demyan et al., "The Oxazolidinone Linezolid Inhibits Translation Initiation in Bacteria", Poster C–102, 37th *Interscience Conference on Antimicrobial Agents and Chemotherepy,* Toronto, Canada, Sep. 28 to Oct. 1, 1997.

Denis et al., "5–aryl–β,γ butenolide, a new class of antibacterial derived from the n–aryl oxazolidinone DUP 721" (1994) *Bioorg. & Med. Chem. Lett.* 4:1925–1930.

de Parrodi et al., "Preparation of enantiomerically pure cis– and trans–N–(propionyl)hexahydrobenzoxazolidin–2–ones" (1997) *Tetrahedron: Asymmetry* 8:1075–1082.

Ding et al., "Transformation of heterocyclic reversible monoamine oxidase–B inactivators into irreversible inactivators by N–methylation" (1993) *J. Med. Chem.* 36:3606–3610.

Eliopoulos et al., "Activities of the new oxazolidinone antimicrobials against enterococci" (1995) *Abstracts of the 35th ICAAC Session 130. Poster. Oxazolidinones.* p. 151. (Abstract F217).

Ford et al., "In vivo efficacy evaluations of U–100592 and U–100766, new oxazolidinone antibiotics" (1995) *Abstracts of the 35th ICAAC Session 130. Poster. Oxazolidinones.* p. 151. (Abstract F221).

Ford et al., "Oxazolidinones: new antibacterial agents", (1997) *Trends in Microbiology,* 5:196–200.

Frost et al., "Antibacterial activity of 3–(1–methyl–5–nitro–2–imidazolymethylideneamino) –2–oxazolidinones" (1975) *J. Appl. Bacteriol.* 38:177–184.

Gadwood et al., "Synthesis of Oxazolidinone Antibacterial Agents Incorporating Morpholine and Piperazine N–Oxides: Oxazolidinone Prodrugs having High Water Solubility", Poster F–20, 37th *Interscience Conference on Antimicrobial Agents and Chemotherepy,* Toronto, Canada, Sep. 28 to Oct. 1, 1997.

Gates et al., "5–(Aminomethyl)–3–aryl–2–oxazolidinones. A Novel Class of Mechanism—Based Inactivators of Monoamine Oxidase B", (1990) *J. Am. Chem. Soc.,* 112:9364–9372.

Getman et al., "Discovery of a novel class of potent HIV–1 protease inhibitors containing the (R)–(hydroxyethyl) urea isostere" (1993) *J. Med. Chem.* 36:288–291.

Geysen et al., "Use of peptide synthesis to probe viral antigens for epitopes to a resolution of a single amino acid" (1984) *Proc. Natl. Acad. Sci. USA* 81:3998–4002.

Gleave et al., "Oxazolidinone antibacterial agents. an enantiselective synthesis of the [6,5,5] tricyclic fused oxazolidinone ring system and application to the synthesis of a rigid DuP 721 analogue" (1996) *J. Org. Chem.* 61:6470–6474.

Gordon et al., "Applications of combinatorial technolgies to drug discovery. 2. Combinatorial organic synthesis, library screening strategies, and future directions" (1994) *J. Med. Chem.* 37:1385–1401.

Grega et al., "Regioselective metalation of phoroanilines. An application to the synthesis of fluorinated oxazolidinone antibacterial agents" (1995) *J. Org. Chem.* 60:5255–5261.

Gregory et al., "Antibacterials. Synthesis and structure–activity studies of 3–aryl–2–oxooxazolidines. 2. The "A"group"(1990) *J. Med. Chem.* 33:2569–2578.

Gregory et al., "Antibacterials. Synthesis and structure–activity studies of 3–aryl–2–oxooxazolidines. 1. The "B"group"(1989) *J. Med. Chem.* 32:1673–1681.

Gualerzi et al., "Initiation of mRNA Translation in Prokaryotes", (1990) *Biochemistry:* 29:5881–5889.

Hermkens et al., "Solid–phase organic reactions: A review of the recent literature" (1996) *Tetrahedron* 52:4527–4554.

Houghten et al., "Generation and use of synthetic peptide combinatorial libraries for basic research and drug discovery" (1991) *Nature* 354:84–86.

Howard et al., Preliminary pharmacokinetic and metabolic study of U–100480, a substituted oxazolidinone antibiotic, in the rat (1995) *Abstracts of the 35th ACAAC Session 130. Poster. Oxazolidinones.* p. 153. (abstract F230).

Hutchins et al., "A general method for the solid phase synthesis of ureas" (1994) *Tetrahedron Lett.* 35:4055–4058.

Hutchinson et al., "Piperazinyl oxazolidinones: Structure activity relationships of a new class of oxazolidinone antibacterial agents" (1995) *Abstracts of the 35th ICAAC Session 130. Poster. Oxazolidinones.* p. 149. (Abstract F207).

Hutchinson et al., "Structure–activity relationships of piperazinylphenyl oxazolidinone antibacterial agents and related developments" (1996) Book of Abstracts, 212th ACS National Meeting, Orlando, FL., Aug. 25029. American Chemical Society, Washington, D.C., Publisher.

Ishii et al. "Highly Selective Aldose Reductase Inhibitors. 1. 3–(Arylalkly)–2,4,5–trioxoimidazolidine–1 acetic Acids", (1996), 39:1224–1927.

Jenkins et al., "Comparative in vitro activities of vancomycin and the oxazolidinones U–100592 and U100766 against 300 clinical staphylococcal isolates" (1995) *Abstracts of the 35th ICAAC Session 130. Poster Oxazolidinones.* p. 150. (Abstract F213).

Jones et al., "In vitro specturm and activity of U–100592 and U–100766, two novel oxazolidinones" (1995) *Abstracts of the 35th ICAAC Session 130. Poster. Oxazolidinones.* p. 149. (Abstract F209).

Kaatz et al., "In vitro activity of oxazolidinone compounds U100592 (592) and U100766 (766) versus *staphylococcus aureus* (SA) and *staphylococcus epidermis* (SE)"(1995) *Abstracts of the 35th ICAAC Session 130. Poster. Oxazolidinones.* p. 150. (abstract F215).

Kalnbergs et al., "Synthesition reactions of carbEnesic hydrocarbons. New derivatives of diazabenzanthracene and triazaphenalene.ang." (1967) *Khim.–Farm. Zh.* 1:47–49. (English translation abstract).

Kick et al., "Expedient method for the solid–phase synthesis of aspartic acid protease inhibitors toward the generation of libraries" (1995) *J. Med. Chem.* 38:1427–1430.

Klemens et al., "Activities of the two novel oxazolidinones against *M. tuberculosis* (*MTB*) in a murine model" (1995) *Abstracts of the 35th ICAAC Session 130. Poster. Oxazolidinones.* p. 152. (abstract F228).

Koike et al., "Drug safety studies with a novel oxazolidinone, U–100766" (1995) *Abstracts of the 35th ICAAC Session 130. Poster. Oxazolidinones.* p. 152. (Abstract F224).

Lam et al., "A new type of synthetic peptide library for identifying ligand–binding activity" (1991) *Nature* 354:82–84.

Lizondo et al., "Linezolid. Oxazolidinone antibacterial U–100766" (1996) *Drugs of the Future* 21:1116–1123.

Lowe et al., "Structure–Activity Relationship of Quinazolinedione Inhibitors of Calcium–Independent Phosphoditerase" (1991) *J. Med. Chem.* 34:623–628.

Luly et al., "New inhibitors of human renin that contain novel Leu–Val replacements. Examination of the $P_1$ site" (1988) *J. Med. Chem.* 31:532–539.

Luly et al., "New inhibitors of human renin that contain novel Leu–Val replacements" (1987) *J. Med. Chem.* 30:1609–1616.

March, "Double and triple covalent bonds" *Advanced Organic Chemistry,* 3d Edition, pp. 16–17, Wiley–Interscience, New York.

Manninen et al., "Investigation into the metal ion dependency of the regiospecific alkylation/cyclization reaction producing 5–(R)–hydroxymethyl–3–aryl–oxazolidinones" (1996) Book of Abstracts, 212th ACS National Meeting, Orlando, FL, Aug. 25–29. American Chemical Society, Washington, D.C., Publisher.

Martin et al., "The metabolism and kinetics of a novel oxazolidinone, U–100592" (1995) *Abstracts of the 35th ICAAC Session 130. Poster. Oxazolidinones.* p. 151. (Abstract F221).

Mason, Jr. et al., "Activity of oxazolidinones U–100592 and U–100766 in vitro against penicillin–resistant and cephalosporin–resistant strains of *S. pneumoniae*" (1995) *Abstracts of the 35th ICAAC Session 130. Poster. Oxazolidinones.* p. 150. (Abstract F212).

Merrifield, R.B., "Solid phase peptide synthesis. 1. The synthesis of a tetrapeptide" (1963) *J. Am. Chem. Soc.* 85:2149–2154.

Montginoul et al., "Activities analgesiques, anticonvulsivates et anti–inflammatories de 1H, 3H–quinazolinediones–2,4", (1988), *Ann Pharmaceutiques Francaises,* 46:223–232. (English translation abstract).

Moureau et al., "Reversible monoamine oxidase inhibitor toloxatone: structural and elecronic properties", (1992) *Eur. J Med Chem,* 27:939–948.

Mulazimoglu et al., "In vitro activity of two novel oxazolidinones (U100592 and U10076), a new fluoroquinolone (CP–99219,27), and a streptogramin (Synercid) against *S. aureus* and *S. epidermidis*" (1995) *Abstracts of the 35th ICAAC Session 130. Poster. Oxazolidinones.* p. 149. (Abstract F210).

Neu et al., "In vitro activities of two oxazolidinone antimicrobial agents, DuP 721 and DuP 105" (1988) *Antimicrob. Agents Chemother.* 32:580–583.

Park et al., "Antibacterials. Synthesis and Structure–Activity Studies of 3–Aryl–2–oxooxazolidines. 4 Multiply–Substituted Aryl Derivitives" (1992) *J. Med. Chem.,* 35:1156–1165.

Pawsey et al., "1st administration of a new oxazolidinone antibiotic (U–100592) to man" *Abstracts of the 35th ICAAC Session 130. Poster. Oxazolidinones.* p. 152. (Abstract F225).

Piper et al., "Drug safety evaluation of U–100592, and oxazolidinone antibiotic, in dogs and rats" (1995) *Abstracts of the 35th ICAAC Session 130. Poster. Oxazolidinones.* p. 152. (Abstract F223).

Poel et al., "Novel Phenyloxazolidinone Antibacterial Agents Containing Saturated and 4,5–Unsaturated 4–Pyridinyl and Thiopyranyl Aryl Substituents", Pharmacia & Upjohn.

Ranaldi et al., "Transport of the antibacterial agent oxazolidinone–2–one and derivatives across intestinal (Caco–2) and renal (MDCK) epithelial cell lines" (1996) *Antimicrob. Agents Chemother.* 40:652–658.

Reisch et al., "Alkylation of Quinazoline–2,4 (1 H, 3H)–diones with 1,4–Dibromo–2–methylbut–2–methylbut–2–ene under Phase–Transfer–Catalysis" *J. Heterocyclic Chem.*, (1993) 30:1117–1120.

Rich et al., "Preparation of a new o–nitrobenzyl resin for solid–phase synthesis of tert–butyloxycarbonyl–protected peptide acids" (1975) *J. Am. Chem. Soc.* 97:1575–1579.

Rotella, D.P., "Solid phase synthesis of olefin and hydroxyethylene peptidomimetics" (1996) *J. Am. Chem. Soc.* 118:12246–12247.

Rybak et al., "Comparative in vitro activity of oxazolidinone compounds U100592 (592) and U100766 (766) versus vancomycin (V) against *staphylococcus aureus* and coagulase–negative staphylococci" (1995) *Abstracts of the 35th ICAAC Session 130. Poster. Oxazolidinones.* p. 150. (Abstract F221).

Schaus et al., "Dynamic kinetic resolution of epichlorohydrin via enantioselective catalytic ring opening with $TMSN_3$. Practical synthesis of aryl oxazolidinone antibacterial agents" (1996) *Tetrahedron Letters* 37:7937–7940.

Seneci et al., "Synthesis and Antimicrobial Activity of Oxazolidinone–2–ones and Related Heterocycles", (1994) *J. Chem. Soc. Perkin Trans.*, 1:2345–2351.

Silverman et al., "The oxazolidinone antibacterial agent DuP 105 does not act on cell wall biosynthesis or on a β–lactamase" (1993) *Biochem. Biophys. Res. Comm.* 195:1077–1080.

Spangler et al., "Susceptibility of 115 pencillin susceptible and resistant pneumococci to two oxazolidinones compared to penicillin G, ceftriaxone, telcoplanin, vancomycin, rifampin and imipenem" (1995) *Abstracts of the 35th ICAAC Session 130. Poster. Oxazolidinones.* p. 151. (Abstract F218).

Ulanowicz et al., "Synthesis and Biological Activity of N–Acetyl Modified Analogs Of Oxazolidinone Antibacterial Agents Linezolid and Eperezolid", Poster F–21, 37th *Interscience Conference on Antimicrobial Agents and Chemotherepy*, Toronto, Canada, Sep. 28 to Oct. 1, 1997.

"Upjohn oxazolidinoneantibacterial agents" *Posters Presented at the 35th Interscience Conference on Antimicrobial Agents and Chemotherapy* San Francisco, Sep. 17–20, 1995.

Van Delft et al., "Preparation of 2–oxazolidinones by intramolecular nucleophilic substitution" (1997) *Synthesis* 450–454.

Wang et al., "Solid phase synthesis of protected peptides via photolytic cleavage of the α–methylphenacyl ester anchoring linkage" (1976) *J. Org. Chem.* 41:3258–3261.

Wang et al., "Chiral synthesis of DuP 721, a new antibacterial agent" (1989) *Tetrahedron* 45:1323–1326.

Watts et al., "In vitro activity of two oxazolidinone antimicrobial agents (U–100592 and U–100766) against Mycoplasma spp." (1995) *Abstracts of the 35th ICAAC Session 130. Poster. Oxazolidinones.* p. 151. (Abstract F220).

Zamkoff et al., "Activity of U–100480, an oxazolidinone, against *M. avium* complex (*MAC*) infection in beige mice" (1995) *Abstracts of the 35th ICAAC Session 130. Poster. Oxazolidinones.* p. 153. (Abstract F229).

Zurenko et al., "In vitro antibacterial activity of U–100592 and U–100766, novel oxazolidinone antibiotics" (1995) *Abstracts of the 35th ICAAC Session 130. Poster. Oxazolidinones.* p. 150. (Abstract F216).

Zurenko et al., "Oxazolidinone antibacterial agents: development of the clinical candidates eperezolid and linezolid" (1997) *Expert Opin. Invest. Drugs* 6:151–158.

Zurenko et al., "In vito activities of Y–100592 and U–100766, novel oxazolidinone antibacterial agents" (1996) *Antimicrob. Agents. Chemother.* 40:839–845.

Grant (1992) *Synthetic Peptides. A User's Guide*, W.H. Freeman and Co., table of contents enclosed herein.

Greene et al. *Protective Groups in Organic Synthesis,* 2nd Ed. (John Wiley & Sons, Inc., New York), table of contents enclosed herein.

* cited by examiner

Synthesis from 5-(S)-azidomethyloxazolidinone

Synthesis from 5-(S)-(protected amino)methyloxazolidinone

OXAZOLIDINONE COMBINATORIAL LIBRARIES, COMPOSITIONS AND METHODS OF PREPARATION

CROSS REFERENCE TO RELATED APPLICATIONS

This application is a divisional application of U.S. patent application Ser. No. 09/235,771, filed Jan. 22, 1999, now U.S. Pat. No. 6,239,152, which is a continuation in part of U.S. patent application Ser. No. 09/086,702, now abandoned, filed May 28, 1998, and which in turn is a CIP of U.S. patent application Ser. No. 09/012,535, now abandoned filed Jan. 23, 1998, under 35 USC 119(e)(i).

FIELD OF THE INVENTION

The present invention is directed to oxazolidinones; oxazolidinone compositions; oxazolidinone combinational libraries; and methods for their preparation and use.

BACKGROUND ART

Oxazolidinones are compounds where an amine group and a hydroxyl group on adjacent carbon atoms have been cyclic to form a 5-membered ring containing a carbonyl group. Certain oxazolidinones have been shown to exhibit a variety of biological activities. For example, some oxazolidinones are inhibitors of monoamine oxidase-B, an enzyme implicated in Parkinson's disease. See, for example, Ding et al., *J. Med. Chem.* 36:3606–3610 (1993).

A a ten step synthesis of oxazolidinone antibiotics has been described. U.S. Pat. No. 5,547,950. A four step synthesis of the antibacterial compound U-100592 also has been reported. Schauss et al., *Tetrahedron Letters*, 37:7937–7940 (1996). A five step preparation of enantiomerically pure cis- and trans-N-(propionyl)hexahydrobenzoxazolidin-2-ones further was reported. De Parrodi et al., *Tetrahedron: Asymmetry*, 8:1075–1082 (1997).

Scientists have reported that certain oxazolidinone derivatives exhibit beneficial antibacterial effects. For instance, N-[3-[3-fluoro-4-(morpholin-4-yl)phenyl]2-oxooxazolidin-5(s)-ylmethyl]acetamide (below) has been reported to be useful for the treatment of bacterial infections. Lizondo et al., *Drugs of the Future*, 21:1116–1123(1996).

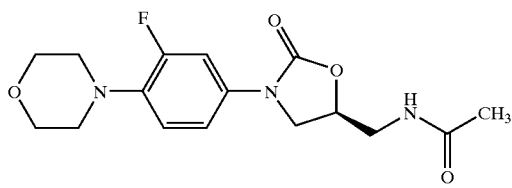

The synthesis of the oxazolidinone antibacterial agent shown below has been reported. Wang et al., *Tetrahedron*, 45:1323–1326 (1989). This oxazolidinone was made using a process that included the reaction of an aniline with glycidol to provide an amino alcohol, and the diethylcarbonate mediated cyclization of the amino alcohol to afford an oxazolidinone.

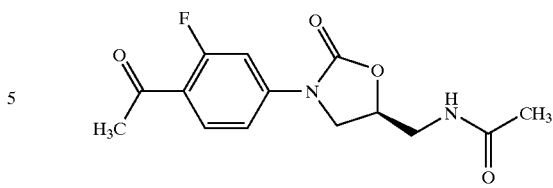

The synthesis of oxazolidinone antibacterial agents, including the compound shown below has been reported. U.S. Pat. No. 4,705,799. The process used to make the compound shown below included a metal mediated reduction of a sulfonyl chloride to provide a sulfide.

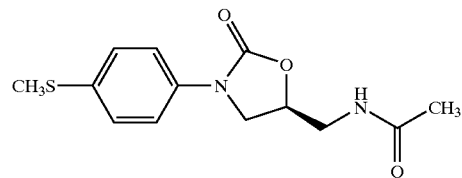

The synthesis of oxazolidinone antibacterial agents, including the pyridyl compound shown below has been reported. U.S. Pat. No. 4,948,801. The process used included an organometallic mediated coupling of an organotin compound and an aryl iodide.

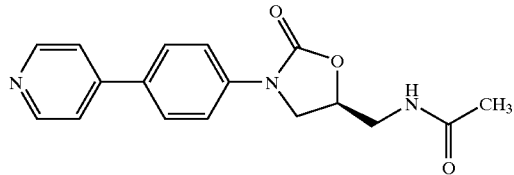

Synthetic routes to oxazolidinones often allow a chemist to produce only one compound at a time. These laborious methods can provide a limited number of compounds for evaluation in a biological screen. These methods cannot, however, provide the number of compounds required to supply a high-throughput biological screen, an assay technique whereby the activity of thousands of drug candidates, for example, per week, may be analyzed. This limitation on compound production is of practical importance since high-throughput screens are desirable and efficient for the discovery of new drugs.

SUMMARY OF INVENTION

Provided are oxazolidinones and combinatorial libraries, compositions comprising oxazolidinones, as well as methods of their synthesis and use. Using the methods provided herein, one of skill in the art can rapidly produce the large number of compounds required for high-throughput screening.

In one embodiment, provided are methods for the solid phase synthesis of oxazolidinones.

In one embodiment, the method comprises attaching an olefin to a solid support oxidizing the olefin to provide an epoxide functionality, opening the epoxide with an amine and cyclizing the resulting amino alcohol using a phosgene equivalent.

In another embodiment, the method comprises attaching an allylic amine to a solid support, oxidizing the olefin of the allylic amine to provide an epoxide, opening the epoxide with an amine, and cyclizing the resulting amino alcohol using a phosgene equivalent.

In another embodiment, the method comprises attaching allylamine to a solid support, oxidizing the olefin of allylamine to provide an epoxide, opening the epoxide with an amine and cyclizing the resulting amino alcohol using a phosgene equivalent.

In another embodiment, the method comprises attaching an olefin to a solid support, oxidizing the olefin to provide an epoxide, opening the epoxide with an amino acid and cyclizing the resulting amino alcohol using a phosgene equivalent.

In another embodiment, the method comprises attaching an olefin to a solid support, oxidizing the olefin to provide an epoxide, opening the epoxide with an aromatic amine and cyclizing the resulting amino alcohol using a phosgene equivalent.

Methods also are provided for the synthesis of oxazolidinone combinatorial libraries.

In one embodiment, the method comprises attaching an olefin group to an array of solid supports, oxidizing the individual olefin groups to provide an array of solid support bound epoxides, opening the epoxides with amine units, and cyclizing the resulting array of amino alcohols using a phosgene equivalent.

In another embodiment, the method comprises attaching an allylic amine to an array of solid supports, oxidizing the individual olefin groups to provide an array of solid support bound epoxides, opening the epoxides with amine units and cyclizing the resulting array of amino alcohols using a phosgene equivalent.

In another embodiment, the method comprises attaching allyl amine to an array of solid supports, oxidizing the individual olefin groups to provide an array of solid support bound epoxides, opening the epoxides with amine units and cyclizing the resulting array of amino alcohols using a phosgene equivalent.

In another embodiment, the method comprises attaching an olefin to an array of solid supports, oxidizing the individual olefin groups to provide an array of solid support bound epoxides, opening the epoxides with amino acid units and cyclizing the resulting array of amino alcohols using a phosgene equivalent.

In another embodiment, the method comprises attaching an olefin to an array of solid supports, oxidizing the individual olefin groups to provide an array of solid support bound epoxides, opening the epoxides with aromatic amine units and cyclizing the resulting array of amino alcohols using a phosgene equivalent.

Provided are a variety of oxazolidinones and combinatorial libraries thereof. In one embodiment, the oxazolidinones have the structure:

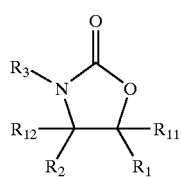

1a where $R_1$ is selected from the group consisting of alkyl, heteroalkyl aryl and heteroaryl; $R_2$ is selected from the group consisting of hydrogen, alkyl, heteroalkyl; aryl and heteroaryl; $R_3$ is selected from the group consisting of hydrogen, alkyl, heteroalkyl, aryl and heteroaryl; $R_{11}$ is selected from the group consisting of hydrogen, alkyl, heteroalkyl, aryl and heteroaryl; and $R_{12}$ is selected from the group consisting of hydrogen, alkyl, heteroalkyl, aryl and heteroaryl.

In another embodiment, oxazolidinones and combinatorial libraries are provided wherein the oxazolidinones are of the structure 1b, wherein $R_2$, $R_3$, $R_4$ and $R_5$ are, independently, hydrogen, alkyl,

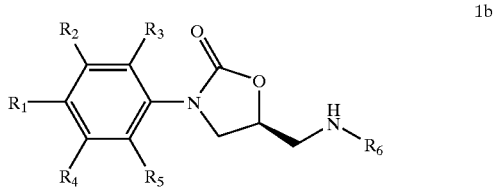

1b heteroalkyl, heteroaryl or an electron withdrawing group; $R_6$ is acyl or sulfonyl; and, $R_1$ is one of the following functional groups: $C(O)NR_7R_8$, wherein $R_7$ and $R_8$ are, independently, hydrogen, alkyl, heteroalkyl, aryl or heteroaryl; $C(O)OR_9$, wherein $R_9$ is hydrogen, alkyl, heteroalkyl, aryl or heteroaryl; $C(O)R_{10}$, wherein $R_{10}$ is hydrogen, alkyl, heteroalkyl, aryl or heteroaryl; $SR_{11}$, wherein $R_{11}$ is hydrogen, alkyl, heteroalkyl, aryl or heteroaryl; $S(O)_2R_{11}$, wherein $R_{11}$ is hydrogen, alkyl, heteroalkyl, aryl or heteroaryl; $S(O)R_{11}$, wherein $R_{11}$ is hydrogen, alkyl, heteroalkyl, aryl or heteroaryl; $NR_{12}R_{13}$, wherein $R_{12}$ and $R_{13}$ are, independently, hydrogen, acyl, sulfonyl, alkyl, heteroalkyl, aryl or heteroaryl; 2-oxazolyl, wherein $R_{14}$ is at the 4-position and $R_{15}$ is at the 5-position of the oxazolyl, and wherein $R_{14}$ and $R_{15}$ are, independently, hydrogen, alkyl, heteroalkyl, aryl, heteroaryl or an electron withdrawing group; 2-aminothiazolyl, wherein $R_{16}$ is at the 4-position and $R_{17}$ is at the 5-position of the thiazole, and wherein $R_{16}$ and $R_{17}$, are, independently, hydrogen, alkyl, heteroalkyl, aryl, heteroaryl or an electron withdrawing group; and, $CH_2NR_{18}R_{19}$, wherein $R_{18}$ and $R_{19}$ are, independently, hydrogen, alkyl, heteroalkyl, aryl, heteroaryl, acyl or sulfonyl.

All compounds disclosed herein can exist as different isomer forms including stereoisomers and enantiomerically pure forms, and all such isomers and forms are within the scope of the invention. For example, while structure 1b is shown with the preferred embodiment of a S isomer at the 5 position of the oxazolidinone, the R isomer is within the scope of the invention. Similarly, in all of the other oxazolidinone compounds, in the case where a preferred stereoisomer is shown at the 5 position of the oxazolidinone, both stereoisomers are within the scope of the invention.

In one embodiment of structure 1b, $R_1$ is $C(O)R_7R_8$.
In another embodiment of structure 1b, $R_1$ is $C(O)OR_9$.
In another embodiment of structure 1b, $R_1$ is $C(O)R_{10}$.
In another embodiment of structure 1b, $R_1$ is $SR_{11}$.
In another embodiment of structure 1b, $R_1$ is $S(O)_2R_{11}$.
In another embodiment of structure 1b, $R_1$ is $S(O)R_{11}$.
In another embodiment of structure 1b, $R_1$ is $NR_{12}R_{13}$. In another embodiment, $R_1$ is $NR_x(C=O)R_y$, wherein $R_x$ and $R_y$ are independently hydrogen, alkyl, heteroalkyl, aryl, or heteroaryl;

or $R_1$ is $NR_x(SO_2)R_y$, wherein $R_x$ and $R_y$ are independently hydrogen, alkyl, heteroalkyl, aryl, or heteroaryl with the proviso that $R_y$ is not H;

In another embodiment of structure 1b, $R_1$ is 2-oxazolyl, wherein $R_{14}$ is at the 4-position and $R_{15}$ is at the 5-position of the oxazole group.

In another embodiment of structure 1b, $R_1$ is 2-aminothiazolyl, wherein $R_{16}$ is at the 4-position and $R_{17}$ is at the 5-position of the aminothiazolyl group.

In another embodiment of structure 1b, $R_1$ is $CH_2NR_{18}R_{19}$.

In another embodiment of structure 1b, $R_1$ is $C(O)NR_7R_8$; and $R_3$, $R_4$ and $R_5$ are hydrogen.

In another embodiment of structure 1b, $R_1$ is $C(O)NR_7R_8$; $R_3$, $R_4$ and $R_5$ are hydrogen; and, $R_2$ is fluorine.

In another embodiment of structure 1b, $R_1$ is $C(O)NR_7R_8$; $R_3$, $R_4$ and $R_5$ are hydrogen; $R_2$ is fluorine; and, $R_6$ is $C(O)CH_3$.

In another embodiment of structure 1b, $R_1$ is $C(O)NR_7R_8$; $R_3$, $R_4$ and $R_5$ are hydrogen; $R_2$ is fluorine; $R_6$ is $C(O)CH_3$; and, $R_7$ is hydrogen.

In another embodiment of structure 1b, $R_1$ is $C(O)NR_7R_8$; $R_3$, $R_4$ and $R_5$ are hydrogen; $R_2$ is fluorine; $R_6$ is $C(O)CH_3$; $R_7$ is hydrogen; and, $R_8$ is heteroaryl.

A variety of methods of preparing combinatorial libraries comprising oxazolidinones are provided.

In one embodiment, the method is for the preparation of oxazolidinones, such as those of structure 1b. The method comprises the steps of: attaching a plurality of aryl oxazolidinones to a plurality of solid supports; functionalizing the 4-position of the aryl groups of the attached oxazolidinones; and, optionally, removing the oxazolidinones from the solid supports.

In another embodiment, the aryl oxazolidinone is attached to a solid support through the reaction of an iminophosphorane with a carbonyl containing resin to form an imine. In another embodiment, the aryl oxazolidinone is attached to a solid support through the reaction of an amine with a carbonyl containing resin to form an imine.

In another embodiment, the aryl oxazolidinone is attached to a solid support through the reaction of an iminophosphorane with a carbonyl containing resin to form an imine, and the imine is reduced to form an amine. In another embodiment, the aryl oxazolidinone is attached to a solid support through the reaction of an amine with a carbonyl containing resin to form an imine, and the imine is reduced to form an amine.

Also provided are biologically active oxazolidinones and compositions comprising biologically active oxazolidinones. For example, the oxazolidinones may have antibiotic activity.

In one embodiment, the biologically active oxazolidinones are of the structure 1b.

In another embodiment, the biologically active oxazolidinones are of the structure 1b, wherein $R_1$ of the oxazolidinone is $C(O)NR_7R_8$.

In another embodiment, the biologically active oxazolidinones are of the structure 1b, wherein $R_1$ of the oxazolidinone is 2 oxazolyl containing $R_{14}$ at the 4-position and $R_{15}$ at the 5-position of the oxazole.

In another embodiment, the biologically active oxazolidinones are of the structure 1b, wherein $R_1$ of the oxazolidinone is 2-aminothiazolyl containing $R_{16}$ at the 4-position and $R_{17}$ at the 5-position of the aminothiazole.

In another embodiment, the biologically active oxazolidinones are of the structure 1b, wherein $R_1$ of the oxazolidinone is $C(O)NR_7R_8$, and wherein $R_3$, $R_4$ and $R_5$ are hydrogen.

In another embodiment, the biologically active oxazolidinones are of the structure 1b, wherein $R_1$ of the oxazolidinone is 2 oxazolyl containing $R_{14}$ at the 4-position and $R_{15}$ at the 5-position of the oxazole, and wherein $R_3$, $R_5$ and $R_6$ are hydrogen.

In another embodiment, the biologically active oxazolidinones are of the structure 1b, wherein $R_1$ of the oxazolidinone is 2-aminothiazolyl containing $R_{16}$ at the 4-position and $R_{17}$ at the 5-position of the aminothiazole, and wherein $R_3$, $R_4$ and $R_5$ are hydrogen.

In another embodiment, the biologically active oxazolidinones are of the structure 1b, wherein $R_1$ of the oxazolidinone is $C(O)NR_7R_8$, and wherein $R_3$, $R_4$ and $R_5$ are hydrogen, and further wherein $R_2$ is fluorine.

In another embodiment, the biologically active oxazolidinones are of the structure 1b, wherein $R_1$ of the oxazolidinone is 2 oxazolyl containing $R_{14}$ at the 4-position and $R_{15}$ at the 5-position of the oxazole, and wherein $R_3$, $R_4$ and $R_5$ are hydrogen, and further wherein $R_2$ is fluorine.

In another embodiment, the biologically active oxazolidinones are of the structure 1b, wherein $R_1$ of the oxazolidinone is 2-aminothiazolyl containing $R_{16}$ at the 4-position and $R_{17}$ at the 5-position of the aminothiazole, and wherein $R_3$, $R_4$ and $R_5$ are hydrogen, and further wherein $R_2$ is fluorine.

In another embodiment, the biologically active oxazolidinones are of the structure 1b, wherein $R_1$ of the oxazolidinone is $C(O)NR_7R_8$, wherein $R_7$ is hydrogen and $R_8$ is 5-chloropyridine-3-yl, thiazole-2-yl, 5'-(5-aminopyridine-2-yl)thiopyridine-3'-yl, or pyridine-3-yl; and wherein $R_3$, $R_4$ and $R_5$ are hydrogen; and further wherein $R_2$ is fluorine; and further wherein $R_6$ is $C(O)CH_3$.

In another embodiment, the biologically active oxazolidinones are of the structure 1b, wherein $R_1$ of the oxazolidinone is $C(O)NR_7R_8$, wherein $R_7$ is hydrogen and $R_8$ is 5-chloropyridine-3-yl; and wherein $R_3$, $R_4$ and $R_5$ are hydrogen; and further wherein $R_2$ is fluorine; and further wherein $R_6$ is $C(O)CH_2SMe$.

In another embodiment, the biologically active oxazolidinones are of the structure 1b wherein $R_1$ of the oxazolidinone is $C(O)NR_7R_8$, wherein $R_7$ is hydrogen and $R_8$ is 5-chloropyridine-3-yl; and wherein $R_3$, $R_4$ and $R_5$ are hydrogen; and further wherein $R_2$ is fluorine; and further wherein $R_6$ is $C(O)CHCH(pyridine-3-yl)$.

In another embodiment, the biologically active oxazolidinones are of the structure 1b wherein $R_1$ of the oxazolidione is 5-amino-4-cyanooxazole-2-yl; and wherein $R_2$ is fluorine; and further wherein $R_3$, $R_4$ and $R_5$ are hydrogen; and still further wherein $R_6$ is $C(O)CH_3$.

In another embodiment, the biologically active oxazolidinones are of the structure 1b wherein $R_1$ of the oxazolidione is 4-phenylthiazole-2-yl-amino; and wherein $R_2$ is fluorine; and further wherein $R_3$, $R_4$ and $R_5$ are hydrogen; and still further wherein $R_6$ is $C(O)CH_3$.

A variety of methods of synthesizing biologically active oxazolidinones are provided.

In one embodiment, methods are provided for the preparation of oxazolidinones, such as those of the structure 1b, and comprise the steps of: providing an iminophosphorane; mixing the iminophosphorane with a resin that comprises carbonyl groups to form an imine intermediate; and, reducing the imine intermediate to afford a compound attached to the resin through an amine linkage. In another embodiment, the iminophosphorane is provided from an azide that is reacted with a phosphine. In another embodiment, the iminophosphorane is provided from an amine that is reacted with a (trisubstituted)phosphine dihalide.

In another embodiment, the resin comprising carbonyl groups is of the structure

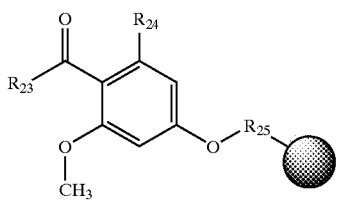

wherein $R_{23}$ is hydrogen, alkyl, aryl, O-alkyl or O-aryl; $R_{24}$ is hydrogen, $CH_3O$ or $NO_2$; $R_{25}$ is ($CH_2CONH$, wherein n is an integer ranging between 1 and about 5; and, the filled circle is a polymeric support.

In another embodiment of structure 1c, $R_{23}$ is hydrogen, $R_{24}$ is $CH_3O$, $R_{25}$ is $(CH_2)_3CONH$ and the filled circle is Tentagel, (cross-linked)polystyrene, (cross-linked) polyethylene glycol or polyethyleneglycol-polystyrene compositions.

Methods also are provided of synthesizing biologically active oxazolidinone compositions from a corresponding amine. In one embodiment, the method is for the preparation of oxazolidinones, for example, of the structure 1b, and comprises the steps of: reacting an amine with a resin that comprises carbonyl groups to form an imine intermediate; and, reducing the imine intermediate to afford a compound attached to the resin through an amine linkage.

DETAILED DESCRIPTION

Definitions

Figure 1:
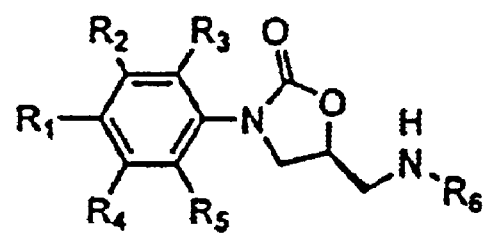
FIG. 1 is shows the structure of an oxazolidinone 1b.

As used herein, the terms and phrases have the meanings and definitions known in the art. Some of the more commuonly used phrases are described in more detail below.

"Combinatorial library" or "array" is an intentionally created collection of differing molecules which can be prepared synthetically and screened for biological activity in a variety of different formats (e.g., libraries of soluble molecules, libraries of molecules bound to a solid support). Typically, combinatorial libraries contain between about 6 and two million compounds. In one embodiment, combinatorial libraries contain between about 48 and 1 million compounds. For example, combinatorial libraries may contain between about 96 and 250,000 compounds. In another embodiment, combinatorial libraries may contain about 40 to 100 compounds.

"Alkyl" refers to a cyclic, branched or straight chain chemical group containing only carbon and hydrogen, such as methyl, pentyl, and adamantyl. Alkyl groups can either be unsubstituted or substituted with one or more substituents, e.g., halogen, alkoxy, acyloxy, amino, hydroxyl, mercapto, carboxy, benzyloxy, phenyl, and benzyl. Alkyl groups can be saturated or unsaturated (e.g., containing —C=C— or —C≡C— subunits), at one or several positions. Typically, alkyl groups will comprise about 1 to 12 carbon atoms, for example about 1 to 10, or about 1 to 8 carbon atoms.

"Heteroalkyl" refers to a cyclic, branched or straight chain chemical group containing carbon, hydrogen and at least one heteroatom. The heteroatom will be typically nitrogen, oxygen or sulfur. Heteroalkyl groups can either be unsubstituted or substituted with one or more substituents, e.g., halogen, alkoxy, acyloxy, amino, hydroxyl, mercapto, carboxy, benzyloxy, phenyl, benzyl. Where the heteroalkyl group contains a nitrogen atom, the nitrogen atom can be primary, secondary, tertiary, quaternary or can be in various forms such as an amide or sulfonamide. Heteroalkyl groups can contain one or more unsaturated (e.g., —C=C— or —C≡C—) subunits. Typically, heteroalkyl groups will comprise 1 to 12 atoms, for example 1 to 8, or 1 to 4 carbon atoms.

"Aryl" refers to a monovalent unsaturated aromatic carbocyclic group having a single ring (e.g. phenyl), multiple rings (e.g. biphenyl), or multiple condensed rings (e.g. naphthyl or anthryl). Aryl groups can be optionally unsubstituted or substituted with amino, hydroxyl, alkyl, heteroalkyl, alkoxy, halo, mercapto and other substituents. Typically, the aryl group is a substituted single ring compound. For example, the aryl group is a substituted phenyl ring.

"Heteroaryl" refers to a monovalent unsaturated aromatic carbocyclic group having a single ring (e.g., pyridyl or furyl) or multiple condensed rings (e.g., indolizinyl or benzothienyl) and having at least one heteroatom within the ring. The heteroatom in the ring is preferably nitrogen, oxygen or sulfur. Heteroaryl groups can be optionally unsubstituted or substituted with amino, hydroxyl, alkyl, heteroalkyl, alkoxy, halo, mercapto and other substituents. In one embodiment, the heteroaryl group is substituted.

"Electron withdrawing group" refers to a substituent that draws electrons to itself more than a hydrogen atom would if it occupied the same position in a molecule. This definition according to field effect is discussed in March, "Advanced Organic Chemistry," 3d Edition, pp. 16–17, Wiley-Interscience, New York. It should be contrasted with a definition based on resonance effects. Examples of electron withdrawing groups include —$NR_2$, —COOH, —OR, —SR, —F, —COR, —Cl, —SH, —$NO_2$, —Br, —$NH_2$, —$SO_2R$, —I, —OH, —CN, —C=$CR_2$, where R is alkyl, heteroalkyl, aryl or heteroaryl.

"Chemical module" refers to a general class of molecules that can be incorporated into a combinatorial library at a discrete step in the library synthesis. For example, thiols are chemical modules that can be coupled to a substrate, where the synthetic route employs a nucleophile to displace a solid support bound leaving group; isocyanates are chemical modules that can be coupled to a substrate, where the synthetic route employs an electrophile to react with a solid support bound amine. Chemical modules can contain tens, hundreds or thousands of different individual members.

"Protecting group" refers to a chemical group that exhibits the following characteristics: (1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) generated in such protection reactions. Examples of protecting groups can be found in Greene et al. (1991) *Protective Groups in Organic Synthesis,* 2nd Ed. (John Wiley & Sons, Inc., New York).

"Biologically active oxazolidinone compounds" or "bioactive oxazolidinone compounds" refers to an oxazolidinone compound, for example, of structure 1b that exhibits biological activity. For instance, a biologically active oxazolidinone can inhibit the interaction between an enzyme or receptor and its respective substrate(s) or endogenous ligand(s), or inhibit cell growth of a microorganism, by about at least 15% at a solution concentration of $10^{-3}$ molar or lower (i.e., it has inhibitory activity). For example, the biologically active oxazolidinone will inhibit such processes at solution concentrations of about $10^{-4}$ M or lower, or $10^{-5}$ M or lower, or, e.g., of about $10^{-6}$ M or lower.

"Allylic amine" refers to a compound of the following structure:

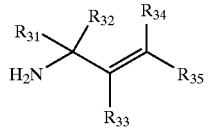

where $R_{31}$, $R_{32}$, $R_{33}$, $R_{34}$ and $R_{35}$ are independently selected from the group consisting of hydrogen, alky, heteroalkyl, aryl and heteroaryl. Where $R_{31}$, $R_{32}$, $R_{33}$, $R_{34}$ and $R_{35}$ are all hydrogen, the allylic amine is allylamine.

"Phosgene equivalent" refers to a chemical reagent that can add a C=O group to a molecule in either one or more than one chemical steps. A nonlimiting example of a phosgene equivalent that can add a C=O group in one chemical step is carbonyldiimidazole (CDI). A nonlimiting example of a phosgene equivalent that can add a C=O group in more than one chemical step is ethyl chloroformate.

"Acyl" refers to a group —(C=O)—R, where R is a substituent such as H, aryl, heteroaryl, alkyl or heteroalkyl. Exemplary acyl groups include formyl, acetyl, propionyl and butyryl.

"Sulfonyl", refers to a group —(SO$_2$)—R, where R is a substituent such as alkyl, heteroalkyl, aryl, or heteroaryl. Exemplary sulfonyl groups include methylsulfonyl and trifluoromethylsulfonyl.

Oxazolidinones

Provided are oxazolidinones and combinatorial libraries thereof, as well as methods for their synthesis, for example by solid phase synthesis methods.

In one embodiment, oxazolidinones have the following structure:

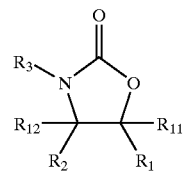

1a where $R_1$ is selected from the group consisting of alkyl, heteroalkyl, aryl and heteroaryl; $R_2$ is selected from the group consisting of hydrogen, alkyl, heteroalkyl, aryl and heteroaryl; $R_3$ is selected from the group consisting of hydrogen, alky, heteroalkyl, aryl and heteroaryl; $R_{11}$ is selected from the group consisting of hydrogen, alkyl, heteroalkyl, aryl and heteroaryl; and $R_{12}$ is selected from the group consisting of hydrogen, alkyl, heteroalkyl, aryl and heteroaryl.

Figure 29:
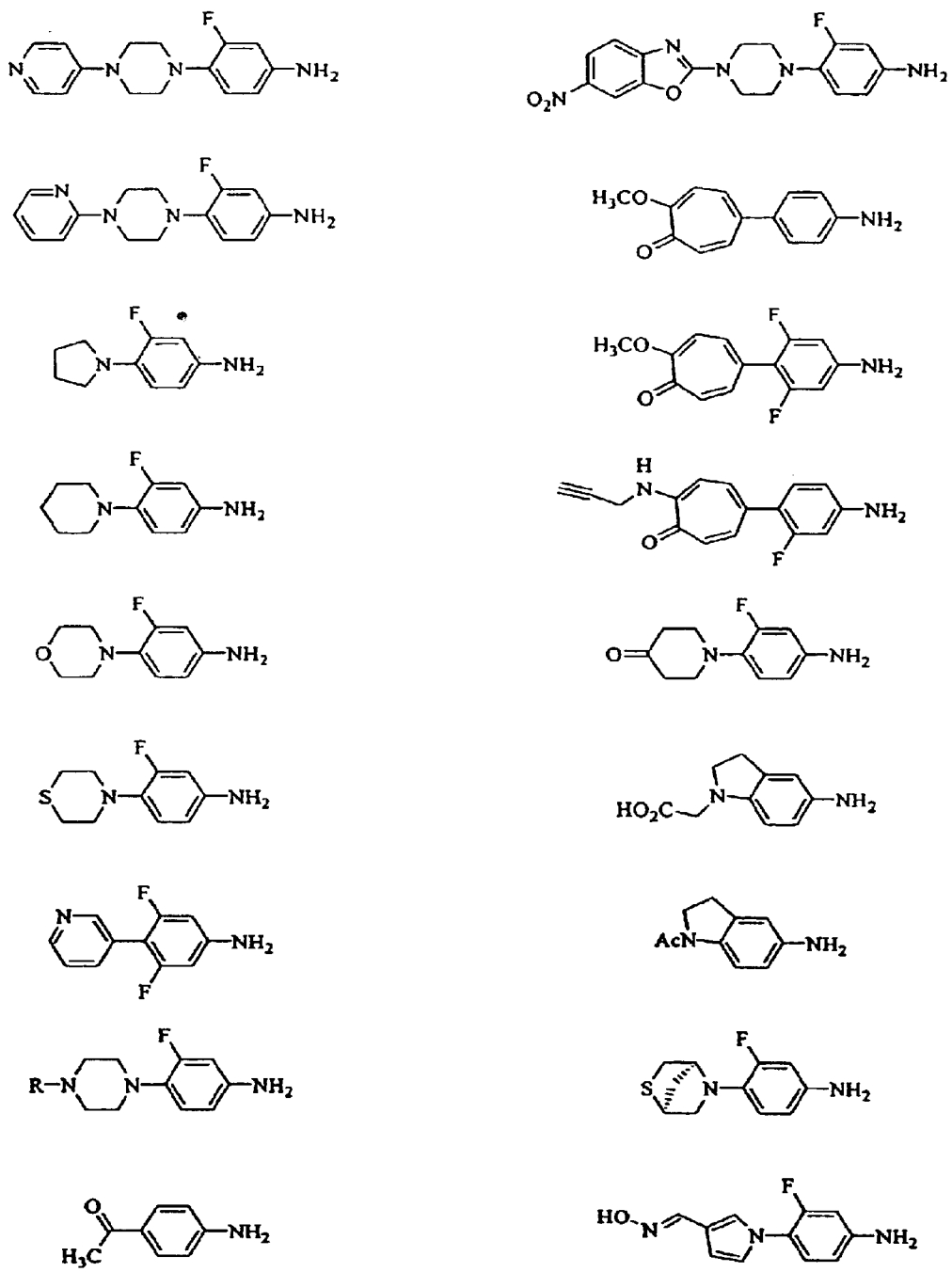
FIG. 29 shows a nonlimiting group of amines that are used in the preparation of sulfonyl, amidyl and ureayl oxazolidinone combinatorial libraries.
Figure 30:
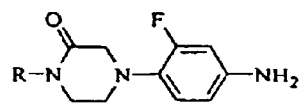
FIG. 30 shows another nonlimiting group of amines that are used in the preparation of sulfonyl, amidyl and ureayl oxazolidinone combinatorial libraries.
Figure 30:
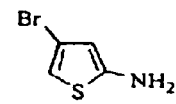
Figure 30:
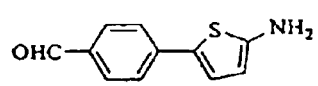
Figure 30:
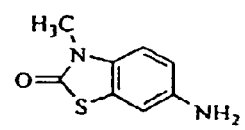
Figure 30:
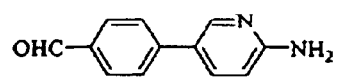
Figure 30:
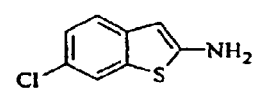
Figure 30:
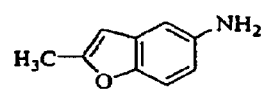
Figure 30:
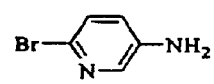
Figure 30:
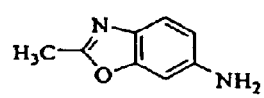
Figure 30:
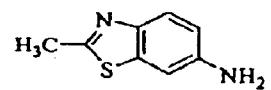
Figure 30:
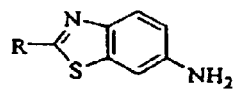
Figure 30:
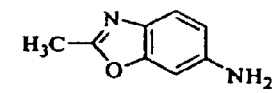
Figure 30:
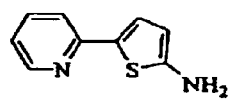
Figure 30:
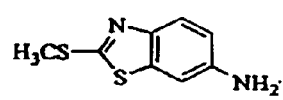
Figure 30:
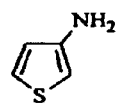
Figure 30:
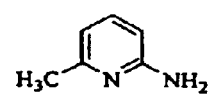
Figure 30:
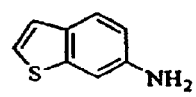
Figure 30:
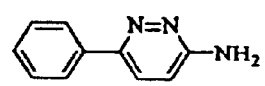
Figure 31:
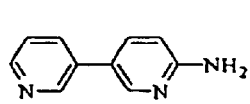
FIG. 31 shows another nonlimiting group of amines that are used in the preparation of sulfonyl, amidyl and ureayl oxazolidinone combinatorial libraries.
Figure 31:
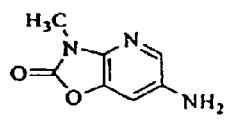
Figure 31:
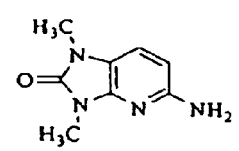
Figure 31:
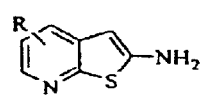
Figure 31:
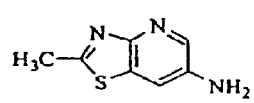
Figure 31:
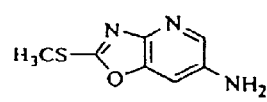
Figure 31:
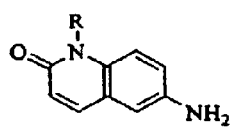
Figure 31:
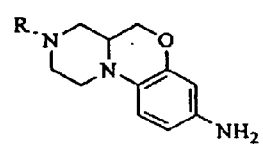
Figure 31:
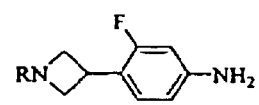
Figure 31:
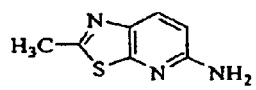
Figure 31:
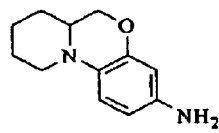
Figure 31:
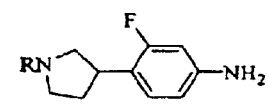
Figure 31:
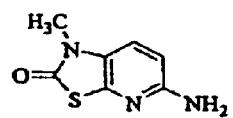
Figure 31:
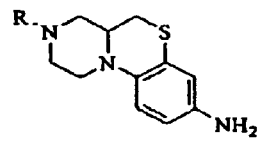
Figure 31:
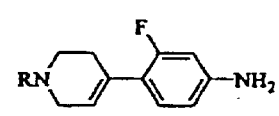
Figure 31:
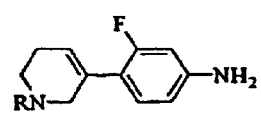
Figure 31:
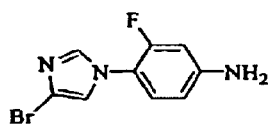
Figure 32:
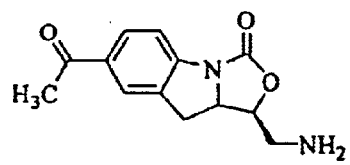
FIG. 32 shows a nonlimiting group of amines that are attached to a solid support in a manner analogous to amine 32a in FIG. 26 and then used to construct sulfonamide, amide and urea oxazolidinone libraries in an manner analogous to solid support bound amine 33a in FIG. 27.
Figure 32:
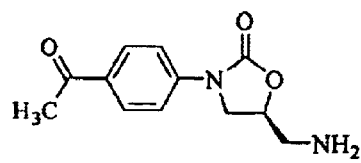
Figure 32:
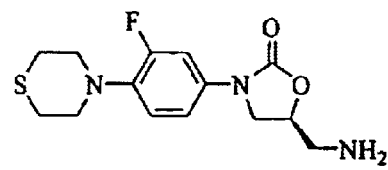
Figure 32:
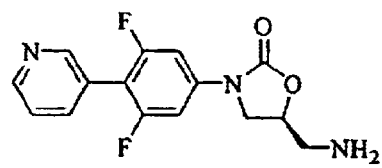
Figure 32:
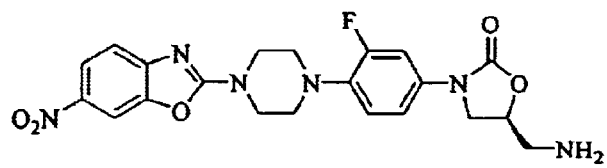
Figure 32:
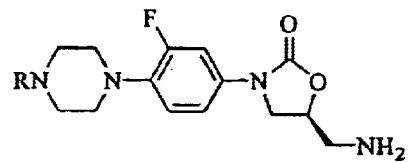
Figure 33A:
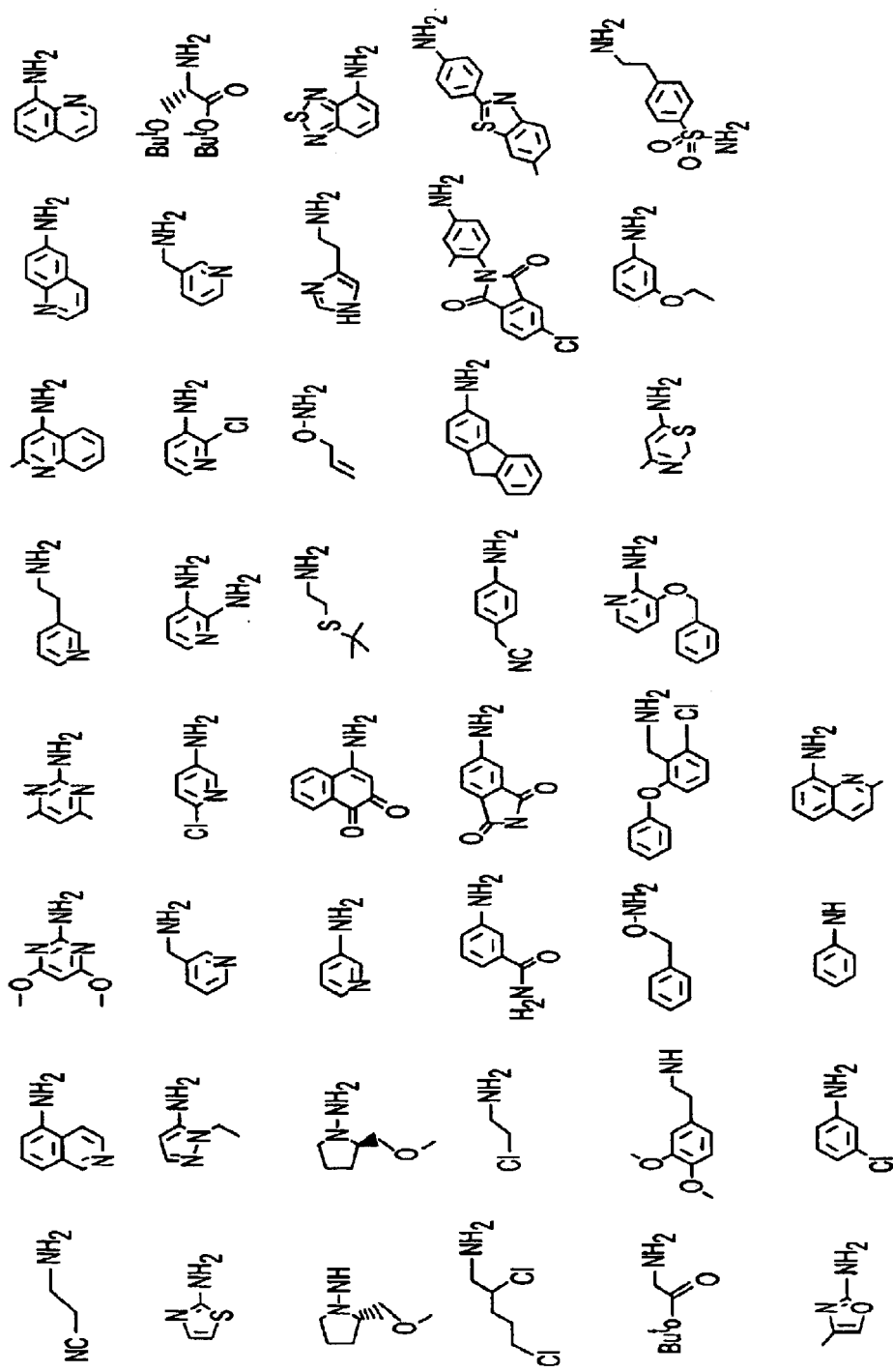
FIG. 33 is a group of amines for use in the preparation of oxazolidononones that was for example used to prepare combinatorial libraries comprising oxazolidinones of structure 1b, wherein $R_1$ is derived from the shown amine, $R_2$ is fluorine, $R_3$ is hydrogen, $R_4$ is hydrogen, $R_5$ is hydrogen and $R_6$ is $C(O)CH_3$.
Figure 33B:
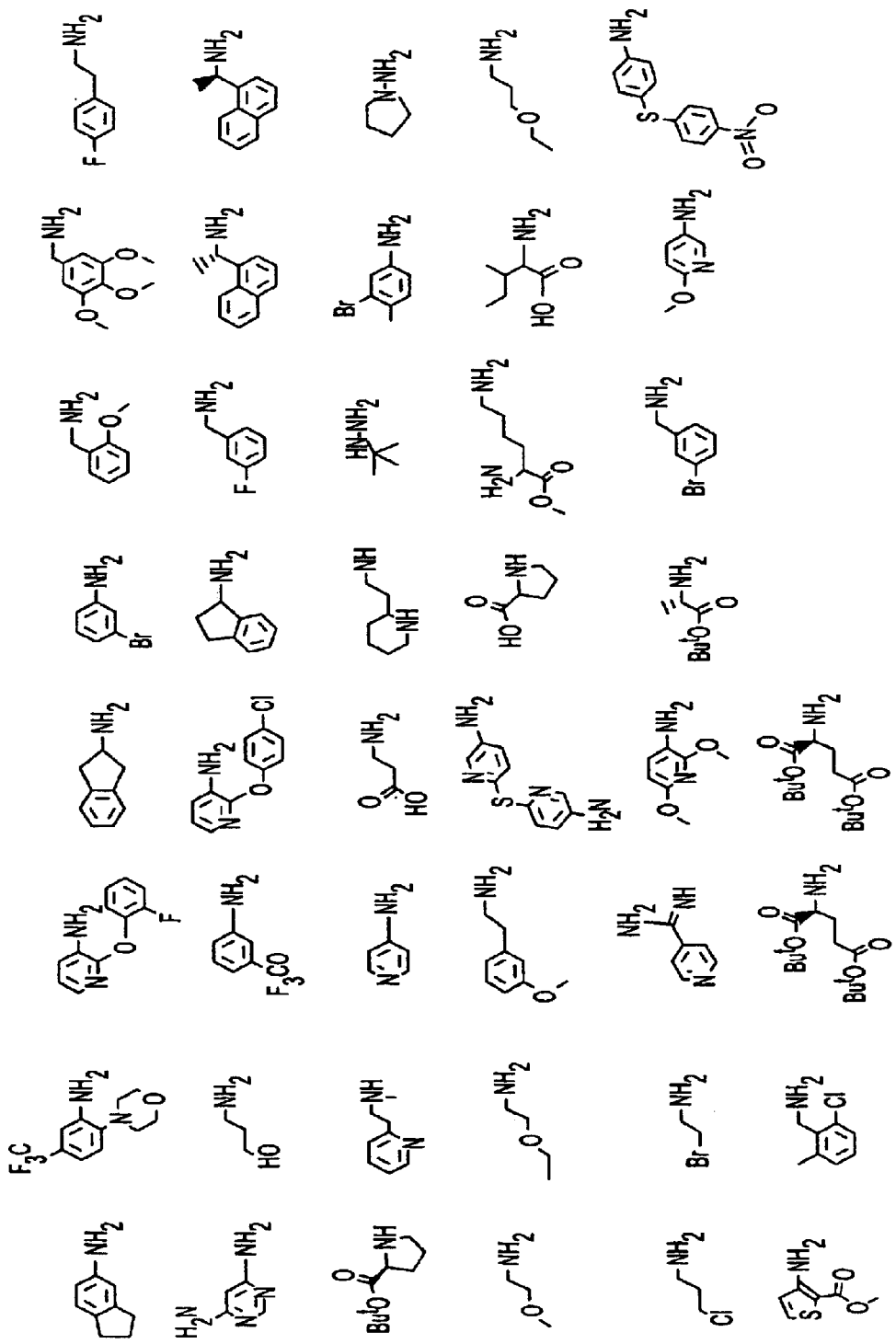
Figure 34A:
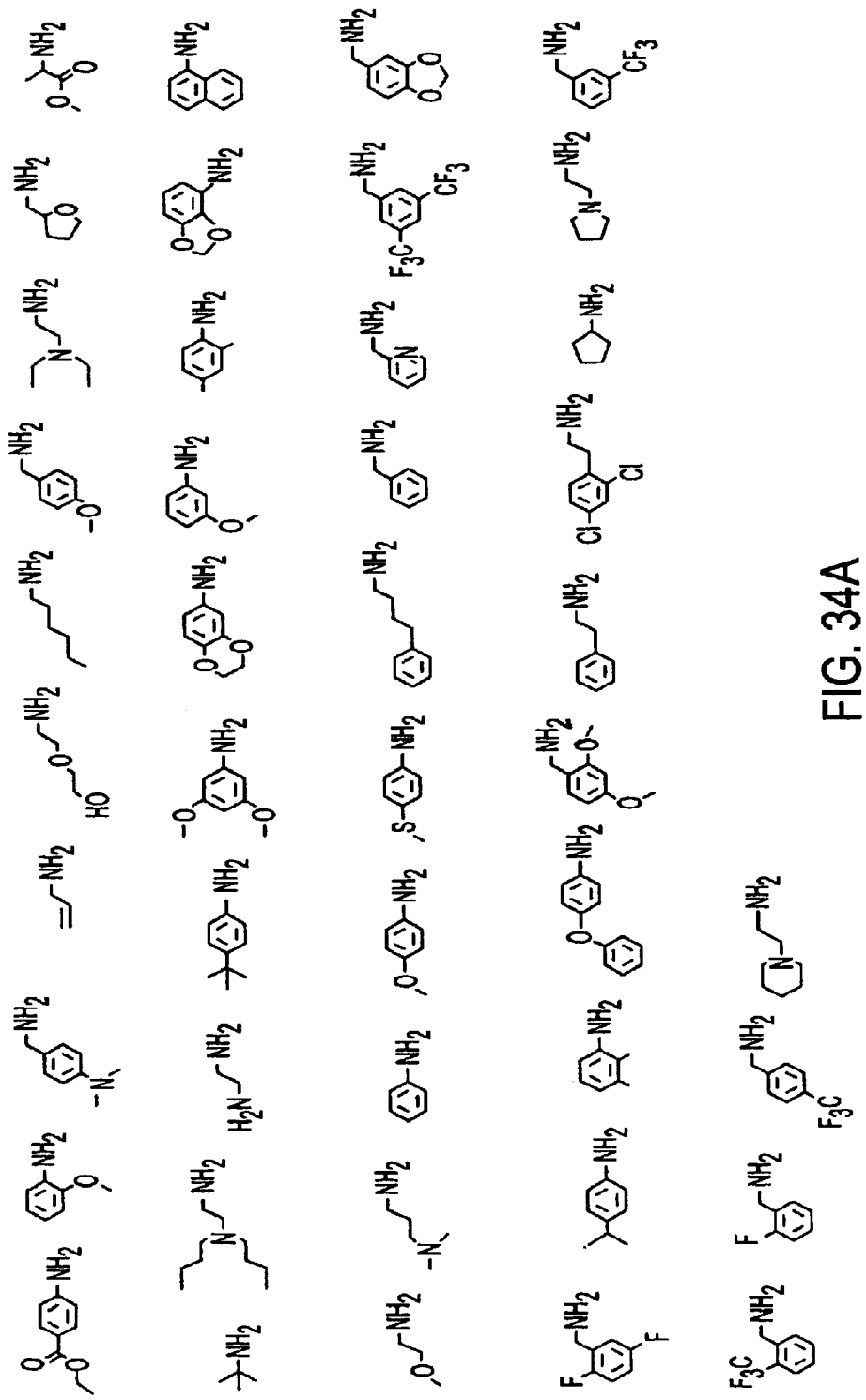
FIG. 34 is a group of amines for use in the preparation of oxazolidinones that was for example used to prepare combinatorial libraries comprising oxazolidinones of structure 1b, wherein $R_1$ is derived from the shown amine, $R_2$ is fluorine, $R_3$ is hydrogen, $R_4$ is hydrogen, $R_5$ is hydrogen and $R_6$ is $C(O)CH_3$.
Figure 34B:
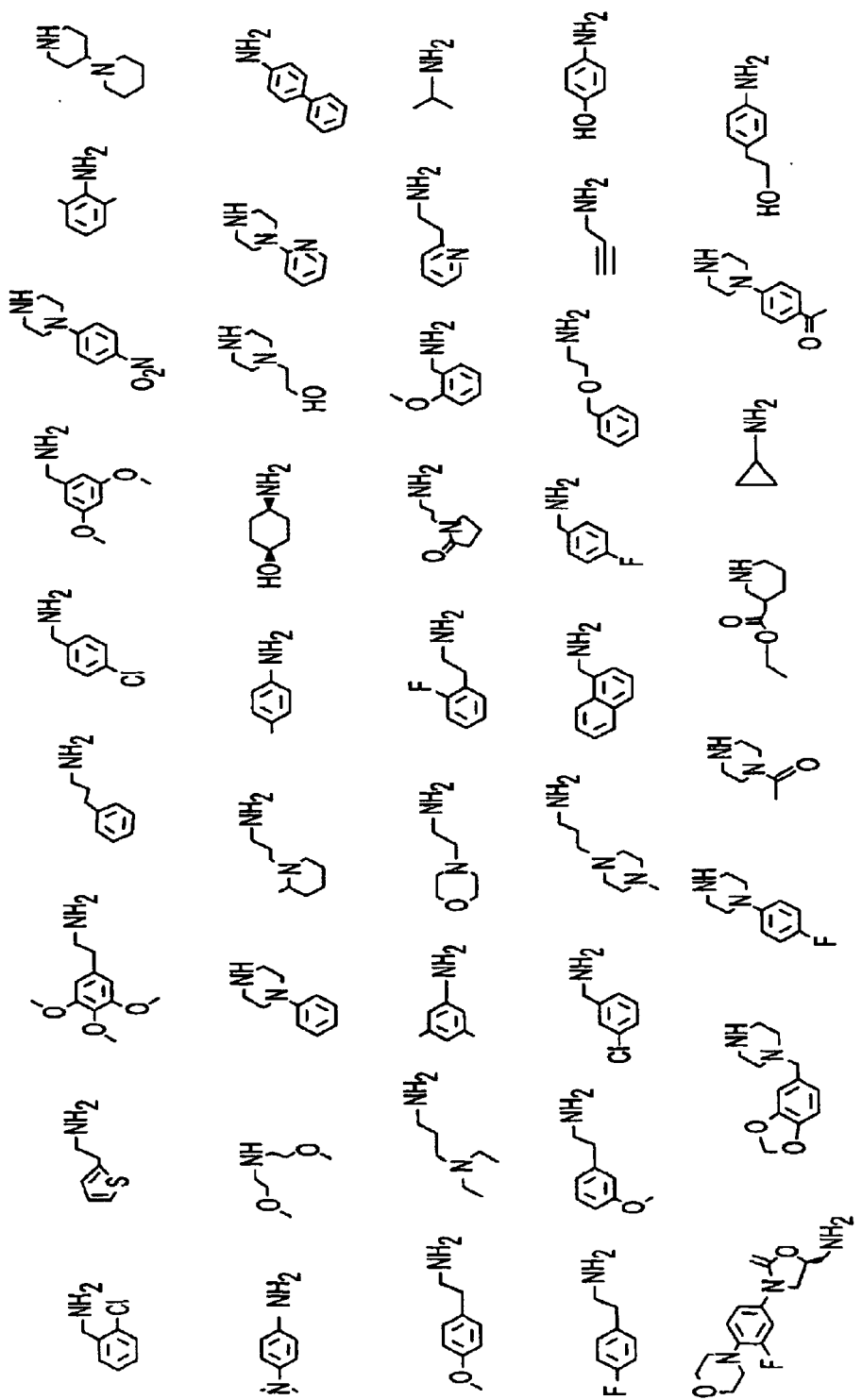
Figure 35A:
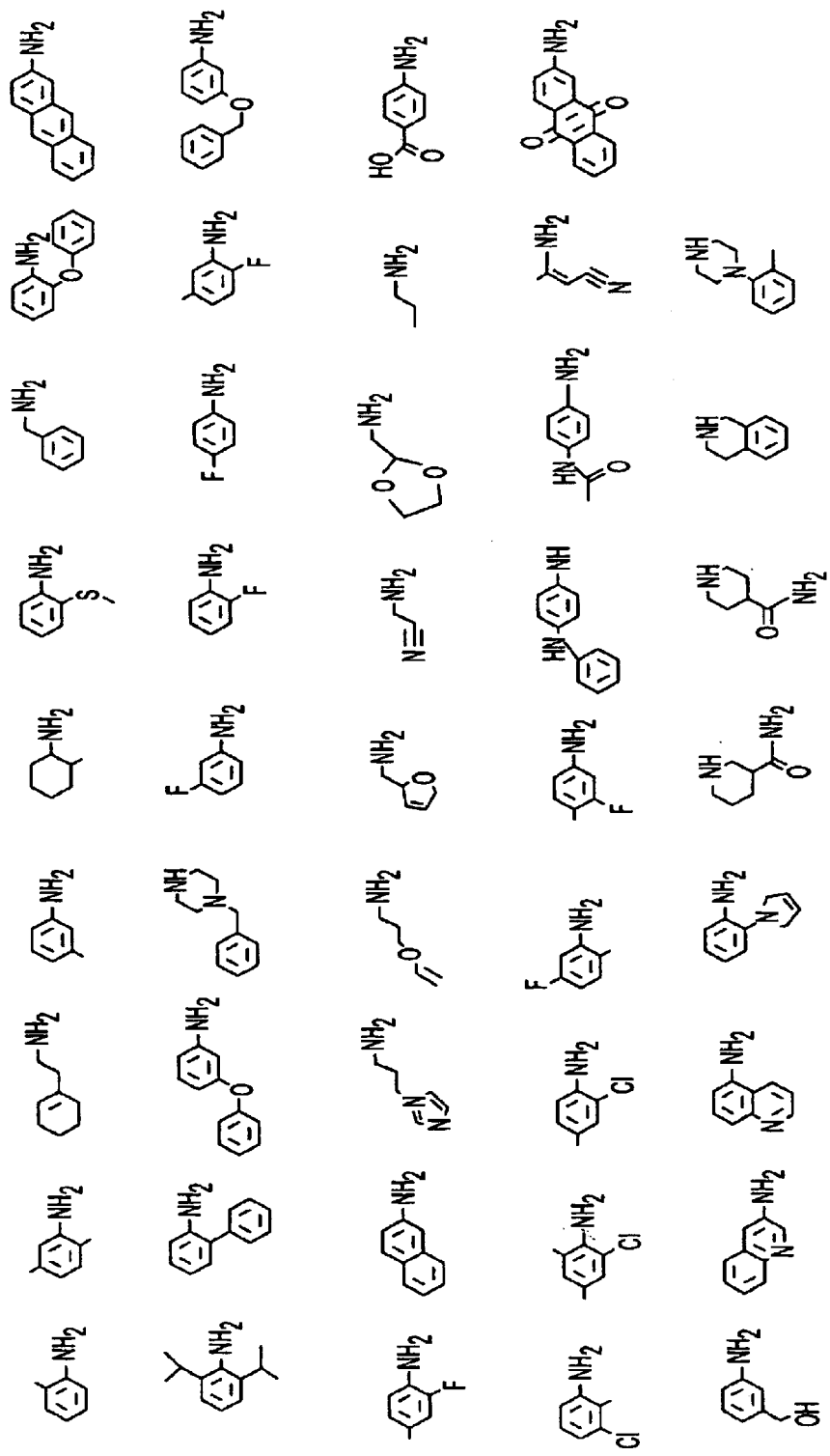
FIG. 35 is a group of amines for use in the preparation of oxazolidinones that was for example used to prepare combinatorial libraries comprising oxazolidinones of structure 1b, wherein $R_1$ is derived from the shown amine, $R_2$ is fluorine, $R_3$ is hydrogen, $R_4$ is hydrogen, $R_5$ is hydrogen and $R_6$ is $C(O)CH_3$.
Figure 35B:
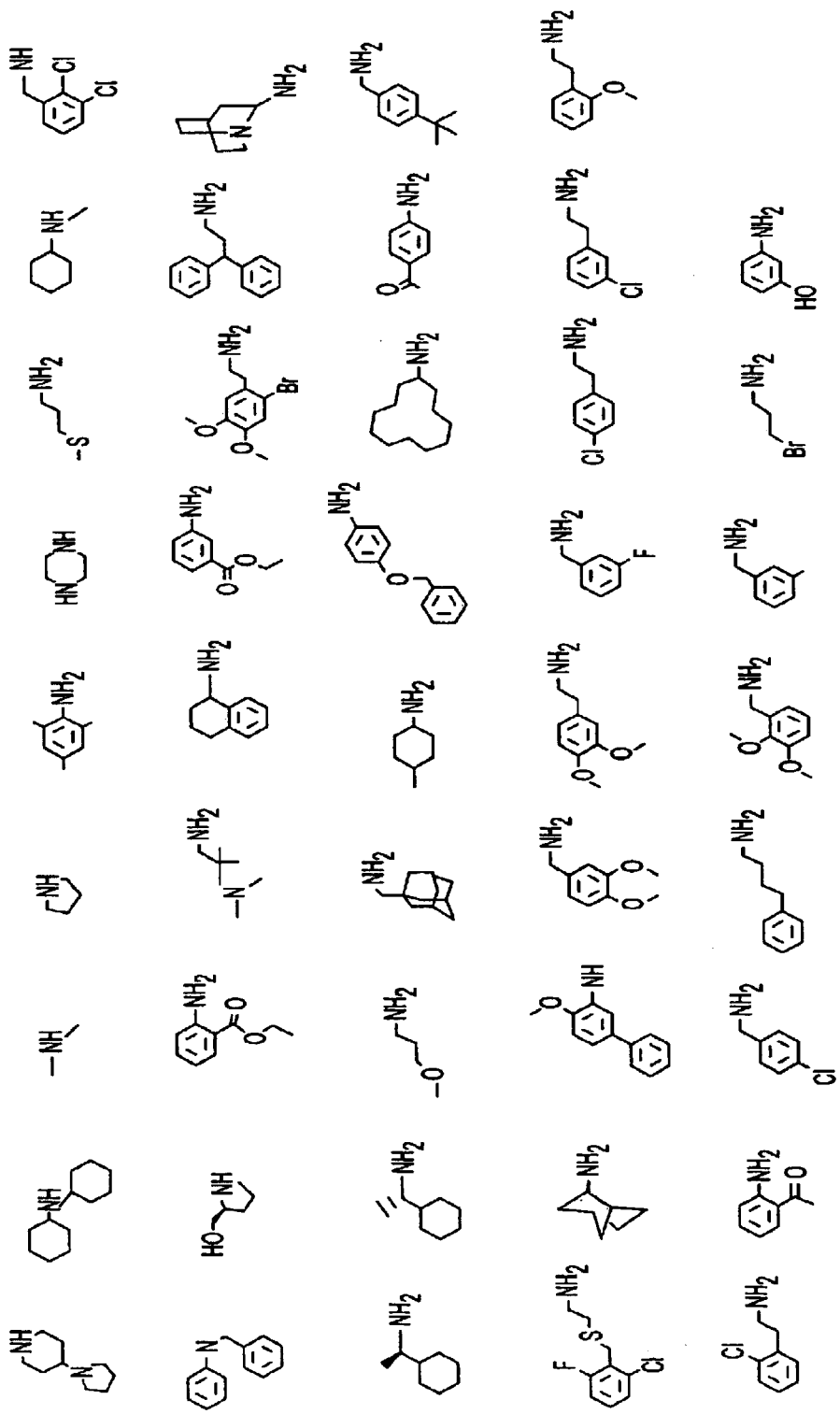
Figure 36:
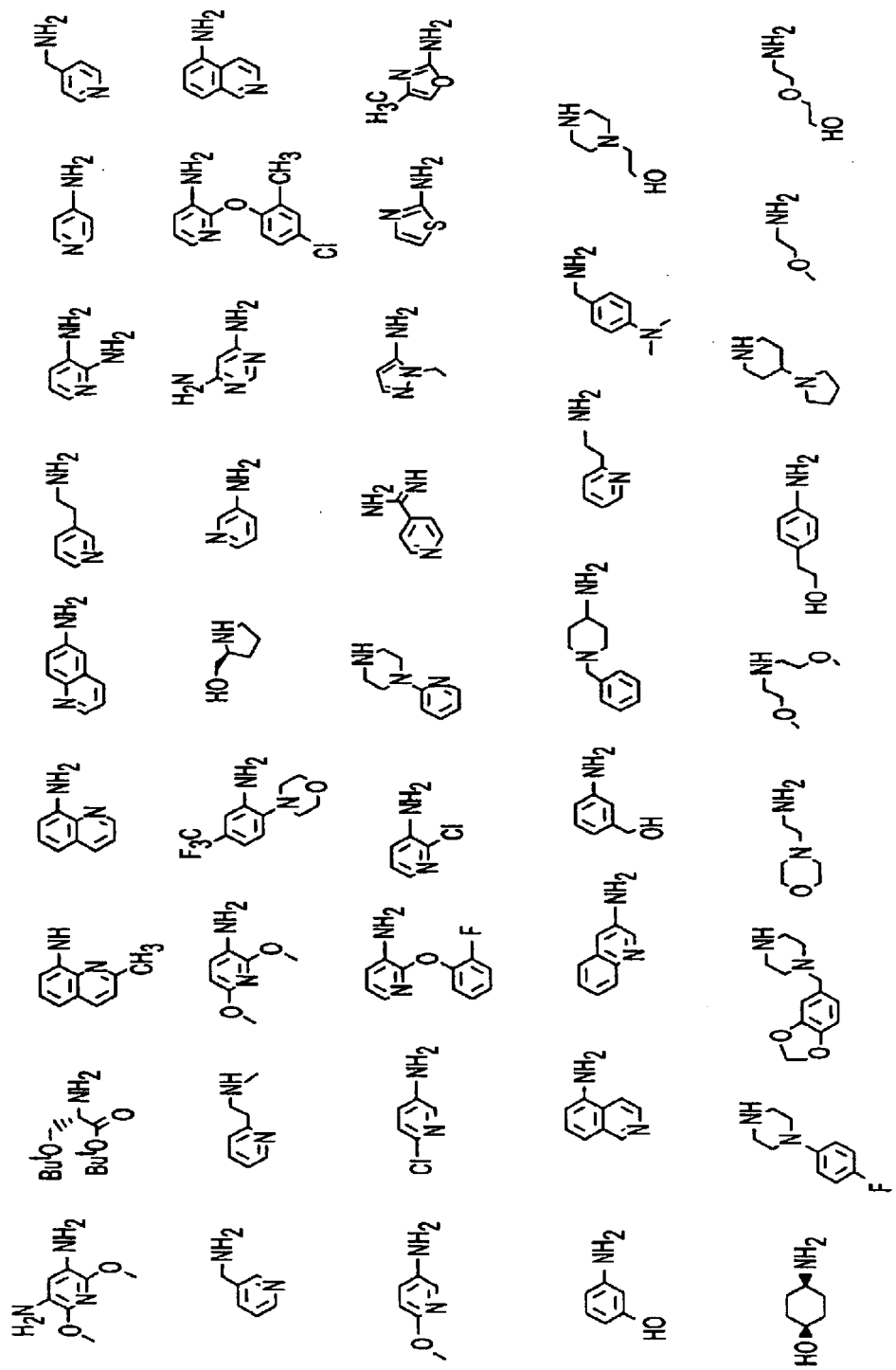
FIG. 36 is a group of amines for use in the preparation of oxazolidinones that was used for example to prepare combinatorial libraries comprising oxazolidinones of structure 1b, wherein $R_1$ is derived from the shown amine, $R_2$ is fluorine, $R_3$ is hydrogen, $R_4$ is hydrogen, $R_5$ is hydrogen and $R_6$ is $C(O)CHCHC_6H_4CH(p-NOCH_3)$ or $C(O)CHCHC_6H_4$ (p-$OCH_3$).
Figure 37:
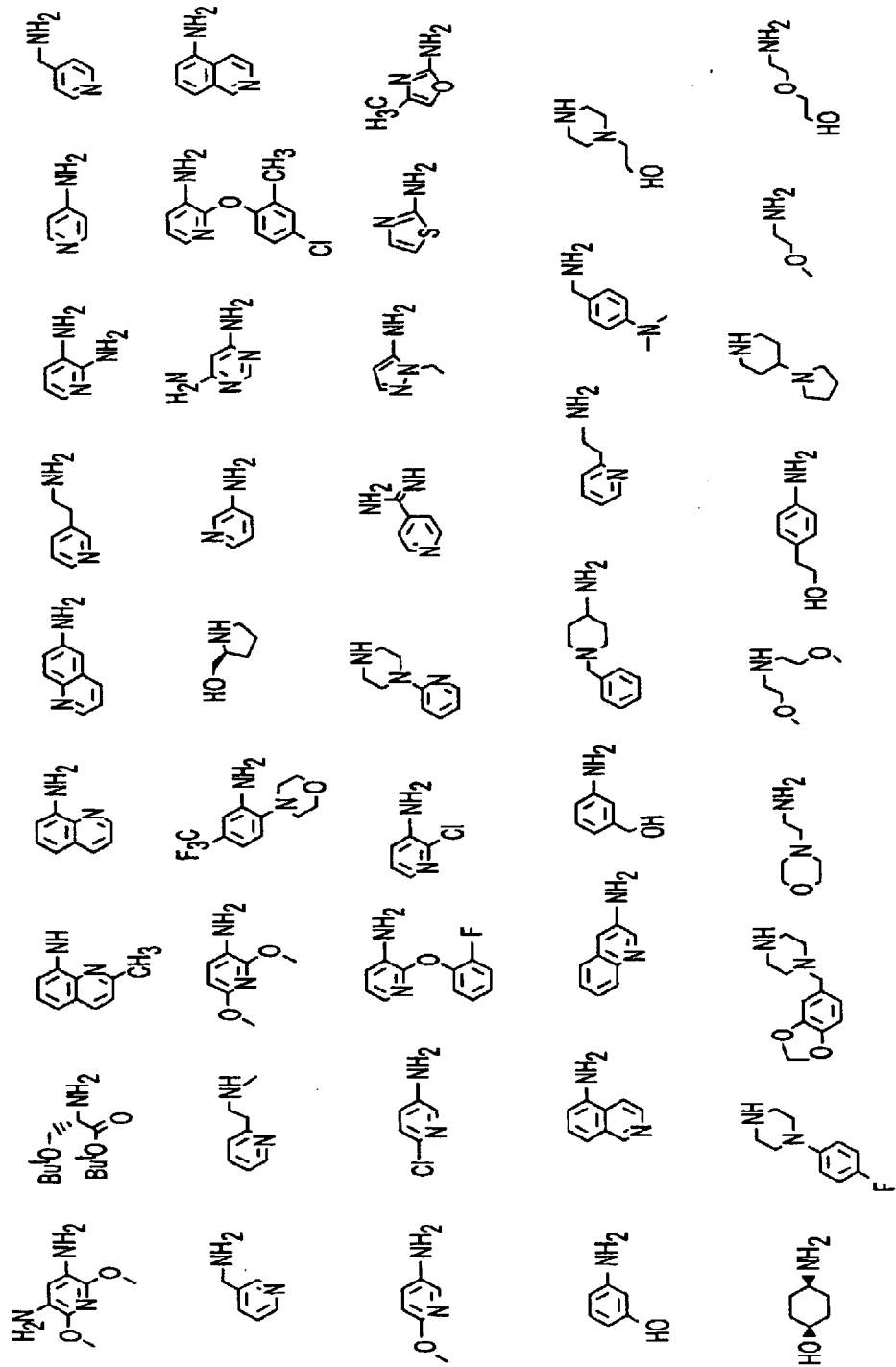
FIG. 37 is a group of amines for use in the preparation of oxazolidinones that was used for example to prepare combinatorial libraries comprising oxazolidinones of structure 1b, wherein $R_1$ is derived from the shown amine, $R_2$ is fluorine, $R_3$ is hydrogen, $R_4$ is hydrogen, $R_5$ is hydrogen and $R_6$ is $C(O)CH_2SCH_3$ or $C(O)CHCH(3-C_5H_4N)$.
Figure 38:
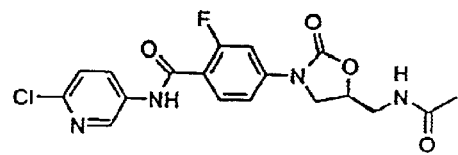
FIG. 38 shows a group of biologically active oxazolidinone compounds, with an MIC range of about 1.25–20 μg/ml against E. faecium.
Figure 38:
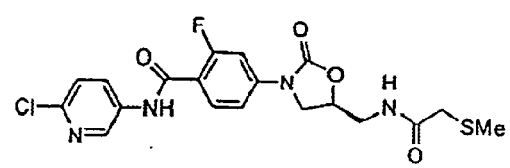
Figure 38:
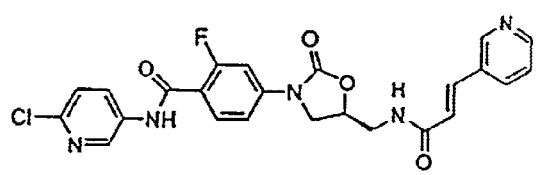
Figure 38:
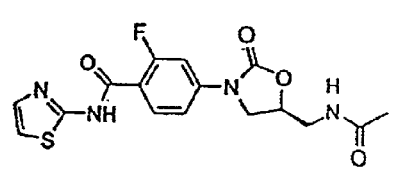
Figure 38:
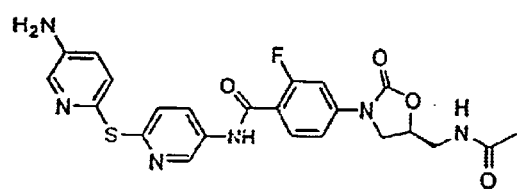
Figure 38:
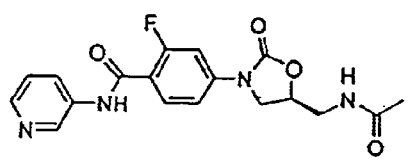
Figure 38:
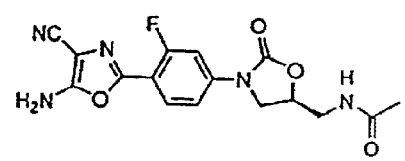
Figure 38:
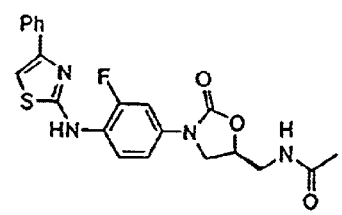

In another embodiment, $R_3$ of the oxazolidinones 1a is selected from the group consisting of aryl and heteroaryl, where the aryl and heteroaryl groups are the aryl and heteroaryl groups attached to the amines of Table 2 and FIGS. 29, 30 and 31.

In another embodiment, $R_3$ of the oxazolidinones 1a is a heteroaryl group such as a pyridyl group, a thienylphenyl group, an oxazolyl group or a pyrrolyl group, or is a (morpholino)fluorophenyl group.

In another embodiment, the oxazolidinones have the structure

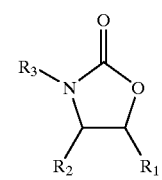

1d where $R_1$ is selected from the group consisting of alkyl, heteroalkyl, aryl and heteroaryl, $R_2$ is selected from the group consisting of hydrogen, alkyl, heteroalkyl, aryl and heteroaryl, and $R_3$ has the structure

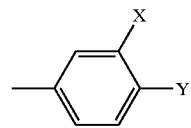

where 'X' is selected from the group consisting of hydrogen, electron withdrawing groups, alkyl, heteroalkyl, aryl and heteroaryl, and 'Y' is selected from the group consisting of hydrogen, electron withdrawing groups, alkyl, heteroalkyl, aryl and heteroaryl.

In another embodiment, $R_3$ of the oxazolidinones 1d is the following structure:

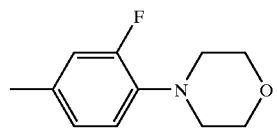

In another embodiment, $R_1$ of the oxazolidinones 1d is the following structure:

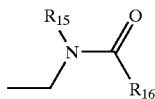

where $R_{15}$ is selected from the group consisting of hydrogen, alkyl, heteroalkyl, aryl and heteroaryl, and where $R_{16}$ is selected from the group consisting of alkyl, heteroalkyl, aryl and heteroaryl.

In one embodiment, oxazolidinones are provided that are antimicrobial compounds. In one embodiment, the antimicrobial compounds have the structure:

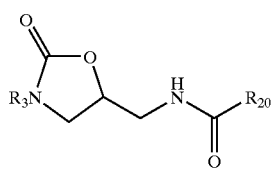

1e where $R_3$ is selected from the group consisting of aryl and heteroaryl, and where $R_{20}$ is selected from the group consisting of structures A, B, C, I, J and K:

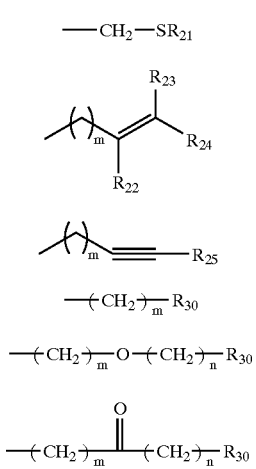

A

B

C

I

J

K where m is 0, 1, 2 or 3, and where n is 0, 1, 2 or 3, and where $R_{21}$ is selected from the group consisting of alkyl, heteroalkyl, aryl and heteroaryl, and where $R_{22}$, $R_{23}$ and $R_{24}$ are independently selected from the group consisting of hydrogen, alkyl, heteroalkyl and heteroaryl, and where $R_{25}$ is selected from the group consisting of hydrogen, alkyl, heteroalkyl, aryl and heteroaryl, and where $R_{30}$ is selected from the group consisting of alkyl, heteroalkyl, aryl and heteroaryl.

In another embodiment, $R_3$ of the antimicrobial compound 1e is selected from the group consisting of aryl and heteroaryl, where the aryl and heteroaryl groups are the aryl and heteroaryl groups attached to the amines of Table 2 and FIGS. 29, 30 and 31.

In another embodiment, $R_3$ of the antimicrobial compound 1e has the following structure:

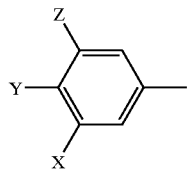

where X and Z are independently selected from the group consisting of hydrogen and fluoride, and where Y is selected from the group consisting of structures D, E, F, G and H:

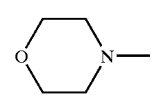

D

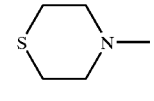

E

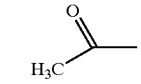

F

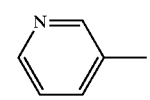

G

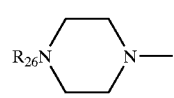

H where $R_{26}$ is selected from the group consisting of hydrogen, alkyl, heteroalkyl, aryl and heteroaryl.

In another embodiment, Y of the antimicrobial compound 1e has the structure D:

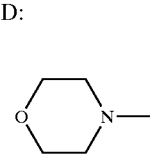

D

In another embodiment, the antimicrobial compound has the structure:

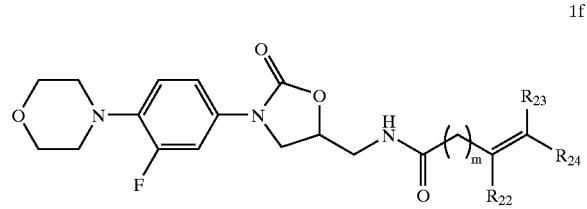

1f where m is 0, 1, 2 or 3, and where $R_{22}$, $R_{23}$ and $R_{24}$ are independently selected from the group consisting of hydrogen, alkyl, heteroalkyl and heteroaryl.

In another embodiment, m in the antimicrobial compound 1f is 0, $R_{22}$ and $R_{23}$ are hydrogen, and $R_{24}$ is an aryl group.

In another embodiment, the antimicrobial compound is of the structure

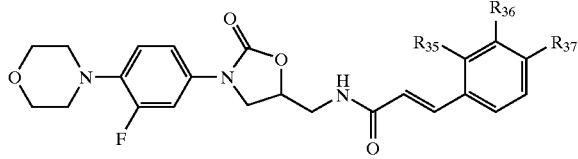

where $R_{35}$, $R_{36}$ and $R_{37}$ are independently selected from the group consisting of hydrogen, an electron withdrawing group, alky, heteroalkyl, aryl and heteroaryl.

In another embodiment, oxazolidinones and combinatorial libraries thereof, of the structure 1b shown in FIG. 1 are provided:

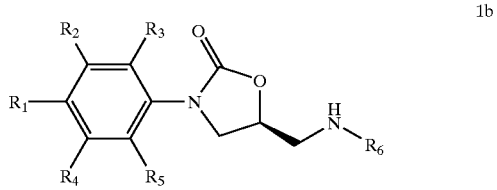

1b

In one embodiment, substituent $R_1$ of compound 1b is one of the following functional groups: $C(O)NR_7R_8$, wherein $R_7$ and $R_8$ are, independently, hydrogen, alkyl, heteroalkyl, aryl or heteroaryl (See FIGS. 33, 34, 35, 36 and 37 for nonlimiting examples of amines used to construct such libraries); $C(O)OR_9$, wherein $R_9$ is hydrogen, alkyl, heteroalkyl, aryl or heteroaryl; $C(O)R_{10}$, wherein $R_{10}$ is hydrogen, alkyl, heteroalkyl, aryl or heteroaryl; $SR_{11}$, wherein $R_{11}$ is hydrogen, alkyl, heteroalkyl, aryl or heteroaryl; $S(O)_2R_{11}$, wherein $R_{11}$ is hydrogen, alkyl, heteroalkyl, aryl or heteroaryl; $S(O)R_{11}$, wherein $R_{11}$ is hydrogen, alkyl, heteroalkyl, aryl or heteroaryl; $NR_{12}R_{13}$, wherein $R_{12}$ and $R_{13}$ are, independently, hydrogen, acyl, sulfonyl, alkyl, heteroalkyl, aryl or heteroaryl; $NR_x(C=O)R_y$, wherein $R_x$ and $R_y$ are independently hydrogen, alkyl, heteroalkyl, aryl, or heteroaryl; $NR_x(SO_2)R_y$, wherein $R_x$ and $R_y$ are independently hydrogen, alkyl, heteroalkyl, aryl, or heteroaryl, provided $R_y$ is not H; 2-oxazolyl, wherein $R_{14}$ is at the 4-position and $R_{15}$ is at the 5-position, and wherein $R_{14}$ and $R_{15}$ are, independently, hydrogen, alkyl, heteroalkyl, aryl, heteroaryl or an electron withdrawing group; 2-aminothiazolyl, wherein $R_{16}$ is at the 4-position and $R_{17}$ is at the 5-position, and wherein $R_{16}$ and $R_{17}$ are, independently, hydrogen, alkyl, heteroalkyl, aryl, heteroaryl or an electron withdrawing group; and, $CH_2NR_{18}R_{19}$, wherein $R_{18}$ and $R_{19}$ are, independently, hydrogen, alkyl, heteroalkyl, aryl, heteroaryl, acyl or sulfonyl. The substituents $R_2$, $R_3$, $R_4$ and $R_5$ are, independently, hydrogen, alkyl, heteroalkyl, heteroaryl or an electron withdrawing group; and, $R_6$ is acyl or sulfonyl.

In one embodiment, the substituents of compound 1b are defined as follows:. $R_1$ is $C(O)NR_7R_8$, wherein $R_7$ is hydrogen and $R_8$ is alkyl, heteroalkyl aryl or heteroaryl; $R_2$ is an electron withdrawing group; $R_3$, $R_4$ and $R_5$ are hydrogen; and $R_6$ is acyl. In one embodiment, the substituents are as follows: $R_1$ is $C(O)NR_7R_8$, wherein $R_7$ is hydrogen and $R_8$ is aryl or heteroaryl; $R_2$ is a halogen; $R_3$, $R_4$ and $R_5$ are hydrogen; and $R_6$ is acyl, wherein the acyl group is of the structure $C(O)(CH_2)_nCH_3$, and wherein n is an integer ranging from 0 to about 5. In one embodiment, the substituents are as follows: $R_1$ is $C(O)NR_7R_8$, wherein $R_7$ is hydrogen and $R_8$ is heteroaryl; $R_2$ is fluorine (F); $R_3$,$R_4$ and $R_5$ are hydrogen; and $R_6$ is acyl, wherein the acyl group is of the structure $C(O)CH_3$.

In another embodiment, the substituents of compound 1b are defined as follows: $R_1$ is $C(O)OR_9$, wherein $R_9$ is alkyl heteroalkyl, aryl or heteroaryl; $R_2$ is an electron withdrawing group; $R_3$, $R_4$ and $R_5$ are hydrogen; and $R_6$ is acyl. In one embodiment the substituents are as follows: $R_1$ is $C(O)OR_9$, wherein $R_9$ is alkyl or heteroalkyl; $R_2$ is a halogen; $R_3$, $R_4$ and $R_5$ are hydrogen; and $R_6$ is acyl, wherein the acyl group is of the structure $C(O)(CH_2)_nCH_3$, and wherein n is an integer ranging from 0 to about 5. For example, the substituents are as follows: $R_1$ is $C(O)OR_9$, wherein $R_9$ is alkyl; $R_2$ is fluorine; $R_3$, $R_4$ and $R_5$ are hydrogen; and, $R_6$ is acyl, wherein the acyl group is of the structure $C(O)CH_3$.

In another embodiment, the substituents of compound 1b are defined as follows: $R_1$ is $C(O)R_{10}$, wherein $R_{10}$ is hydrogen, alkyl, heteroalkyl, aryl or heteroaryl; $R_2$ is an electron withdrawing group; $R_3$, $R_4$ and $R_5$ are hydrogen; and $R_6$ is acyl. In one embodiment, the substituents are as follows: $R_1$ is $C(O)R_{10}$, wherein $R_{10}$ is alkyl or aryl; $R_2$ is a halogen; $R_3$, $R_4$ and $R_5$ are hydrogen; and $R_6$ is acyl wherein the acyl group is of the structure $C(O)(CH_2)_nCH_3$, and wherein n is an integer ranging from 0 to about 5. For example, the substituents are as follows: $R_1$ is $C(O)R_{10}$, wherein $R_{10}$ is alkyl; $R_2$ is fluorine; $R_3$, $R_4$ and $R_5$ are hydrogen; and $R_6$ is acyl, wherein the acyl group is of the structure $C(O)CH_3$.

In another embodiment, the substituents of compound 1b are defined as follows: $R_1$ is $SR_{11}$, wherein $R_{11}$ is alkyl, heteroalkyl, aryl or heteroaryl; $R_2$ is an electron withdrawing group; $R_3$, $R_4$ and $R_5$ are hydrogen; and, $R_6$ is acyl. In one embodiment, the substituents are as follows: $R_1$ is $SR_{11}$, wherein $R_{11}$ is alkyl or heteroalkyl; $R_2$ is a halogen; $R_3$, $R_4$ and $R_5$ are hydrogen; and, $R_6$ is acyl, wherein the acyl group is of the structure $C(O)(CH_2)_nCH_3$. For example, the substituents are as follows: $R_1$ is $SR_{11}$, wherein $R_{11}$ is alkyl; $R_2$ is fluorine; $R_3$, $R_4$ and $R_5$ are hydrogen; and $R_6$ is acyl, wherein the acyl group is of the structure $C(O)CH_3$.

In another embodiment, the substituents of compound 1b are defined as follows: $R_1$ is $S(O)_2R_{11}$, wherein $R_{11}$ is alkyl, heteroalkyl, aryl or heteroaryl; $R_2$ is an electron withdrawing group; $R_3$, $R_4$ and $R_5$ are hydrogen; and, $R_6$ is acyl. In one embodiment, the substituents are as follows: $R_1$ is $S(O)_2R_{11}$, wherein $R_{11}$ is alkyl or heteroalkyl; $R_2$ is a halogen; $R_3$, $R_4$ and $R_5$ are hydrogen; and, $R_6$ is acyl, wherein the acyl group is of the structure $C(O)(CH_2)_nCH_3$. For example, the substituents are as follows: $R_1$ is $S(O)_2R_{11}$, wherein $R_{11}$ is alkyl; $R_2$ is fluorine; $R_3$, $R_4$ and $R_5$ are hydrogen; and $R_6$ is acyl, wherein the acyl group is of the structure $C(O)CH_3$.

In another embodiment, the substituents of compound 1b are defined as follows: $R_1$ is $S(O)R_{11}$, wherein $R_{11}$ is alkyl, heteroalkyl, aryl or heteroaryl; $R_2$ is an electron withdrawing group; $R_3$, $R_4$ and $R_5$ are hydrogen; and, $R_6$ is acyl. In one embodiment, the substituents are as follows: $R_1$ is $S(O)R_{11}$, wherein $R_{11}$ is alkyl or heteroalkyl; $R_2$ is a halogen; $R_3$, $R_4$ and $R_5$ are hydrogen; and, $R_6$ is acyl, wherein the acyl group is of the structure $C(O)(CH_2)_nCH_3$. For example, the substituents are as follows: $R_1$ is $S(O)R_{11}$, wherein $R_{11}$ is alkyl; $R_2$ is fluorine; $R_3$, $R_4$ and $R_5$ are hydrogen; and $R_6$ is acyl, wherein the acyl group is of the structure $C(O)CH_3$.

In another embodiment, the substituents of compound 1b are defined as follows: $R_1$ is $NR_{12}R_{13}$, wherein $R_{12}$ is hydrogen and $R_{13}$ is hydrogen, alkyl, heteroalkyl, aryl, heteroaryl, acyl or sulfonyl; $R_2$ is an electron withdrawing group; $R_3$, $R_4$ and $R_5$ are hydrogen; $R_6$ is acyl. In one embodiment, the substituents are as follows: $R_1$ is $NR_{12}R_{13}$, wherein $R_{12}$ is hydrogen and $R_{13}$ is acyl or sulfonyl; $R_2$ is a halogen; $R_3$, $R_4$ and $R_5$ are hydrogen; and, $R_6$ is acyl, wherein the acyl group is of the structure $C(O)(CH_2)_nCH_3$, and wherein n is an integer ranging from 0 to about 5. For example, the substituents are as follows: $R_1$ is $NR_{12}R_{13}$, wherein $R_{12}$ is hydrogen and $R_{13}$ is acyl; $R_2$ is fluorine; $R_3$, $R_4$ and $R_5$ are hydrogen; and, $R_6$ is acyl, wherein the acyl group is of the structure $C(O)CH_3$.

In another embodiment, the substituents of compound 1b are defined as follows: $R_1$ is 2-oxazolyl, wherein $R_{14}$ is at the 4-position and $R_{15}$ is at the 5-position, and wherein $R_{14}$ and $R_{15}$ are, independently, hydrogen, alkyl, heteroalkyl, aryl, heteroaryl or an electron withdrawing group; $R_2$ is an electron withdrawing group; $R_3$, $R_4$ and $R_5$ are hydrogen; and, $R_6$ is acyl. In one embodiment, the substituents are as follows: $R_1$ is 2-oxazolyl, wherein $R_{14}$ is at the 4-position and $R_{15}$ is at the 5-position, and wherein $R_{14}$ and $R_{15}$ are, independently, an electron withdrawing group; $R_2$ is a halogen; $R_3$, $R_4$ and $R_5$ are hydrogen; and, $R_6$ is acyl, wherein the acyl group is of the structure $C(O)(CH_2)_nCH_3$. For example, the substituents are as follows: $R_1$ is 2-oxazolyl, wherein $R_{14}$ is at the 4-position and $R_{15}$ is at the 5-position, and wherein $R_{14}$ and $R_{15}$ are, independently, an electron withdrawing group; $R_2$ is fluorine; $R_3$, $R_4$ and $R_5$ are hydrogen; and, $R_6$ is acyl, wherein the acyl group is of the structure $C(O)CH_3$.

In another embodiment, the substituents of compound 1b are defined as follows: $R_1$ is 2-aminothiazolyl, wherein $R_{16}$ is at the 4-position and $R_{17}$ is at the 5-position, and wherein $R_{16}$ and $R_{17}$ are, independently, hydrogen, alkyl, heteroalkyl, aryl, heteroaryl or an electron withdrawing group; $R_2$ is an electron withdrawing group; $R_3$, $R_4$ and $R_5$ are hydrogen; and, $R_6$ is acyl. In one embodiment, the substituents are as follows: $R_1$ is 2-aminothiazolyl, wherein $R_{16}$ is at the 4-position and $R_{17}$ is at the 5-position, and wherein $R_{16}$ and $R_{17}$ are, independently, an electron withdrawing group; $R_2$ is a halogen; $R_3$, $R_4$ and $R_5$ are hydrogen; and, $R_6$ is acyl, wherein the acyl group is of the structure $C(O)(CH_2)_nCH_3$, and wherein n is an integer ranging from 0 to about 5. For example, the substituents are as follows: $R_1$ is 2-aminothiazolyl, wherein $R_{16}$ is at the 4-position and $R_{17}$ is at the 5-position, and wherein $R_{16}$ and $R_{17}$ are, independently, an electron withdrawing group; $R_2$ is fluorine; $R_3$, $R_4$ and $R_5$ are hydrogen; and, $R_6$ is acyl, wherein the acyl group is of the structure $C(O)CH_3$.

In another embodiment, the substituents of compound 1b are defined as follows: $R_1$ is $CH_2NR_{18}R_{19}$, wherein $R_{18}$ is hydrogen and $R_{19}$ is alkyl, heteroalkyl, aryl, heteroaryl, acyl or sulfonyl; $R_2$ is an electron withdrawing group; $R_3$, $R_4$ and $R_5$ are hydrogen; and, $R_6$ is acyl. In one embodiment, the substituents are as follows: $R_1$ is $CH_2NR_{18}R_{19}$, where $R_{18}$ is hydrogen and $R_{19}$ is acyl or sulfonyl; $R_2$ is a halogen; $R_3$, $R_4$ and $R_5$ are hydrogen; and $R_6$ is acyl, wherein the acyl group is of the structure $C(O)(CH_2)_nCH_3$. For example, the substituents are as follows: $R_1$ is $CH_2NR_{18}R_{19}$, wherein $R_{18}$ is hydrogen and $R_{19}$ is acyl; $R_2$ is fluorine; $R_3$, $R_4$ and $R_5$ are hydrogen; and, $R_6$ is acyl, wherein the acyl group is of the structure $C(O)CH_3$.

Synthesis of Combinatorial Libraries of Oxazolidinones 1b

Provided are methods for the preparation of combinatorial libraries comprising oxazolidinones, for example, of the structure 1b. (For a general discussion of combinatorial library synthesis, see U.S. Pat. No. 5,549,974, which is hereby incorporated by reference for all purposes.) In one embodiment, the methods comprise attaching an aryl oxazolidinone to a solid support; functionalizing the 4position of the aryl group; and removing the oxazolidinone from the solid support.

Figure 2:
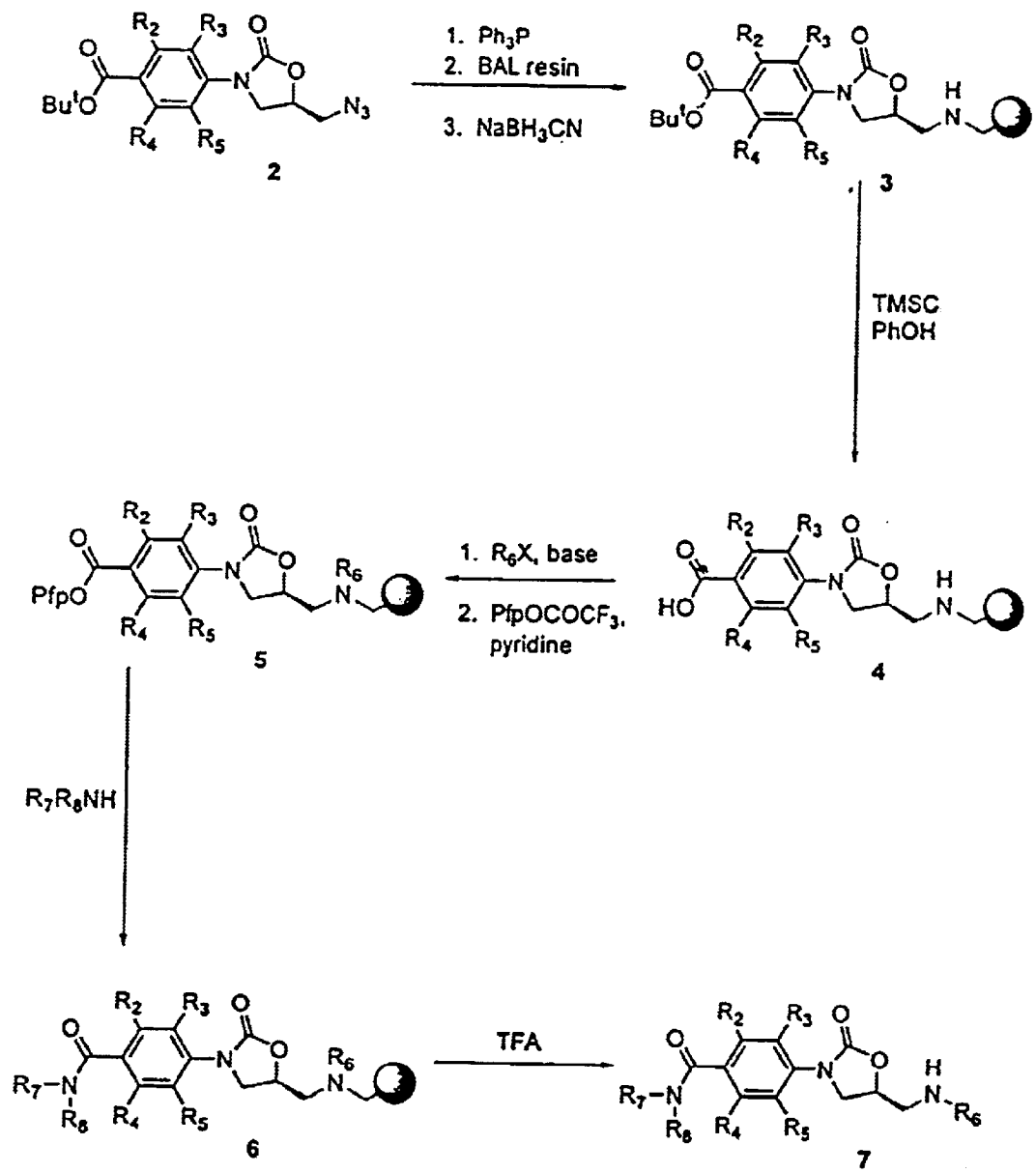
FIG. 2 is a scheme showing the synthesis of a combinatorial library comprising oxazolidinones of structure 1b, wherein $R_1$ is $C(O)R_7R_8$.

FIG. 2 shows a method for the preparation of combinatorial libraries comprising oxazolidinones of the structure 1b, wherein $R_1$ is $C(O)NR_7R_8$. A plurality of azides 2 are converted to the corresponding iminophosphoranes upon reaction with a phosphine. The ylides are mixed with a plurality of solid supports containing a carbonyl functional group, producing a plurality of amines. The imines are reduced (e.g., $NaBH_3CN$) to provide a plurality of amines 3. The ester group of 3 is deprotected to afford a plurality of acids 4. Acylation of the amine and activation of the acid of 4 yields a plurality of activated esters 5. The activated esters are reacted with an $R_7R_8NH$ amine unit, providing a plurality of amides 5. The solid support bound amides 5 are removed from the solid support using a suitable reagent (e.g., TFA) to afford a plurality of amides 7 in solution.

Figure 3:
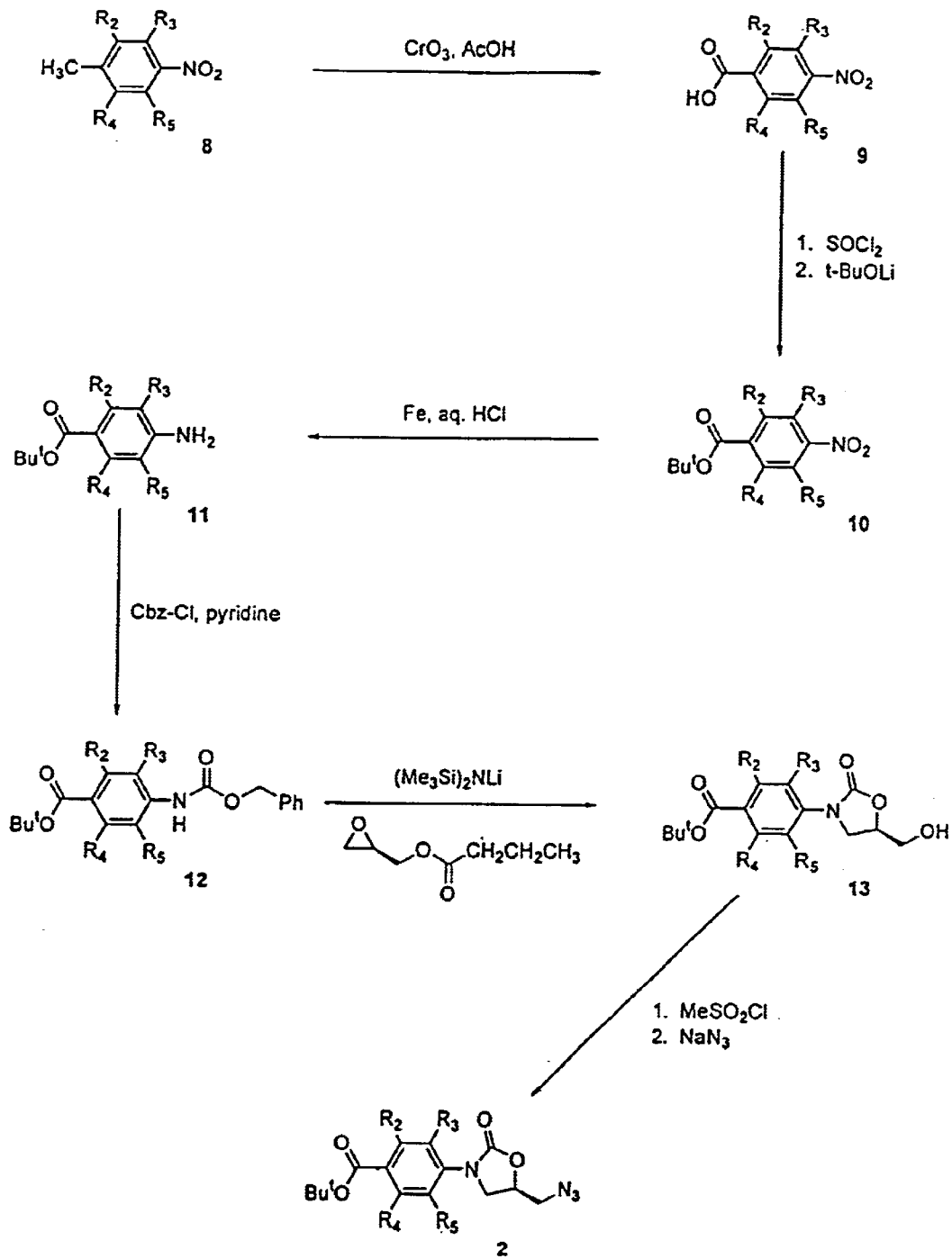
FIG. 3 is a scheme showing the synthesis of a set of azido oxazolidinones.

The plurality of azides 2 is produced starting from a set of substituted methylnitrobenzenes (8, FIG. 3). The methyl group of 8 is oxidized to provide the corresponding carboxylic acids 9. The acids are esterified, affording a set of nitro esters 10. The nitro group of 10 is reduced to yield a set of amines 11. Acylation of 11 provides a set of protected amines 12. Amines 12 are reacted with a substituted epoxide to afford a set of amino alcohols, which are cyclized to a set of oxazolidinones 13. Displacement of the primary alcohol of 13 yields the azides 2.

Figure 4:
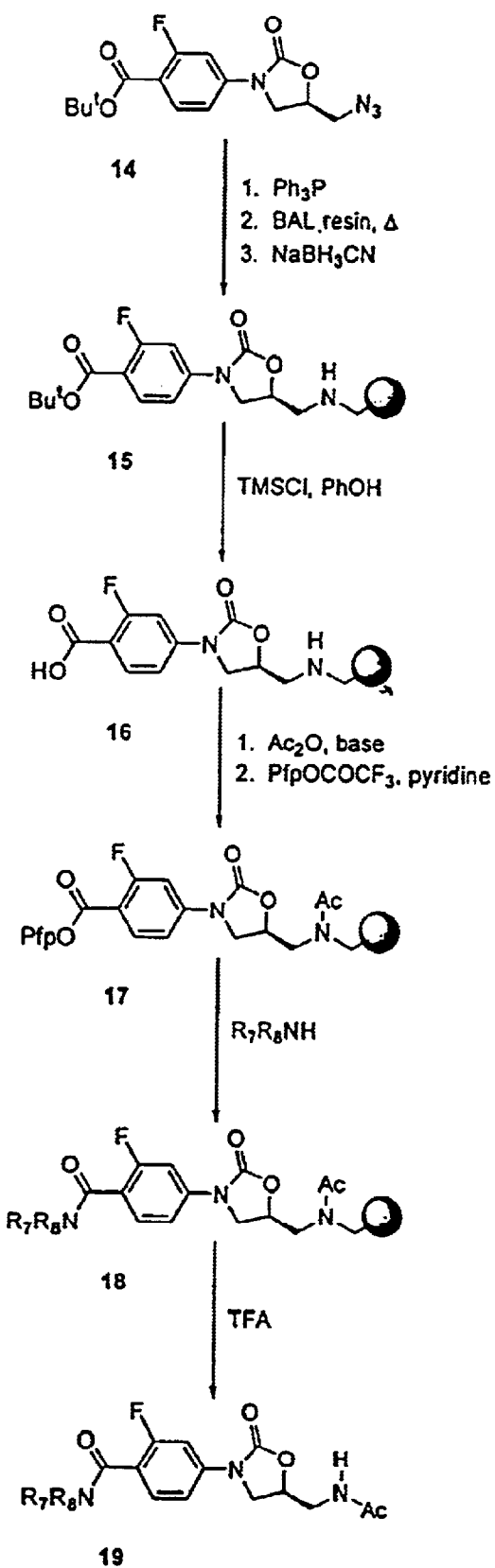
FIG. 4 is a scheme showing the synthesis of a combinatorial library comprising oxazolidinones of structure 1b, wherein $R_1$ is $C(O)R_7R_8$, and wherein $R_3$, $R_4$ and $R_5$ are hydrogen; and wherein in FIG. 4, the N—Ac group of 17, 18 and 19 also may be $NCOR_1$, wherein $R_1$ is a substituent, such as H, alkyl, heteroalkyl, aryl, or heteroaryl.
Figure 47A:
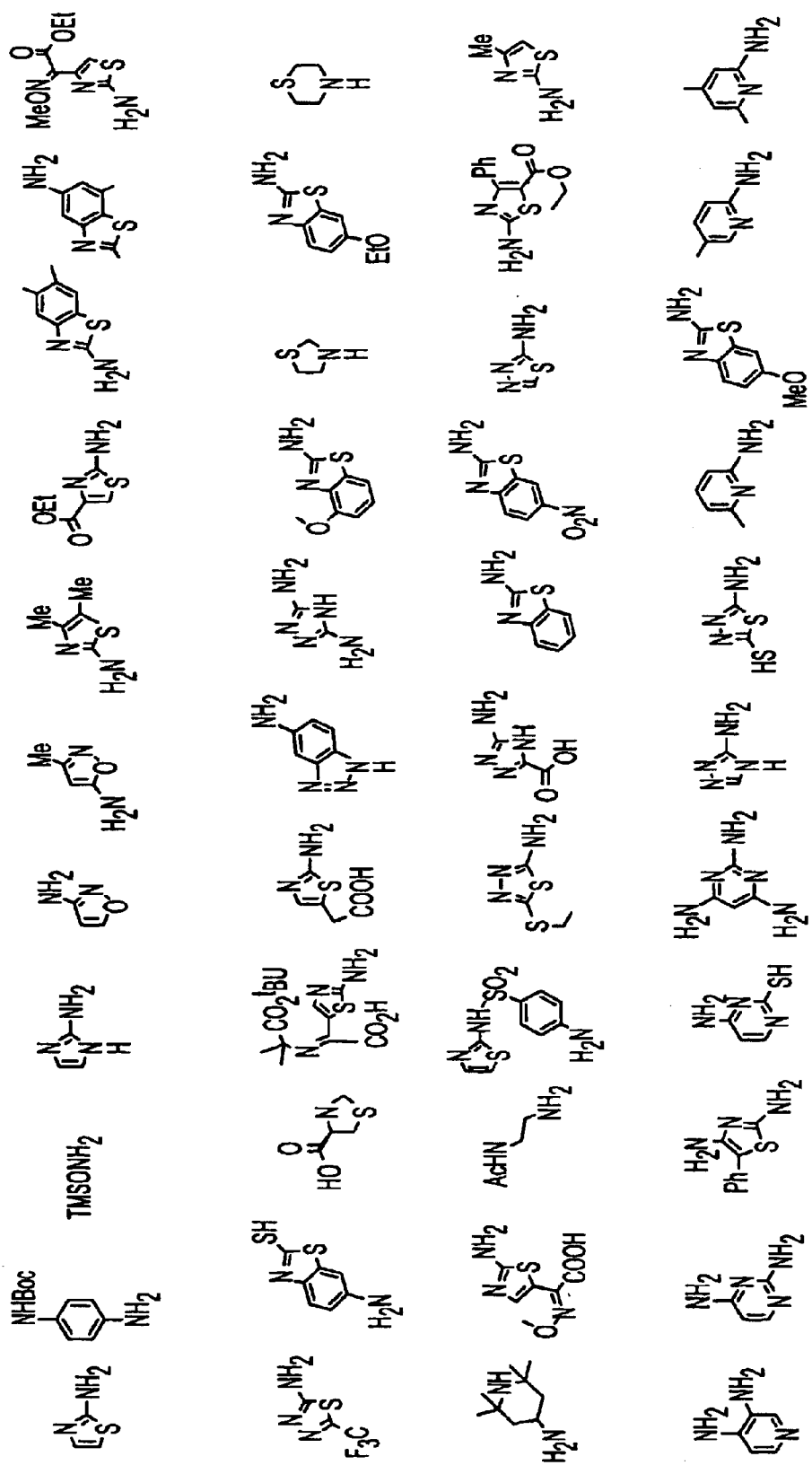
FIG. 47 illustrates amine building blocks $R_7R_8NH$ that may be used in the synthesis of oxazolidinone libraries and compounds as shown in FIG. 4.
Figure 47B:
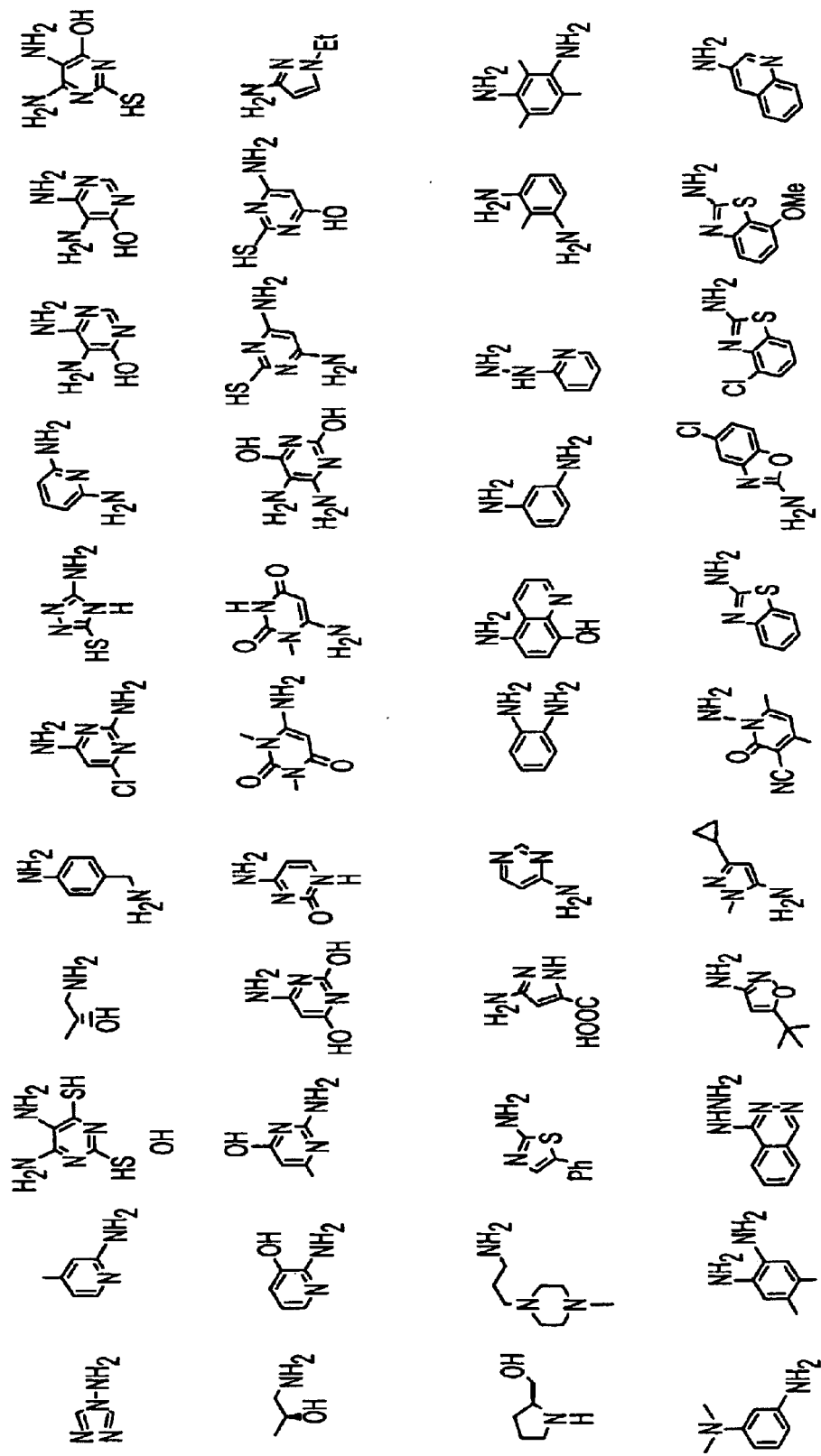

FIG. 4 shows an exemplary method for the preparation of combinatorial libraries comprising oxazolidinones of the structure 1b, wherein the substituents are defined as follows: $R_1$ is $C(O)NR_7R_8$, wherein $R_7$ is hydrogen and $R_8$ is alkyl, heteroalkyl, aryl or heteroaryl; $R_2$ is fluorine; $R_3$, $R_4$ and $R_5$ are hydrogen; and, $R_6$ is acyl, wherein the acyl group is of the structure $C(O)CH_3$. A plurality of azides 14 were converted to the corresponding iminophosphoranes upon reaction with triphenylphosphine. The iminophosphoranes were mixed with a plurality of 5-formyldimethoxyphenoxybutyric acid resin beads (BAL resin beads, Novabiochem), producing a plurality of imines. The imines were reduced with $NaBH_3CN$ to provide a plurality of amines 15. The ester group of 15 was deprotected using trimethylsilylchloride (TMSCl) to afford a plurality of acids (16). Acylation of the amine with $Ac_2O$ and activation of the acid with $PfpOCOCF_3$ yielded a plurality of activated esters 17. The activated esters were reacted with an $R_7R_8NH$ unit, providing a plurality of amides 18. The solid support bound amides 18 were removed from the solid support using TFA to afford a plurality of amides 19 in solution. FIG. 47 illustrates amine building blocks $R_7R_8NH$ that may be used in the synthesis of oxazolidinone libraries and compounds as shown in FIG. 4.

Figure 5:
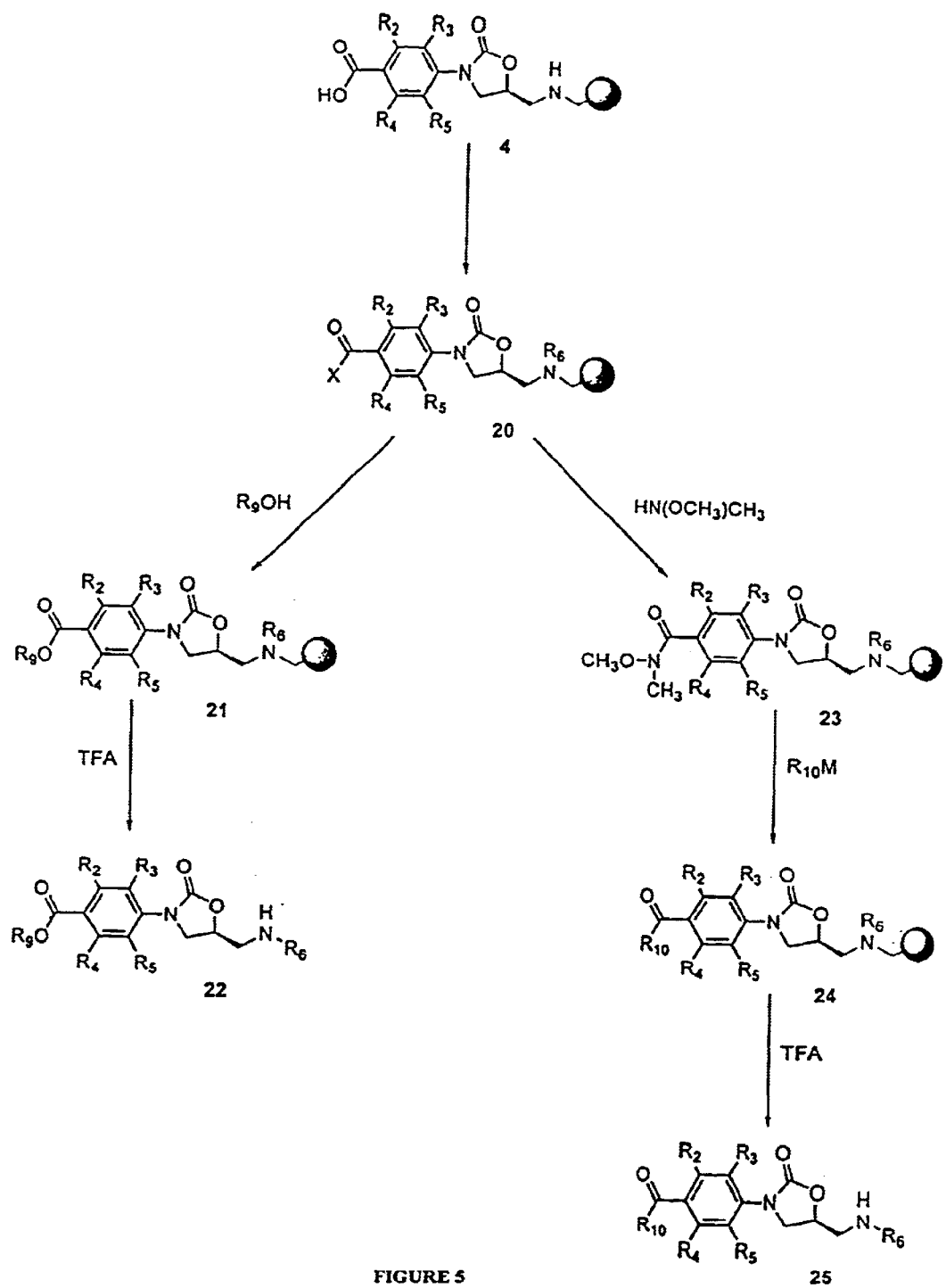
FIG. 5 is a scheme showing the synthesis of combinatorial libraries comprising oxazolidinones of structure 1b, wherein $R_1$ is $C(O)OR_9$ or $C(O)R_{10}$.

FIG. 5 shows exemplary methods for the preparation of combinatorial libraries comprising oxazolidinones of the structure 1b, wherein $R_1$ is either $C(O)OR_9$ or $C(O)R_{10}$. A plurality of solid support bound acids 4 are converted into activated acids 20. To prepare an oxazolidinone library, wherein $R_1$ is $C(O)OR_9$, the activated acids 20 are reacted with an $R_9OH$ unit, providing a plurality of esters 21. The esters are removed from the solid support upon treatment with a suitable reagent, affording a plurality of amides 22 in solution. To prepare an oxazolidinone library, wherein $R_1$ is $C(O)R_{10}$, the activated acids 20 are reacted with an amine, providing a plurality of Weinreb amides 23. The Weinreb amides are reacted with an organometallic unit (e.g., LiAlH4 or MeMgBr), affording a plurality of ketones 24. The ketones 24 are removed from the solid support upon treatment with a suitable reagent, producing a plurality of ketones 25 in solution.

Figure 6:
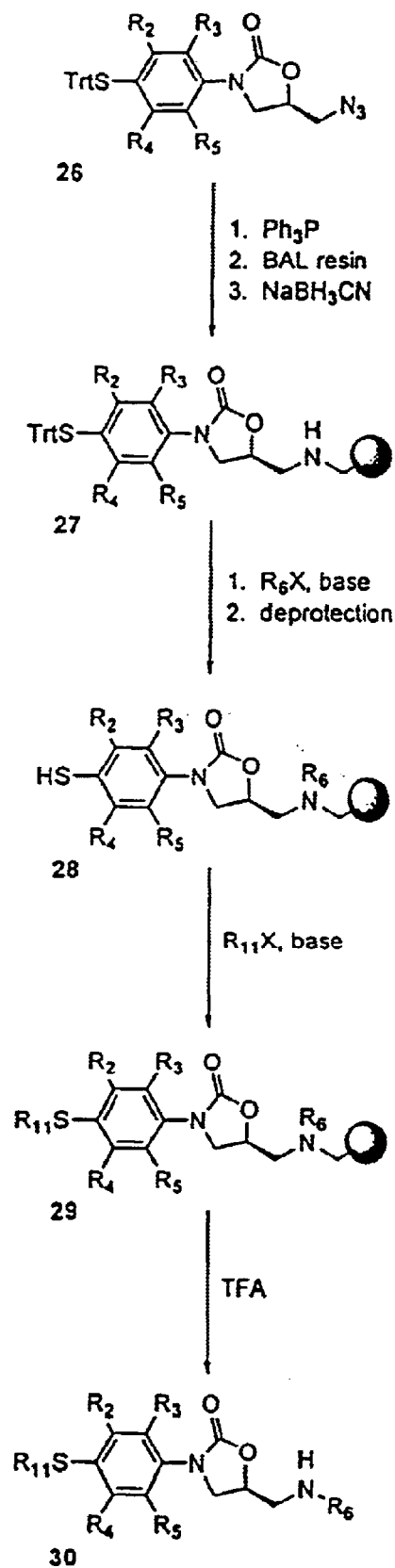
FIG. 6 is a scheme showing the synthesis of combinatorial libraries comprising oxazolidinones of structure 1b, wherein $R_1$ is $SR_{11}$.
Figure 41:
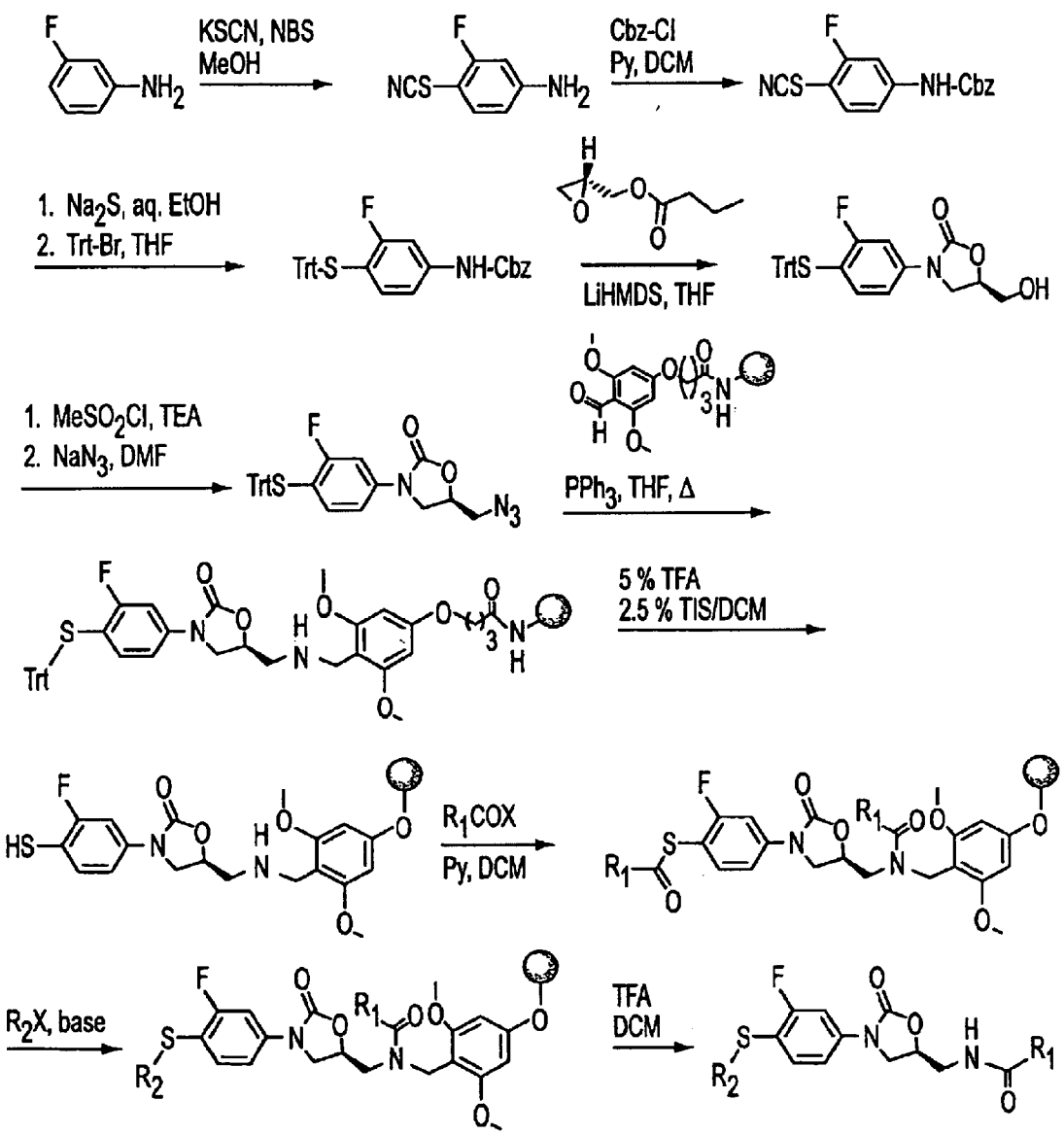
FIG. 41 is a scheme showing the synthesis of sulfide oxazolidinone compounds and libraries, wherein $R_1$ is a substituent, for example, H, alkyl, heteroalkyl, aryl, heteroaryl, or alkoxy.
Figure 44A:
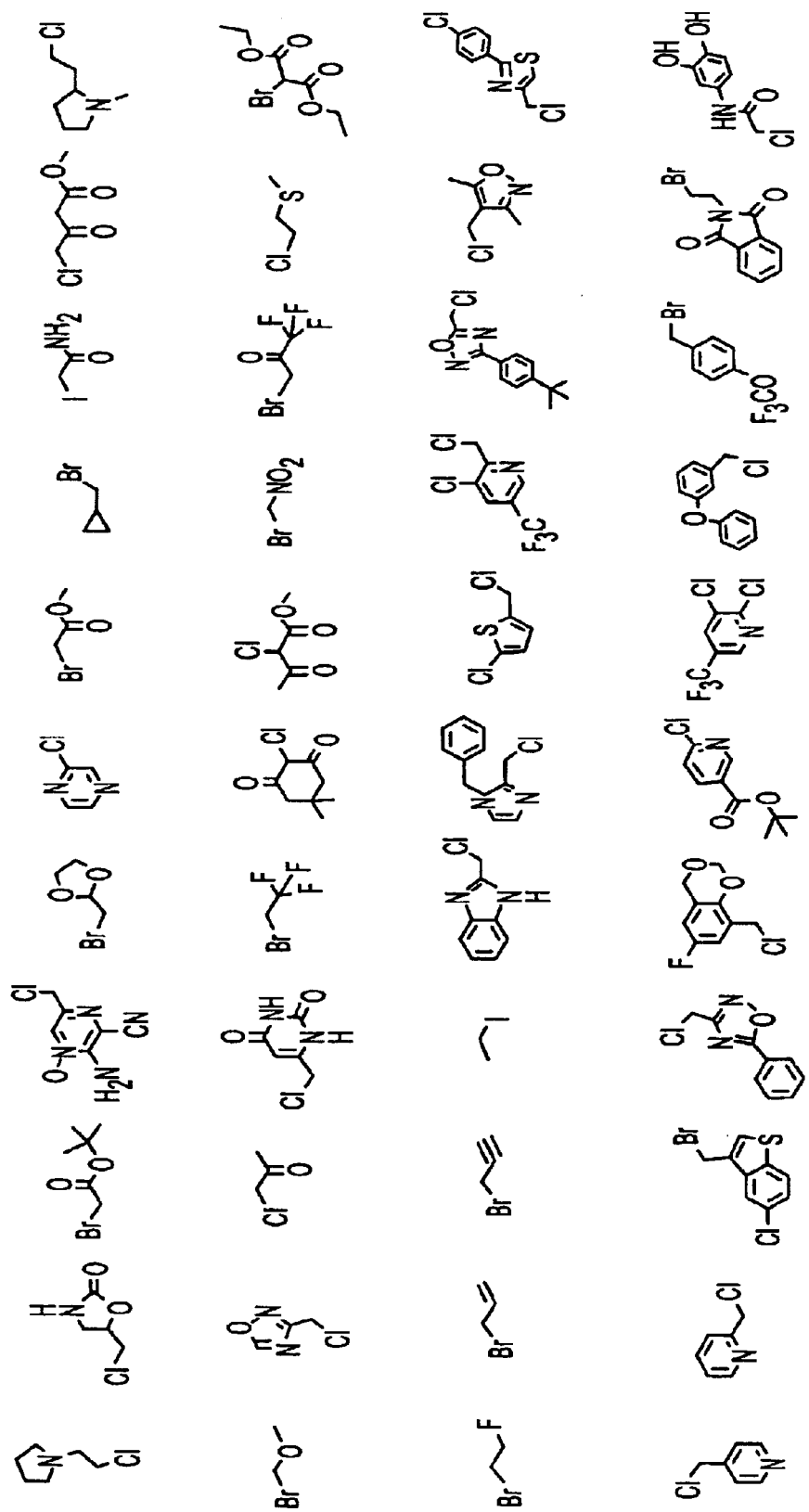
FIGS. 44 and 45 illustrate building blocks $R_2X$, where X is halo, which may be used in the synthesis of sulfide oxazolidinone libraries and compounds as shown in FIG. 41 and also can be used as $R_{11}X$ in the synthesis shown in FIG. 6.
Figure 44B:
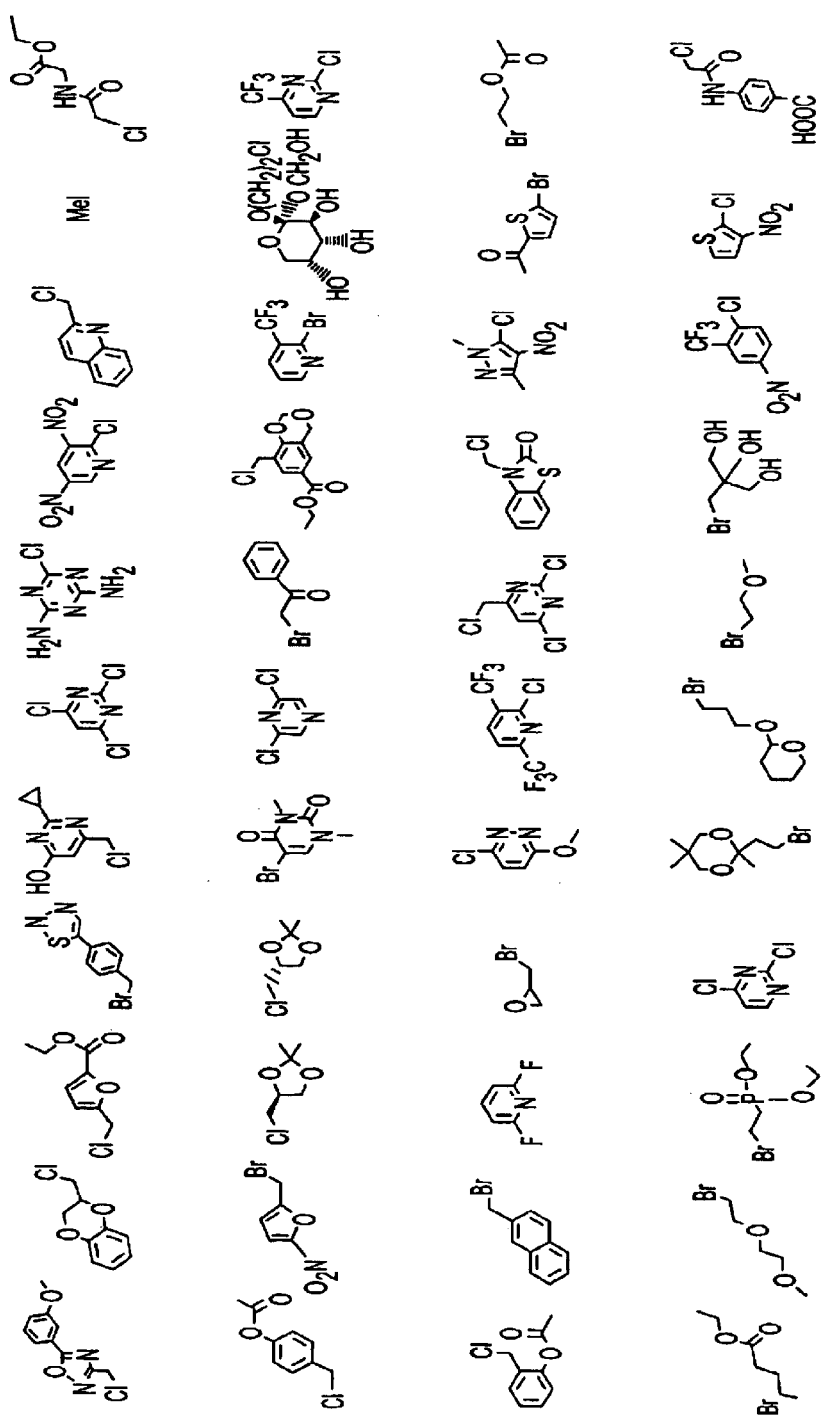
Figure 45:
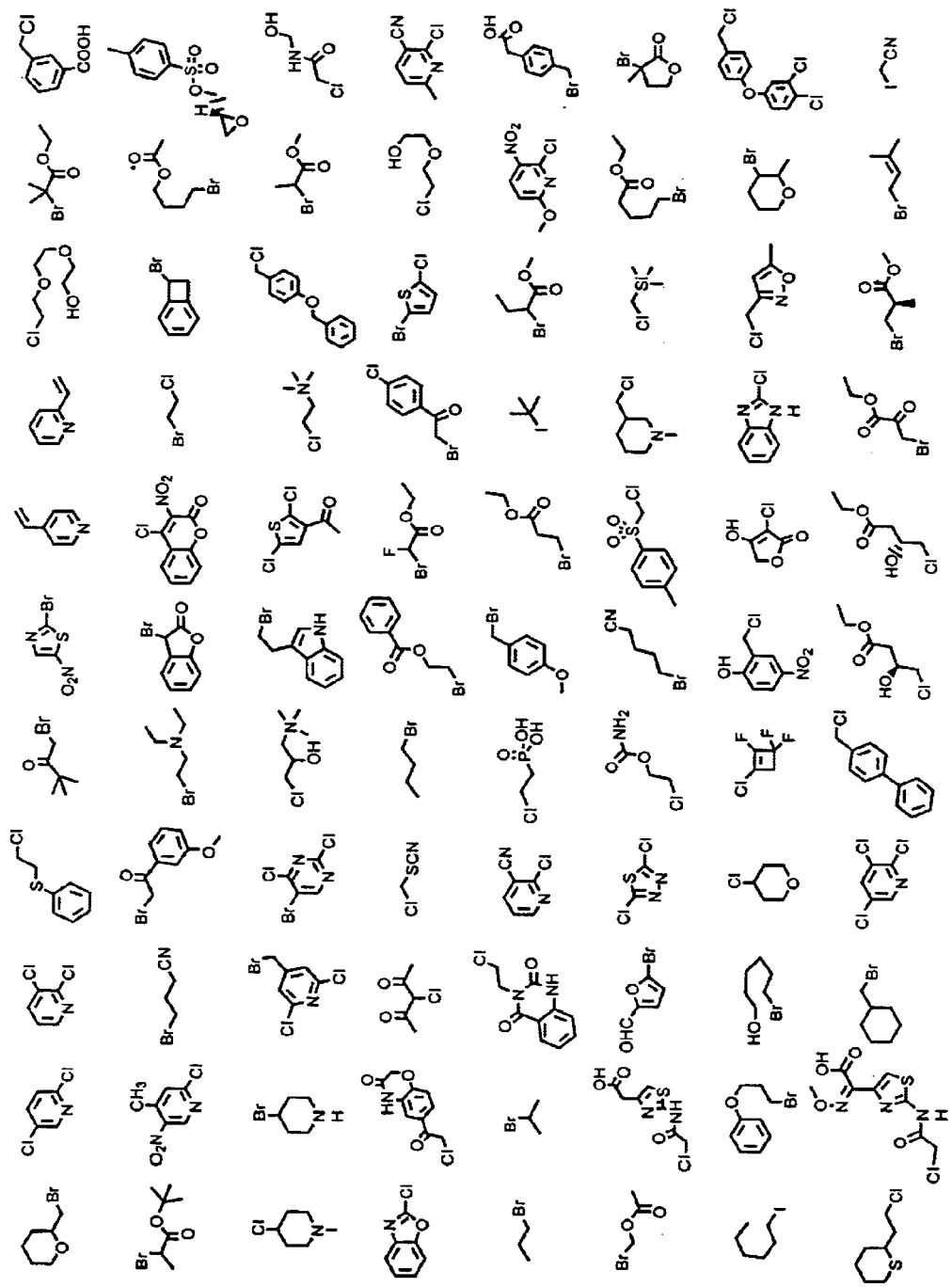

FIG. 6 shows an exemplary method for the preparation of combinatorial libraries comprising oxazolidinones of the structure 1b, wherein $R_1$ is $SR_{11}$. A plurality of azides 26 are converted to the corresponding iminophosphoranes upon reaction with a phosphine. The iminophosphoranes are mixed with a plurality of solid supports containing a carbonyl functional group, producing a plurality of imines. The imines are reduced to provide a plurality of amines 27. Acylation of the amine and deprotection of the sulfide of 27 yields a plurality of thiols 28. Alkylation of 28 with an electrophile provides a plurality of sulfides 29. The solid support bound sulfides 29 are removed from the solid support using a suitable reagent to afford a plurality of sulfides 30 in solution. Another embodiment is shown in FIG. 41. FIGS. 44 and 45 illustrate building blocks $R_2X$, where X is halo, which may be used in the synthesis of sulfide oxazolidinone libraries and compounds as shown in FIG. 41 and also can be used as $R_{11}X$ in the synthesis shown in FIG. 6.

Figure 7:
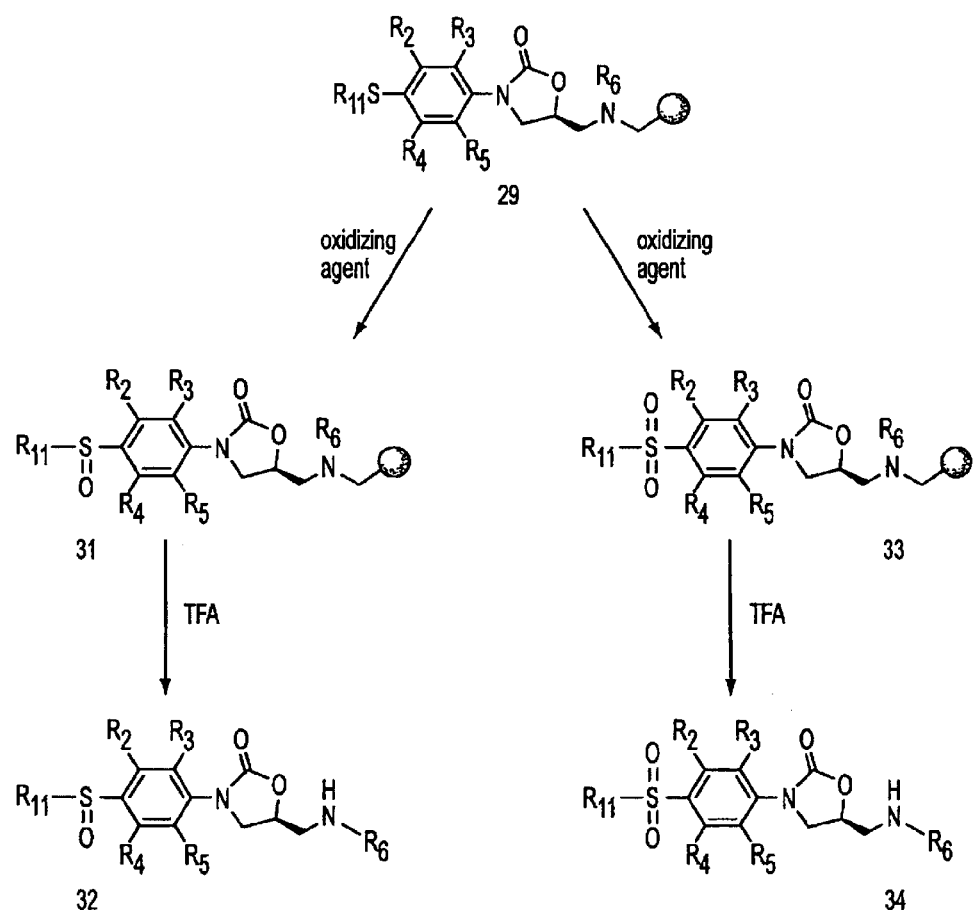
FIG. 7 is a scheme showing the synthesis of combinatorial libraries comprising oxazolidinones of structure 1b, wherein $R_1$ is $S(O)R_{11}$ or $S(O)_2R_{11}$.

FIG. 7 shows an exemplary method for the preparation of combinatorial libraries comprising oxazolidinones of the structure 1b, wherein $R_1$ is $S(O)R_{11}$ or $S(O)_2R_{11}$. To prepare an oxazolidinone library, wherein R1 is $S(O)R_{11}$, a plurality of solid support bound sulfides 29 is converted into a plurality of sulfoxides 31 upon oxidation. The sulfoxides are removed from the solid support upon treatment with a suitable reagent, affording a plurality of sulfoxides 32 in solution. To prepare an oxazolidinone library, wherein $R_1$ is $S(O)_2R_{11}$, a plurality of solid support bound sulfides 29 is converted into a plurality of sulfones 33 upon oxidation. The sulfones are removed from the solid support upon treatment with a suitable reagent, affording a plurality of sulfones 34 in solution.

Figure 8:
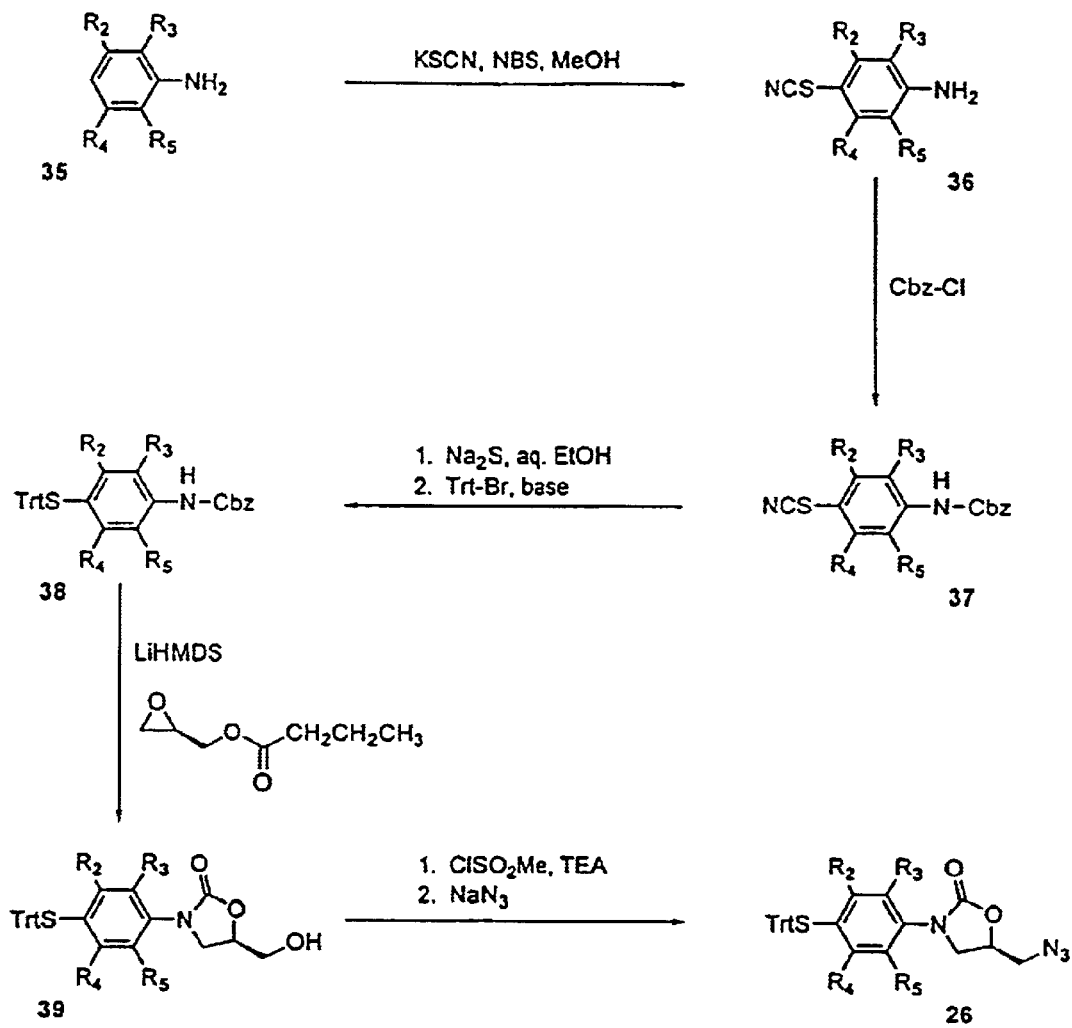
FIG. 8 is a scheme showing the synthesis of a set of thio substituted azido oxazolidinones.

The plurality of azides 26 is produced starting from a set of substituted anilines 35. The aniline is subjected to electrophilic aromatic substitution at the 4-position, providing a set of isothiocyanates 36. The amine portion of 36 is protected to produce 37. The isothiocyanate group of 37 is reacted with sodium sulfide and trityl bromide to afford a set of protected sulfides 38. The protected aniline of 38 is reacted with a substituted epoxide and cyclized, yielding a set of oxazolidinones 39. Conversion of the primary alcohol of 39 to an azide produces the set of azides 26. See FIG. 8.

Figure 9:
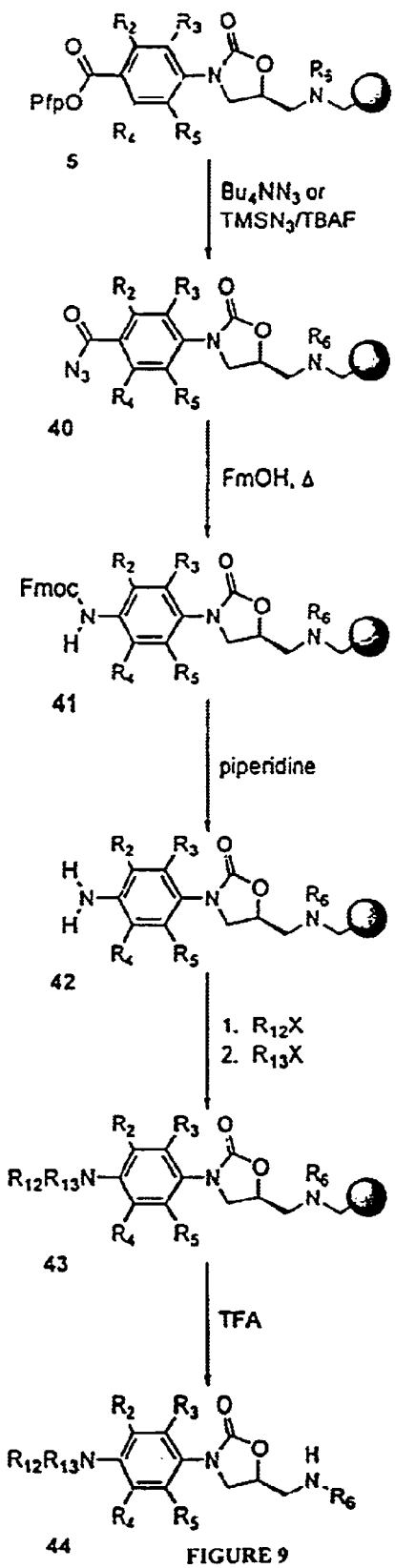
FIG. 9 is a scheme showing the synthesis of a combinatorial library comprising oxazolidinones of structure 1b, wherein $R_1$ is $NR_{12}R_{13}$.
Figure 39:
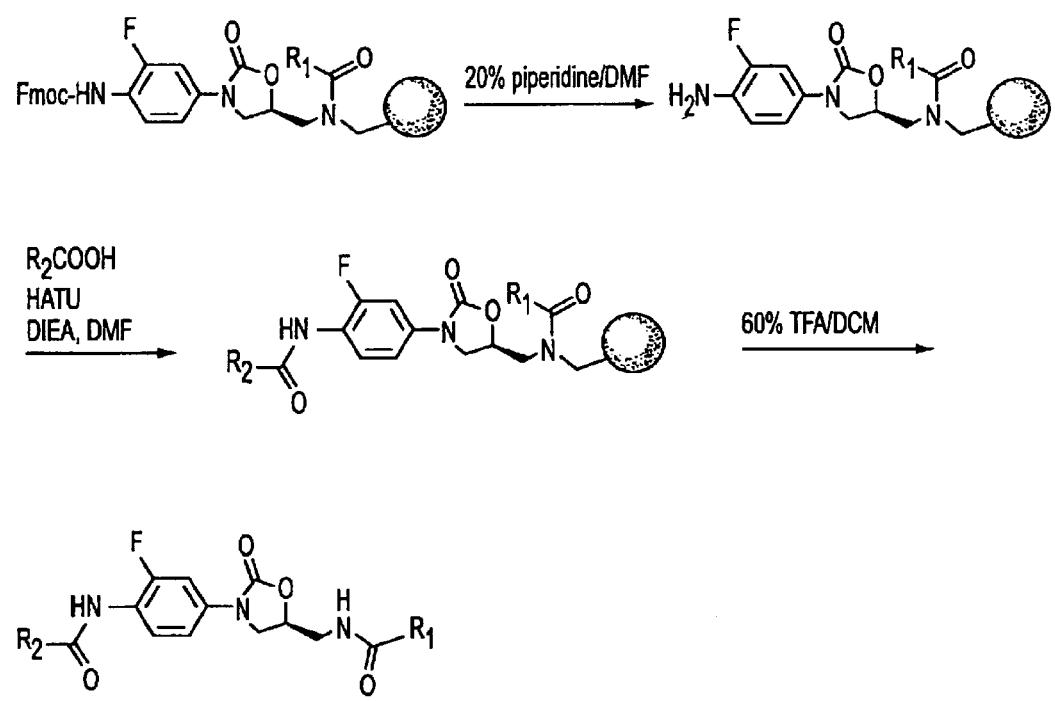
FIG. 39 is a scheme showing the synthesis of acylamino oxazolidinone compounds and libraries, wherein $R_1$ and $R_2$ are substituents, for example, H, alkyl, heteroalkyl, aryl, heteroaryl, or alkoxy.
Figure 42A:
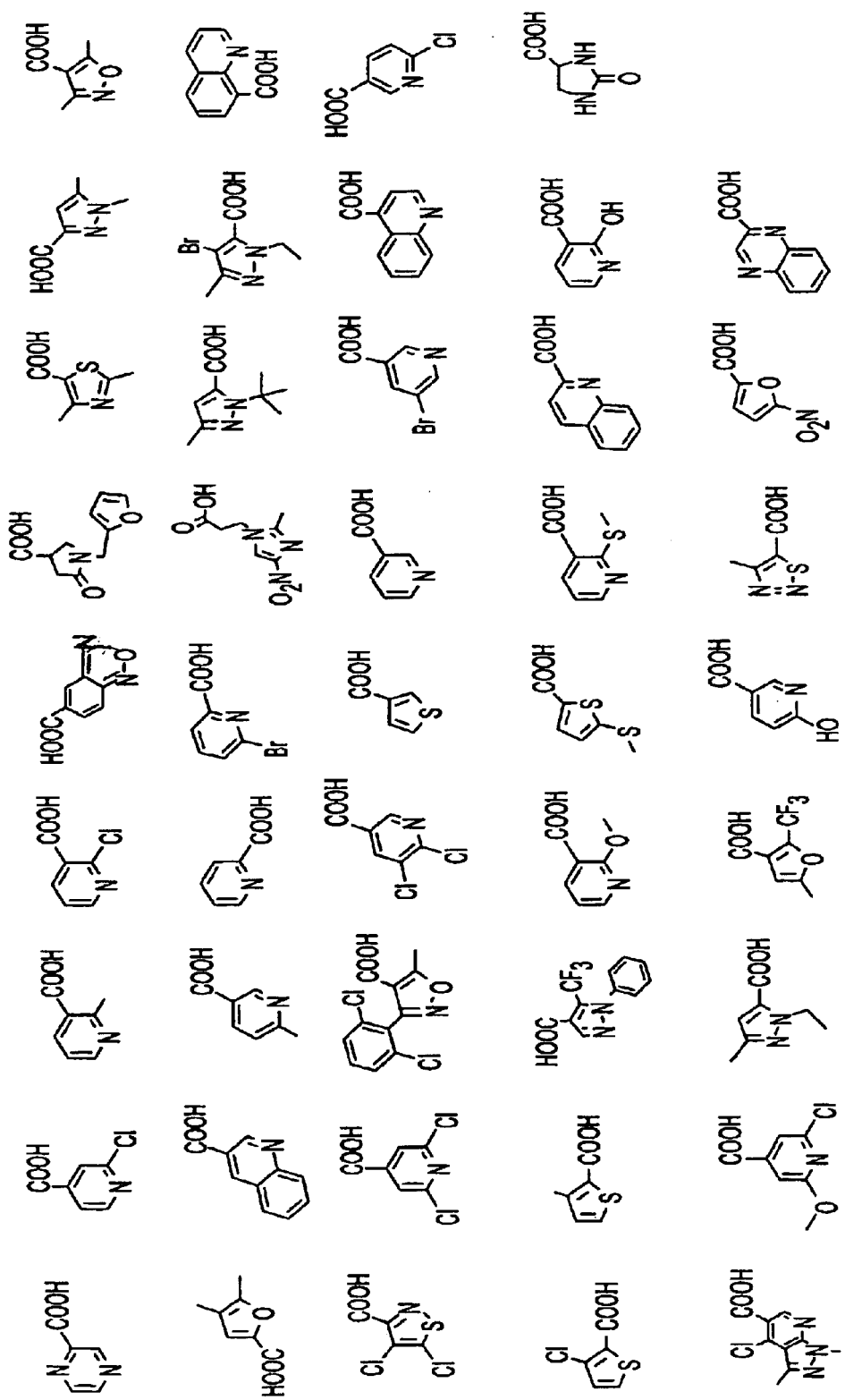
FIGS. 42 and 43 illustrate building blocks $R_2COOH$ that may be used for synthesis of acylamino oxazolidinone libraries and compounds as shown in FIG. 39, and also may be used in other syntheses such as those shown in FIG. 9.
Figure 42B:
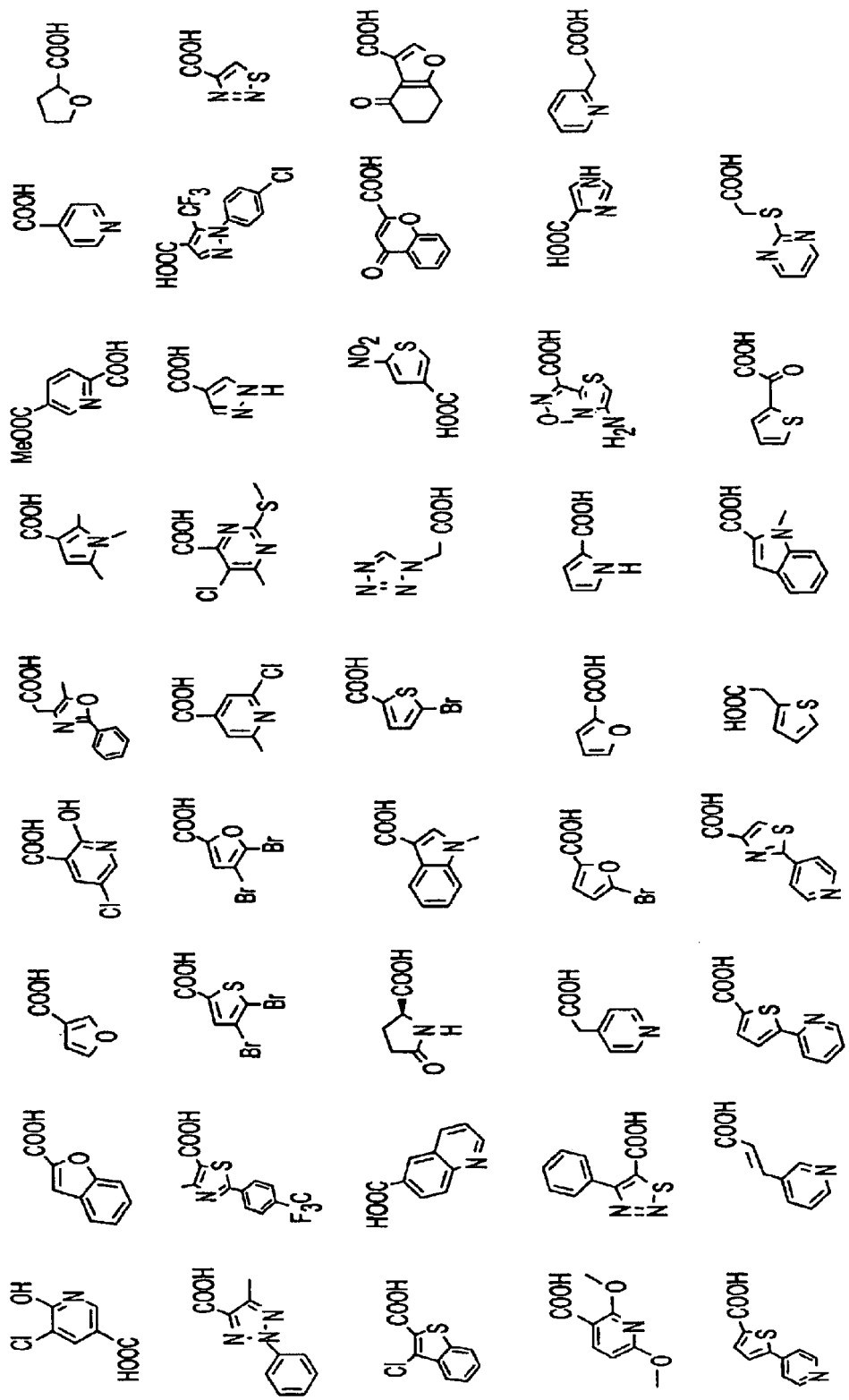
Figure 43A:
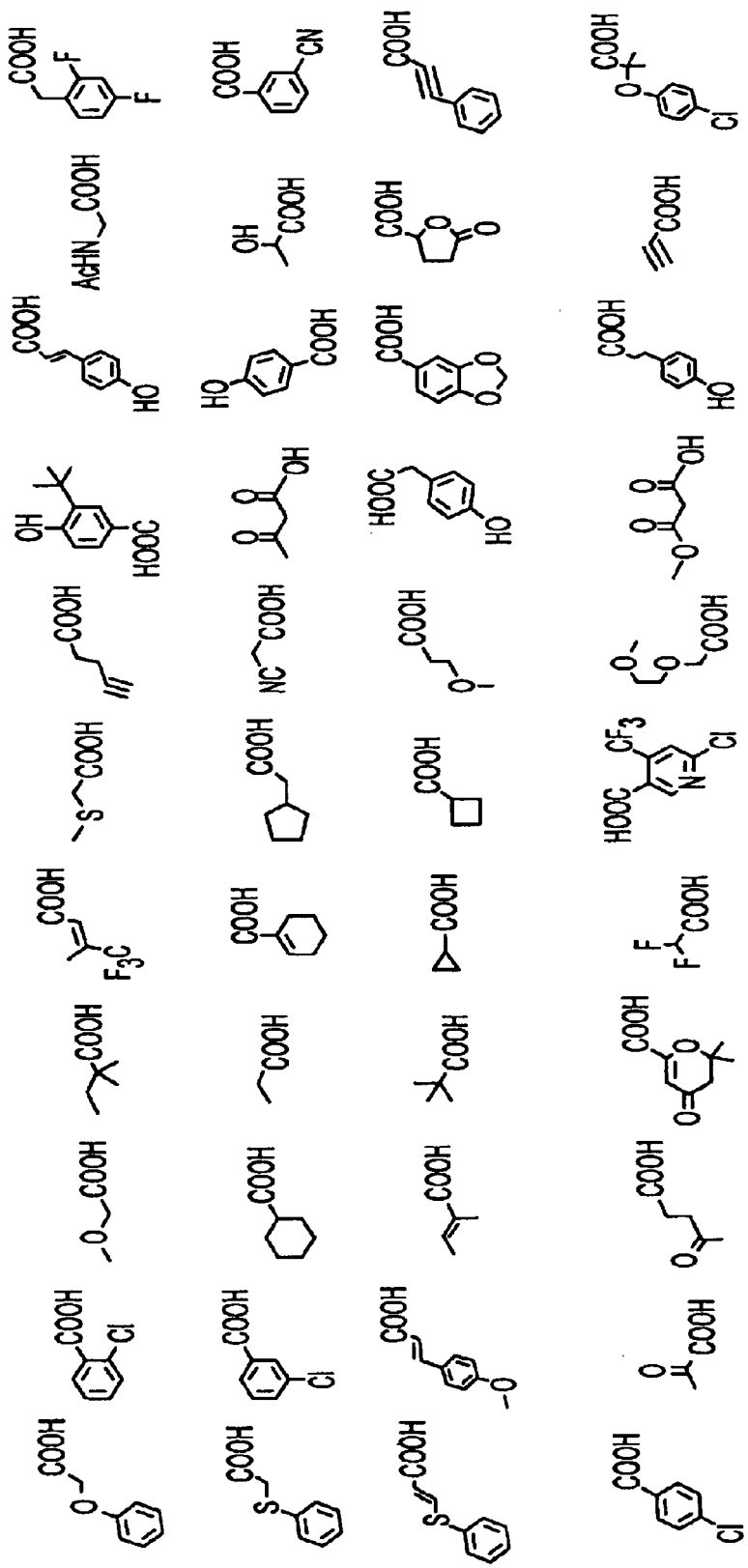
Figure 43B:
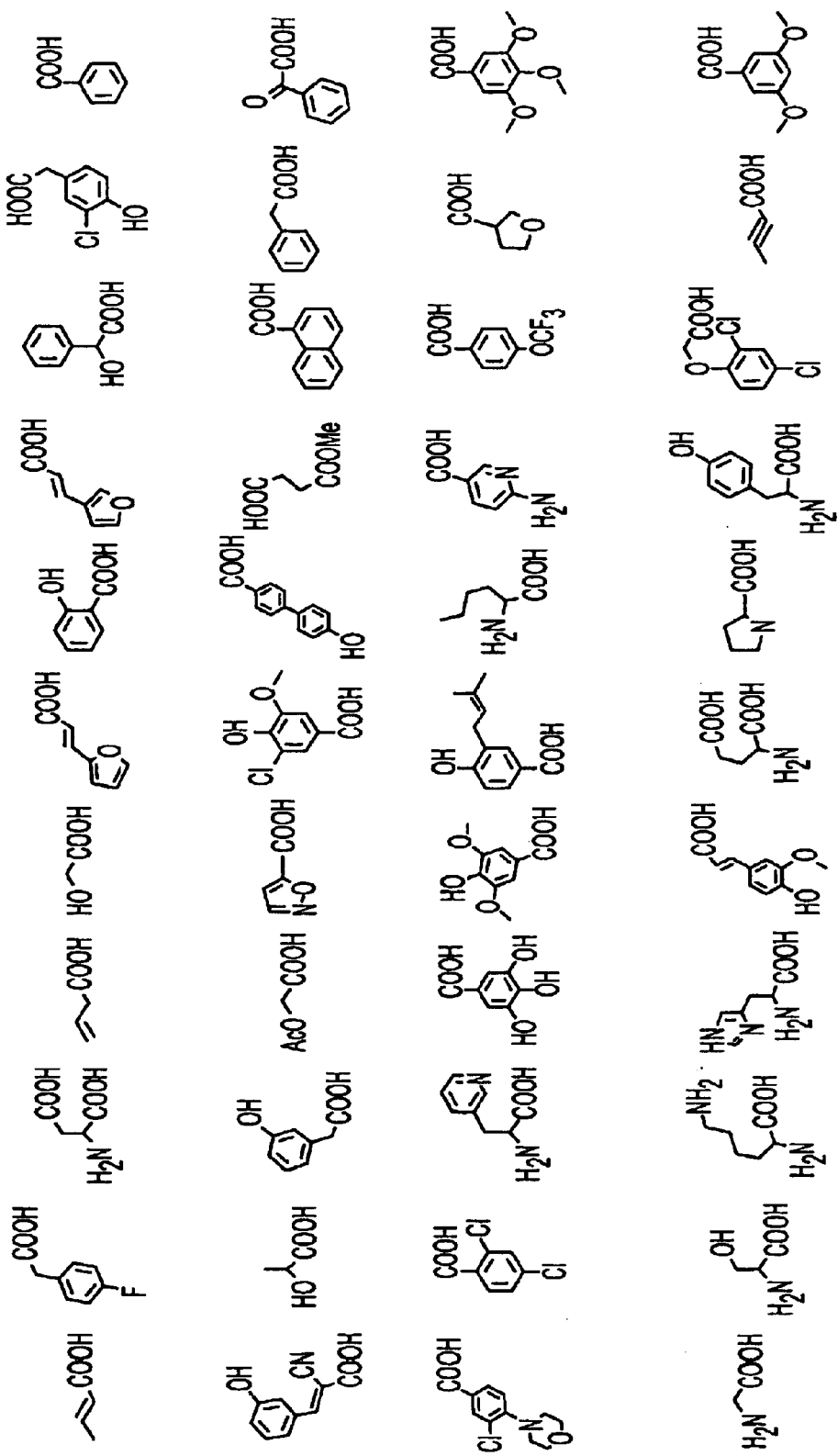

FIG. 9 shows an exemplary method for the preparation of combinatorial libraries comprising oxazolidinones of the structure 1b, wherein $R_1$ is $NR_{12}R_{13}$. A plurality of solid support bound azides 5, which contain an activated ester, are converted into a plurality of acyl azides 40. The acyl azides are rearranged, providing a plurality of protected anilines 41. Deprotection of 41 affords a plurality of anilines 42, which are reacted with electrophilic units $R_{12}X$ and $R_{13}X$ to yield a plurality of substituted anilines 43. The solid support bound substituted anilines 43 are removed from the solid support using a suitable reagent to afford a plurality of substituted anilines 44 in solution. Another embodiment is shown in FIG. 39, which is a scheme showing the synthesis of acylamino oxaaolidinone compounds and libraries, wherein $R_1$ and $R_2$ are substituents, for example, H, alkyl, heteroalkyl, aryl, heteroaryl, or alkoxy. FIGS. 42 and 43 illustrate building blocks $R_2COOH$ that may be used for synthesis of acylamino oxazolidinone libraries and compounds as shown in FIG. 39, and also may be used in other syntheses such as those shown in FIG. 9.

Figure 10:
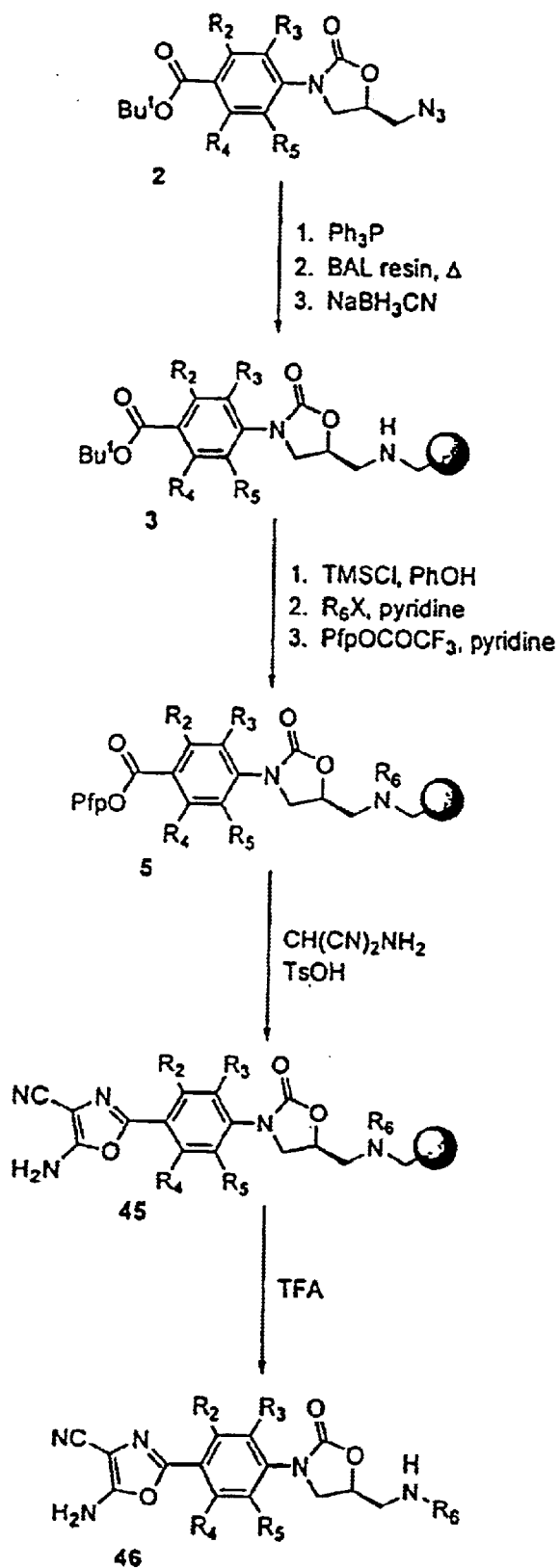
FIG. 10 is a scheme showing the synthesis of a combinatorial library comprising oxazolidinones of structure 1b, wherein $R_1$ is an oxazole.

FIG. 10 shows an exemplary method for the preparation of combinatorial libraries comprising oxazolidinones of the structure 1b, wherein $R_1$ is 2-oxazolyl with a cyano group at the 4-position and an amino group at the 5-position. A plurality of azides 2 are converted to the corresponding iminophosphoranes upon reaction with a phosphine. The ylides are mixed with a plurality of solid supports containing a carbonyl functional group, producing a plurality of amines 3. The ester group of 3 is deprotected to provide plurality of carboxylic acids. The amine is acylated and the carboxylic acid activated, yielding a plurality of esters 5. Reaction of 5 with amino malonitrile affords a plurality of oxazoles 45. The solid support bound oxazoles are removed from the solid support using a suitable reagent to produce a plurality of oxazoles 46 in solution.

Figure 11:
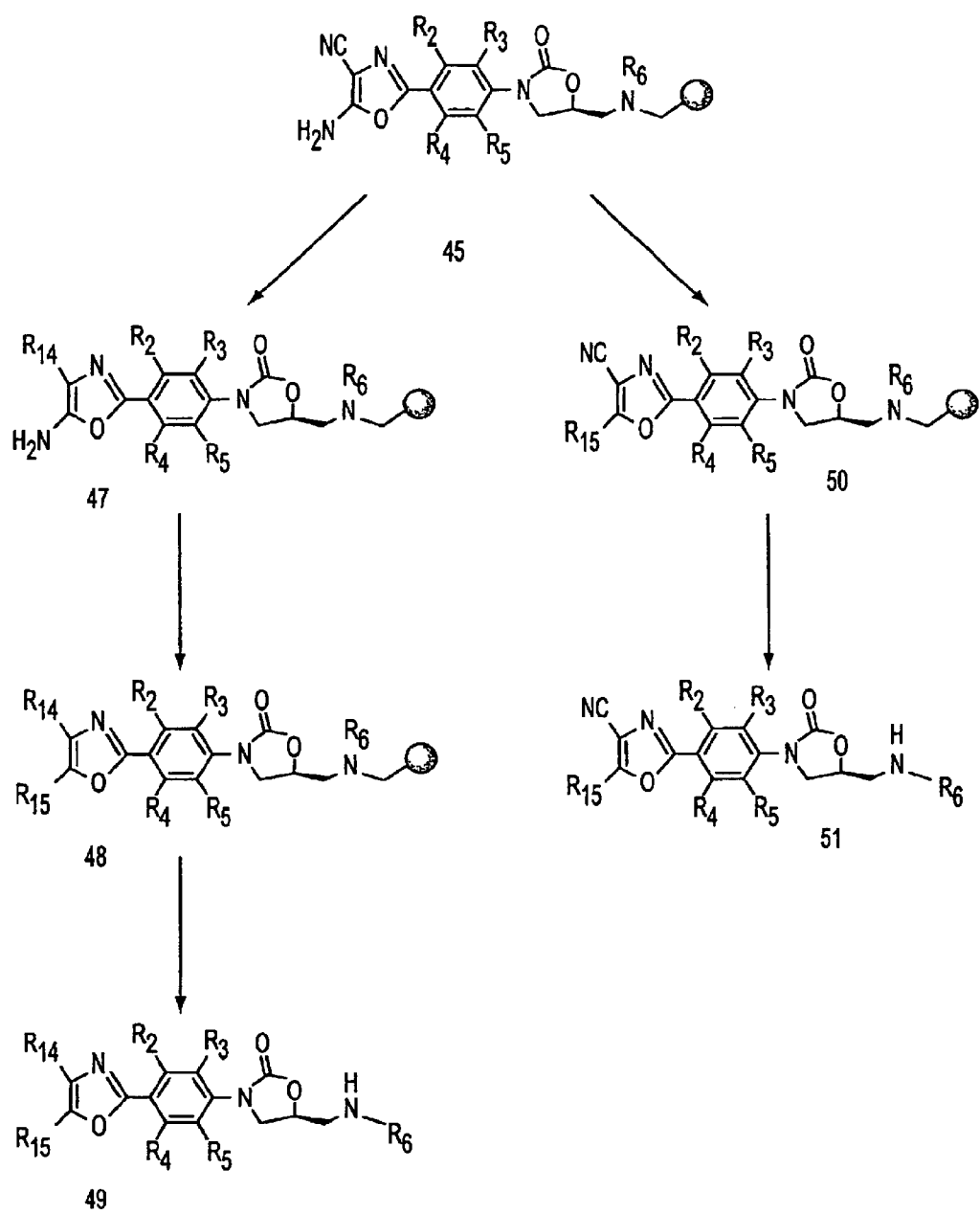
FIG. 11 is a scheme showing the synthesis of combinatorial libraries comprising oxazolidinones of structure 1b, wherein $R_1$ is an oxazole.

FIG. 11 shows exemplary methods for the preparation of combinatorial libraries comprising oxazolidinones of the structure 1b, wherein $R_1$ is either 2-oxazolyl containing $R_{14}$ at the 4-position and $R_{15}$ and the 5-position, or 2-oxazolyl containing cyano at the 4-position and $R_{15}$ at the 5-position. To prepare an oxazolidinone library, wherein $R_1$ is 2-oxazolyl containing $R_{14}$ at the 4-position and $R_{15}$ at the 5-position, a plurality of solid support bound oxazoles 45 is reacted with a reagent capable of converting the 4-cyano group to a different functionality (e.g. hydrolysis to acid) to provide a plurality of oxazole compounds 47. The 5-amino substituent of 47 is alkylated or acylated to produce a plurality of compounds 48. The solid support bound oxazoles 48 are removed from the solid support using a suitable reagent to afford a plurality of $R_{14}$, $R_{15}$-substituted oxazoles 49 in solution. To prepare an oxazolidinone library, wherein $R_1$ is 2-oxazolyl containing cyano at the 4-position and $R_{15}$ at the 5-position, the 5-amino substituent of 45 is alkylated or acylated to produce a plurality of compounds 50. The solid support bound oxazoles 50 are removed from the solid support using a suitable reagent to afford a plurality of cyano, $R_{15}$ substituted oxazoles 51 in solution.

Figure 12:
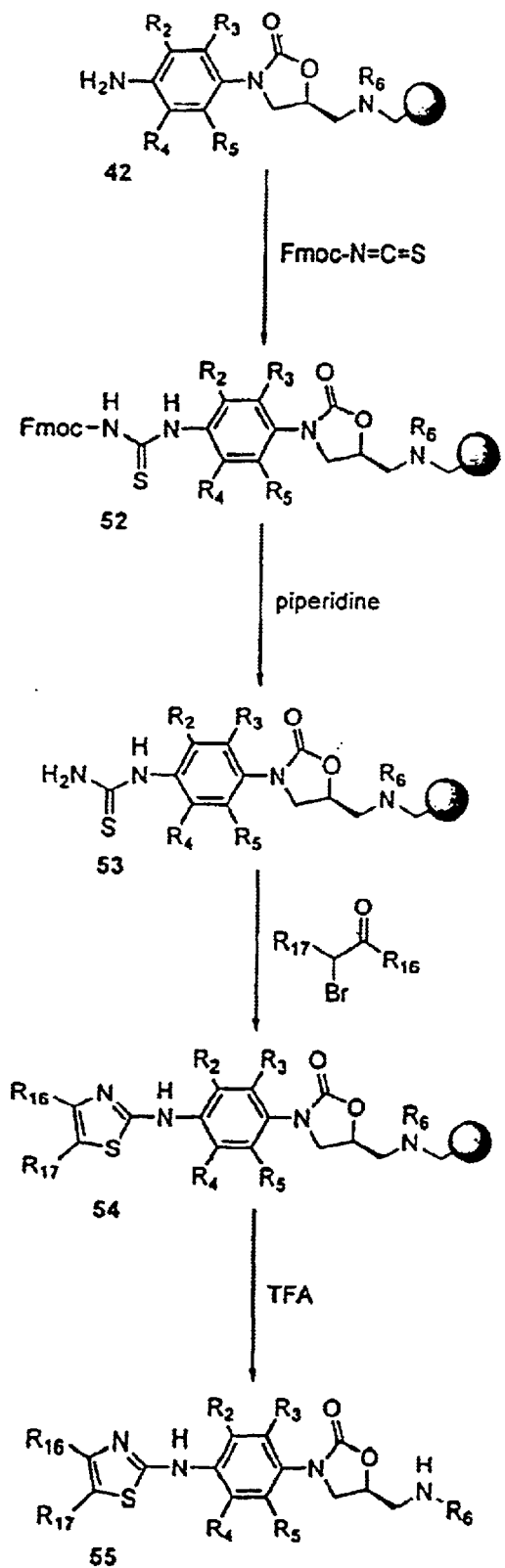
FIG. 12 is a scheme showing the synthesis of combinatorial libraries comprising oxazolidinones of structure 1b, wherein $R_1$ is an aminothiazole.

FIG. 12 shows an exemplary method for the preparation of combinatorial libraries comprising oxazolidinones of the structure 1b, wherein $R_1$ is 2-aminothiazolyl containing $R_{16}$ at the 4-position and $R_{17}$ at the 5-position. A plurality-of anilines 42 is reacted with a protected isothiocyanate to provide a plurality of protected thiocarbamates 52. The thiocarbamates are deprotected, producing a plurality of thiocarbamates 53. Reaction of 53 with an α-halo ketone yields a plurality of aminothiazoles 54. The solid support bound amino thiazoles are removed from the solid support using a suitable reagent to afford a plurality of aminothiazoles 55 in solution.

Figure 13:
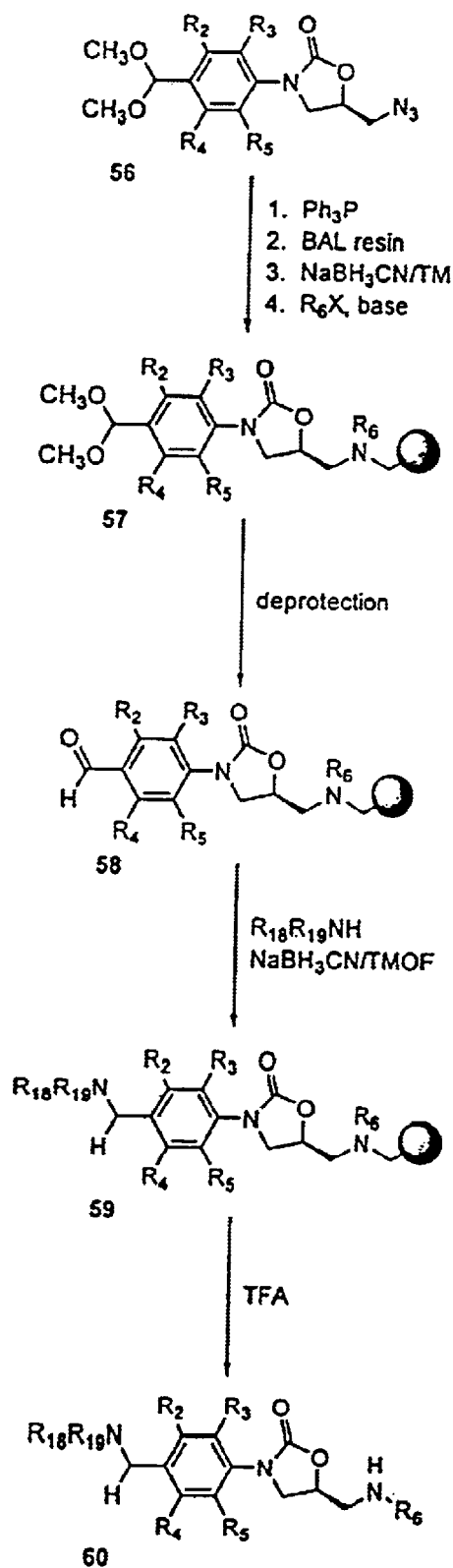
FIG. 13 is a scheme showing the synthesis of combinatorial libraries comprising oxazolidinones of structure 1b, wherein $R_1$ is $CH_2NR_{18}R_{19}$.

FIG. 13 shows an exemplary method for the preparation of combinatorial libraries comprising oxazolidinones of the structure 1b, wherein $R_1$ is $CH_2NR_{18}R_{19}$. A plurality of azides 56 is converted to the corresponding iminophosphoranes upon reaction with a phosphine. The iminophosphoranes are mixed with a plurality of solid supports, producing a plurality of imines. The imines are reduced and acylated to provide a plurality of acetals 57. The acetals are removed, yielding a plurality of aldehydes 58. Reductive amination of the aldehydes affords a plurality of amines 59. The solid support bound amines are removed from the solid support using a suitable reagent to afford a plurality of amines 60 in solution.

Figure 14:
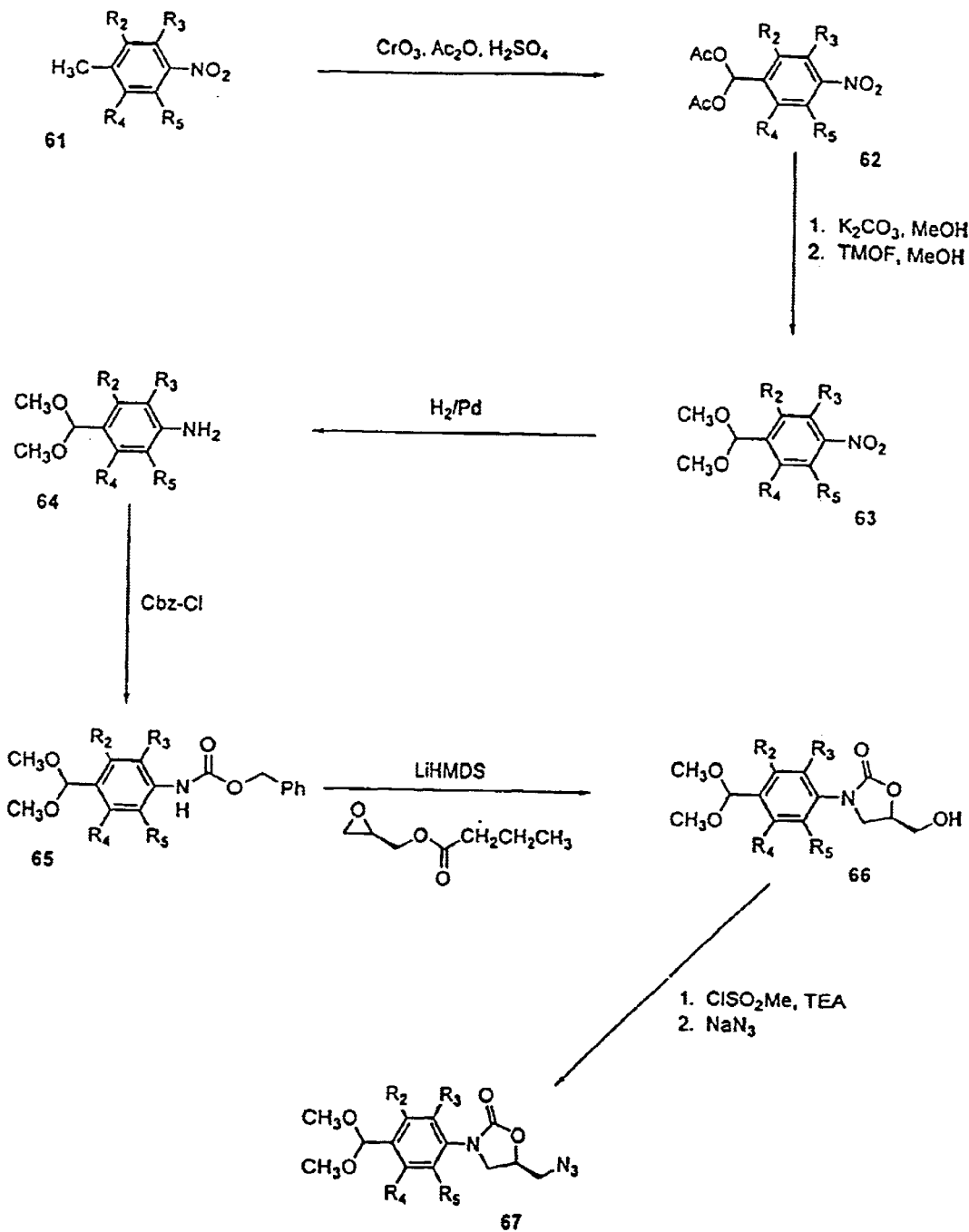
FIG. 14 is a scheme showing the synthesis of a set of acetal containing azido oxazolidinones.

The plurality of azides 67 is produced starting from a set of substituted methylnitrobenzenes 61 (FIG. 14). The methyl group of 61 is oxidized to provide the acetals 62. Transacetalization of 62 yields a set of dimethyl acetals 63. The nitro group of 63 is reduced, affording a set of anilines 64, which are protected 65. The protected anilines are reacted with a substituted epoxide, and the resulting amino alcohols are cyclized to yield a set of oxazolidinones 66. The primary of alcohol of 66 is displaced with azide, producing 67.

Embodiments of Biologically Active Oxazolidinone Compounds

In one embodiment, biologically active oxazolidinones, for example with antibiotic activity, are provided, for example, of the structure 1b:

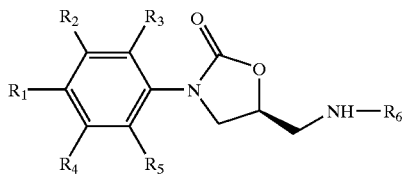

In one embodiment, the substituents on 1b are as follows: Substituent $R_1$ of compound 1b is one of the following functional groups: $C(O)NR_7R_8$, wherein $R_7$ and $R_8$ are, independently, hydrogen, alkyl, heteroalkyl, aryl or heteroaryl; $C(O)OR_9$, wherein $R_9$ is hydrogen, alkyl, heteroalkyl, aryl or heteroaryl; $C(O)R_{10}$, wherein $R_{10}$ is hydrogen, alkyl, heteroalkyl, aryl or heteroaryl; $SR_{11}$, wherein $R_{11}$ is hydrogen, alkyl, heteroalkyl, aryl or heteroaryl; $S(O)_2R_{11}$, wherein $R_{11}$ is hydrogen, alkyl, heteroalkyl, aryl or heteroaryl; $S(O)R_{11}$, wherein $R_{11}$ is hydrogen, alkyl, heteroalkyl, aryl or heteroaryl; $NR_{12}R_{13}$, wherein $R_{12}$ and $R_{13}$ are, independently, hydrogen, acyl, sulfonyl, alkyl, heteroalkyl, aryl or heteroaryl; 2-oxazolyl, wherein $R_{14}$ is at the 4-position and $R_{15}$ is at the 5-position, and wherein $R_{14}$ and $R_{15}$ are, independently, hydrogen, alkyl, heteroalkyl, aryl, heteroaryl or an electron withdrawing group; 2-aminothiazolyl, wherein $R_{16}$ is at the 4-position and $R_{17}$ is at the 5-position, and wherein $R_{16}$ and $R_{17}$ are, independently, hydrogen, alkyl, heteroalkyl, aryl, heteroaryl or an electron withdrawing group; and $CH_2NR_{18}R_{19}$, wherein $R_{18}$ and $R_{19}$ are, independently, hydrogen, alkyl, heteroalkyl, aryl, heteroaryl, acyl or sulfonyl. The substituents $R_2$, $R_3$, $R_4$ and $R_5$ are, independently, hydrogen, alkyl, heteroalkyl, heteroaryl or an electron withdrawing group; and, $R_6$ is acyl or sulfonyl.

In one embodiment, the biologically active oxazolidinones of structure 1b are substituted as follows: $R_1$ is $C(O)NR_7R_8$, wherein $R_7$ is hydrogen and $R_8$ is alkyl, heteroalkyl, aryl or heteroaryl; $R_2$ is fluorine; $R_3$, $R_4$ and $R_5$ are hydrogen; and, $R_6$ is acyl, wherein the acyl group is of the structure $C(O)CH_3$. In one embodiment, the oxazolidinone is substituted as follows: $R_1$ is $C(O)NR_7R_8$, wherein $R_7$ is hydrogen and $R_8$ is aryl or heteroaryl; $R_2$ is fluorine; $R_3$, $R_4$ and $R_5$ are hydrogen; and, $R_6$ is acyl, wherein the acyl group is of the structure $C(O)CH_3$. In another embodiment, the oxazolidinone is substituted as follows: $R_1$ is $C(O)NR_7R_8$, wherein $R_7$ is hydrogen and $R_8$ is heteroaryl; $R_2$ is fluorine; $R_3$, $R_4$ and $R_5$ are hydrogen; and $R_6$ is acyl, wherein the acyl group is of the structure $C(O)CH_3$.

In another embodiment, the biologically active oxazolidinones of structure 1b are substituted as follows: $R_1$ is 2-oxazolyl, containing a cyano group at the 4-position and an amino group at the 5-position of the oxazole; $R_2$ and $R_3$ are, independently, hydrogen or an electron withdrawing group; $R_3$ and $R_5$ are hydrogen; and, $R_6$ is acyl or sulfonyl. The oxazolidinone is, for example, substituted as follows: $R_1$ is 2-oxazolyl, containing a cyano group at the 4-position and an amino group at the 5-position of the oxazole; $R_2$ is a halogen; $R_3$, $R_4$ and $R_5$ are hydrogen; and, $R_6$ is acyl. In another embodiment, the oxazolidinone is substituted as follows: $R_1$ is 2-oxazolyl, containing a cyano group at the 4-position and an amino group at the 5-position of the oxazole; $R_2$ is fluorine; $R_3$, $R_4$ and $R_5$ are hydrogen; and $R_6$ is acyl, wherein the acyl group is of the structure $C(O)CH_3$.

In another embodiment, the biologically active oxazolidinones of structure 1b are substituted as follows: $R_1$ is 2-aminothiazolyl, wherein the 4-position of the thiazole contains $R_{16}$ and the 5-position contains $R_{17}$, and wherein $R_{16}$ and $R_{17}$ are, independently, hydrogen, alkyl, aryl or heteroaryl; $R_2$ and $R_4$ are, independently, hydrogen or an electron withdrawing group; $R_3$ and $R_5$ are hydrogen; and, $R_6$ is acyl. For example, the oxazolidinone is substituted as follows: $R_1$ is 2-aminothiazolyl, wherein the 4-position of the thiazole contains $R_{16}$ and the 5-position contains $R_{17}$, and wherein $R_{16}$ and $R_{17}$ are, independently, hydrogen, alkyl or aryl; $R_2$ is a halogen; $R_3$, $R_4$ and $R_5$ are hydrogen; and, $R_6$ is acyl, wherein the acyl group is of the structure $C(O)CH_3$. In another embodiment, the oxazolidinone is substituted as follows: $R_1$ is 2-aminothiazolyl, wherein the 4-position of the thiazole contains $R_{16}$ and the 5-position contains $R_{17}$, and wherein $R_{16}$ and $R_{17}$ are, independently, hydrogen or aryl; $R_2$ is fluorine; $R_3$, $R_4$ and $R_5$ are hydrogen; and, $R_6$ is acyl, wherein the acyl group is of the structure $C(O)CH_3$.

Synthesis of Biologically Active Oxazolidinone Compounds 1b

Exemplary methods for the solid phase synthesis of biologically active oxazolidinones, for example, of the structure 1b are provided. The methods comprise: providing an iminophosphorane; mixing the iminophosphorane with a resin that comprises carbonyl groups to form an imine intermediate; and reducing the imine intermediate to afford a compound attached to the resin through an amine linkage.

Figure 15:
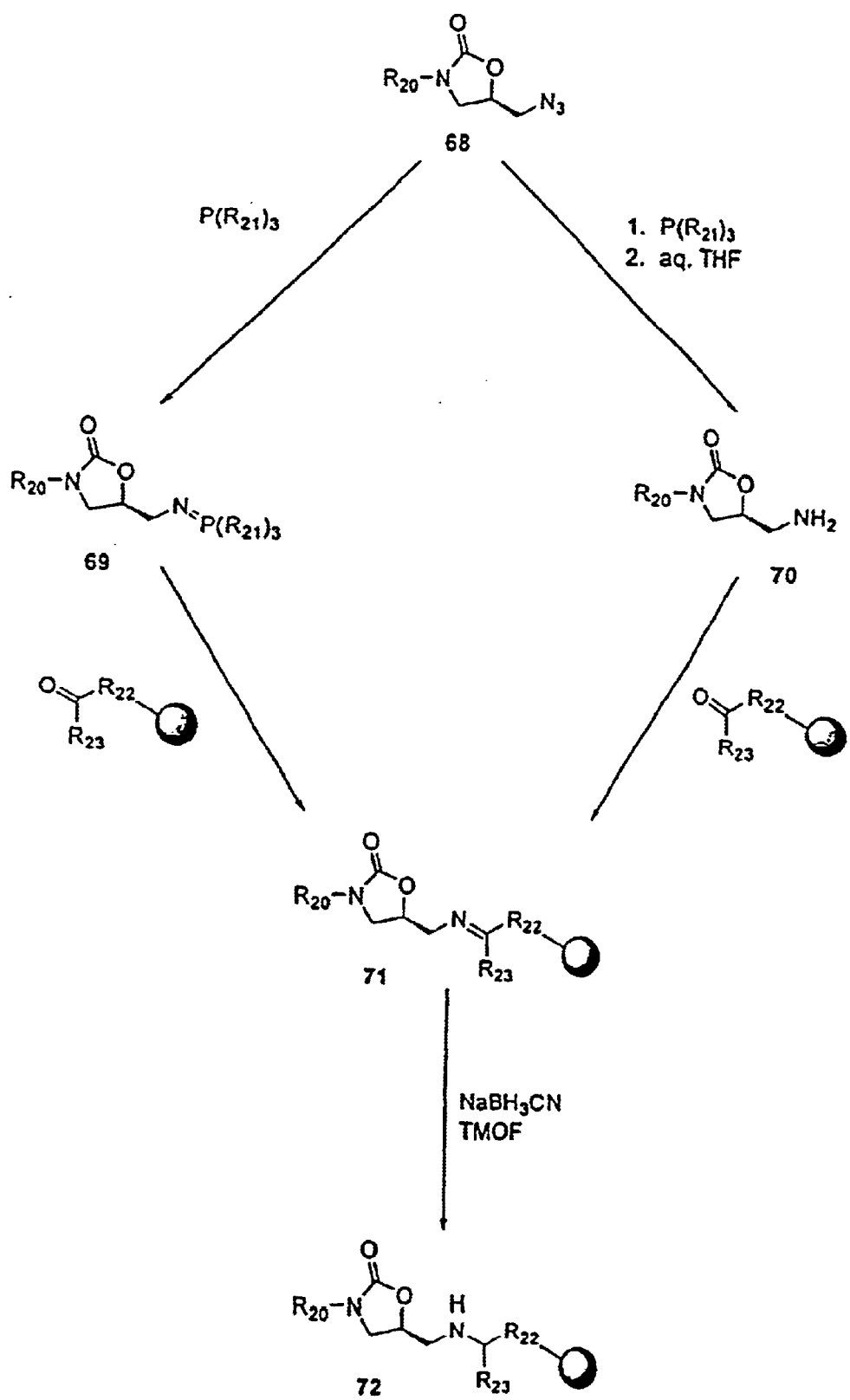
FIG. 15 is a scheme showing a general synthetic method for the preparation of oxazolidinones.

FIG. 15 generally shows the solid phase synthesis of oxazolidinone compounds. Oxazolidinone 68, wherein $R_{20}$ is $(4-R_1)$-aryl (1), is converted into imine 71 by 1 of 2 pathways: azide 68 is treated with a phosphine ($R_{21}$ is alkyl or aryl) to provide iminophosphorane 69, which is reacted with a carbonyl containing resin; or, azide 68 is reduced to amine 70, which is reacted with a carbonyl containing resin. Imine 71 is reduced using an appropriate reducing agent (e.g., NaBH$_3$CN), affording compound 72, which is attached to the resin through an amine linkage.

Figure 16:
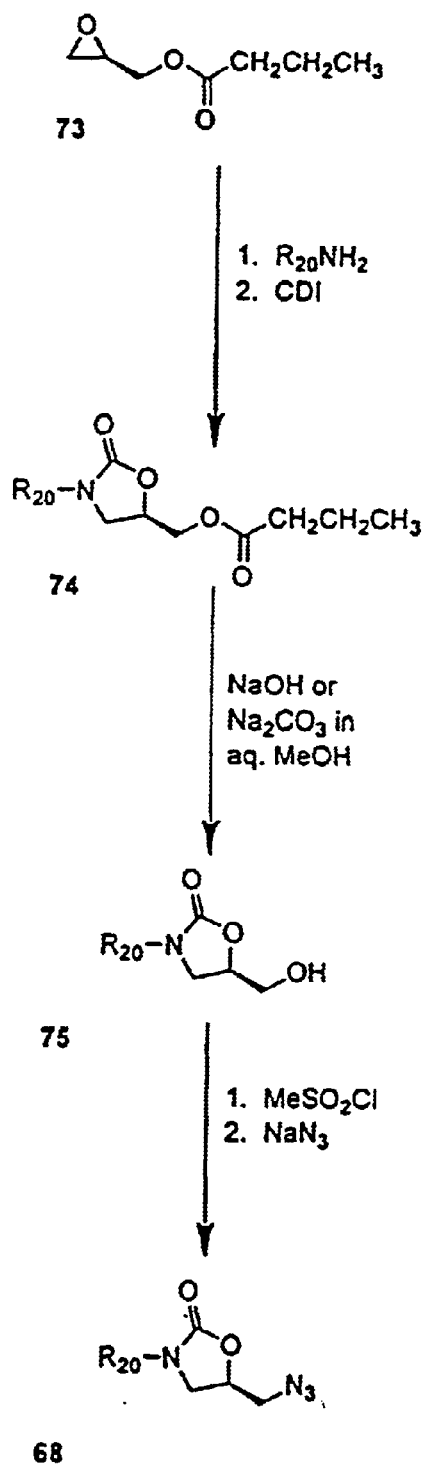
FIG. 16 is a scheme showing a general synthetic method for the preparation of azido oxazolidinones.

FIG. 16 generally shows the synthesis of compound 68. Epoxide 73 is subjected to nucleophilic attack by $R_{20}NH_2$, producing an amino alcohol. The amino alcohol is cyclized to provide oxazolidinone 74. Removal of the ester protecting group of 74 affords a primary alcohol 75. Displacement of the primary alcohol with azide yields 68.

Figure 17:
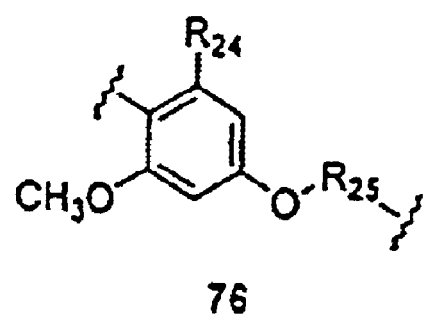
FIG. 17 is a graphical depiction of a linking portion connecting an oxazolidinone to a solid support.

The carbonyl containing resin is graphically depicted on FIG. 15. Substituent $R_{23}$ is hydrogen, alkyl, aryl, O-alkyl or O-aryl. The polymeric support (filled circle) is composed of a variety of materials, including, without limitation, Tentagel, (cross-linked)polystyrene, (cross-linked) polyethyleneglycol, poly-ethyleneglycol-polystyrene compositions, and polyacrylate. Substituent R22 is shown on FIG. 17: R24 is hydrogen, $CH_3O$, $NO_2$; and, $R_{25}$ is $(CH_2)_nCONH$, wherein n is an integer ranging from 1 to about 5.

Figure 18:
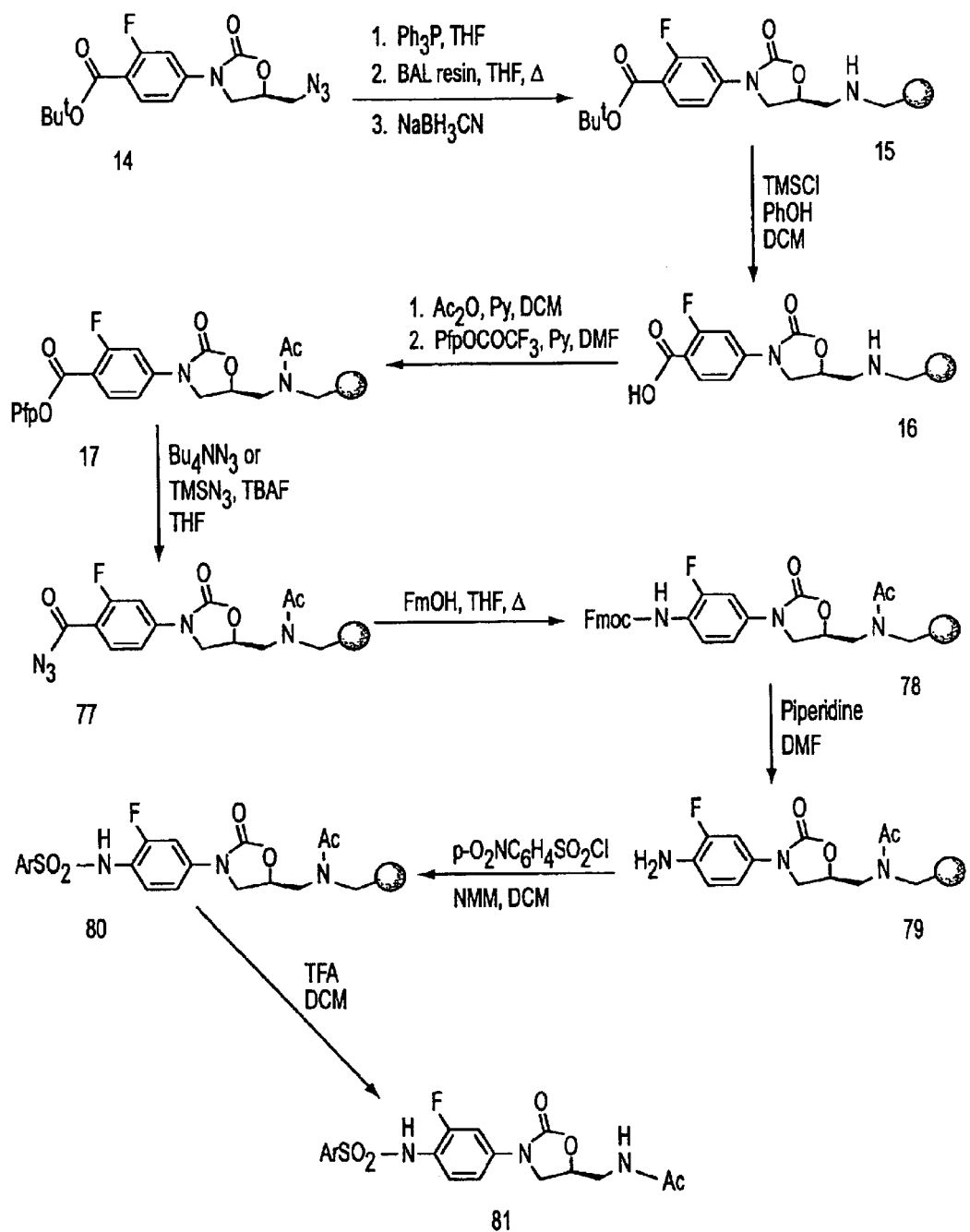
FIG. 18 is a scheme showing the synthesis of an oxazolidinone of structure 1b, wherein $R_1$ is $NR_{12}R_{13}$.
Figure 40:
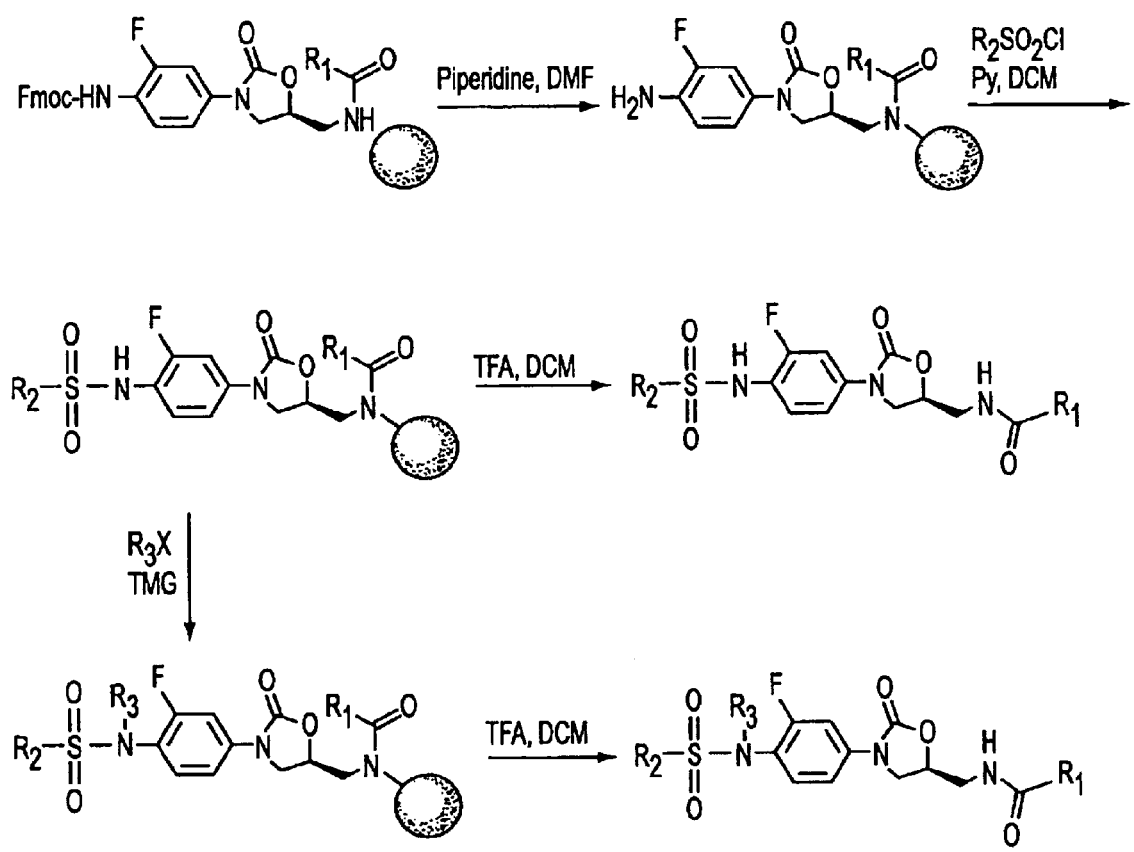
FIG. 40 is a scheme showing the synthesis of sulfonamide oxazolidinone compounds and libraries, wherein $R_1$ is a substituent, for example, H, alkyl, heteroalkyl, aryl, heteroaryl, or alkoxy.
Figure 46:
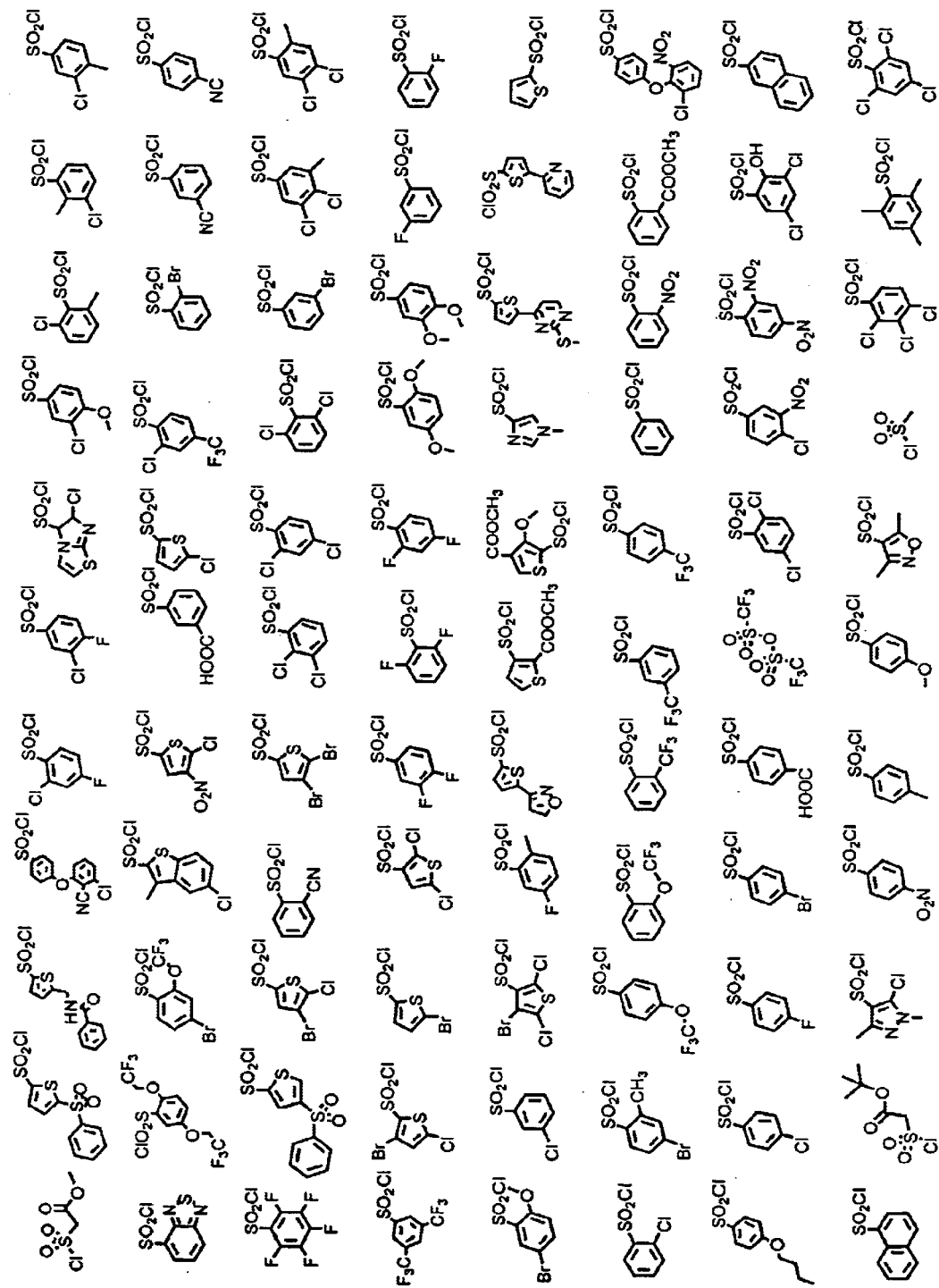
FIG. 46 illustrates sulfonyl chloride building blocks $R_2SO_2Cl$ that may be used in the synthesis of sulfonamide oxazolidinone libraries and compounds as shown in FIG. 40, and also may be used in the syntheses shown in FIG. 18.

FIG. 18 shows an embodiment of the solid phase synthesis methods. Azide 14 is converted into an iminophosphorane upon treatment with triphenylphosphine. The iminophosphorane is reacted with BAL resin to provide an imine, which is reduced with NaBH$_3$CN, affording amine 15. Compound 15 is reacted with TMSCl to remove the ester group (16). The amine of 16 is acylated and the carboxylic acid is transformed into an activated ester (17). Treatment of the activated ester with Bu$_4$NN$_3$ or TMSN3 affords acyl azide 77. Acyl azide 77 is rearranged, yielding a protected aniline (78). The Fmoc protecting group is removed (79), and the resulting aniline is sulfonated with p-O₂NC₆H₄SO₂Cl (80). The sulfonated aniline (80) is removed from the solid support upon reaction with TFA, providing 81. Another embodiment is shown in FIG. 40. FIG. 46 illustrates sulfonyl chloride building blocks R₂SO₂Cl that may be used in the synthesis of sulfonamide oxazolidinone libraries and compounds as shown in FIG. 40, and also may be used in the syntheses shown in FIG. 18.

Figure 19:
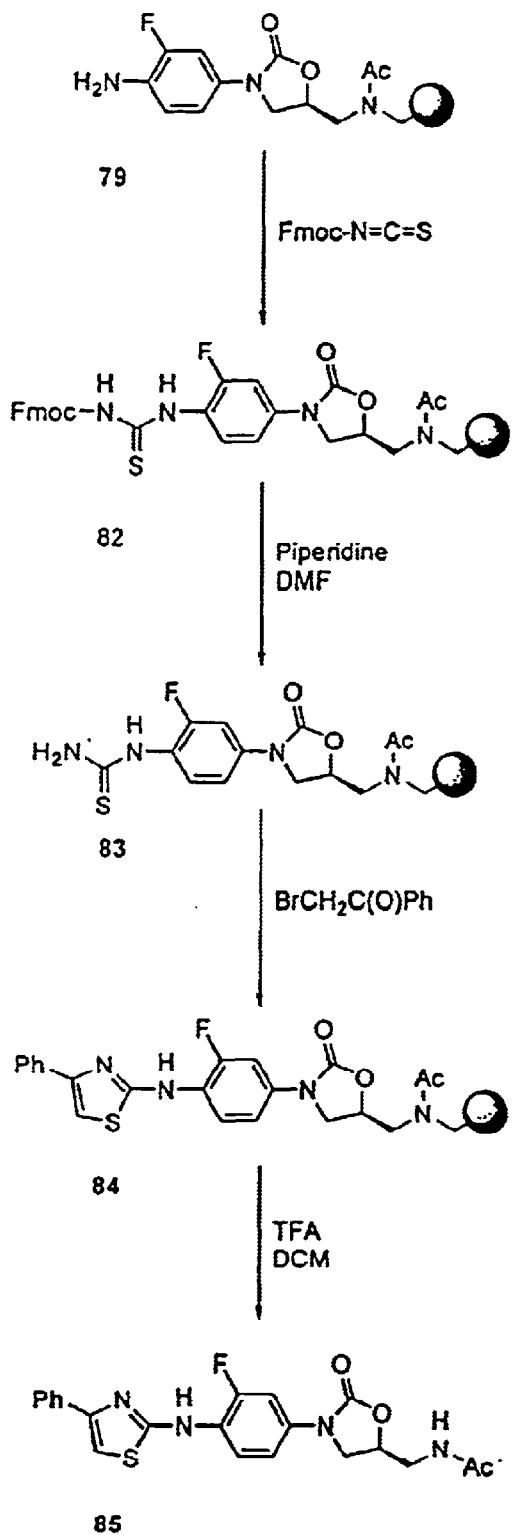
FIG. 19 is a scheme showing the synthesis of an oxazolidinone of structure 1b wherein $R_1$ is an aminothiazole.

FIG. 19 shows another embodiment of the solid phase synthesis methods. Aniline 79 is reacted with Fmoc-N=C=S to provide protected thiourea 82. The protected thiourea is treated with piperidine, affording a deprotected thiocarbamate (83). Reaction of 83 with 2-bromoacetophenone yields thiazole 84. Treatment of 84 with TFA cleaves the thiazole from the solid support, providing 85.

Figure 20:
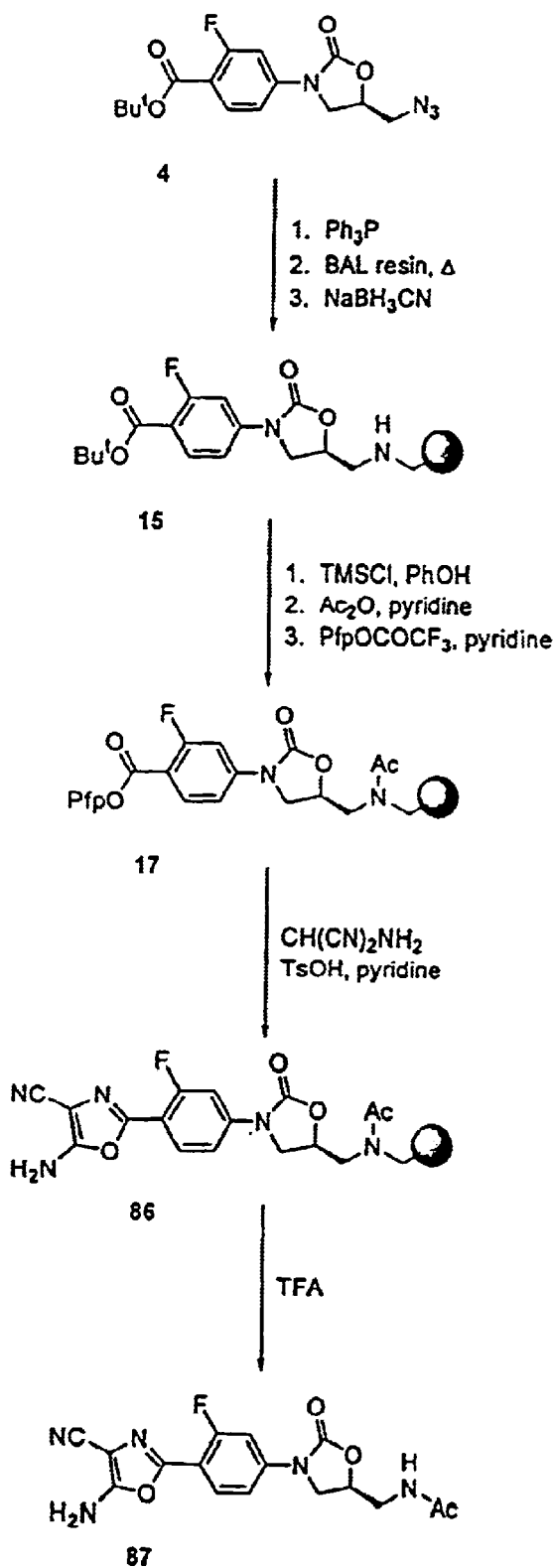
FIG. 20 is a scheme showing the synthesis of an oxazolidinone of structure 1b, wherein $R_1$ is an oxazole.

FIG. 20 shows another embodiment of the solid phase synthesis methods. Azide 4 is converted into an iminophosphorane upon treatment with triphenyl phosphine. The iminophosphorane is reacted with BAL resin, providing an imine. The imine is reduced using NaBH₃CN to afford solid support bound amine 15. The ester of 15 is deprotected using TMSCl, yielding a carboxylic acid; the amine is acylated upon reaction with Ac₂O; and, the acid is activated using PfpOCOCF3, yielding 17. Reaction of 17 with aminomalonitrile provides oxazole 86. Treatment of 86 with TFA cleaves the oxazole from the solid support to afford 87.

Figure 21:
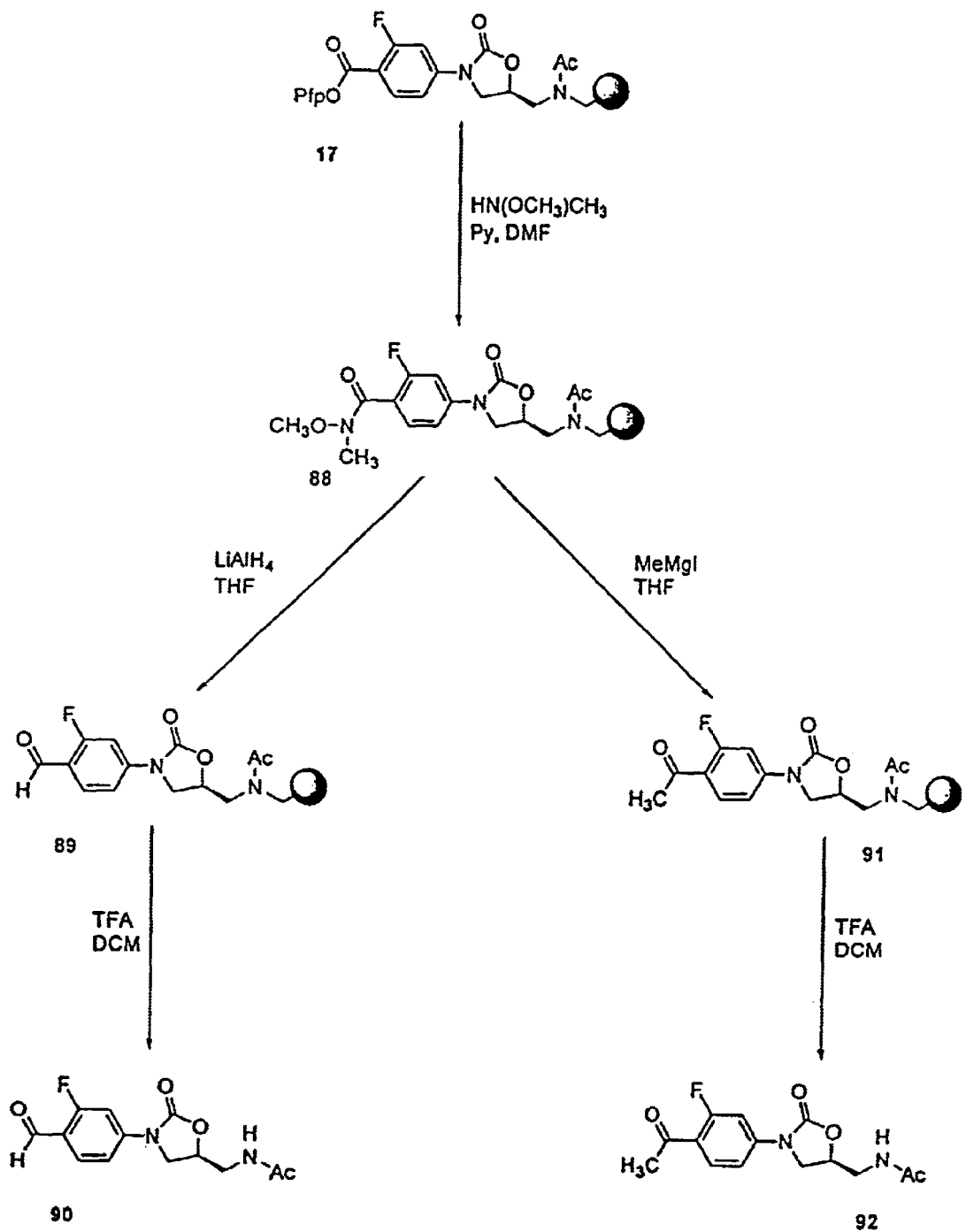
FIG. 21 is a scheme showing the synthesis of oxazolidinones of structure 1b wherein $R_1$ is $C(O)R_{10}$.

FIG. 21 shows two embodiments of the solid phase synthesis methods. Compound 17 is treated with HN(OCH₃)CH₃ to provide Weinreb amide 88. Amide 88 is either reduced with LiAlH₄ to afford aldehyde 89 or reacted with MeMgI, a Grignard reagent, to yield ketone 91. Treatment of either aldehyde 89 or ketone 91 with TFA provides, respectively, cleaved products 90 and 92.

Figure 22:
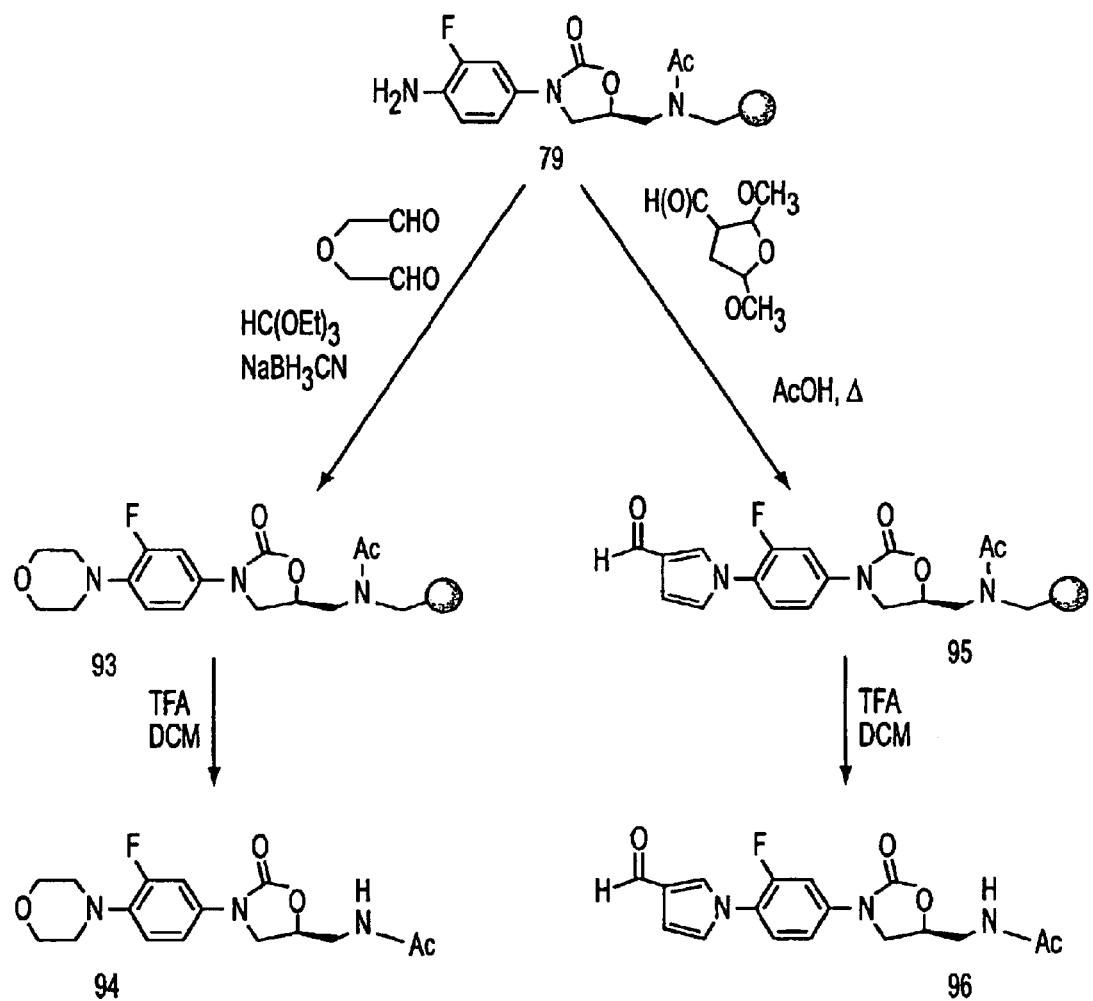
FIG. 22 is a scheme showing the synthesis of oxazolidinones of structure 1b, wherein $R_1$ is $NR_{12}R_{13}$.

FIG. 22 shows two embodiments of the solid phase synthesis methods. Compound 79 is treated with either a dialdehyde to provide morpholine 93 or a diacetal to afford pyrrole 95. Treatment of either morpholine 93 or pyrrole 95 with TFA provides, respectively, cleaved products 94 and 96.

Figure 48:
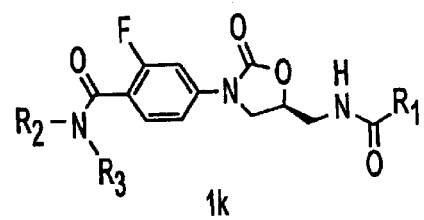
FIG. 48 shows building blocks $R_2R_3NH$ and $R_1COOH$ that may be used to make compounds of formula 1k and libraries thereof.
Figure 48:
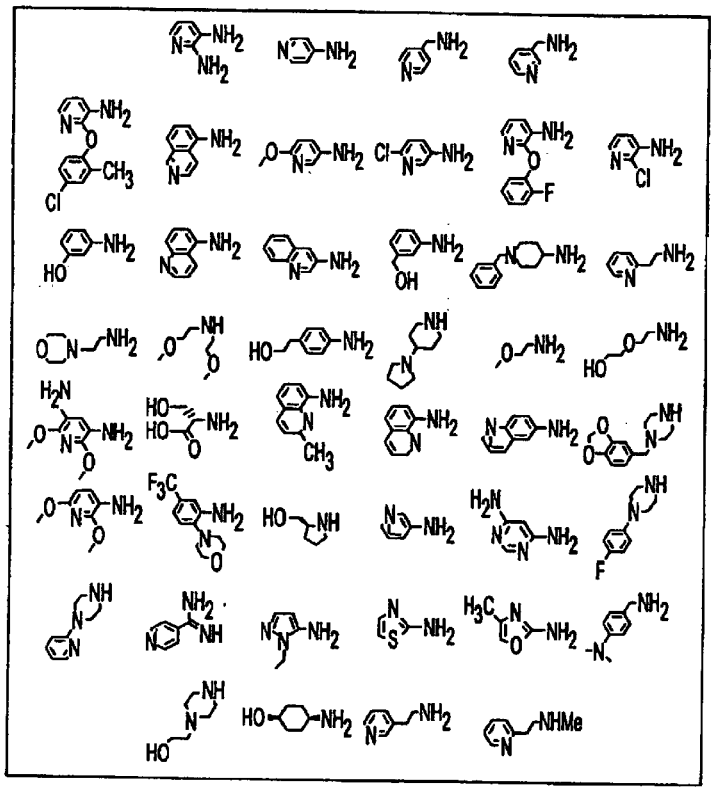
Figure 48:
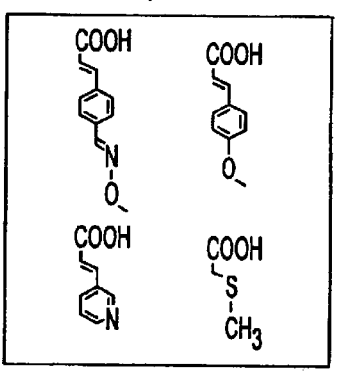

FIG. 48, shows building blocks R₂R₃NH and R₁COOH that may be used to make exemplary oxazolidinone compounds of formula 1k and libraries thereof.

Synthesis of Oxazolidinone Compounds 1a

Oxazolidinone compounds 1a and precursors thereof may be made by a variety of methods as disclosed herein.

Figure 23:
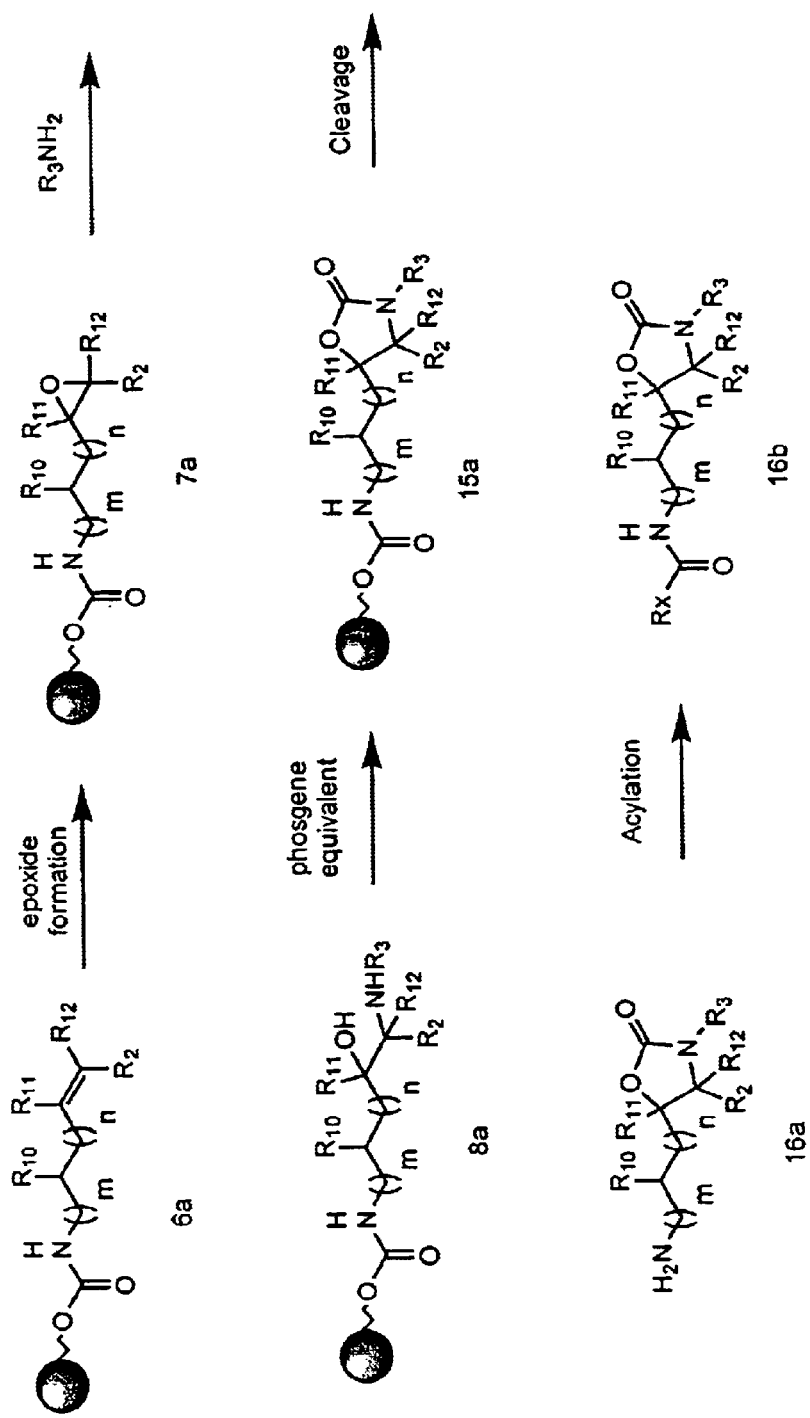
FIG. 23 is a scheme showing a general synthetic method for the preparation of oxazolidinones.

An embodiment of a solid phase synthesis method to make amino alcohols, where R₁ is an alkyl, is shown in FIG. 23. An olefin group is attached to the surface of a solid support (5a) providing the functionalized resin 6a. The olefin can have the following functionality: "m" is 0, 1, or 2; "n" is 0, 1, or 2; R₁₀, R₁₁ R₁₂, R₂ and R₃ are independently hydrogen, alkyl, heteroalkyl, aryl or heteroaryl. The olefin is chemically modified yielding epoxide 7a. Addition of a substituted amine to the distal carbon of immobilized epoxide 7a affords solid support bound amino alcohol 8a. Solid support bound amino alcohol 8a is treated with a phosgene equivalent providing oxazolidinone 15a, which is cleaved under standard conditions to yield free oxazolidinone 16a. Acylation of 16a yields oxazolidinone 16b.

Figure 24:
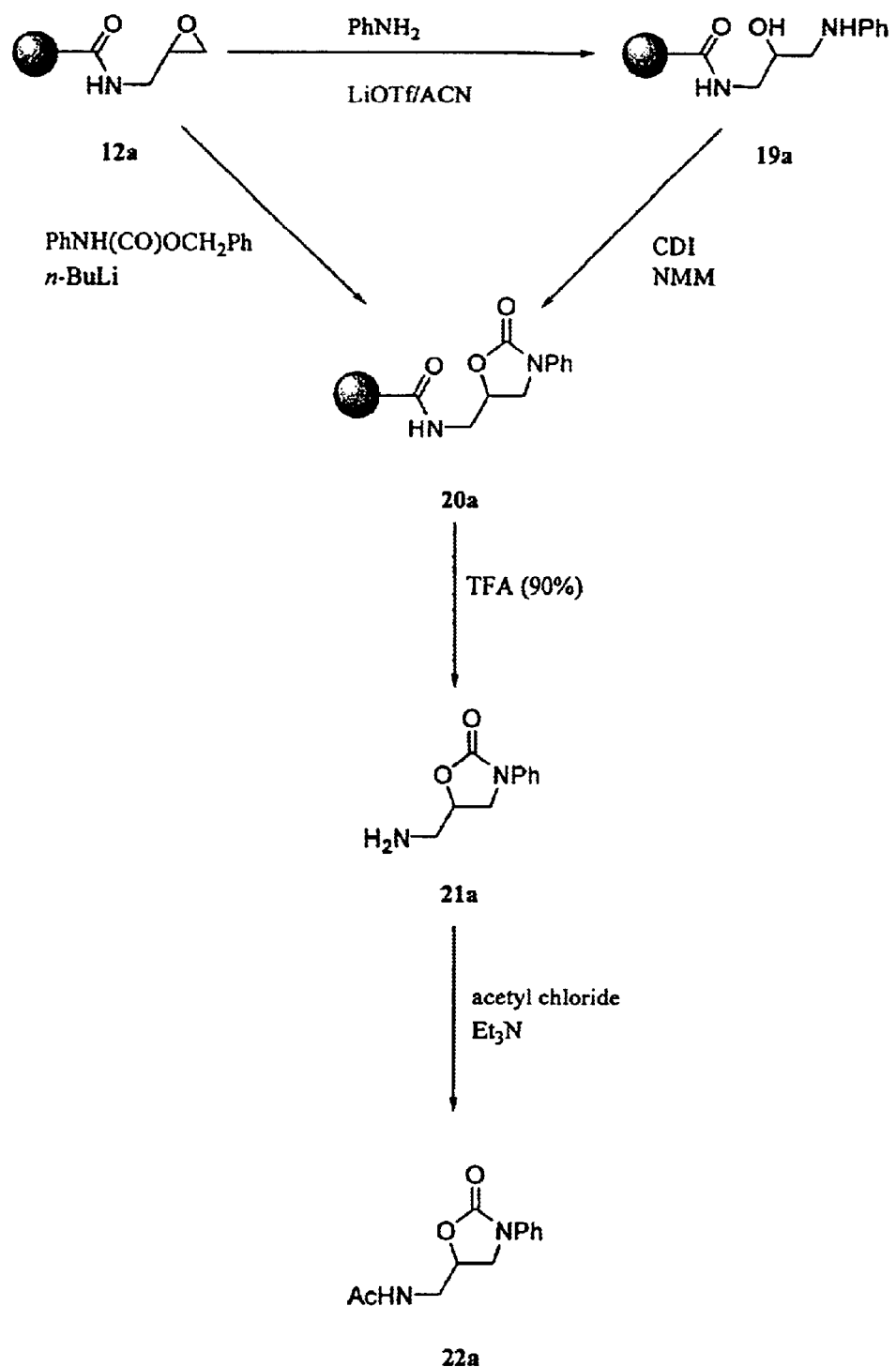
FIG. 24 is a scheme showing a method of preparation of N-[(3-phenyl-2-oxo-5-oxazolidinyl)methyl]acetamide.

Another embodiment of the solid phase synthesis method to make oxazolidinones is shown in FIG. 24. Immobilized epoxide 12a was treated with aniline in the presence of lithium triflate to provide solid support bound amino alcohol 19a. Reaction of 19a with CDI yielded oxazolidinone 20a. Alternatively, 20a was prepared directly from epoxide 12a upon treatment with a lithium salt of aniline benzylcarbamate. Addition of TFA to oxazolidinone 20a provided free oxazolidinone 21a, which was acetylated to yield acetamide 22a.

Figure 25:
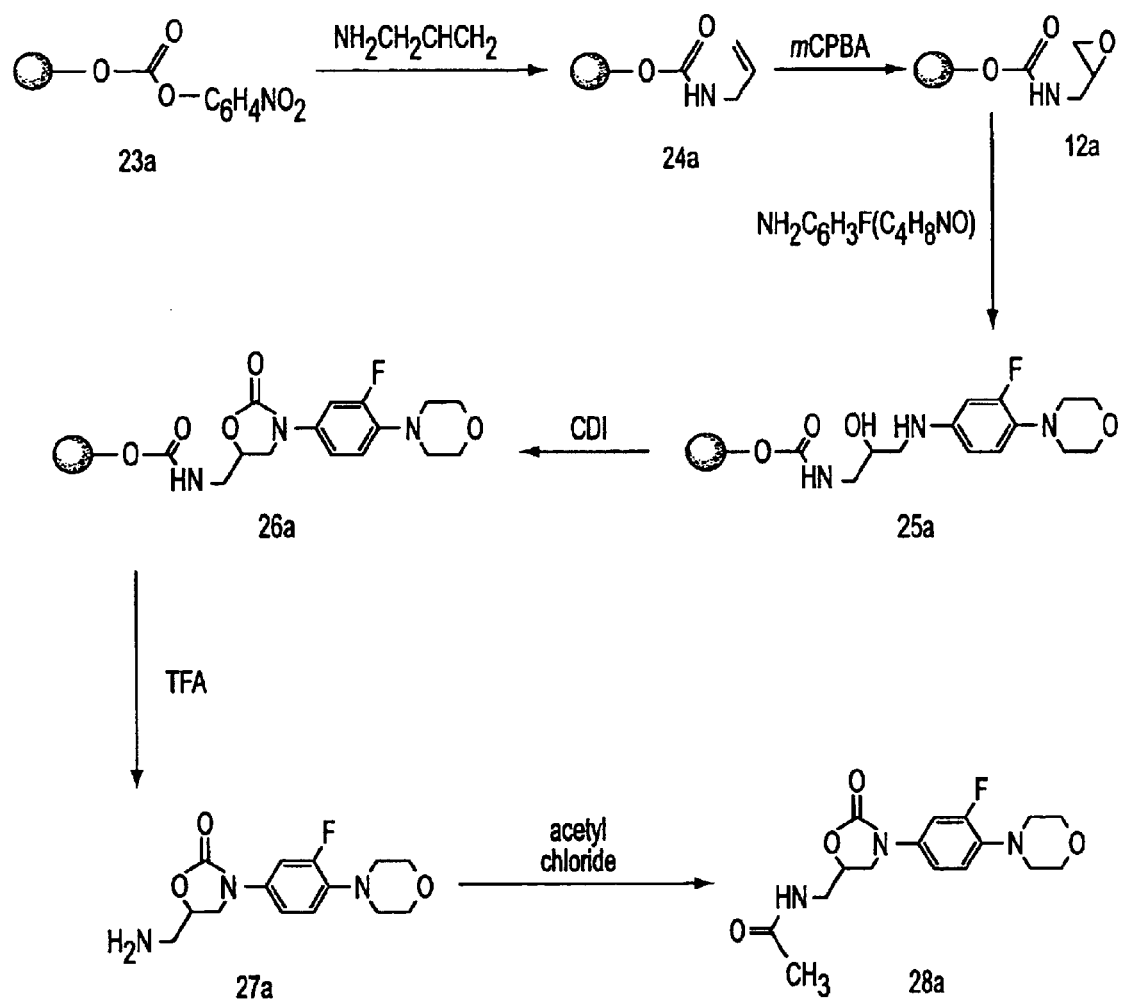
FIG. 25 is a scheme showing a method of preparation of N-[[3-(3-fluoro-4-morpholinylphenyl)-2-oxo-5-oxazolidinyl]methyl]acetamide.

Another embodiment of the solid phase synthesis method to make oxazolidinones is shown in FIG. 25. PNP Wang Resin (23a) was reacted with allyl amine to provide carbamate 24a. The terminal olefin of carbamate 24a was oxidized with mCPBA to yield immobilized epoxide 12a. Addition of 3-fluoro-4-morpholino aniline to 12a produced amino alcohol 25a, which was cyclized to oxazolidinone 26a upon treatment with CDI. Reaction of 26a with TFA provided free amine 27a. Addition of acetyl chloride to 27a produced acetamide 28a.

Synthesis of Combinatorial Libraries Comprising Oxazolidinones 1a

In one embodiment, provided are methods for the synthesis of combinatorial libraries comprising oxazolidinones 1a and compositions formed from this method. In one embodiment, oxazolidinones 1a are compounds of the following structure:

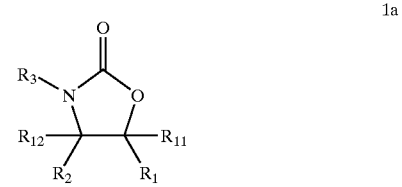

1a where R₁ is selected from the group consisting of alkyl, heteroalkyl, aryl and heteroaryl; R₂ is selected from the group consisting of hydrogen, alkyl, heteroalkyl, aryl and heteroaryl; R₃ is selected from the group consisting of hydrogen, alkyl, heteroalkyl, aryl and heteroaryl; R₁₁ is selected from the group consisting of hydrogen, alkyl, heteroalkyl, aryl and heteroaryl; and R₁₂ is selected from the group consisting of hydrogen, alkyl, heteroalkyl, aryl and heteroaryl.

An embodiment of the solid phase method to make oxazolidinone libraries, where R₁ is an alkyl group, is described in reference to FIG. 23. Olefin groups are attached to the surface of a plurality of solid supports 5a providing functionalized resins 6a. The olefin groups can have the following funtionality "m" is 0, 1, or 2; "n" is 0, 1, or 2; R₂, R₃, R₁₀, R₁₁ and R₁₂ are independently hydrogen, alkyl, heteroalkyl, aryl or heteroaryl. The individual olefin groups are chemically modified to yield epoxides 7a. Addition of different amine units to the distal carbon of the epoxides 7a affords a plurality of amino alcohols 8a.

A plurality of solid support bound amino alcohols 8a is treated with a phosgene equivalent to provide a plurality of oxazolidinones 15a, which are cleaved under standard conditions to yield the free oxazolidinones 16a.

Figure 26:
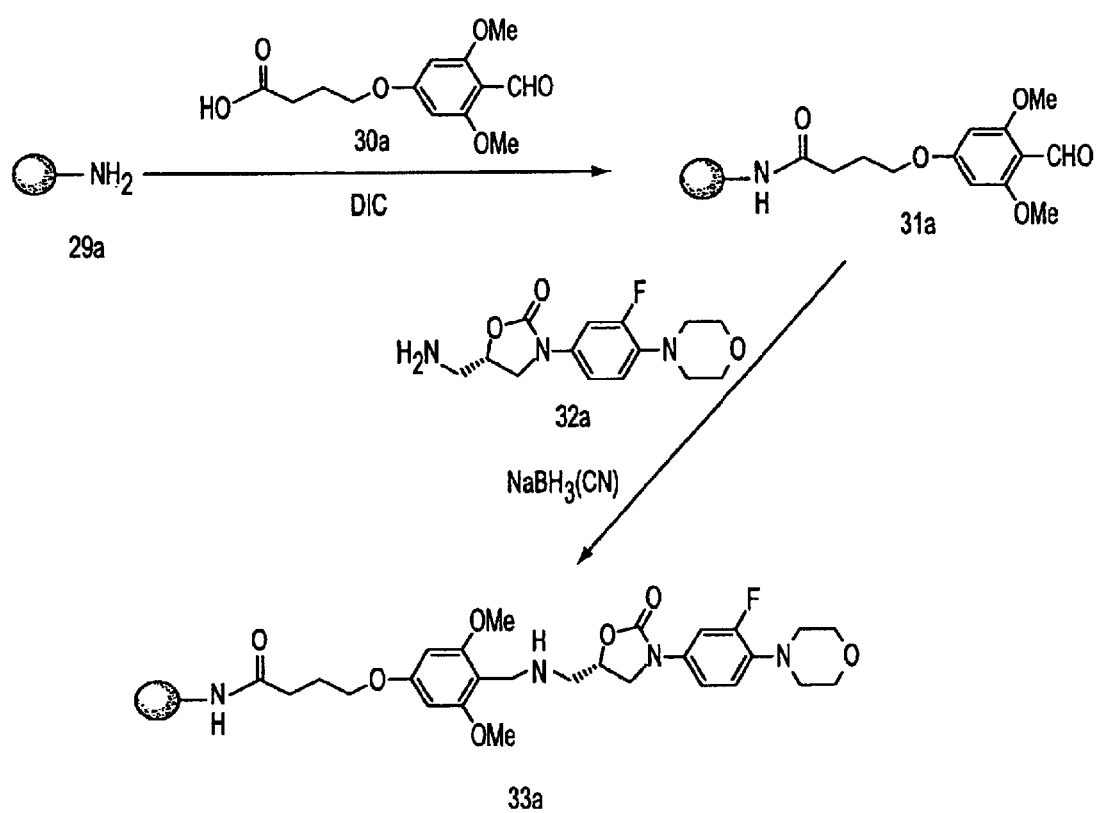
FIG. 26 is a scheme showing a method of preparation for solid support bound (S)-N-[[3-(3-fluoro-4-morpholinylphenyl)-2-oxo-5-oxazolidinyl]-methyl] acetamide.
Figure 27:
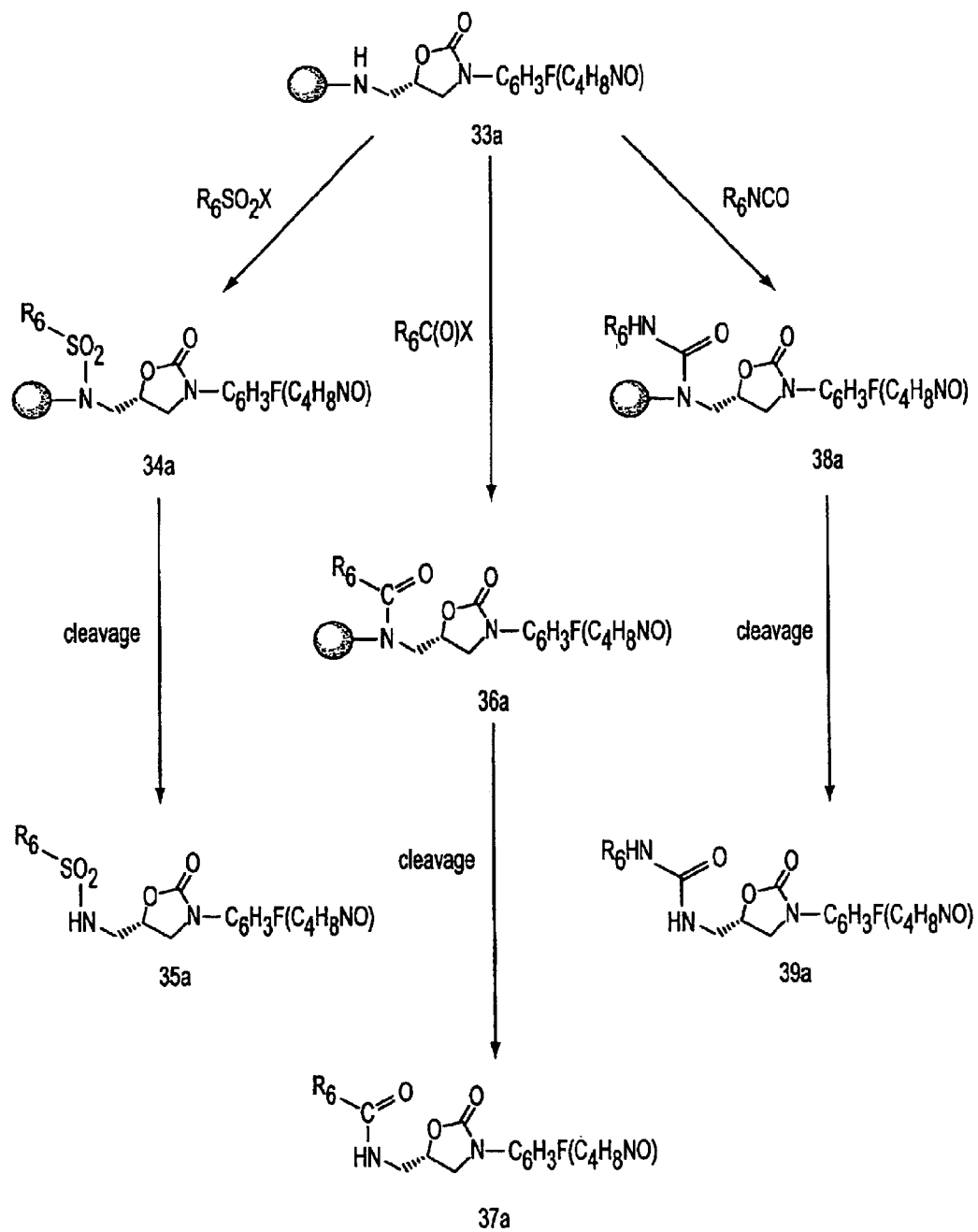
FIG. 27 is a scheme showing a method of preparation for sulfonyl, amidyl and ureayl derivatives of (S)-N-[[3-(3-fluoro-4-morpholinylphenyl)-2-oxo-5-oxazolidinyl]-methyl]acetamide.

Another embodiment of the solid phase method to make oxazolidinone libraries is shown in FIGS. 26 and 27. Carboxylic acid 30a is attached to amine resin 29a to provide amide 31a. Reductive amination of 31a employing amine 32a yields the functionalized amine 33a, which is added to an array of individual reaction chambers. Addition of sulfonyl chloride units to a plurality of amines 33a produces the sulfonamides 34a. The sulfonamides are cleaved from the solid support using standard conditions providing a plurality of free sulfonamides 35a. Addition of carboxylic acid or carboxylic acid derivative units to a plurality of amines 33a produces the amides 36a. The amides 36a are cleaved from the solid support using standard conditions providing a plurality of free amides 37a. Addition of isocyanate units to a plurality of amines 33a produces the ureas 38a. The ureas 38a are cleaved from the solid support using standard conditions providing a plurality of free ureas 39a.

Figure 28:
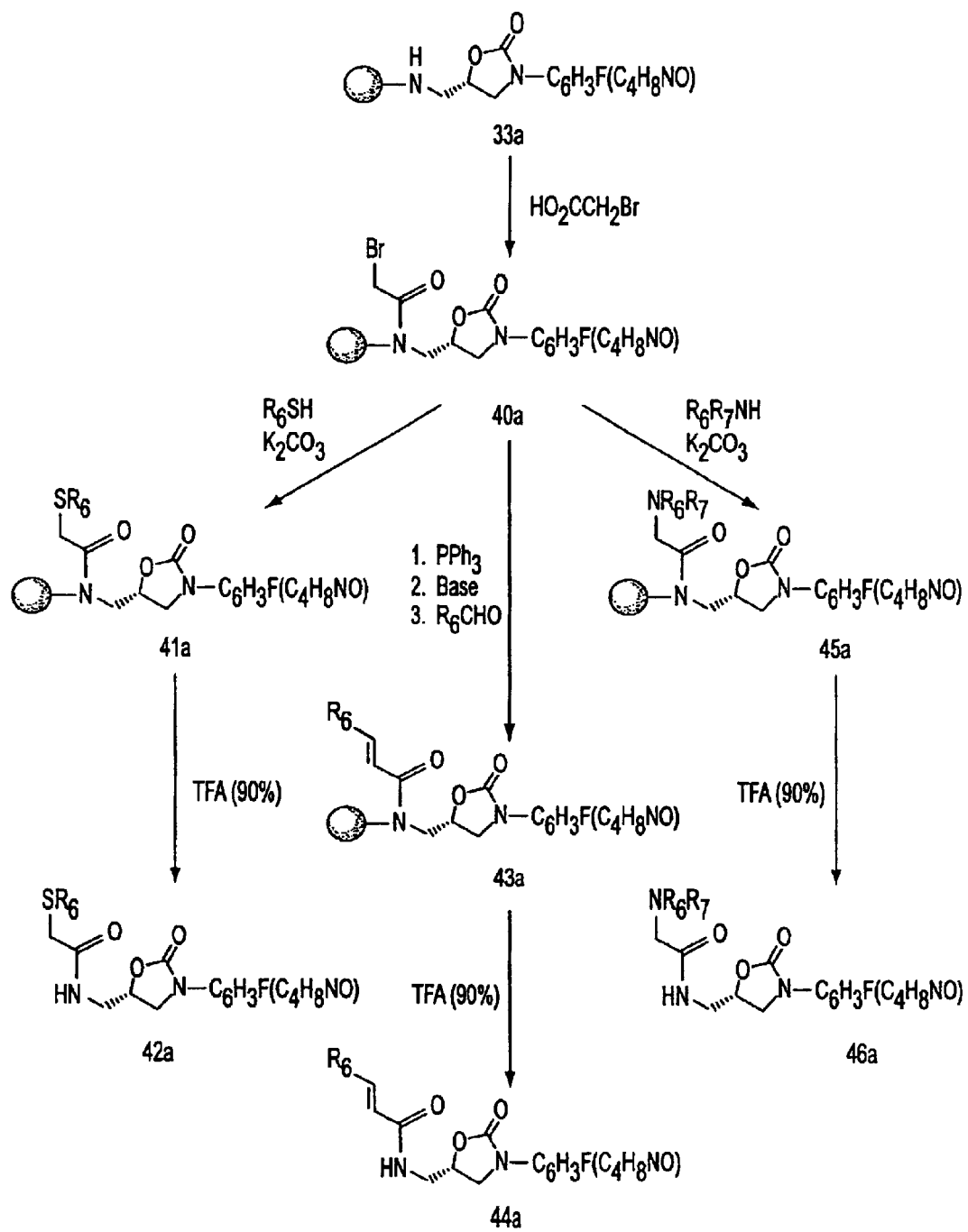
FIG. 28 is a scheme showing the preparation of α-thio acetamide, α, β-unsaturated acetamide and α-amino acetamide derivatives of (S)-N-[[3-(3-fluoro-4-morpholinylphenyl)-2-oxo-5-oxazolidinyl]-methyl]acetamide.

Another embodiment of the solid phase method to make oxazolidinone libraries is shown in FIG. 28. Coupling of α-bromo acetic acid to amine 33a provides amide 40a, which is divided into an array of individual reaction chambers. Nucleophilic addition of thiol units to a plurality of amides 40a yields the α-thio amides 41a, which are cleaved from the solid support upon treatment with TFA producing a plurality of free α-thio amides 42a. Nucleophilic addition of triphenylphospine to a plurality of amides 40a yields solid support bound Wittig reagents that are coupled with aldehyde units affording a plurality of α, β-unsaturated amides 43a. The amides were cleaved from the solid support upon treatment with TFA to produce a plurality of free α, β-unsaturated amides 44a. Nucleophilic addition of amine units to a plurality of amides 40a yields the (α-amino amides 45a, which are cleaved from the solid support upon treatment with TFA producing a plurality of free α-amino amides 46a.

3-(Polysubstituted)oxazolidinones

A variety of 3polysubstituted)oxazolidinones are provided, which optionally have biological activity, such as antimicrobial activity.

In one embodiment, 3-(polysubstituted)oxazolidinones 2c as well as combinatorial libraries comprising the compounds are provided:

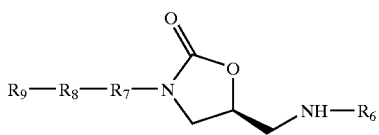

2c

In 2c, in one embodiment:

R$_6$ is acyl or sulfonyl;

R$_7$ is aryl or heteroaryl;

R$_8$ is C$_1$–C$_7$ alkyl, NR, O, S, C(=O)NR, NRC(=O), C(=O), C(=O)O, OC(=O), S(=O), SO$_2$, SO$_2$NR, NRSO$_2$, NRCONR', or (CH$_2$)$_n$O, where n=0–6, and R and R' are substituents, for example, independently H, or alkyl, such as C$_1$–C$_7$ alkyl, or heteroalkyl, aryl or heteroaryl; and R$_9$ is hydrogen, OH, alkyl, aryl, heteroalkyl, or heteroaryl.

In another embodiment, 3-[4-(heteroaryl) aminocarbonylaryl]-oxazolidinones and 3-[4-(N-oxide heteroaryl)aminocarbonylaryl]-oxazolidinones are provided.

In one embodiment of 2c:

R$_6$ is C(=O)R, where R is a substituent, for example, H or alkyl, such as C$_1$–C$_7$ alkyl, such as methyl or ethyl, or, e.g., heteroalkyl, aryl or heteroaryl;

R$_7$ is aryl;

R$_8$ is an amide group, such as NH(C=O) or NR'(C=O), where R' is a substituent, for example, H, heteroalkyl, aryl, heteroaryl, or alkyl, such as C$_1$–C$_7$ alkyl, such as methyl; and R$_9$ is hydrogen or a heteroaryl group, such as an unsubstituted or substituted heteroaryl group, wherein the heteroaryl group is for example pyridinyl, thiazolyl, benzothiazolyl, isothiazolyl, quinolinyl, 1,3,4-triazolyl, or 1,3,4-thiadiazolyl.

For example, compounds of formula 2d are provided:

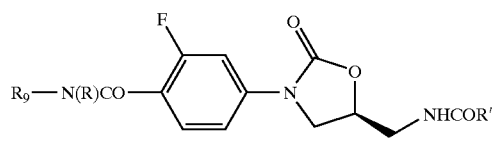

2d wherein

R$_9$ is hydrogen or an unsubstituted or substituted heteroaryl group, such as pyridinyl, thiazolyl, benzothiazolyl, isothiazolyl, quinolinyl, 1,3,4-triazolyl, or 1,3,4-thiadiazolyl; and R and R' are substituents, for example, independently H or alkyl, such as C$_1$–C$_7$ alkyl, such as methyl, or, e.g., heteroalkyl, aryl or heteroaryl.

Exemplary compounds are shown below.

In one embodiment the following nine preferred compounds are provided, which have an MIC against S. aureus of about 0.5 to 1 μg/mL using a standard whole cell assay as disclosed herein.

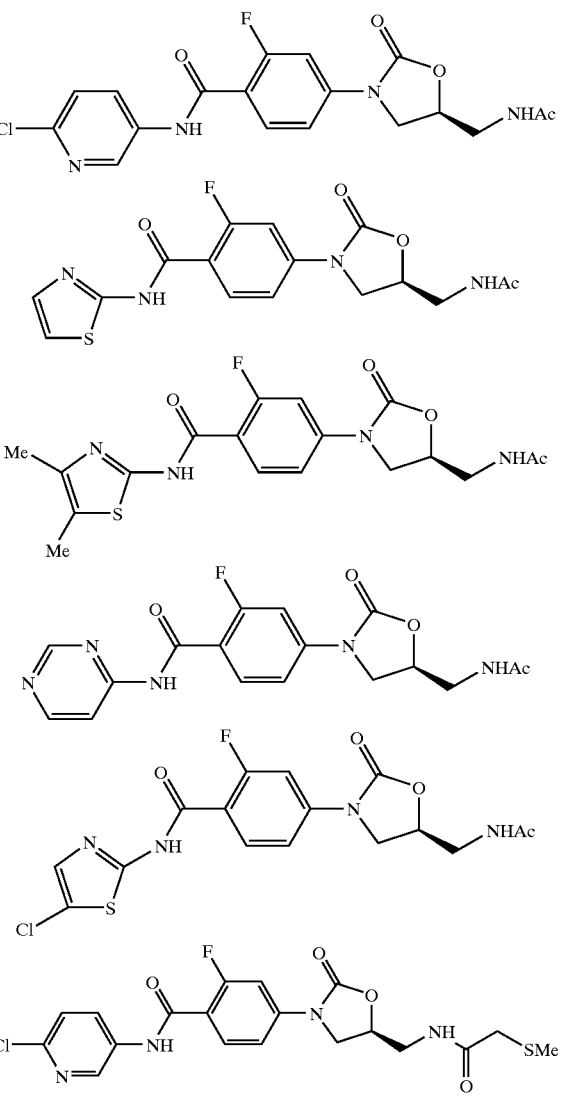

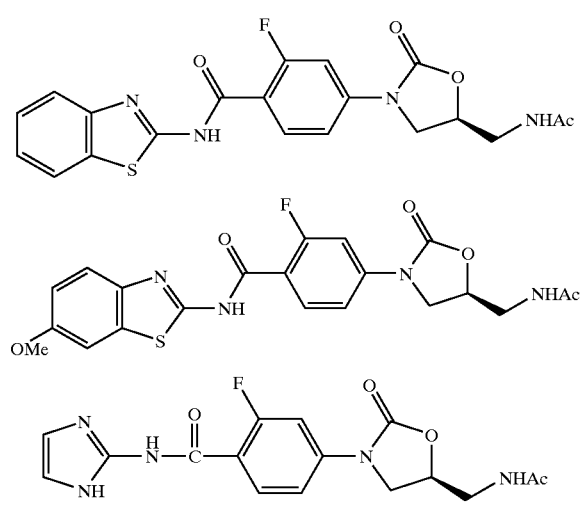
The following nine compounds also are provided that have an MIC against *S. aureus* of about 2 to 4 μg/mL using a standard whole cell assay as disclosed herein.
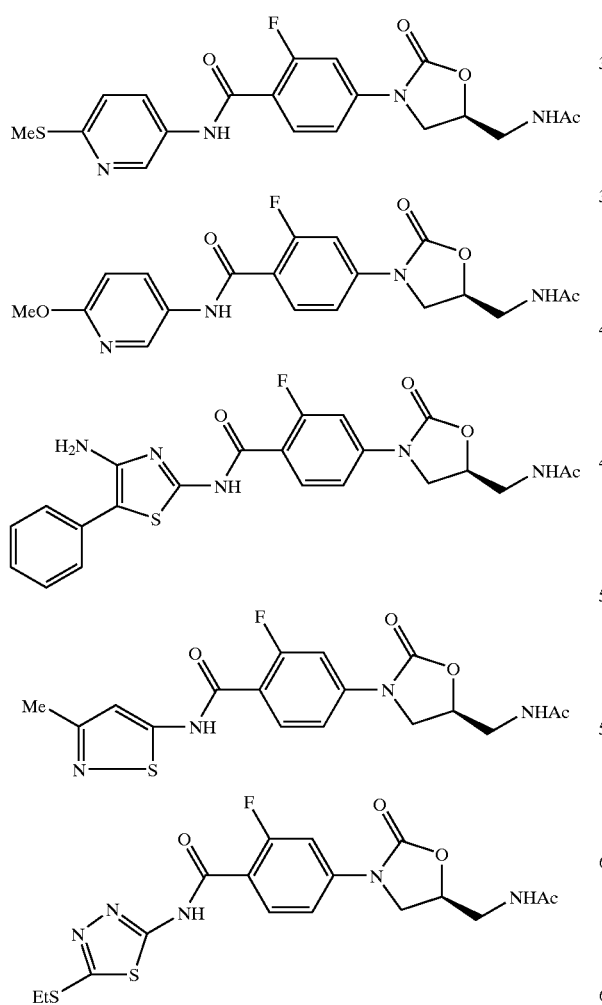
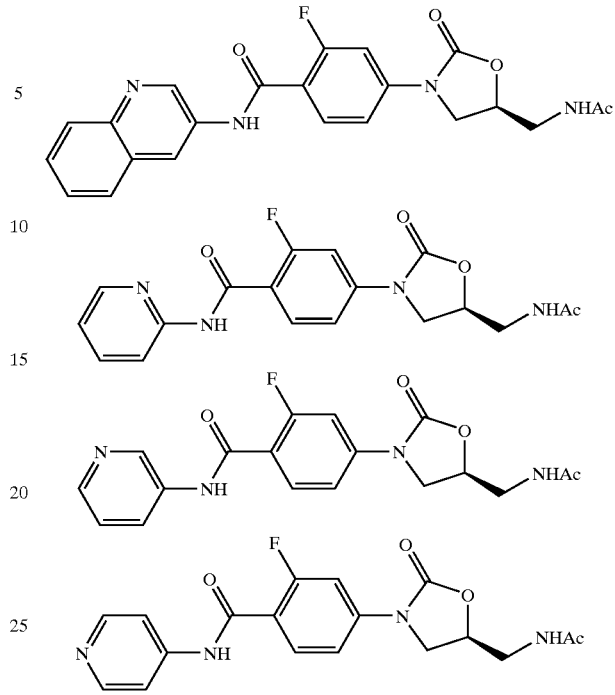
Also provided are the following compounds.
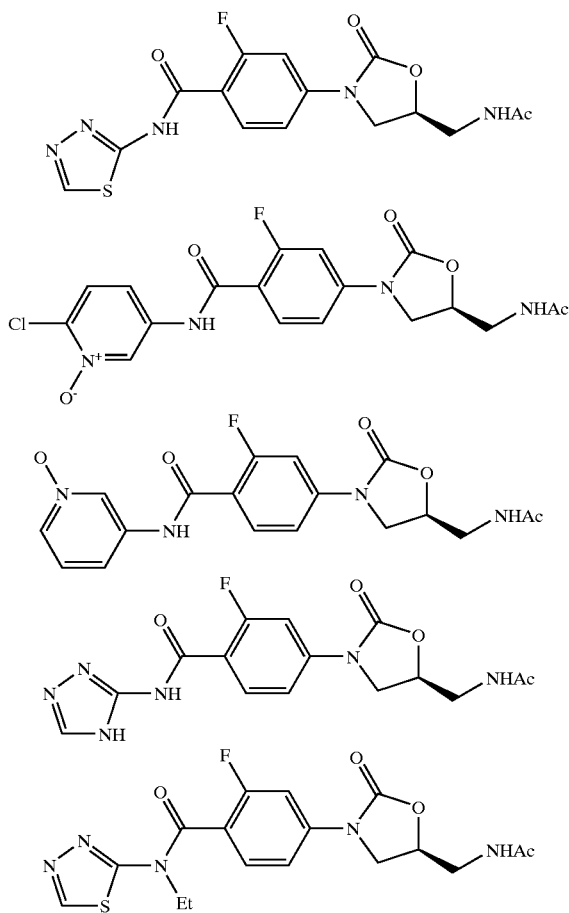

Other exemplary oxazolidinone compounds within the scope of the invention are shown below:

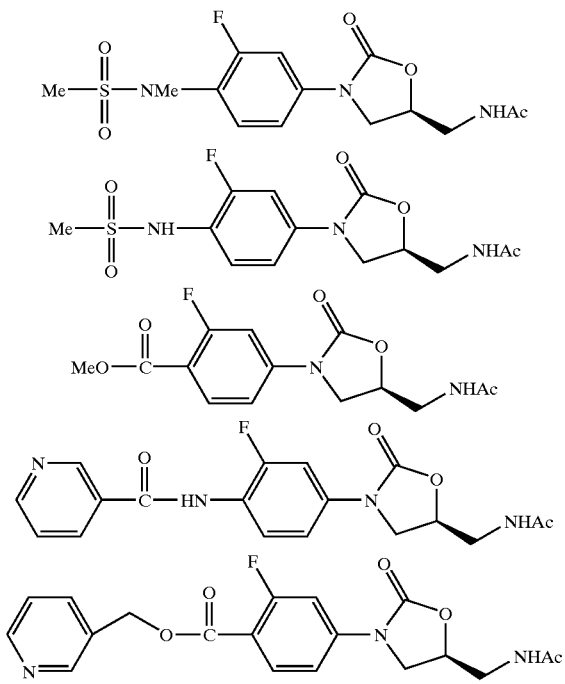

Further provided are 3-(aminocarbonyl)oxazolidinones of formula 2c, wherein:

$R_6$ is an acyl group, such as C(=O)R, where R is a substituent, for example, H or alkyl, such as $C_1$–$C_7$ alkyl, including methyl, or e.g., heteroaryl, aryl or heteroaryl;

$R_7$ is aryl;

$R_8$ is NH(C=O); and $R_9$ is hydrogen or OH;

Exemplary compounds are shown below:

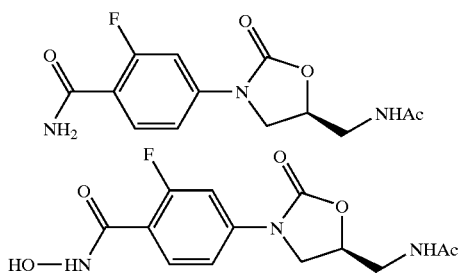

In one embodiment the following compound is provided, which has an MIC against S. aureus of about 0.5 µg/mL using a standard whole cell assay as disclosed herein.

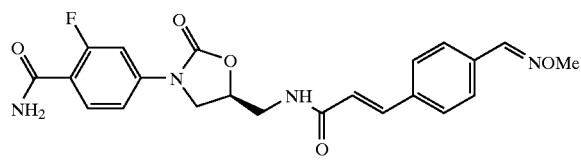

3-[(Substituted)aryl]oxazolidinones

A variety of 3-[(substituted)aryl]oxazolidinones are provided, which optionally are biologically active, for example as antimicrobial compounds.

In one embodiment oxazolidinones of formula 3c, and combinatorial libraries comprising compounds of formula 3c are provided:

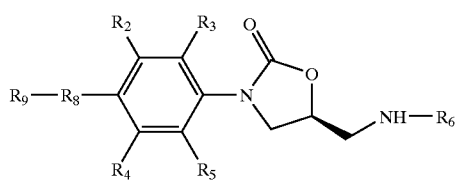

In one embodiment in 3c:

$R_2$, $R_3$, $R_4$ and $R_5$ are, independently, hydrogen, alkyl, heteroalkyl, heteroaryl or an electron withdrawing group;

$R_6$ is acyl or sulfonyl;

$R_8$ is $C_1$–$C_7$ alkyl, NR, O, S, C(=O)NR, NRC(=O), C(=O), C(=O)O, OC(=O), S(=O), $SO_2$, $SO_2$NR, $NRSO_2$, NRCONR', or $(CH_2)_nO$, where n=0–6, and where R and R' are substituents, for example, independently H or alkyl, such as $C_1$–$C_7$ alkyl, or, e.g., heteroalkyl, aryl or heteroaryl; and $R_9$ is alkyl, aryl, heteroalkyl, or heteroaryl.

In a further embodiment, 3-[4-(alkylthio)aryl] oxazolidinones are provided. For example, compounds of formula 3c are provided, wherein:

$R_2$, $R_3$, $R_4$ and $R_5$ are, independently, hydrogen, alkyl, heteroalkyl, heteroaryl or an electron withdrawing group;

$R_6$ is acyl, such as C(=O)CH$_3$;

$R_7$ is an aryl group;

$R_8$ is thio group, such as S; and $R_9$ is a heteroalkyl group.

In another embodiment, compounds of formula 3d are provided:

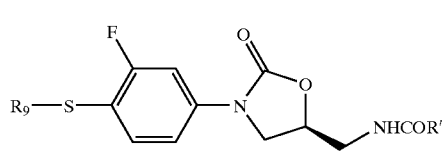

wherein $R_9$ is alkyl, aryl, heteroalkyl, or heteroaryl; and

R' is a substituent, for example, H or alkyl, such as $C_1$–$C_7$ alkyl, or, e.g., heteroalkyl, aryl or heteroaryl.

Exemplary compounds are shown below.

In one preferred embodiment, the following three compounds are provided that have an MIC against S. aureus of about 2 µg/mL using a standard whole cell assay as disclosed herein.

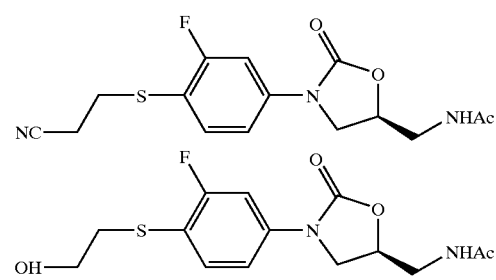

-continued

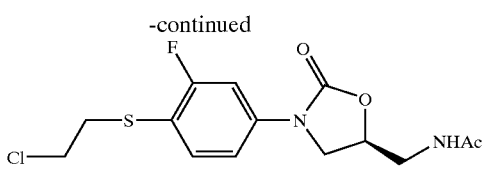

In another embodiment, the following four compounds are provided that have an MIC against *S. aureus* of about 8 µg/mL using a standard whole cell assay as disclosed herein.

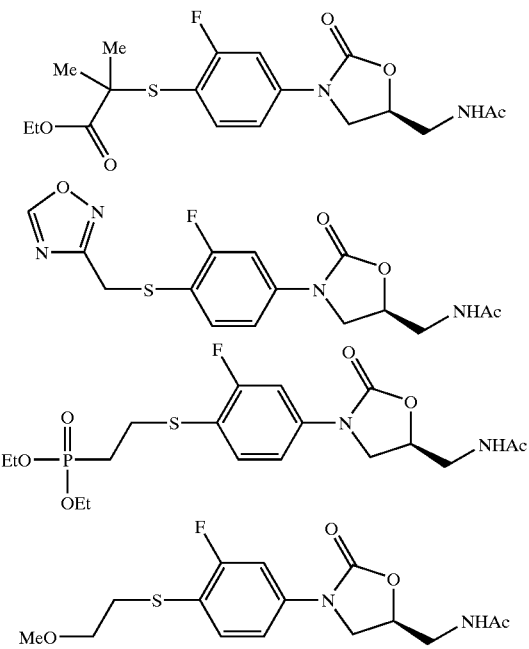

Also provided are the following compounds:

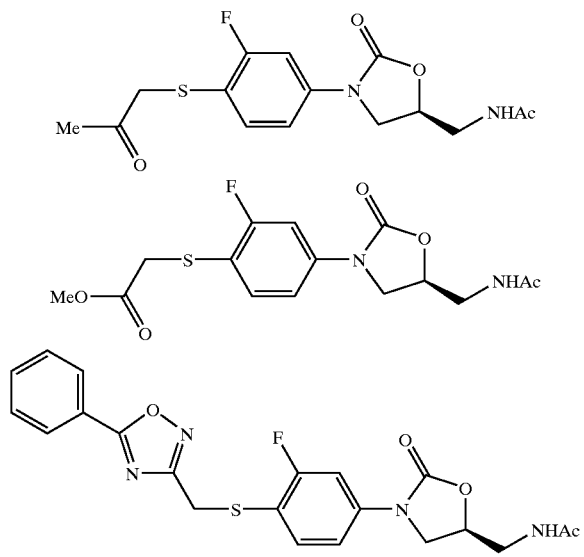

In another embodiment, 3-[4-(ester group)aryl] oxazolidinones useful as antimicrobial agents are provided. For example, compounds of formula 3c are provided wherein:

$R_2$, $R_3$, $R_4$ and $R_5$ are, independently, hydrogen, alkyl, heteroalkyl, heteroaryl or an electron withdrawing group;

$R_6$ is an acyl group, such as C(=O)CH$_3$;
$R_8$ is an ester, such as OC(=O); and
$R_9$ is an alkyl group, such as a $C_1$–$C_7$ alkyl group.

In one embodiment, compounds of structure 3e are provided:

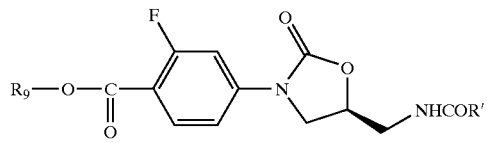

wherein $R_9$ is alkyl, aryl, heteroalkyl, or heteroaryl; and

R' is a substituent, for example, H or alkyl, such as $C_1$–$C_7$ alkyl, or, e.g., heteroalkyl, aryl or heteroaryl.

Exemplary compounds are shown below:

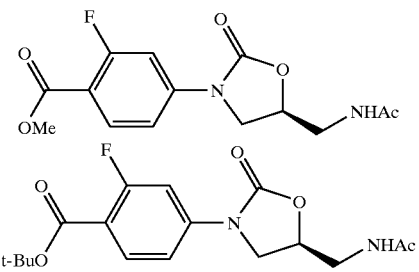

3-[(Substituted)heteroaryl]oxazolidinones

In another embodiment, a variety of 3-[(substituted) heteroaryl]oxazolidinones, which optionally are biologically active, for example, as antimicrobial compounds, are provided.

In one embodiment, compounds of the formula 4c, and combinatorial libraries thereof are provided:

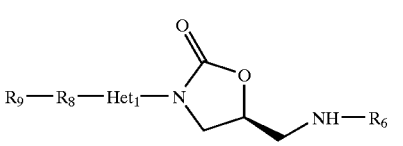

In one embodiment of 4c:

$R_6$ is acyl or sulfonyl;

$Het_1$ is heterocyclic group such as an unsubstituted or substituted heteroaryl group, such as thienylphenyl, thiazolyl, 1,3,4-thiadiazolyl, pyridinyl, or pyrimidinyl;

$R_8$ is $C_1$–$C_7$ alkyl, NR, O, S, C(=O)NR, C(=O)NOR, NRC(=O), C(=O), C(=O)O, OC(=O), S(=O), SO$_2$, SO$_2$NR, NRSO$_2$, NRCONR', or (CH$_2$)$_n$O, where n=0–6, and R and R' are substituents, for example, independently, H, or alkyl, such as $C_1$–$C_7$ alkyl, or, e.g., heteroalkyl, aryl or heteroaryl; and $R_9$ is alkyl, aryl, heteroalkyl, or heteroaryl.

In 4c, substituents on the heteroaryl group Het$_1$ are, for example, independently, hydrogen, alkyl, aryl, heteroalkyl, electron withdrawing group, F, Cl, CN, NO$_2$, NR"R'", OH, OR", SR", S(=O)R", SO$_2$R", C(=O)R", C(=O)OR", OC(=O)R", C(=O)NR"R'", N(R")C(=O)R'", or N-oxide group in the Het$_1$ nuclei, and R" and R'" are substituents, for example are independently H or alkyl, such as $C_1$–$C_7$ alkyl, or, e.g., heteroalkyl, aryl or heteroaryl.

3-[4-Linked heteroaryl)aryl]oxazolidinones

In a further embodiment, 3-[4-(linked heteroaryl)aryl] oxazolidinones are provided, which optionally have biological activity, for example, as antimicrobial compounds.

For example, compounds of the formula 5c, and combinatorial libraries thereof are provided:

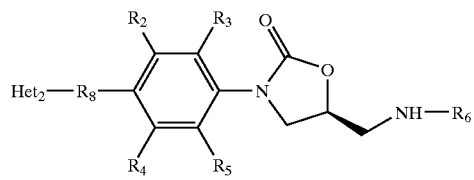

In one embodiment of 5c:

$R_2$, $R_3$, $R_4$ and $R_5$ are, independently, hydrogen, alkyl, heteroalkyl, heteroaryl or an electron withdrawing group;

$R_6$ is acyl or sulfonyl;

$R_8$ is $C_1$–$C_7$ alkyl, NR, O, S, C(=O)NR, NRC(=O), C(=O)NOR C(=O), C(=O)O, OC(=O), S(=O), $SO_2$, $SO_2$NR, $NRSO_2$, NRCONR', or $(CH_2)_nO$, where n=0–6, and R and R' are substituents, for example, independently H or alkyl, such as $C_1$–$C_7$ alkyl, or, e.g., heteroalkyl, aryl or heteroaryl; and $Het_2$ is a heterocyclic group, such as an unsubstituted or substituted heterocyclic group, such as an oxazolyl, isoxazolyl, 1,2,4-oxadiazolyl, 1,3,4-oxadiazolyl, 1,2,3-oxadiazolyl, thienylphenyl, thiazolyl, isothiazolyl, 1,2,3-thiadiazolyl, 1,2,4-thiadiazolyl, 1,3,4-thiadiazolyl, pyrrolyl, imidazolyl, pyrazolyl, 1,2,3-triazolyl, 1,2,4-triazolyl, 1,2,3-triazinyl, 1,2,4-triazinyl, tetrazolyl, pyridinyl, pyrazinyl, pyrimidinyl, pyridazinyl, 1,2,4-triazinyl, 1,3,5-triazinyl, or 1,2,4,5-tetrazinyl;

wherein substituents in heteroaryl group $Het_2$ are, for example, independently, hydrogen, alkyl, aryl, heteroalkyl, electron withdrawing group, F, Cl, CN, $NO_2$, NR''R''', OH, OR'', SR'', S(=O)R'', $SO_2$R'', C(=O)R'', C(=O)OR'', OC(=O)R'', C(=O)NR''R''', N(R'')C(=O)R''', or N-oxide group in the $Het_2$ nuclei, where R'' and R''' are substituents, for example, independently H or alkyl, such as $C_1$–$C_7$ alkyl, or, e.g., heteroalkyl, aryl or heteroaryl.

In another embodiment, 3-[4-linked heteroaryl)aryl] oxazolidinones are provided, which optionally have antimicrobial activity, of formula 5c wherein:

$R_2$, $R_3$, $R_4$ and $R_5$ are, independently, hydrogen, alkyl, heteroalkyl, heteroaryl or an electron withdrawing group;

$R_6$ is acyl, for example, C(=O)$CH_3$;

$R_7$ is an aryl group;

$R_8$ is a thio group, such as S; and $Het_2$ is a substituted or unsubstituted thienylphenyl or thiazolyl heteroaryl group.

Also provided are compounds of structure 5d:

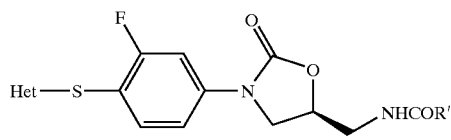

wherein $Het_2$ is a substituted or unsubstituted thienylphenyl or thiazolyl heteroaryl group; and R' is a substituent, for example, H or alkyl, such as $C_1$–$C_7$ alkyl, or, e.g., heteroalkyl, aryl or heteroaryl.

Exemplary compounds are shown below:

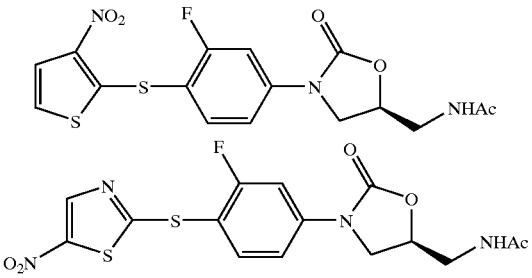

In another embodiment, 3-[4-(triazinylamino)aryl] oxazolidinones are provided, which are optionally antimicrobial compounds. For example, compounds of formula 5c are provided wherein:

$R_2$, $R_3$, $R_4$ and $R_5$ are, independently, hydrogen, alkyl, heteroalkyl, heteroaryl or an electron withdrawing group;

$R_6$ is acyl, such as C(=O)$CH_3$;

$R_8$ is amino group, such as NH; and $Het_2$ is 1,3,5-triazinyl.

Additionally, compounds of structure 5e are provided:

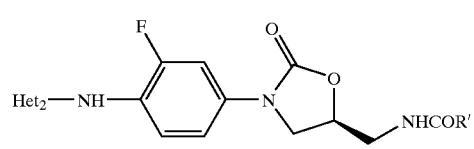

wherein $Het_2$ is a unsubstituted or substituted 1,3,5-triazinyl; and

R' is a substituent, for example, H or alkyl, such as $C_1$–$C_7$ alkyl, or, e.g., heteroalkyl, aryl or heteroaryl.

Exemplary compounds are shown below:

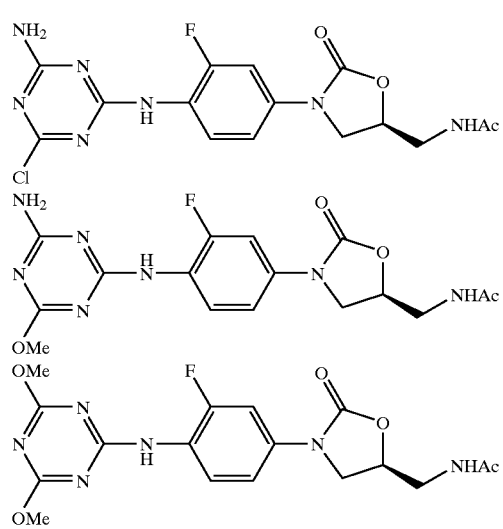

3-[4-(Linked heteroaryl)heteroaryl]oxazolidinones

In another embodiment, 3-[4-(linked heteroaryl) heteroaryl]oxazolidinones are provided, which are optionally biologically active, for example, as antimicrobial compounds.

For example, compounds of formula 6c, and combinatorial libraries thereof are provided:

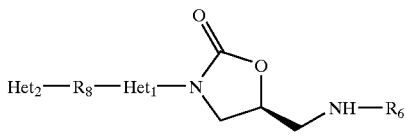

6c

In one embodiment of 6c:

$R_6$ is acyl or sulfonyl;

$R_8$ is $C_1$–$C_7$ alkyl, NR, O, S, C(=O)NR, NRC(=O), C(=O)NOR C(=O), C(=O)O, OC(=O), S(=O), SO$_2$, SO$_2$NR, NRSO$_2$, NRCONR', or (CH$_2$)$_n$O, where n=0–6, and R and R' are substituents, for example, independently H or alkyl, such as $C_1$–$C_7$ alkyl, or, e.g., heteroalkyl, aryl or heteroaryl;

Het$_1$ is a heterocyclic group such as an unsubstituted or substituted heterocyclic group, for example, thienylphenyl, thiazolyl, 1,3,4-thiadiazolyl, pyridinyl, pyrimidinyl, phenyl or fluorophenyl;

wherein substituents in heteroaryl group Het$_1$ are independently, for example, hydrogen, alkyl, aryl, heteroalkyl, electron withdrawing group, F, Cl, CN, NO$_2$, NR"R'", OR", SR", S(=O)R", SO$_2$R", C(=O)R", C(=O)OR", OC(=O)R", C(=O)NR"R'", N(R")C(=O)R'", or N-oxide group in the Het$_1$ nuclei, where R" and R'" are substituents, for example, independently H or alkyl, such as $C_1$–$C_7$ alkyl, or, e.g., heteroalkyl, aryl or heteroaryl; and Het$_2$ is an unsubstituted or substituted heterocyclic preferably heteroaryl group, such as an oxazolyl, isoxazolyl, 1,2,4-oxadiazolyl, 1,3,4-oxadiazolyl, 1,2,3-oxadiazolyl, thienylphenyl, thiazolyl, isothiazolyl, 1,2,3-thiadiazolyl, 1,2,4-thiadiazolyl, 1,3,4-thiadiazolyl, pyrrolyl, imidazolyl, pyrazolyl, 1,2,3-triazolyl, 1,2,4-triazolyl, 1,2,3-triazinyl, 1,2,4-triazinyl, tetrazolyl, pyridinyl, pyrazinyl, pyrimidinyl, pyridazinyl, 1,2,4-triazinyl, 1,3,5-triazinyl, or 1,2,4,5-tetrazinyl;

wherein substituents in heteroaryl group Het$_2$ are independently, for example, hydrogen, alkyl, aryl, heteroalkyl, electron withdrawing group, F, Cl, CN, NO$_2$, NR$_x$R$_y$, OH, OR$_x$, SR$_x$, S(=O)R$_x$, SO$_2$R$_x$, C(=O)R$_x$, C(=O)OR$_x$, OC(=O)R$_x$, C(=O)NR$_x$R$_y$, N(R$_x$)C(=O)R$_y$, or N-oxide group in the Het$_2$ nuclei, where R$_x$ and R$_y$ are substituents, for example, independently H or alkyl, such as $C_1$–$C_7$ alkyl, or, e.g., heteroalkyl, aryl or heteroaryl.

3-(Substituted pyridyl)oxazolidinones

Also provided are 3-(substituted pyridyl)oxazolidinones, which are optionally biologically active, for example as antimicrobial compounds.

In one embodiment, compounds of the formulas 7c or 8c and combinatorial libraries thereof are provided:

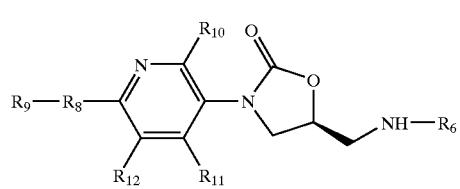

7c

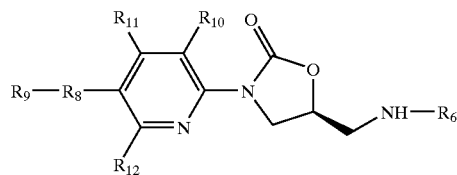

8c

In one embodiment, in 7c and 8c;

$R_6$ is acyl or sulfonyl;

$R_8$ is $C_1$–$C_7$ alkyl, NR, O, S, C(=O)NR, C(=O)NOR, NRC(=O), C(=O), C(=O)O, OC(=O), S(=O), SO$_2$, SO$_2$NR, NRSO$_2$, NRCONR', or (CH$_2$)$_n$O, wherein n=0–6, and wherein R and R' are substituents, for example, independently H or alkyl, such as $C_1$–$C_7$ alkyl, or, e.g., heteroalkyl, aryl or heteroaryl;

$R_9$ is alkyl, aryl, heteroalkyl, or heteroaryl; and $R_{10}$, $R_{11}$ and $R_{12}$ are, for example, independently hydrogen, alkyl, aryl, heteroalkyl, electron withdrawing group, F, Cl, CN, NO$_2$, NR"R'", OR", SR", S(=O)R", SO$_2$R", C(=O)R", C(=O)OR", OC(=O)R", C(=O)NR"R'", N(R")C(=O)R'", or N-oxide group in the pyridine nuclei, where R" and R'" are substituents, for example, independently H or alkyl, such as $C_1$–$C_7$ alkyl, or, e.g., heteroalkyl, aryl or heteroaryl.

3-(Substituted pyrimidinyl)oxazolidinones

A variety of 3-(substituted pyrimidinyl)oxazolidinones, which optionally have biological activity, such as antimicrobial activity, also are provided.

In one embodiment, compounds of the formulas 9c and 10c, as well as combinatorial libraries thereof, are provided:

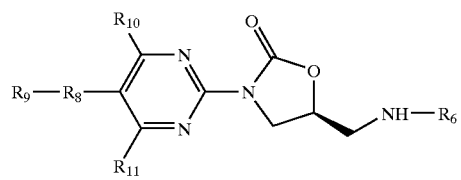

9c

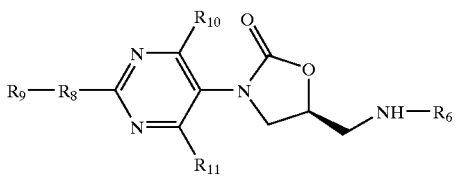

10c

In one embodiment of 9c and 10c:

$R_6$ is acyl or sulfonyl;

$R_8$ is $C_1$–$C_7$ alkyl group, NR, O, S, C(=O)NR, C(=O)NOR, NRC(=O), C(=O), C(=O)O, OC(=O), S(=O), SO$_2$, SO$_2$NR, NRSO$_2$, NRCONR', or (CH$_2$)$_n$O, where n=0–6, and where R and R' are substituents, for example, independently H or alkyl, such as $C_1$–$C_7$ alkyl, or, e.g., heteroalkyl, aryl or heteroaryl;

$R_9$ is alkyl, aryl, heteroalkyl, or heteroaryl; and $R_{10}$ and $R_{11}$ are independently hydrogen, alkyl, aryl, heteroalkyl, electron withdrawing group, F, Cl, CN, NO$_2$, NR"R'", OR", SR", S(=O)R", SO$_2$R", C(=O)R", C(=O)OR", OC(=O)R", C(=O)NR"R'", N(R")C(=O)R'", or N-oxide group in the pyrimidine nuclei, where R" and R'" are substituents, for example, independently H or alkyl, such as $C_1$–$C_7$ alkyl, or, e.g., heteroalkyl, aryl or heteroaryl.

3-(Thienyl)oxazolidinones

A variety of 3-(thienyl)oxazolidinones are provided, which optionally have biological activity, such as antimicrobial activity.

In one embodiment, compounds of formulas 11c, 12c and 13c, and combinatorial libraries thereof are provided:

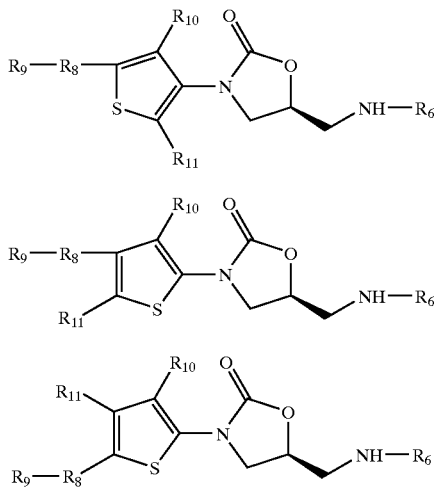

11c

12c

13c

In one embodiment of formulas 11c, 12c and 13c:

$R_6$ is acyl or sulfonyl;

$R_8$ is $C_1$–$C_7$ alkyl, NR, O, S, C(=O)NR, C(=O)NOR, NRC(=O), C(=O), C(=O)O, OC(=O), S(=O), $SO_2$, $SO_2NR$, $NRSO_2$, NRCONR', or $(CH_2)_nO$, where n=0–6, and where R and R' are substituents, for example, independently H or alkyl, such as $C_1$–$C_7$ alkyl, or, e.g., heteroalkyl, aryl or heteroaryl;

$R_9$ is an alkyl, aryl, heteroalkyl, or heteroaryl group; and $R_{10}$ and $R_{11}$ are independently hydrogen, alkyl, aryl, heteroalkyl, electron withdrawing group, F, Cl, CN, $NO_2$, NR"R'", OR", SR", S(=O)R", $SO_2R"$, C(=O)R", C(=O)OR", OC(=O)R", C(=O)NR"R'", N(R")C(=O)R'", where R" and R'" are substituents, for example, independently H or alkyl, such as $C_1$–$C_7$ alkyl, or, e.g., heteroalkyl, aryl or heteroaryl.

3-(Thiazolyl)oxazolidinones

Also provided are 3-(thiazolyl)oxazolidinones, which optionally have biological activity, such as antimicrobial activity.

In one embodiment, compounds of formulas 14c, 15c and 16c, and combinatorial libraries thereof are provided:

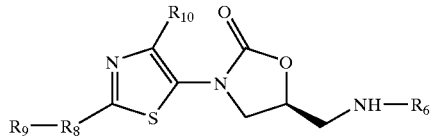

14c

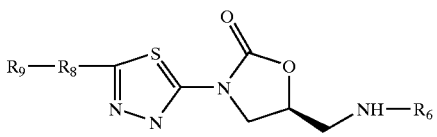

15c

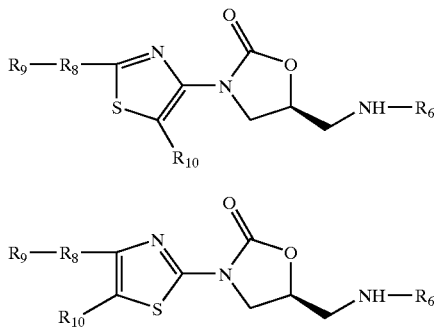

16c

In one embodiment of 14c, 15c and 16c:

$R_6$ is acyl or sulfonyl;

$R_8$ is $C_1$–$C_7$ alkyl, NR, O, S, C(=O)NR, C(=O)NOR, NRC(=O), C(=O), C(=O)O, OC(=O), S(=O), $SO_2$, $SO_2NR$, $NRSO_2$, NRCONR', or $(CH_2)_nO$, wherein n=0–6, and wherein R and R' are substituents, for example, independently H or alkyl, such as $C_1$–$C_7$ alkyl, or, e.g., heteroalkyl, aryl or heteroaryl;

$R_9$ is an alkyl, aryl, heteroalkyl, or heteroaryl group; and $R_{10}$ is hydrogen, alkyl, aryl, heteroalkyl, electron withdrawing group, F, Cl, CN, $NO_2$, NR"R'", OR", SR", S(=O)R", $SO_2R"$, C(=O)R", C(=O)OR", OC(=O)R", C(=O)NR"R'", or N(R")C(=O)R'", where R" and R'" are substituents, for example, independently H or alkyl, such as $C_1$–$C_7$ alkyl, or, e.g., heteroalkyl, aryl or heteroaryl.

3-(1,3,4-Thiadiazolyl)oxazolidinones

A variety of 3-(1,3,4-thiadiazolyl)oxazolidinones are provided, which optionally have biological activity, such as antimicrobial activity.

In one embodiment, compounds of formula 17c and combinatorial libraries thereof are provided:

17c

In one embodiment of 17c:

$R_6$ is acyl or sulfonyl;

$R_8$ is $C_1$–$C_7$ alkyl, NR, O, S, C(=O)NR, C(=O)NOR, NRC(=O), C(=O), C(=O)O, OC(=O), S(=O), $SO_2$, $SO_2NR$, $NRSO_2$, NRCONR', or $(CH_2)_nO$, where n=0–6, and where R and R' are substituents, for example, independently H or alkyl, such as $C_1$–$C_7$ alkyl, or, e.g., heteroalkyl, aryl or heteroaryl; and $R_9$ is alkyl, aryl, heteroalkyl, or heteroaryl.

Figure 49:
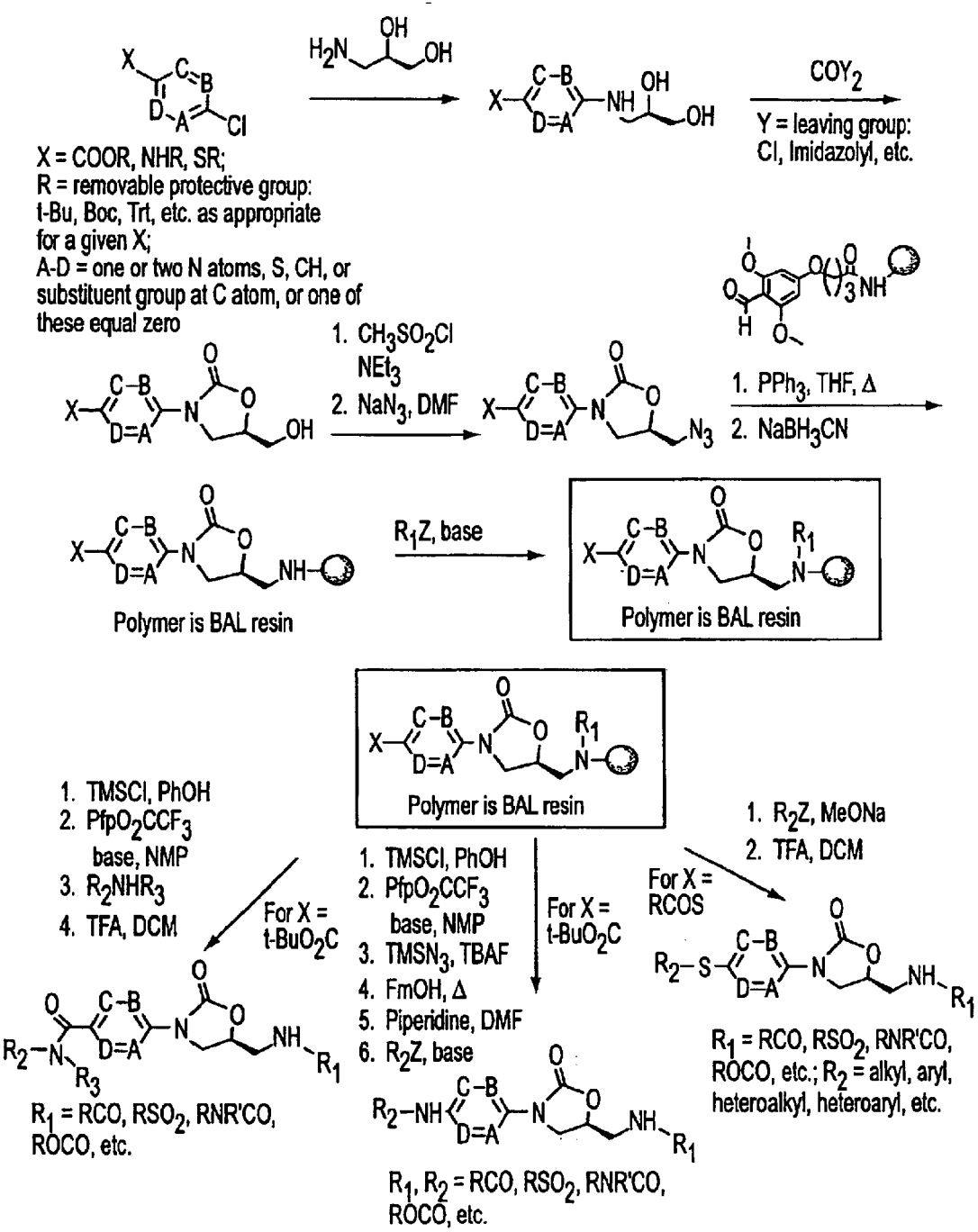
FIG. 49 is a general scheme showing routes of synthesis of 3-(heteroaryl)oxazolidinones.

Synthesis of 3-(Heteroaryl)Oxazolidinones 3-(Heteroaryl)oxazolidinones and other oxazolidinones may be synthesized by a variety of routes as disclosed herein. In one embodiment, the synthesis may be conducted as shown in FIG. 49, wherein the synthesis includes: reaction of an appropriate heteroaryl halide with 3-aminopropane-1,2-diol; cyclization of the resulting (heteroaryl)aminodiol with phosgene or equivalent; conversion of 5-(R)-hydroxymethyl-3-heteroaryloxazolidinone into resin immobilized 5-(S)-aminomethyl-3-heteroaryl oxazolidinone. Further reaction of this reagent produces the desired oxazolidinone.

Figure 50:
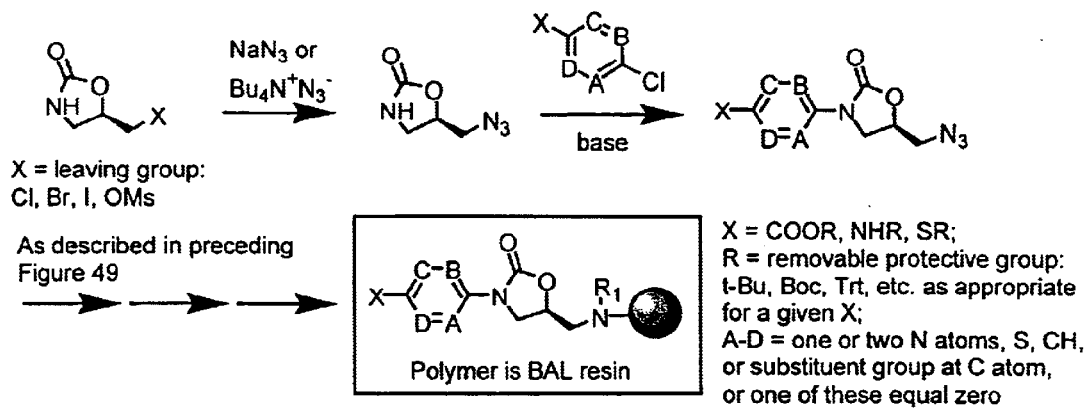
FIG. 50 is another general scheme showing routes of synthesis of 3-(heteroaryl)oxazolidinones.
Figure 50:
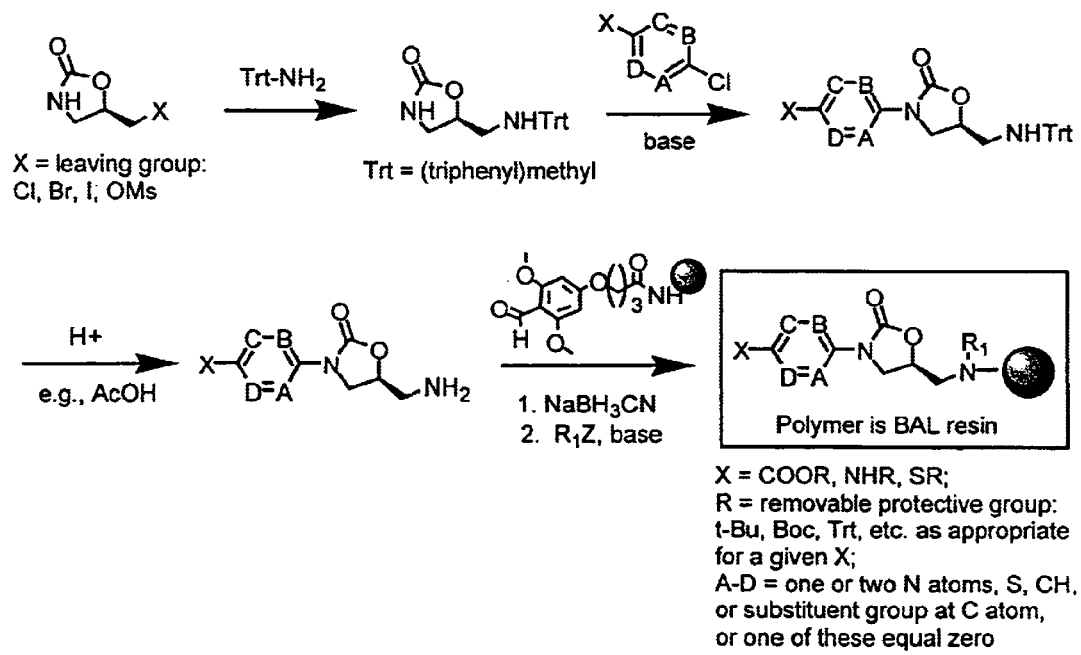

In another embodiment, which is illustrated in FIG. 50, the 5-(S)-azidomethyl-3-heteroaryloxazolidinone reagent is produced from an appropriate heteroarylhalide and 5-(S)-azidomethyloxazolidinone or equivalent thereof in the presence of a base. The resulting azide or amine intermediate is then immobilized on a BAL linker resin. Further reaction of the X group and or the amine group attached to the solid phase provides an array of desired 3-heteroaryloxazolidones.

As will be appreciated by those skilled in the art, using these and other methods disclosed herein, based on the teachings of the specification, the oxazolidinones disclosed herein can be readily synthesized.

Combinatorial Library Synthesis

Combinatorial library synthesis is typically performed on a solid support. See, for example, Lam et al. (1991) *Nature* 354:82–84; and Houghten et al. (1991) *Nature* 354:84–86. There are two general technologies for the construction of combinatorial libraries: "mix and split" technology and "multiple parallel synthesis" technology.

For the "mix and split" technology, a large number of beads or particles are suspended in a suitable carrier (such as a solvent) in a parent container. The beads, for example, are provided with a functionalized point of attachment for a chemical module. The beads are then divided and placed in various separate reaction vessels. The first chemical module is attached to the bead, providing a variety of differently substituted solid supports. Where the first chemical module includes 3 different members, the resulting substituted beads can be represented as $A_1$, $A_2$ and $A_3$.

The beads are washed to remove excess reagents and subsequently remixed in the parent container. This bead mixture is again divided and placed into various separate reaction vessels. The second chemical module is coupled to the first chemical module. Where the second chemical module includes 3 different members, $B_1$, $B_2$ and $B_3$, 9 differently substituted beads result: $A_1B_1$, $A_1B_2$, $A_1B_3$, $A_2B_1$, $A_2B_2$, $A_2B_3$, $A_3B_1$, $A_3B_2$ and $A_3B_3$. Each bead will have only a single type of molecule attached to its surface.

The remixing/redivision synthetic process can be repeated until each of the different chemical modules has been incorporated into the molecule attached to the solid support. Through this method, large numbers of individual compounds can be rapidly and efficiently synthesized. For instance, where there are 4 different chemical modules, and where each chemical module contains 20 members, 160,000 beads of different molecular substitution can be produced.

Combinatorial library synthesis using the "mix and split" technology can be performed either manually or through the use of an automated process. For the manual construction of a combinatorial library, a scientist would perform the various chemical manipulations. For the construction of a combinatorial library through an automated process, the various chemical manipulations will typically be performed robotically. For example, see U.S. Pat. No. 5,463,564.

For the "multiple parallel synthesis" technology, beads or particles are suspended in a suitable carrier (such as a solvent) in an array of reaction chambers. The beads or particles are provided with a functionalized point of attachment for a chemical module. Different members of a chemical module are added to each individual reaction chamber, providing an array of differently functionalized beads. Where there are 96 separate reaction chambers and 96 different chemical module members, a combinatorial library of 96 compounds is formed. The compounds can be assayed on the solid support, cleaved from the solid support and then assayed, or subjected to the addition of another chemical module.

Combinatorial library synthesis using the "multiple parallel synthesis" technology can be performed either manually or through the use of an automated process. For the manual construction of a combinatorial library, a scientist would perform the various chemical manipulations. For the construction of a combinatorial library through an automated process, the various chemical manipulations will typically be performed robotically.

Solid Supports

The solid phase synthesis of the compositions provided herein in one embodiment is performed on a solid support. "Solid support" includes an insoluble substrate that has been appropriately derivatized such that a chemical module can be attached to the surface of the substrate through standard chemical methods. Solid supports include, but are not limited to, beads and particles such as peptide synthesis resins. For example, see Merrifield (1963) *J. Am. Chem. Soc.* 85:2149–2154; U.S. Pat. No. 4,631,211; and Geysen et al. (1984) *Proc. Natl. Acad. Sci. USA* 81:3998–4002.

Solid supports can consist of many materials, limited primarily by the capacity of the material to be functionalized through synthetic methods. Examples of such materials include, but are not limited to, polymers, plastics, resins, polysaccharides, silicon or silica based materials, carbon, metals, inorganic glasses and membranes. Preferred resins include Sasrin resin (a polystyrene resin available from Bachem Bioscience, Switzerland), Wang resin or p-nitrophenylcarbonate Wang resin (PNP resin, Novabiochem), and TentaGel S AC, TentaGel PHB, or TentaGel S $NH_2$ resin (polystyrene-polyethylene glycol copolymer resins available from Rapp Polymere, Tubingen, Germany or from Perseptive, Boston).

The solid support can be purchased with suitable functionality already present such that a chemical module can be attached to the support surface (e.g., Novabiochem, Bachem Bioscience, Rapp Polymere). Alternatively, the solid support can be chemically modified such that a chemical module can be attached to the support surface. Grant (1992) *Synthetic Peptides. A User's Guide*, W.H. Freeman and Co.; and Hermkens et al. (1996) *Tetrahedron* 52:4527–4554. One of ordinary skill in the art will understand that the choice of functionality used for attaching a molecule to the solid support will depend on the nature of the compound to be synthesized and the type of solid support. Examples of functionality present on the solid support that can be used to attach a chemical module include, but are not limited to, alkyl or aryl halides, aldehydes, alcohols, carbonates, ketones, amines, sulfides, carboxyl groups, aldehyde groups and sulfonyl groups.

The functional group on the solid support that permits the attachment of a chemical module is, for example, an alcohol, an amine, an aldehyde, a carbonate, or a diol group. Gordon el al. (1994) *J. Med Chem.* 37:1385–1401; and Hermkens el al. (1996) *Tetrahedron* 52:4527–4554.

For making certain combinatorial libraries, one can purchase a solid support with an existing, protected chemical module already attached. An example of such a support is FmocGly Sasrin, which is commercially available from Bachem. Typically, however, the first step of the combinatorial library synthesis is the attachment of a chemical module to the solid support through the existing functionality on the support surface. Examples of chemical reactions that can be used to attach a chemical module to the support include, but are not limited to, nucleophilic displacement of a halide or other leaving group, etherification of an alcohol, esterification of an alcohol, amidation of an amine, carbamation of an amine, reductive amination of a carbonyl compound, acetalization of an aldehyde and ketalization of a ketone. Hermkens et al. (1996) *Tetrahedron* 52:4527–4554.

The reaction used to attach the chemical module to the solid support is, for example, a carbamation of an amine, a reductive amination of a carbonyl compound or a nucleophilic displacement of a halide or other leaving group. For example, see Hermkens et al. (1996).

For the attachment of certain chemical modules to the solid support, it may be necessary to mask functionality that is not involved in the attachment process, but that is incompatible with the mode of attachment. A non-limiting example of this type of process is the esterification of an alcohol functionalized solid support, using a hydroxyl-substituted carboxylic acid as the coupling partner. Prior to the esterification reaction, the hydroxyl group of the carboxylic acid would be "protected" through alkylation, silylation, acetylation, or through another method known to one of skill in the art. Strategies for the use of masking or protecting groups have been well-described in the art, such as in Green (1985) *Protecting Groups in Organic Synthesis*, Wiley.

Methods of Compound Cleavage from a Solid Support

The cleavage of oxazolidinones from a solid support to produce the corresponding "free" compounds can be accomplished using a variety of methods. For example, a compound can be photolytically cleaved from a solid support (Wang et a. (1976) *J. Org. Chem.* 41:3258; Rich et al. (1975) *J. Am. Chem. Soc.* 97:1575–1579), and through nucleophilic attack (U.S. Pat. No. 5,549,974), or through hydrolysis (Hutchins et al. (1994) *Tetrahedron Lett.* 35:4055–4058). The cleavage of compounds from a solid support to produce soluble compounds is accomplished, for example, using hydrolytic conditions, such as through the addition of trifluoroacetic acid.

Screening

The libraries of this invention can be used to select one or more bioactive molecules. Preferably, the bioactive molecules possess activity against a cellular target, including but not limited to enzymes and receptors, or a microorganism. A target cellular ligand or microorganism is one that is known or believed to be of importance in the etiology or progression of a disease. Examples of disease states for which amino alcohol, thio alcohol, oxazolidinone and sulfone libraries can be screened include, but are not limited to, inflammation, infection, hypertension, central nervous system disorders, and cardiovascular disorders.

Several methods have been developed in recent years to screen libraries of compounds to identify bioactive molecules. Methods for isolating library compound species that demonstrate desirable affinity for a receptor or enzyme are well-known in the art.

For example, an enzyme solution can be mixed with a solution of the compounds of a particular combinatorial library under conditions favorable to enzyme-ligand binding. See Bush et al. (1993) *Antimicrobial Agents and Chemotherapy* 37:851–858; and Daub et al. (1989) *Biochemistry* 27:3701–3708. Specific binding of library compounds to the enzyme can be detected, for instance, by any of the numerous enzyme inhibition assays which are well known in the art Compounds which are bound to the enzyme are separated readily from compounds which remain free in solution by applying the solution to a suitable separation material such as Sephadex G-25 gel filtration column. Free enzyme and enzyme-ligand complexes pass through the column quickly, while free library compounds are retarded in their progress through the column. The mixture of enzyme-ligand complex and free enzyme is then treated with a suitable denaturing agent, such as guanidinium hydrochloride or urea, to cause release of the ligand from the enzyme. The solution is then injected onto an HPLC column (for example, a Vydac C-4 reverse-phase column, and eluted with a gradient of water and acetonitrile ranging from 0% acetonitrile to 80% acetonitrile). Diode array detection provides discrimination of the compounds of the combinatorial library from the enzyme. The compound peaks are then collected and subjected to mass spectrometry for identification.

An alternate manner of identifying compounds that inhibit an enzyme is to divide the library into separate sublibraries where one step in the synthesis is unique to each sublibrary. To generate a combinatorial library, reactants are mixed together during a step to generate a wide mixture of compounds. At a certain step in the synthesis, however, the resin bearing the synthetic intermediates is divided into several portions, with each portion then undergoing a unique transformation. The resin portions are then (separately) subjected to the rest of the synthetic steps in the combinatorial synthetic method. Each individual resin portion thus constitutes a separate sublibrary. When testing the compounds, if a given sublibrary shows more activity than the other sublibraries, the unique step of that sublibrary is then held fixed. The sublibrary then becomes the new library, with that step fixed, and forms the basis for another round of sublibrary synthesis, where a different step in the synthesis is optimized. This procedure is executed at each step until a final compound is arrived at. The aforementioned method is the generalization of the method described in Geysen, WO 86/00991, for determining peptide "mimotopes," to the synthetic method of this invention.

Finding a compound that inhibits an enzyme is performed most readily with free compound in solution. The compounds can also be screened while still bound to the resin used for synthesis; in some applications, this may be the preferable mode of finding compounds with the desired characteristics. For example, if a compound that binds to a specific antibody is desired, the resin-bound library of compounds is contacted with an antibody solution under conditions favoring a stable antibody-compound-resin complex. A fluorescently labeled second antibody that binds to the constant region of the first antibody is then contacted with the antibody-compound-resin complex. This allows identification of a specific bead as carrying the compound recognized by the first antibody binding site. The bead is then physically removed from the resin mixture and subjected to mass spectral analysis. If the synthesis is conducted in a manner such that only one compound is likely to be synthesized on a particular bead, then the binding compound has been identified. If the synthesis is carried out so that many compounds are present on a single bead, the information derived from analysis can be utilized to narrow the synthetic choices for the next round of synthesis and identification.

The enzyme, antibody, or receptor target need not be in solution. Antibody or enzyme can be immobilized on a column. The library of compounds is then passed over the column, resulting in the retention of strongly binding compounds on the column after weaker-binding and non-binding compounds are washed away. The column is then washed under conditions that dissociate protein-ligand binding, which removes the compounds retained in the initial step. These compounds are then analyzed, and synthesized separately in quantity for further testing. Similarly, cells bearing surface receptors are contacted with a solution of library compounds. The cells bearing bound compounds are readily separated from the solution containing non-binding compounds. The cells are then washed with a solution which dissociates the bound ligand from the cell surface receptor. Again, the cells are separated from the solution, and the solution analyzed.

Pharmaceutical Compositions

The present invention also provides pharmaceutical compositions which comprise a bioactive oxazolidinone compound or a pharmaceutically acceptable salt thereof and a pharmaceutically acceptable carrier. The compositions of the invention include those in a form adapted for oral, topical or parenteral use and can be used for the treatment of bacterial infection in mammals including humans.

The antibiotic compounds, also referred to herein as antimicrobial compounds, according to the invention can be formulated for administration in any convenient way for use in human or veterinary medicine, by analogy with other antibiotics. Such methods are known in the art and are not described in detail herein.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present, for example, from about 1% up to about 98% of the formulation. For example, they may form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods will known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifing agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl phydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, e.g., from about 10–60% by weight, of the active material, depending on the method of administration. Where the compositions comprise dosage units, each unit will contain, for example, from about 50–500 mg of the active ingredient The dosage as employed for adult human treatment will range, for example, from about 100 to 3000 mg per day, for instance 1500 mg per day depending on the route and frequency of administration. Such a dosage corresponds to about 1.5 to 50 mg/kg per day. Suitably the dosage is, for example, from about 5 to 20 mg/kg per day.

Pharmaceutical Applications

The oxazolidinones disclosed herein can be used in a variety of pharmaceutical applications.

The compounds may be used, for example, as pharmaceutically active agents that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system autocoid systems, the alimentary and excretory systems, the histamine system and central nervous systems as well as other biological systems. Thus, the compounds may be used as sedatives, psychic energizers, tranquilizers, anticonvulsants, muscle relaxants, anti-Parkinson agents, analgesics, antiinflammatories, local anesthetics, muscle contractants, antibiotic, antiviral, antiretroviral, antimalarials, diuretics, lipid regulating agents, antiandrogenic agents, antiparasitics, neoplastics, antineoplastics and chemotherapy agents. These compounds could further be used to treat cardiovascular diseases, central nervous system diseases, cancer, metabolic disorders, infections and dermatological diseases as well as other biological disorders and infections. The compounds also may be used as monoamine oxidase inhibitors.

In one embodiment, the compounds may be used as antimicrobial agents for the treatment of infectious disorders that are caused by microbial agents, such as bacteria.

In one embodiment, compositions for treating or preventing infectious disorders are provided, comprising an oxazolidone compound as disclosed herein in combination with a pharmaceutically acceptable carrier.

In another embodiment, there is provided a dosage amount of an oxazolidinone as disclosed herein in an effective amount for the treatment, prevention or alleviation of a disorder, such as an infectious disorder.

Oxazolidinones can be screened for activity against different microbial agents and appropriate dosages may be determined using methods available in the art. Advantageously, the methods of making combinatorial libraries as disclosed herein permit large quantities of oxazolidinones to be made and screened against a wide variety of microbial agents to permit the rapid isolation of an effective oxazolidinone for a particular target microbe. The method also may be used to determine new oxazolidinones for use after and if bacterial resistance occurs.

The compounds may be used to treat a subject to treat, prevent, or reduce the severity of an infection. Subjects include animals, plants, blood products, cultures and surfaces such as those of medical or research equipment, such as glass, needles and tubing.

In one embodiment, methods of treating or preventing an infectious disorder in a subject, such as a human or other animal subject, are provided, by administering an effective amount of an oxazolidinone as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as bacterial infections. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, may be adjusted as needed.

The compounds of the invention may be used for the treatment or prevention of infectious disorders caused by a variety of bacterial organisms. Examples include Gram positive and Gram negative aerobic and anaerobic bacteria, including Staphylococci, for example *S. aureus*; Enterococci, for example *E. faecalis*; Streptococci, for example *S. pneumoniae*; *Haemophilus*, for example *H. influenza*; *Moraxella*, for example *M. catarrhalis*; and *Escherichia*, for example *E. coli*. Other examples include Mycobacteria for example *M. tuberculosis*; intercellular microbes, for example *Chlamydia* and Rickettsiae; and *Mycoplasma*, for example *M. pneumoniae*.

The following examples are provided to illustrate but not limit the claimed invention.

EXAMPLES

Abbreviations: ACN, acetonitrile; CDI, carbonyldiimidazole; DIEA, diethylisopropylamine; DCM, dichloromethane; DIC, diisopropyldiimide; DMF, dimethylformamide; HATU, O-(7-azabenzotriazol-1-yl)-1,1,3,3-bis(tetramethylene)-uronium hexafluorophosphate; NMM, N-methyl morpholine; mCPBA, m-chloro-peroxybenzoic acid; TFA, trifluoroacetic acid; THF, tetrahydrofuran; TMOF, trimethylorthoformate.

General. Reagents were obtained from Aldrich (St. Louis, Mo.), Sigma (St. Louis, Mo.), Bachem Biosciences, Rapp Polymere, Perseptive, and Novabiochem, and used without further purification. The resin Tentagel S NTi was purchased from Rapp Polymere. Concentration of solutions after workup was performed by reduced pressure rotary evaporation, or using the Savant's SpeedVac instrument. Reactions with moisture-sensitive reagents were performed under nitrogen atmosphere.

Mass-spectra were obtained using ESI technique. HTLC analysis and purification were performed using Beckman System Gold R®; detection at 220 nm. Analytical EPLC was performed on YMC 5 micron C18 (4.6 mm×50 mm) reverse phase column (gradient from 100% of the aq. 0.1% TFA to 100% of 0.1% TFA in MECN over 6 min$^1$, flow rate 2.0 m l/min). Preparative TLC was performed using EM silica gel 60 $F_{254}$ plates (20×20 cm, thickness 2 min).

NMR spectra were obtained on a Varian Gemini 300 MHz instrument with $CDCl_3$ as solvent, unless otherwise noted. 1H NMR spectra were reported as follows: chemical shift relative to tetramethylsilane (0.00 ppm), multiplicity (s=singlet, d=doublet, t=triplet, q=quartet, m=multiplet, b=broad), coupling, and integration.

2-Fluoro-4-Nitrobenzoic Acid

Concentrated sulfuric acid (32 ml) was added carefully with stirring to a solution of 2-fluoro-4-nitrotoluene (16.5 g, 0.106 mol) in acetic acid (200 ml). The mixture was warmed up to 95° C., and solution of chromium trioxide (37.1 g, 0.371 mol) in water (32 ml) was added dropwise with stirring over 2 h. The mixture was heated with stirring for another 30 minutes, allowed to cool down to r.t, and poured into water (1000 ml). The product was extracted with diethyl ether (3×200 ml). Combined ether layers were washed with water and evaporated to dryness. The residue was dissolved in 10% aqueous potassium carbonate and washed with ether. The aqueous layer was acidified with con. HCl, and the resulting white precipitate filtered and dried (16.3 g, 83%), m.p. 174–177° C. $^1$H NMR.

Tert-Butyl 2-Fluoro-4-Nitrobenzoate

Thionyl chloride (45 ml, 0.62 mol) was added to 2-fluoro-4-nitrobenzoic acid (23.0 g, 0.124 mol), and the mixture was stirred under reflux for 2 h. Solvent was removed under vacuum, and the residue thoroughly dried under vacuum to give crystalline acid chloride (25.2 g, 99%). The acid chloride was dissolved in tetrahydrofuran (150 ml) under nitrogen, and 1M lithium tert-butoxide in tetrahydrofuran (136 ml, 0.136 mol) was added dropwise with stirring at room temperature. The mixture was stirred overnight, diluted with water (300 ml) and extracted with ether. The ether layer was washed with saturated aqueous sodium bicarbonate, brine, and dried ($MgSO_4$). Solvent was removed under vacuum to gave the product as a white crystalline solid (24.2 g, 81%); mp 81–82° C. $^1$H NMR.

tert-Butyl-2-Fluoro-4-Aminobenzoate

Tert-butyl 2-fluoro-4-nitrobenzoate (24.2 g, 0.100 mol) was added to a warm (95° C.) solution of ammonium chloride (53.5 g, 1.00 mol), dissolved in ethanol (300 ml) and water (150 ml). Iron powder (325 mesh, 16.8 g, 0.300 mol) was added with stirring in small portions over ca. 1 h. The reaction mixture was stirred and heated at 95° C. for another 30 minutes and then filtered while still warm. The filter cake was washed thoroughly with excess ethanol. The filtrate and washings were diluted with water (1 L) and extracted with ether (3×150 ml). Combined ether extracts were washed with water and brine, dried ($MgSO_4$), and evaporated to give the product as an off-white solid (21.1 g, 98%); mp 100–101° C. $^1$H NMR.

O-Benzyl-N-(3-fluoro-4-butoxycarbonylphenyl) carbamate

Benzyl chloroformate (15.9 ml, 0.112 mol) was added dropwise with stirring to a mixture of tert-butyl-2-fluoro-4-aminobenzoate (21.5 g, 0.102 mol) and pyridine (16.5 ml, 0.204 mol) in dichloromethane (200 ml) at 0° C. The reaction mixture was stirred for 30 minutes at 0° C., allowed to warm up to room temperature, and then poured into water (ca. 300 ml). The organic layer was separated, washed with water, brine and dried (MgSO$_4$). Evaporation gave a white solid, which was washed with hexane and dried under vacuum to afford the product (32.8 g, 93%); mp 117–118° C. $^1$H NMR.

5-(R)-Hydroxymethyl-3-[4'-tert-butoxycarbonyl-3'-fluorophenyl]oxazolidine-2-one

1M Lithium bis(trimethylsilyl)amide in tetrahydrofuran (104 ml, 0.104 mol) was added dropwise with stirring at −78° C. to a solution of O-benzyl-N-(3-fluoro-4-butoxycarbonylphenyl)-carbamate (32.8 g, 0.0948 mol) in tetrahydrofuran (150 ml). The mixture was stirred at −78° C. for 1 hour, and then (R)-glycidyl butyrate (15.0 g, 0.104 mol) was added dropwise with stirring. The mixture was allowed to warm to room temperature overnight, and was then quenched with saturated aqueous ammonium chloride (100 ml). The mixture was extracted with ethyl acetate, and the combined organic layers washed with water, brine, and dried (MgSO$_4$). Solvent was removed under vacuum, and the crude product purified by silica gel column chromatography (eluent: 30% ethyl acetate in hexanes) to afford the product as a white solid (20.0 g, 68%); mp 148–149° C. $^1$H NMR.

5-(S)-Azidomethyl-3-[4'-tert-butoxycarbonyl-3'-fluorophenyl]oxazolidine-2-one

Methanesulfonyl chloride (2.61 ml, 0.0337 mol) was added dropwise with stirring to a solution of 5-(R)-hydroxymethyl-3-[4'-tert-butoxycarbonyl-3'-fluorophenyl]oxazolidine-2-one (10.0 g, 0.0321 mol) and triethylamine (6.71 ml, 0.0482 mol) in dichloromethane (150 ml) at 0° C. over ca. 15 minutes. The reaction mixture was allowed to warm up to room temperature and then poured into water. The organic layer was separated, washed with water, saturated aq. NaHCO$_3$, brine, and dried (MgSO$_4$). Solvent was removed under vacuum to afford the mesylate intermediate as an oil (11.6 g, 99%). A mixture of the mesylate (13.4 g, 0.0370 mol) and sodium azide (12.0 g, 0.185 mol) in DMF (130 ml) was heated with stirring at 75° C. for 12 h. The reaction mixture was cooled to room temperature, diluted with water (300 ml), and extracted with ethyl acetate (3×100 ml). Combined organic layers were washed with water and brine, dried (MgSO$_4$) and evaporated. The residue was washed with diethyl ether to give the pure azide as a white solid (9.76 g, 90.5%); mp 91–92° C. $^1$H NMR.

S-(S)-Azidomethyl-3-[4'-N-methyl-N-methoxyamido-3'-fluorophenyl]oxazolidine-2-one 5-(S)-Azidomethyl-3-[4'-tert-butoxycarbonyl-3'-fluorophenyl]oxazolidine-2-one (3.36 g, 0.01 mol) is dissolved in dichloromethane (ca. 100 ml), and trifluoroacetic acid (50 ml) added with stirring. The mixture is kept at room temperature for 3–4 h, solvent removed under vacuum, and residue washed with diethyl ether-hexanes (1:3, ca. 20 ml) to afford an intermediate acid. The acid (1.40 g, 0.005 mol) is dissolved in dichloromethane (100 ml) and dimethylformamide (50 ml), and 1-(3-dimethylaminopropyl)-3 ethyl-carbodiimide hydrochloride (0.96 g, 0.005 mol) added. The mixture is stirred for ca. 2 h, and N-methyl-N-methoxyamine hydrochloride (0.48 g, 0.005 mmol) added, followed by triethylamine (1.5 ml, 0.015 mmol). The mixture is stirred at room temperature for 3–4 h, poured into water (ca. 200 ml), and extracted with ethyl acetate (3×150 ml). Combined organic layers are washed with water (4×250 ml), brine, and dried (MgSO$_4$). Solvent is removed under vacuum to afford the Weinreb amide.

2-Fluoro-4-nitrobenzylidene diacetate

2-Fluoro-4-nitrotoluene (21.65 g, 0.140 mol) was dissolved in acetic anhydride (145 ml) and concentrated sulfuric acid (30 ml) was added slowly with stirring. The mixture was cooled to 0° C., and a solution of chromium trioxide (42.0 g, 0.420 mol) in acetic anhydride (200 ml) added at such a rate that the temperature did not exceed 10° C. The reaction mixture was stirred at 0° C. for another 2 h, and then poured into ice water (1000 ml). The resulting precipitate was filtered, washed with water and then dissolved in ethyl acetate. The ethyl acetate solution was washed with saturated aq. sodium bicarbonate, brine, and dried (MgSO$_4$). Solvent was removed under vacuum to afford the product as a white crystalline solid (37.9 g, 70%); mp 116–117° C. $^1$H NMR.

2-Fluoro-4-nitrobenzaldehyde Dimethyl Acetal

2-Fluoro-4-nitrobenzylidene diacetate (9.30 g, 0.0343 mol) was dissolved in methanol (200 ml), and potassium carbonate (4.74 g, 0.0343 mol) was added in one portion. The mixture was stirred at room temperature for 2 h and then evaporated to dryness. The residue was dissolved in diethyl ether, washed with water, brine, and dried (MgSO$_4$). Solvent was removed under vacuum to afford an aldehyde intermediate (5.68 g, 98%) The aldehyde (6.00 g, 0.0355 mol) was dissolved in a mixture of methanol (4.5 ml) and trimethyl orthoformate (4.27 ml, 0.0390 mol). Ammonium chloride (0.10 g, 0.00178 mol) was added, and the mixture was refluxed for 2 h. Solvent was removed under vacuum, and the residue was washed with diethyl ether. The resulting ether solution was washed with water, brine, and dried (MgSO$_4$). Solvent was removed under vacuum to afford the product as a colorless oil. Yield 7.60 g (99%). $^1$H NMR.

4-Amino-3-fluorobenzaldehyde Dimethyl Acetal

2-Fluoro-4-nitrobenzaldehyde dimethyl acetal (0.59 g, 2.74 mmol) was dissolved in methanol: (20 ml), and 5% palladium on carbon (0.059 g) was added. The flask was charged with hydrogen gas, and the mixture was stirred at room temperature for 20 h. The catalyst was filtered through Celite, and solvent was removed under vacuum to afford the product. Yield 0.40 g (78%). $^1$H NMR.

O-Benzyl-N-[3-fluoro-4-(dimethoxymethyl)phenyl]carbamate

Benzyl chloroformate (0.34 ml, 2.38 mmol) was added dropwise with stirring to a solution of 4-amino-3-fluorobenzaldehyde dimethyl acetal (0.40 g, 2.16 mmol) and pyridine (0.26 ml, 3.24 mmol) in dichloromethane (10 ml) at 0° C. The reaction mixture was allowed to warm to room temperature, and was washed with water, brine, and dried (MgSO$_4$). Solvent was removed under vacuum to give the desired product as a white solid. Yield 0.56 g (81%). $^1$H NMR.

S-(R)-Hydroxymethyl-3-[4-dimethoxymethyl-3'-fluorophenyl]oxazolidine-2-one

1 M Lithium bis(trimethylsflyl)amide in tetrahydrofuran (0.86 ml, 0.941 mmol) was added dropwise with stirring at −78° C. to O-benzyl-N-[3-fluoro-4-(dimethoxymethyl)phenyl]carbamate (0.273 g, 0.855 mmol) in tetrahydrofuran (5 ml). The mixture was stirred at −78° C. for 1 h, and then (R)-glycidyl butyrate (0.145 ml, 1.03 mmol) was added dropwise with stirring. The mixture was allowed to warm to room temperature overnight, and was then quenched with saturated aq. ammonium chloride (5 ml). The mixture was extracted with ethyl acetate, and the product was washed with water, brine, and dried (MgSO$_4$). Solvent was removed in vacuum, and the crude product purified by silica gel column chromatography (eluent: 30% ethyl acetate in hexanes) to give the alcohol as an oil. Yield 0.24 g, 99%. $^1$H NMR.

5-(S)-Azidomethyl-3-[4'-dimethoxymethyl-3'-fluorophenyl]oxazolidine-2-one

Methanesulfonyl chloride (0.0664 ml, 0.858 mmol) was added with stirring to a solution of S-(R)-hydroxymethyl-3-[4'-dimethoxymethyl-3'-fluorophenyl]oxazolidine-2-one (0.233 g, 0.817 mmol) and triethylamine (0.228 ml, 1.63 mmol) in dichloromethane (10 ml) at 0° C. The reaction was allowed to warm to room temperature, and was then poured into water. The organic layer was separated and washed with water, saturated aq. NaHCO$_3$, brine, and dried (MgSO$_4$). Solvent was removed under vacuum to give a mesylate intermediate as an oil (0.246 g, 83%). A mixture of the mesylate (0.189 g, 0.520 mmol) and sodium azide (0.170 g, 2.60 mmol) in DMF (5 ml) was heated at 75° C. for 12 h. The reaction was cooled to room temperature, diluted with water (50 ml) and extracted with ethyl acetate (3×30 ml). The combined organic layers were washed with water, brine, and then dried (MgSO$_4$). Solvent was removed in vacuum, and the crude product was purified by silica gel column chromatography (eluent: 50% ethyl acetate in hexanes) to give the desired product as a colorless oil (0.154 g, 95%). MS (m/z): 311 [M+H]$^+$. $^1$H NMR.

3-Fluoro-4-thiocyanoaniline

N-Bromosuccinimide (1.76 g, 9.89 mmol) and potassium thiocyanate (1.75 g, 18.0 mmol) in methanol (30 ml) were stirred for 15 minutes at room temperature. The reaction mixture was cooled to 0° C., and 3-fluoroaniline (1.00 g, 9.0 mmol) was added dropwise. The mixture was stirred at 0° C. for 2 h. Solvent was removed under vacuum, and the residue was washed with dichloromethane. The mixture was filtered to remove succinimide by-product, and the solution was washed with water, brine, and dried (MgSO$_4$). Solvent was removed under vacuum to afford the desired product as a colorless oil. Yield 1.45 g (96%). $^1$H NMR.

O-Benzyl-N-[3-fluoro-4-(thiocyano)phenyl]carbamate

Benzyl chloroformate (1.87 ml, 13.1 mmol) was added to a mixture of 3-fluoro-4-thiocyanoaniline (2.00 g, 11.9 mmol) and pyridine (2.12 ml, 26.2 mmol) in dichloromethane (30 ml) at 0° C. The mixture was stirred for 30 minutes at 0° C., allowed to warm to room temperature, and then poured into water. The organic layer was separated, washed with brine, and dried (MgSO$_4$). Solvent was removed under vacuum. The crude product was washed with ether-hexanes and dried under vacuum to afford the desired product. Yield 3.64 g (92%); m.p. 74–75 ° C. $^1$H NMR.

O-Benzyl-N-[3-fuoro-4-(triphenylmethylthio)phenyl]carbamate

Sodium sulfide nonahydrate (0.794 g, 3.31 mmol) in water (3 ml) was added dropwise at room temperature to a solution of O-benzyl-N-[3-fluoro-4-(thiocyano)phenyl]carbamate (1.00 g, 3.31 mmol) in ethanol (10 ml). The reaction mixture was stirred at room temperature for 30 minutes, and then triphenylmethyl bromide (1.07 g, 3.31 mol) in 1,4-dioxane (5 ml) was added dropwise. The reaction was stirred overnight. Organic solvent was removed under vacuum, and the residue taken up in ethyl acetate. The solution was washed with water, brine, and dried (MgSO$_4$). Solvent was removed under vacuum, and the crude product purified by silica gel column chromatography (eluent: 10% ethyl acetate in hexanes) to give the desired compound as a white solid. Yield 1.10 g, (64%); mp 152–153° C. $^1$H NMR.

5-(R)-Hydroxymethyl-3-[4'-triphenylmethylthio-3'-fluorophenyl]oxazolidine-2-one

1M Lithium bis(trimethylsilyl)amide in tetrahydrofuran (54 mL, 69.9 mmol) was added dropwise with stirring at −78° C. to a solution of O-benzyl-N-[3-fluoro-4-triphenylmethylthio)phenyl]carbamate (33.0 g, 63.5 mmol) in tetrahydrofuran (250 ml). The mixture was stirred at −78° C. for 1 hour, and then (R)-glycidyl butyrate (11.0 g, 76.2 mmol) was added dropwise with stirring. The mixture was allowed to warm up to room temperature overnight, and then quenched with saturated aqueous ammonium chloride (125 ml). The mixture was extracted with ethyl acetate, and combined organic layers washed with water, brine, and dried (MgSO$_4$). Solvent was removed under vacuum, and the crude product purified by silica gel column chromatography (gradient from 30% to 75% of ethyl acetate in hexane) to afford the product. TLC: R$_f$ 0.2 (ethyl acetate-hexanes 1:1). MS 486 [M+H]$^+$. $^1$H NMR.

5-(S)-Azidomethyl-3-[4'-triphenylmethylthio-3'-fluorophenyl]oxazolidine-2-one

Methanesulfonyl chloride (3.91 mL, 50.6 mmol) was added dropwise with stirring to a solution of 5-(R)-hydroxymethyl-3-[4'-triphenylmethylthio-3'-fluorophenyl]oxazolidine-2-one (23.4 g, 48.2 mmol) and triethylamine (10.1 mL, 73.8 mmol) in dichloromethane (200 mL) at 0° C. over ca. 10 minutes. The reaction mixture was allowed to warm up to room temperature and then poured into water. The organic layer was separated, washed with water, saturated aq. NaHCO$_3$, brine, and dried (MgSO$_4$). Solvent is removed under vacuum to afford the mesylate intermediate as an oil (27.2 g, 990%). The mesylate (27.2 g, 48.2 mmol) and sodium azide (15.7 g, 241.0 mmol) in DMF (150 ml) was heated with stirring at 70° C. for 12 h. The reaction mixture was cooled to room temperature, diluted with water (750 mL), and extracted with ethyl acetate. Combined organic layers were washed with water, brine, and dried (MgSO$_4$). Solvent was removed under vacuum and the crude product purified by silica gel column chromatography (eluent: 30% ethyl acetate in hexanes) to afford the azide product as a white solid. Yield 18.1 g (73%). M.p. 77–79° C., $[\alpha]^D$=−114° (c=1, methanol). $^1$H NMR.

5-Benzyloxycarbonylaminoindazole

Benzyl chloroformate (9.9 ml, ca. 66 mmol) in tetrahydrofuran (66 ml) was added dropwise with stirring to 5-aminoindazole (4.44 g, 33 mmol) in tetrahydrofuran (150 ml) and pyridine (12.0 ml, 150 mmol) at −5° C. The mixture was allowed to warm to room temperature, stirred for 4 h, and concentrated under vacuum. Ethyl acetate (100 ml) and water (150 ml) were added, and the aqueous layer was extracted with ethyl acetate (2×100 ml). The combined organic laters were washed with 0.3 N aq. HCl (2×100 ml), water, brine, and dried (MgSO$_4$). Solvent was removed under vacuum to afford the crude product as a mixture of two regioisomers. MS (m/z): 402.1 [M+H]$^+$. 0.3 M lithium hydroxide monohydrate in methanol (250 ml, ca. 75 mmol) was added. The mixture was stirred at room temperature for 45 min and then carefully acidified with 6 N aq. HCl until the pH of the solution was 2. The resulting product was filtered off, washed with water and dried under vacuum to afford the desired compound. R$_t$ 4.2 min. MS (m/z): 268.1 [M+H]$^+$. $^1$H NMR.

5-Benzyloxycarbonylamino-1-triphenylmethylindazole

5-Benzyloxycarbonylaminoindazole (0.534 g, 2 mmol) was stirred with trityl chloride (0.556 g, 2 mmol) and tetrabutylammonium iodide (0.074 g, 0.2 mmol) in tetrahydrofuran (5 ml) and triethylamine (0.42 ml, 3 mmol) for 3 days at room temperature. Solvent was removed under vacuum, and the solid residue was triturated with methanol (3 ml). The solid was washed with a mixture of methanol-water (5:1, ca. 15 ml) and dried under vacuum to afford the desired product. Yield 0.73 g (72%). $^1$H NMR.

5-[5-(R)-Hydroxymethyloxazolidine-2-one-3-yl]-1-triphenylmethylindazole

1 M Lithium bis(trimethylsilyl)amide in tetrahydrofuran (1.1 mL, 1.1 mmol) was added dropwise with stirring at −78° C. to 5-benzyloxycarbonylamino-1-tritylindazole (0.510 g, 1 mmol) in tetrahydrofuran (10 mL) under nitrogen atmosphere. The mixture was stirred at −78° C. for 1.5 h. (R)-Glycidyl butyrate (0.160 mL, 1.2 mmol) was added dropwise with stirring. The mixture was allowed to warm to r.t. overnight. Saturated aq. NH$_4$Cl (10 mL) was added, and the mixture was extracted with EtOAc (2×20 mL). The combined organic layers were washed with water (10 mL), brine (10 mL), and dried (MgSO$_4$). Solvent was evaporated to 3 mL, and the residue was triturated with hexanes (50 mL). White crystalline product was filtered off, washed with hexanes, and dried in vacuo. Yield 0.440 g (93%). MS (m/z): 232.1 [M−Trt]$^-$. $^1$H NMR.

5-[5-(S)-Azidomethyloxazolidine-2-one-3-yl]-1-triphenylmethylindazole

Methanesulfonyl chloride (0.066 ml, 0.85 mmol) was added dropwise with stirring to a solution of 5-[5-(R)-hydroxymethyloxazolidine-2-one-3-yl]-1-triphenylmethylindazole (0.300 g, 0.63 mmol) and triethylamine (0.18 ml, 1.3 mmol) in dichloromethane (7.0 ml) at −30° C. over 5 minutes. The reaction mixture was stirred at 5° C. for 2 h and quenched with water (15 ml). Ethyl acetate (20 ml) was added, and the organic layer was washed with water, brine, and dried (MgSO$_4$). Solvent was removed under vacuum to afford a mesylate intermediate. The mesylate and sodium azide (0.205 g, 3.15 mmol) in DMF (4 ml) was heated with stirring at 75° C. for 4 h. The reaction mixture was cooled to room temperature, diluted with water (ca. 10 ml), and extracted with ethyl acetate (2×15 ml). The combined organic layers were washed with water, brine, and dried (MgSO$_4$). Solvent was removed under vacuum to afford the desired product as off-white crystals. Yield 0.31 g (95%). MS (m/z): 257.1 [M−Trt]$^-$. $^1$H NMR.

BAL Aldehyde Resin 4-(4-Formyl-3,5-dimethoxyphenoxy)butyric acid (9.33 g, 34.8 mmol), pyridine (15 ml), and diisopropylcarbodiimide (3.00 ml, 19.1 mmol) in dichloromethane (135 ml) were stirred at room temperature for 1 h. Tentagel S—NH$_2$ resin (Rapp Polymere, 0.29 mmol/g, 8.7 mmol) was added, and the mixture was agitated at room temperature overnight. The resin was filtered, washed liberally with MeOH and dichloromethane and dried under vacuum.

5-[5-(S)-Acetamidomethyloxazolidine-2-one-3-yl]-1-indazole

Tetrahydrofuran (1.0 mL) was added to the mixture of 5-[5-(S)-azidomethyloxazolidine-2-one-3-yl]-1-triphenylmethylindazole (0.065 g, 0.13 mmol, ca. 3 eq. with respect to the resin reagent), triphenylphosphine (0.034 g, 0.13 mmol), and BAL aldehyde resin (150 mg, ca 0.044 mmol). The mixture was stirred at r.t. for 2 h. A rubber septum was replaced with a teflon-coated cap, and the mixture was agitated at 75° C. for ca. 10 h. A tetrahydrofuran-triethylorthoformate mixture (1:1, 1 mL) was added to the resulting imine resin, followed by 0.5 M NaBH$_3$CN (0.5 mL, 0.25 mmol). The mixture was agitated at room temperature for 3 h. The resulting amine resin was washed liberally with MeOH and dichloromethane, and dried under vacuum. An acetic anhydride-pyridine-dichloromethane solution (1 to 1.5 to 3, 4 mL) was added, and the mixture was agitated for 2 h (until negative ninhydrine test indicated completion of the acylation). The trityl protection was removed by treatment with 1% TFA in DCM (2×4 mL, 15 min), and the product was cleaved with 60% TFA in DCM (2 mL) over 2 h. HPLC purity for the cleaved product was 90% (Rt 2.95 min). Solvent was removed under vacuum, and the product was purified by preparative silica gel TLC (eluent: dichloromethane-MeOH 5:1). Yield 7.0 mg (58%). R$_t$ 2.9 min. (given below). MS (m/z): 275.1 [M+H]$^+$. $^1$H NMR.

BAL Resin Immobilized 5-(S)-Aminomethyl-3-[4'-dimethoxymethyl-3'-fluorophenyl]-oxazolidine-2-one Triphenylphosphine (0.130 g, 0.496 mmol) was added to a mixture of BAL aldehyde resin (0.57 g, 0.165 mmol) and 5-(S)-azidomethyl-3-[4'-dimethoxymethyl-3'-fluorophenyl]-oxazolidine-2-one (0.154 g, 0.496 mmol) in THF (3 ml) at room temperature. The mixture was stirred at room temperature for 2 h, and then at 75° C. for 16 h. The mixture was cooled to room temperature, and 1M sodium cyanoborohydride in THF (0.99 ml, 0.992 mmol) was added in one portion. The reaction mixture was agitated for 8 h. The resulting amine resin was washed liberally with methanol and dichloromethane and dried under vacuum.

BAL Resin Immobilized 5-(S)-Acetamidomethyl-3-[4'-dimethoxymethyl-3'-fluorophenyl]-oxazolidine-2-one Acetic anhydride-pyridine-dichloromethane solution (1 to 1.5 to 3, 4 mL) was added to BAL resin immobilized 5-(S)-aminomethyl-3-[4'-dimethoxymethyl-3'-fluorophenyl]oxazolidine-2-one, and the mixture was agitated for ca. 2 h (until negative ninhydrine test indicated completion of the acylation). The resin was filtered, washed liberally with methanol and dichloromethane and dried under vacuum.

5-(S)-Acetamidomethyl-3-[4'-formyl-3'-fluorophenyl]oxazolidine-2-one

BAL resin immobilized 5-(S)-acetamidomethyl-3-[4'-dimethoxymethyl-3'-fluorophenyl]-oxazolidine-2-one (0.100 g, 0.029 mmol) was suspended in 60% trifluoroacetic acid in dichloromethane (2 ml) for 2 h at room temperature. The mixture was filtered, and supernatant was evaporated under vacuum to give the crude product. The crude product was purified by preparative HPLC to afford the desired product as an oil. Yield 4.9 mg, (60%). R$_t$ 3.0 min. MS (m/z): 281.1 [M+H]$^+$. $^1$H NMR.

BAL Resin Immobilized 5-(S)-Aminomethyl-3-[4'-tert-butoxycarbonyl-3'-fluorophenyl]-oxazolidine-2-one Triphenylphosphine (7.61 g, 29.0 mmol) was added to a mixture of BAL aldehyde resin (33.3 g, 9.67 mmol) and 5-(S)-azidomethyl-3-[4'-tert-butoxycarbonyl-3'-fluorophenyl]-oxazolidine-2-one (9.76 g, 29.0 mmol) in tetrahydrofuran (170 ml) under nitrogen at room temperature. The mixture was agitated at room temperature for 2 h and then at 75° C. for 16 h. The mixture was cooled to room temperature, and 1 M sodium cyanoborohydride in THF (58.0 ml, 58.0 mmol) was added in one portion The reaction mixture was agitated for 8 h. The resulting amine resin was filtered, washed liberally with methanol and dichloromethane, and dried under vacuum.

BAL Resin Immobilized 5-(S)-Aminomethyl-3-[4'-carboxy-3'-fluorophenyl]oxazolidine-2-one A mixture of 1 M chlorotrimethylsilane in dichloromethane (290 ml, 0.29 mol) and 1 M phenol in dichloromethane (290 ml, 0.29 mol) was added to BAL resin immobilized 5-(S)-aminomethyl-3-[4'-tert-butoxycarbonyl-3'-fluorophenyl]-oxazolidine-2-one, and the reaction mixture was agitated at room temperature for 36 h. The resulting acid resin was filtered, washed liberally with methanol and dichloromethane, and dried under vacuum.

General Procedure for the Synthesis of Immobilized 5-(S)-Acylaminomethyl-3-[4'-carboxy-3'-fluorophenyl]-oxazolidine-2-ones A selected carboxylic acid (18.0 mmol), pyridine (1.46 ml,18.0 n-tmol) and diisopropylcarbodiimide (1.35 ml, 9.90 mmol) in a mixture of dimethylformamide-dichloromethane (4:1, 8 ml) were stirred at room temperature for 1 h. An appropriate BAL resin immobilized 5-(S)-aminomethyl-3-[4'-carboxy-3'-fluorophenyl]oxazolidine-2-one (1.80 mmol) was added and the mixture was agitated at room temperature for 16 h (or until ninhydrin test indicated a completion of the acylation). The resin was filtered, washed liberally with dimethylformamide, MeOH, dichloromethane, and dried under vacuum.

5-(S)-Acetamidomethyl-3-[4'-carboxy-3'-fluorophenyl]-oxazolidine-2-one

Acetic anhydride-pyridine-dichloromethane solution (1:1.5:3, 200 mL). was added to an immobilized 5-(S)-acylaminomethyl-3-[4'-carboxy-3'-fluorophenyl]-oxazolidine-2-one (33.3 g, 9.67 mmol), and the mixture was agitated overnight. The resin was filtered, washed liberally with methanol and dichloromethane and dried under vacuum. The acylated resin (0.100 g, 0.029 mmol) was suspended in 60% trifluoroacetic acid in dichloromethane for 2 h at room temperature. The mixture was filtered, and the supernatant was evaporated under vacuum to give a white solid which was washed with ether and dried under vacuum. Yield 7.6 mg (88%); mp 252–253° C. $^1$H NMR.

BAL Resin immobilized 5-(S)-Acetamidomethyl-3-[4'-(pentafluorophenyl)oxycarbonyl-3'-fluorophenyl]-oxazolidine-2-one Pentafluorophenyl trifluoroacetate (7.10 ml, 41.3 mmol) was added to a mixture of BAL resin immobilized 5-(S)-acetamidomethyl-3-[4'-carboxy-3'-fluorophenyl]-oxazolidine-2-one (20.4 g, 5.90 mmol) and pyridine (8 ml) in N-methylpyrrolidine-2-one (35 ml). The reaction mixture was agitated at room temperature for 16 h. The resin was filtered, washed with N-methylpyrrolidine-2-one and dichloromethane, and dried under vacuum. The resin was analyzed by cleavage with 60% trifluoroacetic acid in dichloromethane (2 ml per 0.100 g. 0.029 mmol of the resin, 2 h). The resulting supernatant was evaporated under vacuum to give the released pentafluorophenyl ester as a white solid. The solid was purified by preparative TLC (eluent 10% MEOH in dichloromethane). Yield 8.0 mg (60%); m.p. 172–173° C. $^1$H NMR.

5-(S)-Acetamidomethyl-3-[4'-(4"-morpholinophenylamino)carbonyl-3'-fluorophenyl]-oxazolidine-2-one BAL resin immobilized 5-(S)-acetamidomethyl-3-[4'-(pentafluorophenyl)oxycarbonyl-3'-fluorophenyl]oxazolidine-2-one (0.100 g, 0.029 mmol) was agitated with 4-morpholinoaniline (0.155 mg, 0.87 mmol) in 10% pyridine in dimethylformamide (2 ml) for 24 h. The resin was filtered and washed liberally with dimethylformamide, MeOH, DCM, and dried under vacuum. The dry resin was cleaved in 60% trifluoroacetic acid in dichloromethane (2 ml) for 2 h at room temperature. The supernatant was evaporated under vacuum, and the crude product was purified by preparative TLC (eluent: 10% methanol in dichloromethane to give product as a white solid. Yield 6.6 mg (50%). MS (m/z): 457.2 [M+H]$^+$. $^1$H NMR.

5-(S)-Acetamidomethyl-3-[4'-(3"-pyridylamino)carbonyl-3'-fluorophenyl]-oxazolidine-2-one BAL resin immobilized 5-(S)-acetamidomethyl-3-[4'-(pentafluorophenyl)oxycarbonyl-3'-fluorophenyl]oxazolidine-2-one (0.100 g, 0.029 mmol) was agitated with 3-aminopyridine (0.082 mg, 0.87 mmol) in 10% pyridine in dimethylformamide (2 ml) for 24 h. The resin was filtered and washed liberally with dimethylformamide, MeOH, DCM, and dried under vacuum. The dry resin was cleaved in 60% trifluoroacetic acid in dichloromethane (2 ml) for 2 h at room temperature. The supernatant was evaporated under vacuum, and the crude product was purified by preparative TLC (eluent: 10% methanol in dichloromethane) to give the product as a white solid. Yield 4.3 mg (40%). MS(m/z): 373.1 [M+H]$^+$. $^1$H NMR.

5-(S)-Acetamidomethyl-3-[4'-(4"-morpholino)carbonyl-3'-fluorophenyl]oxazolidine-2-one BAL resin immobilized 5-(S)-acetamidomethyl-3-[4'-(pentafluorophenyl)oxycarbonyl-3'-fluorophenyl]oxazolidine-2-one (0.100 g, 0.029 mmol) was agitated with morpholine (0.10 ml, 0.116 mmol) in N-methylpyrrolidine-2-one (2 ml) for 16 h. The resin was filtered and washed liberally with N-methylpyrrolidine-2-one, MeOH, dichloromethane, and dried under vacuum. The dry resin was cleaved in 60% trifluoroacetic acid in dichloromethane (2 ml) for 2 h at room temperature. The resin was filtered, the filtrate evaporated under vacuum, and the crude product was purified by preparative TLC (eluent: 10% MeOH in dichloromethane) to give the product as a white solid. Yield 5.6 mg (53%); m.p. 210–211° C. $^1$H NMR.

BAL Resin Immobilized Weinreb Amide: 5-(S)-Acetamidomethyl-3-[4'-N-methoxy-N-methylaminocarbonyl-3'-fluorophenyl]-oxazolidine-2-one BAL resin immobilized 5-(S)-acetamidomethyl-3-[4'-(pentafluorophenyl)oxycarbonyl-3'-fluorophenyl]oxazolidine-2-one (1.00 g, 0.29 mmol) was agitated with N-methoxy-N-methylamine hydrochloride (0.59 g, 6.0 mmol) and triethylamine (0.84 ml, 6.0 mmol) in N-methylpyrrolidine-2-one for 16 h at room temperature. The resin was filtered, washed liberally with N-methylpyrrolidine-2-one, MeOH, dichloromethane, and dried under vacuum. A small portion of the resin (ca. 10 mg) was cleaved in 60% trifluoroacetic acid in dichloromethane (0.20 ml) for 2 h at room temperature. The supernatant was concentrated under vacuum to afford the cleaved Weinreb amide as an oil. R$_t$ 2.8 min. MS (m/z): 340.1 [M+H]$^+$. $^1$H NMR.

BAL Resin Immobilized Aldehyde 5-(S)-Acetamidomethyl-3-[4'-formyl-3'-fluorophenyl]-oxazolidine-2-one 0.1 M Lithium aluminum hydride in tetrahydrofuran (0.52 ml) was added dropwise with stirring to BAL resin immobilized 5-(S)-acetamidomethyl-3-[4'-N-methoxy-N-methylaminocarbonyl-3'-fluorophenyl]oxazolidine-2-one (0.150 g, 0.044 mmol) in tetrahydrofuran (2 ml) at −78° C. The mixture was agitated at −78° C. for 4–6 h. It was then allowed to warm to room temperature overnight. The resin was filtered, washed liberally with tetrahydrofuran, MeOH, dichloromethane, and dried under vacuum. $^1$H NMR.

5-(S)-Acetamidomethyl-3-[4'-formyl-3'-fluorophenyl]oxazolidine-2-one

BAL resin immobilized 5-(S)-acetamidomethyl-3-[4'-formyl-3'-fluorophenyl]-oxazolidine-2-one (0.150 g, 0.0435 mol) was cleaved with 60% trifluoroacetic acid in dichloromethane (2 ml) for 2 h at room temperature. Supernatant was evaporated under vacuum to give the crude product as an oil. MS (m/z): 281.1 [M+H]$^+$. $^1$H NMR.

5-(S)-Acetamidomethyl-3-[4'-acetyl-3'-fluorophenyl] oxazolidine-2-one 3.0 M Methylmagnesium iodide in diethyl ether (0.022 ml, 0.066 mmol) is added dropwise with stirring to BAL resin immobilized 5-(S)-acetamidomethyl-3-[4'-N-methoxy-N-methylaminocarbonyl-3'-fluorophenyl]-oxazolidine-2-one (0.150 g, 0.044 mmol) in tetrahydrofuran (2 ml) at −78° C. The mixture is agitated at 78° C. for 5–10 h, and then allowed to warm to room temperature overnight. The resin is filtered, washed liberally with tetrahydrofuran, MeOH, dichloromethane, and dried under vacuum. The resulting ketone resin is cleaved with 60% trifluoroacetic acid in dichloromethane (2 ml) for 2 h at room temperature. The supernatant is evaporated under vacuum to afford the desired product.

BAL Resin Immobilized Acyl Azide 5-(S)-Acetamidomethyl-3-[4'-azidocarbonyl-3'-fluorophenyl]oxazolidine-2-one Method A: with azidotrinethylsilane and tetrabutylammonium fluoride. 1 M Tetrabutylammonium fluoride in tetrahydrofuran (0.609 ml, 0.609 mmol) was added to azidotrimethylsilane (0.34 ml, 2.6 mmol) in tetrahydrofuran (3.5 ml), and the mixture was kept at room temperature for 0.5 h. The resulting solution was added to BAL resin immobilized 5-(S)-acetamidomethyl-3-[4'-(pentafluorophenyl)oxycarbonyl-3'-fluorophenyl]-oxazolidine-2-one, and the mixture was agitated at room temperature for 4–5 h. The acyl azide resin was filtered, washed with dichloromethane and acetone. IR (cm$^{-1}$): 2136 ($N_3$). The resin was further analyzed by cleavage with 60% trifluoroacetic acid in dichloromethane (2 ml per 0.100 g, 0.029 mmol of the resin, 2 h). The resulting supernatant was evaporated under vacuum to give the released acyl azide product. $R_t$ 3.3 min. IR (cm$^{-1}$): 2138 ($N_3$). MS (m/z): 278.1 [M−$N_2$+H]$^+$. $^1$H NMR.

Method B: with tetrabutylammonium azide. BAL resin immobilized 5-(S)-acetamidomethyl-3-[4'-(pentafluorophenyl)oxycarbonyl-3'-fluorophenyl]oxazolidine-2-one (Tentagel HL $NH_2$ resin, 1.00 g, ca 0.40 mmol/g) was agitated with tetrabutylammonium azide (0.797 g, 2.8 mmol) in tetrahydrofuran (10 ml) for 5 h at room temperature. The resin was filtered, washed liberally with dichloromethane and acetone, and dried under vacuum.

BAL Resin Immobilized Protected Amine 5-(S)-Acetamidomethyl-3-[4'-(9"-fluorenylmethoxycarbonyl)amino-3'-fluorophenyl]-oxazolidine-2-one BAL resin immobilized acyl azide 5-(S)-acetamidomethyl-3-[4'-azidocarbonyl-3'-fluorophenyl]oxazolidine-2-one (0.75 g, 0.22 mmol) and (9-fluorenyl)methanol (1.18 g, 6.0 mmol) in tetrahydrofuran (7.0 ml) were agitated at 80° C. for 4 h. The resulting Fmoc-protected amine resin was washed with tetrahydrofuran, MeOH, dichloromethane, and dried under vacuum.

5-(S)-Acetamidomethyl-3-[4'-(9"-fluorenylmethoxycarbonyl)amino-3'-fluoro-phenyl]-oxazolidine-2-one Method A. BAL resin immobilized 5-(S)-acetamidomethyl-3-[4'-(9"-fluorenylmethoxycarbonyl)amino-3'-fluorophenyl]oxazolidine-2-one (0.200 g) was cleaved with 60% trifluoroacetic acid in dichloromethane (2 ml) for 2 h. The resulting supernatant was evaporated under vacuum to give the released Fmoc carbamate product. $R_t$ 4.3 min. MS (m/z): 490.2 [M+H]$^+$. $^1$H NMR.

Method B. 9-Fluorenylmethyl chloroformate (0–039 g, 0.15 mmol) in dichloromethane (0.300 ml) and pyridine (0.05 ml, 0.62 mmol) was added to BAL resin immobilized 5-(S)-acetamidomethyl-3-[4'-amino-3'-fluorophenyl]oxazolidine-2-one, and the mixture was agitated at room temperature for 2 h. The resulting resin was worked up and cleaved as described above for Method A. $R_t$ 4.3 min. MS (m/z): 490.2 [M+H]$^+$. $^1$H NMR.

BAL Resin Immobilized Amine 5-(S)-Acetamidomethyl-3-[4'-amino-3'-fluorophenyl]-oxazolidine-2-one Method A. BAL resin immobilized .5-(S)-acetamidomethyl-3-[4'-(9"-fluorenylmethoxycarbonyl)amino3'-fluorophenyl]oxazolidine-2-one (ca. 0.200 g) was deprotected with 20% piperidine in dimethylformamide (2 ml) for 20 min. The resulting amine resin was washed liberally with MeOH, dichloromethane, and dried under vacuum. The resin was analyzed by cleavage with 60% trifluoroacetic acid in dichloromethane (2 ml, 2 h). The resulting supernatant was evaporated under vacuum to give the released' amine product. MS (m/z): 268.1 [M+H]$^+$. $^1$H NMR.

Method B. BAL resin immobilized 5-(S)-acetamidomethyl-3-[4'-(pentafluorophenyl)-oxycarbonyl-3'-fluorophenyl]oxazolidine-2-one (0.200 mg), azidotrimethylsilane (0.240 ml, 1.74 mmol) and catalytic tetrabutylammonium fluoride (0.05 ml, 0.05 mmol) in tetrahydrofuran (5 ml) were agitated at 80° C. for 4 h. The resulting amine resin was washed liberally with MeOH and dichloromethane. It was dried under vacuum and analyzed as described above for Method A. MS (m/z): 268.1 [M+H]$^+$. $^1$H NMR.

5-(S)-Acetamidomethyl-3-[4'-(para-nitrobenzene)sulfonamido-3'-fluorophenyl]oxazolidine-2-one BAL resin immobilized 5-(S)-acetamidomethyl-3-[4'-amino-3'-fluorophenyl]-oxazolidine-2-one (0.200 g) was agitated with para-nitrobenzenesulfonyl chloride (0.108 g, 0.50 mmol) in dichloromethane (2.0 ml) with N-methylmorpholine (0.200 ml) for 14 h at room temperature. The resulting sulfonamide resin was filtered, washed liberally with dimethylformamide, MeOH, dichloromethane, and dried under vacuum. The dry resin was cleaved with 60% trifluoroacetic acid in dichloromethane (2 ml, 2 h). The resulting supenatant was evaporated under vacuum to give the sulfonamide product. MS (m/z): 453.1 [M+H]$^+$. $^1$H NMR.

$N^1$-(9-Fluorenylmethoxycarbonyl)-$N^2$-[4'-(5"-(S)-acetamidomethyloxazolidine-2-one-3"-yl)-3'-fluorophenyl]thiourea BAL resin immobilized 5-(S)-acetamidomethyl-3-[4'-amino-3'-fluorophenyl]-oxazolidine-2-one (0.200 g) was agitated with 9-fluorenylmethoxycarbonylisocyanate (0.140 g, 0.50 mmol) in dichloromethane (2.0 ml) for 14 h at room temperature. The resulting thiourea resin was filtered, washed liberally with dimethylformamide, MeOH, dichloromethane, and dried under vacuum. The dry resin was cleaved with 60% trifluoroacetic acid in dichloromethane (2 ml, 2 h). The resulting supernatant was evaporated under vacuum to give the sulfonamide product. $R_t$ 4.5 min. MS (m/z): 549.1 [M+H]$^+$. $^1$H NMR.

5-(S)-Acetamidomethyl-3-[4'-(4"-phenylthiazole-2"-yl)amino-3'-fluoro-phenyl]oxazolidine-2-one BAL resin immobilized $N^1$-(9-Fluorenyhmethoxycarbonyl)-$N^2$-[4'-(5"-(S)-acetamidomethyloxazolidine-2-one-3"-yl)-3'-fluorophenyl]thiourea was deprotected with 20% piperidine in dimethylformamide (2 ml) for 40 min, filtered, washed liberally with MeOH, dichloromethane, and dried under vacuum. 2-Bromoacetophenone (0.100 g, 0.50 mnol) in tetrahydrofuran (2.0 ml) was added, and the mixture was agitated at room temperature for 2 h. The resulting thiazole resin was washed liberally with MeOH, dichloromethane, and dried under vacuum. The dry resin was cleaved with 60% trifluoroacetic acid in dichloromethane (2 ml, 2 h). The resulting supernatant was evaporated under vacuum to give the thiazole product. $R_t$ 3.9 min. MS (m/z): 427.1 [M+H]$^+$. $^1$H NMR.

5-(S)-Acetamidomethyl-3-[4'-(5"-amino-4"-cyanooxazole-2"-yl)-3'-fluorophenyl]-oxazolidine-2-one BAL resin immobilized 5-(S)-acetamidomethyl-3-[4-(pentafluorophenyl)-oxycarbonyl-3'-fluorophenyl] oxazolidine-2-one (0.100 g) was agitated with aminomalonitrile tosylate (0.253 g,1 mmol) in a mixture of dry pyridine and N-methylpyrrolidine-2-one (1:1, 2.0 ml) at 60° C. for 8–10 h. The resulting aminooxazole resin was washed liberally with MeOH, dichloromethane, and dried under vacuum. The dry resin was cleaved with 60% trifluoroacetic acid in dichloromethane (2 ml, 2 h). The resulting supernatant was evaporated under vacuum to give the oxazole product. $R_t$ 3.2 min. MS (m/z): 360.1 $[M+H]^+$. $^1$H NMR.

5-(S)-Acetamidomethyl-3-[4'-triphenylmethylthio-3'-fluorophenyl]oxazolidine-2-one Triphenylphosphine (2.82 g, 10.8 mmol) was added portionwise to a solution of 5-(S)-azidomethyl-3-[4'-triphenylmethylthio-3'-fluorophenyl]-oxazolidine-2-one (5.00 g, 9.79 mmol) in THF (40 mL), and the mixture stirred for 2 h at room temperature. Water (1.41 mL, 78.3 mmol) was added, and the mixture heated at 40° C. overnight. Solvent was removed under vacuum, and the oily residue dissolved in dichloromethane (50 mL). Acetic anhydride (4.62 ml, 49.0 mmol) and pyridine (7.92 ml, 97.9 mmol) were added, and the mixture stirred for 8 h at r.t Solvent was removed under vacuum and the crude product purified by silica gel flash column chromatography (eluent: 30% ethyl acetate in hexanes) to give the product as a foam (4.98 g, 97%); MS: 527 $[M+H]^+$. $^1$H NMR.

BAL Resin Immobilized 5-(S)-Aminomethyl-3-[4'-triphenylmethylthio-3'-fluorophenyl]-oxazolidine-2-one Diisopropylcarbodiiimide (4.24 ml, 27.0 mmol) aws added to 4-(4-formyl-3,5-dimethoxyphenoxy)butyric acid (13.19 g, 49.2 mmol) and pyridine (20 mL) in dichloromethane (190 mL), and the mixture was stirred at room temperature for 1 h. Tentagel S—NH$_2$ resin (Rapp Polymere, 30.0 g, 12.3 mmol) was added, and the mixture agitated at room temperature overnight. Resulted BAL resin was filtered, washed liberally with methanol and dichloromethane and dried under vacuum. Triphenylphosphine (7.97 g, 0.0304 mol) was added to a mixture of above BAL aldehyde resin (50.9 g, 0.0209 mol) and 5-(S)-azidomethyl-3-[4'-triphenylmethylthio-3'-fluorophenyl]oxazolidine-2-one (1 5.5g, 30.4 mmol) in TBF (200 ml) under nitrogen at r.t (room temperature). The mixture was agitated at r.t. for 2 h and then heated at 75° C. for 16 h. The mixture was cooled to r.t, and 1M sodium cyanoborohydride in THF (62.7 ml, 62.7 mmol) was added. The mixture was agitated for 8 h at r.t. The resin was filtered, washed liberally with methanol and dichloromethane and dried under vacuum.

BAL Resin Immobilized 5-(S)-Acetamidomethyl-3-[4'-acetylthio-3'-fluorophenyl]oxazolidine-2-one BAL resin immobilized 5-(S)-Aminomethyl-3-[4'-triphenylmethylthio-3'-fluorophenyl]-oxazolidine-2-one (5.00 g, 2.05 mmol) was suspended in 5% trifluoroacetic acid and 2.5% triisopropylsilane in dichloromethane (50 mL), and the mixture was agitated for 1 h. The resin was filtered and the procedure repeated with fresh 5% trifluoroacetic acid and 2.5% triisopropylsilane in dichloromethane (50 mL) for another 30 minutes. The resin was filtered and washed liberally with dichloromethane. Resulted thiol resin was immediately suspended in a mixture of acetic anhydride (20 mL) and pyridine (30 mL) in DCM (50 mL), and the mixture was agitated overnight at r.t. The resin was filtered, washed liberally with dichloromethane and dried under vacuum.

5-(S)-Acetamidomethyl-3-[4'-acetylthio-3'-fluorophenyl] oxazolidine-2-one

BAL resin immobilized 5-(S)-acetamidomethyl-3-[4'-acetylthio-3'-fluorophenyl]oxazolidine-2-one. (0.15 g, 0.041 mmol) was suspended in 60% trifluoroacetic acid in dichloromethane for 2 at r.t. Supernatant was evaporated under vacuum and the crude product was purified by TLC (10% methanol in dichloromethane). Yield 8.7 mg (67%). MS: 327 $[M+H]^+$. $^1$H NMR.

Ester Oxazolidinone Derivatives

General Procedures for Preparation of 5-(S)-(N-Acylaminomethyl)-3-[4'-(substituted)thio-3'-fluorophenyl] oxazolidine-2-ones Method A. 4.37 M Sodium methoxide in methanol (0.0927 ml, 0.405 mmol) was added to an appropriate BAL resin immobilized 5-(S)-amidomethyl-3-[4'-acylthio-3'-fluorophenyl]oxazolidine-2-one (prepared as described above; 0.15 g, 0.041 mmol) in a polar aprotic solvent (preferably, N-methylpyrrolidine-2-one, 1.5 mL), and the mixture was agitated for 5–25 min (typically completed within 5 min for acetylated compounds). Optionally, an organic base was used instead of sodium methoxide (e.g., tetramethylguanidine or alkylamine). An appropriate alkylating or (hetero)arylating reagent (0.8–1.6 mmol) was added, and the mixture agitated at r.t. for 12–36 h (typically, complete overnight). The resin wash washed thoroughly with N-methylpyrrolidine-2-one, dichloromethane, and methanol. The resin was suspended in 60% trifluoroacetic acid in dichloromethane and agitated at room temperature for 2 h. Supenatant was evaporated under vacuum and the crude product purified by TLC (methanol-dichloromethane mixtures).

Method B. 5% Trifluoroacetic acid and 2.5% triisopropylsilane in dichloromethane (2.0 mL) was added to 5-(S)-acetamidomethyl-3-[4'-triphenylmethylthio-3'-fluorophenyl]oxazolidine-2-one (0.10, 0.19 mmol), and the mixture was stirred at r.t. for 1 h. and the mixture stirred for 1 h at room temperature. Solvent was removed under vacuum, and the residue dissolved in methanol (3 mL). An appropriate alkylating or (hetero)arylating reagent (19–0.38 mmol) was added, followed by dropwise addition of 4.37 M sodium methoxide in methanol'(0.087 ml, 0.380 mmol). Optionally, an organic base was used instead of sodium methoxide (e.g., tetramethylguanidine or alkylamine). The mixture was stirred at 20–70° C. for 2–24 h (typically, 2 h at r.t.). Solvent was removed under vacuum and the crude product purified by TLC (methanol-dichloromethane mixtures).

5-(S)-Acetamidomethyl-3-[4-(6"chloropyridazine-3"-yl) thio-3'-fluorophenyl]-oxazolidine-2-one Prepared according to Method A of the General Procedures for Preparation of 5-(S)-(N-Acylaminomethyl)-3-[4'-(substituted)thio-3'-fluorophenyl]oxazolidine-2-ones from BAL resin immobilized 5-(S)-acetamidomethyl-3-[4'-acetylthio-3'-fluorophenyl]oxazoli-dine-2-one with 3,6-dichloropyridazine (0.12 g, 0.81 mmol) in N-methylpyrrolidine-2-one (1 mL). The synthesis was performed at r.t. overnight, and the crude cleaved product purified by TLC (eluent: 10% methanol in dichloromethane). Yield 3.9 mg (24%). MS: 397 $[M+H]^+$. $^1$H NMR.

5-(S)-Acetamidomethyl-3-[4'-(4",6"-dimethoxy-1",3",5"-triazine-2"-yl)thio-3'-fluorophenyl]oxazolidine-2-one Prepared according to Method A of the General Procedures for Preparation of 5-(S)-(N-Acylaminomethyl)-3-[4'-(substituted)thio-3'-fluorophenyl]oxazolidine-2-ones from BAL resin immobilized 5-(S)-acetamidomethyl-3-[4'-acetylthio-3'-fluorophenyl]oxazoli-dine-2-one with 2-chloro4,6-dimethoxy-1,3,5-triazine (0.1 g, 0.81 mmol) in N-methylpyrrolidine-2-one (1 mL). The synthesis was performed at r.t. overnight, and the crude cleaved product purified by TLC (eluent: 10% methanol in dichloromethane). Yield 6.1 mg (36%). MS: 424 [M+H]$^+$. $^1$H NMR.

5-(S)-Acetamidomethyl-3-[4'-(5"-nitropyridine-2"-yl)thio-3'-fluorophenyl]-oxazolidine-2-one Prepared according to Method A of the General Procedures for Preparation of 5-(S)-(N-Acylaminomethyl)-3-[4'-(substituted)thio-3'-fluorophenyl]oxazolidine-2-ones from BAL resin immobilized 5S)-acetamidomethyl-3-[4'-acetylthio-3'-fluorophenyl]oxazoli-dine-2-one with 2-chloro-5-nitropyridine (0.13 g, 0.81 mmol) in N-methylpyrrolidine-2-one (1 mL). The synthesis was performed at r.t overnight, and the crude cleaved product purified by TLC (eluent: 10% methanol in dichloromethane). Yield 7.0 mg (44%). MS: 407 [M+H]$^+$. $^1$H NMR.

5-(S)-Acetamidomethyl-3-(4'-[2"-(4'''-morpholino)ethyl]thio-3'-fluorophenyl)-oxazolidine-2-one Prepared according to Method A of the General Procedures for Preparation of 5-(S)-(N-Acylaminomethyl)-3-[4'-(substituted)thio-3'-fluorophenyl]oxazolidine-2-ones from BAL resin immobilized 5-(S)-acetamidomethyl-3-[4'-acetylthio-3'-fluorophenyl]oxazoli-dine-2-one with 4-(2-chloroethyl)morpholine hydrochloride (0.28 g, 0.81 mmol) in N-methylpyrrolidine-2-one (1 mL). The synthesis was performed at r.t. overnight, and the crude cleaved product purified by TLC (eluent: 10% methanol in dichloromethane). Yield 2.4 mg (15%). MS: 398 [M+H]$^+$. $^1$H NMR.

5-(S)-Acetamidomethyl-3-[4'-(pyridine-3"-yl)methylthio-3'-fluorophenyl)-oxazolidine-2-one Prepared according to Method A of the General Procedures for Preparation of 5-(S)-(N-Acylaminomethyl)-3-[4'-(substituted)thio-3'-fluorophenyl]oxazolidine-2-ones from BAL resin immobilized 5-(S)-acetamidomethyl-3-[4'-acetylthio-3'-fluorophenyl]oxazoli-dine-2-one with 3-(chloromethyl)pyridine hydrochloride (0.13 g, 0.81 mmol) in N-methylpyrrolidine-2-one (1 mL). The synthesis was performed at r.t. overnight, and the crude cleaved product purified by TLC (eluent: 10% methanol in dichloromethane). Yield 3.6 mg (24%). MS: 376 [M+H]$^+$.

5-(S)-Acetamidomethyl-3(4'-methylthio-3'-fluorophenyl)oxazolidine-2-one

Prepared according to Method A of the General Procedures for Preparation of 5-(S)-(N-Acylaminomethyl)-3-[4'-(substituted)thio-3'-fluorophenyl]oxazolidine-2-ones from BAL resin immobilized 5-(S)-acetamidomethyl-3–14'-acetylthio-3'-fluorophenyl]oxazoli-dine-2-one with methyl iodide (0.05 mL, 0.81 mmol) in N-methylpyrrolidine-2-one (1 mL). The synthesis was performed at r.t. overnight, and the crude cleaved product purified by TLC (eluent: 10% methanol in dichloromethane). Yield 6.3 mg (52%). MS: 299 [M+H]$^+$. $^1$H NMR.

5-(S)-Acetamidomethyl-3-[4-(2"-methylthiazole4"-yl)methylthio-3'-fluorophenyl]oxazolidine-2-one Prepared according to Method A of the General Procedures for Preparation of 5-(S)-N-Acylaminomethyl)-3-[4'-(substituted)thio3'-fluorophenyl]oxazolidine-2-ones from BAL resin immobilized 5-(S)-acetamidomethyl-3-[4'-acetylthio-3'-fluorophenyl]oxazoli-dine-2-one with 4-chloromethyl-2-methylthiazole hydrochloride (0.15 g, 0.81 mmol) in N-methylpyrrolidine-2-one (1 mL). The synthesis was performed at r.t. overnight, and the crude cleaved product purified by TLC (eluent: 10% methanol in dichloromethane). Yield 6.9 mg (43%). MS: 396 [M+H]$^+$. $^1$H NMR.

5-(S)-Acetamidomethyl-3-[4'-(1",2",4"-oxadiazole-3"-yl)methylthiazole-4"-yl)methylthio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamidomethyl-3-[4'-(triphenylmethyl)lthio-3'-fluorophenyl]-oxazolidine-2-one with 3-chloromethyl-1,2,4-oxadiazole (0.045 g, 0.38 mmol) in N-methylpyrrolidine-2-one (1 mL). The synthesis was performed at r.t. for 2 h. The crude product was purified by TLC (eluent: 10% methanol in dichloromethane). Yield 0.043 g (62%). MS: 367 [M+H]$^+$.

5-(S)-Acetamidomethyl-3-[4'-(methoxycarbonyl)methylthio-3'-fluorophenyl]-oxazolidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamidomethyl-3-[4'-(triphenylmethyl)lthio-3'-fluorophenyl]oxazolidine-2-one with methyl bromoacetate (0.058 g, 0.38 mmol) in N-methylpyrrolidine-2-one (1 mL). The synthesis was performed at r.t for 2 h. The crude product was purified by TLC (eluent 10% methanol in dichloromethane). Yield 0.056 g (83%). M.p. 119–120° C. MS: 357 [M+H]$^+$. $^1$H NMR.

5-(S)-Acetamidomethyl-3-[4'-(2"-methoxyethyl)thio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamidomethyl-3-[4'-(triphenylmethyl)lthio-3'-fluorophenyl]oxazolidine-2-one with 2chloroethyl methyl ether (0.036 g, 0.38 mmol) in N-methylpyrrolidine-2-one (1 mL). The synthesis was performed at r.t. for 2 h. The crude product was purified by TLC (eluent: 10% methanol in dichloromethane). Yield 0.034 g (52%). MS (m/z): 343 [M+H]$^+$. $^1$H NMR.

5-(S)-Acetamidomethyl-3-[4'-(3"-nitrothien-2"-yl)thio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamidomethyl-3-[4'-(triphenylmethyl)lthio-3'-fluorophenyl]oxazolidine-2-one with 2-chloro-3-nitrothiophene (0.062 g, 0.38 mmol) in N-methylpyrrolidine-2-one (1 mL). The synthesis was performed at r.t. for 2 h. The crude product was purified by TLC (eluent: 10% methanol in dichloromethane). Yield 0.066 g (85%). M.p. 194–195° C. MS (m/z): 412 [M+H]$^+$. $^1$H NMR.

5-(S)-Acetamidomethyl-3-[4'-(acetylmethyl)thio-3'-fluorophenyl]oxazo-lidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamidomethyl-3-[4'triphenylmethyl)-1thio-3'-fluorophenyl]oxazolidine-2-one with chloroacetone (0.062 g, 0.38 mmol) in N-methylpyrrolidine-2-one (1 mL). The synthesis was performed at r.t. for 2 h. The crude product was purified by TLC (eluent: 10% methanol in 5-(S)-Acetamidomethyl-3-[4'-(2"-hydroxyethyl)thio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with 2-bromoethanol (0.048 g, 0.38 mmol) in N-methylpyrrolidine-2-one (1 mL). The synthesis was performed at r.t. for 2 h. The crude product was purified by TLC (eluent: 10% methanol in dichloromethane). Yield 0.045 g (72%). MS (m/z): 329 [M+H]$^+$. $^1$H NMR.

5-(S)-Acetamidomethyl-3-[4'-(5"-carboxypyridine-3"-yl)thio-3'-fluorophenyl]-oxazolidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'-(triphenylmethyl)-1thio-3'-fluorophenyl]oxazolidine-2-one with t-butyl 2-chloronicotinate (0.081 g, 0.38 mmol) in N-methylpyrrolidine-2-one (1 mL). The synthesis was performed at r.t. for 2 h. The intermediate t-butyl ester of the product was deprotected with 20% trifluoroacetic acid in dichloromethane (1 mL, 2 h at r.t.). Solvent was evaporated under vacuum, and the crude product washed with diethyl ether. Yield 0.050 g (65%). MS (m/z): 406 [M+H]$^+$. $^1$H NMR.

5-(S)-Acetamidomethyl-3-(4'-cyclopropylmethylthio-3'-fluorophenyl)oxazo-lidine-2-one Prepared according to Method B of the General Procedures for Preparation of 5-(S)-Acylaminomethyl)-3-[4' (substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with chloromethyl cyclopropane (0.051 g, 0.38 mmol) in N-methylpyrrolidine-2-one (1 mL). The synthesis was performed at r.t. for 2 h. The crude product was purified by TLC (eluent: 10% methanol in dichloromethane). Yield 0.053 g (82%). MS (m/z): 339 [M+H]$^+$. $^1$H NMR.

5-(S)-Acetamidomethyl-3-[4'-(3"-cyanoethyl)thio-3'-fluorophenyl]oxazo-lidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'(triphenylmethyl)lthio-3'fluorophenyl]oxazolidine-2-one with 3-bromopropionitrile (0.051 g, 0.38 mmol) in N-methylpyrrolidine-2-one (1 mL). The synthesis was performed at r.t. for 2 h. The crude product was purified by TLC (eluent: 10% methanol in dichloromethane). Yield 0.032 g (50%). MS (m/z): 338 [M+H]$^+$. $^1$H NMR.

5-(S)-Acetamidomethyl-3-[4'-(5"-nitrothiazole-2"-yl)thio-3'fluorophenyl]-oxazolidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with 2-bromo-5-nitrothiazole (0.079 g, 0.38 mmol) in N-methylpyrrolidine-2-one (1 mL). The synthesis was performed at r.t. for 2 h. The crude product was purified by TLC (eluent: 10% methanol in dichloromethane). Yield 0.061 g (78%). MS (m/z): 413 [M+H]$^+$. $^1$H NMR.

5-(S)-Acetamidomethyl-3-[4'-(5"-phenyl-1",2",4"-oxadiazole-3"-yl)methylthio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamido-methyl-3-[4'-(triphenylmethyl)lthio-3'-fluorophenyl]oxazolidine-2-one with 3-chloromethyl-5-phenyl-1,2,4-oxadiazole (0.074 g, 0.38 mmol) in N-methylpyrrolidine-2-one (1 mL). The synthesis was performed at r.t. for 2 h. The crude product was purified by TLC (eluent: 10% methanol in dichloromethane). Yield 0.040 g (47%). MS (m/z): 443 [M+H]$^+$. $^1$H NMR.

5-(S)-Acetamidomethyl-3-[4'-(3"-methoxycarbonylpropane-2"-one-1,-yl)thio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamido-methyl-3-[4'-(triphenylmethyl)lthio-3'-fluorophenyl]oxazolidine-2-one with methyl 4-chloroacetoacetate (0.057 g, 0.38 mmol) in N-methylpyrrolidine-2-one (1 mL). The synthesis was performed at r.t. for 2 h. The crude product was purified by TLC (eluent: 10% methanol in dichloromethane). Yield 0.027 g (35%). MS (m/z): 399 [M+H]$^+$. $^1$H NMR.

5-(S)-Acetamidomethyl-3-[4'-(2"-chloroethyl)thio-3'-fluorophenyl]oxazolidi-ne-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with 1-bromo-2-chloroethane (0.055 g, 0.38 mmol) in N-methylpyrrolidine-2-one (1 mL). The synthesis was performed at r.t. for 2 h. The crude product was purified by TLC (eluent: 10% methanol in dichloromethane). Yield 0.047 g (72%). MS (m/z): 347 [M+H]$^+$. $^1$H NMR.

54-(S)-Acetamidomethyl-3-[4'-(1"-ethoxycarbonyl-1",1"-dimethyl)methylthio-3'-fluorophenyl]oxazo-lidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with ethyl 2-bromoisobutyrate (0.074 g, 0.38 mmol) in N-methylpyrrolidine-2-one (1 mL). The synthesis was performed at r.t. for 2 h. The crude product was purified by TLC (eluent: 10% methanol in dichloromethane). Yield 0.061 g (80%). MS (m/z): 399 [M+H]$^+$. $^1$H NMR.

5-(S)-Acetamidomethyl-3-[4'-(2"-diethoxyphosphinoyl)ethylthio-3'-fluoro-phenyl]oxazo-lidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with diethyl (2-bromoethyl) phosphonate (0.093 g, 0.38 mmol) in N-methylpyrrolidine-2-one (1 mL). The synthesis was performed at r.t. for 2 h. The crude product was purified by TLC (eluent: 10% methanol in dichloromethane). Yield 0.043 g (50%). MS (m/z): 449 [M+H]$^+$. $^1$H NMR.

5-(S)-Acetamidomethyl-3-[4'-(thiocyano)methylthio-3'-fluorophenyl]oxazolidine-2-one Prepared according to Method B of the General Procedures for Preparation of 5-(S)-(-Acylaminomethyl)-3-[4'-

(substituted)thio-3'-fluorophenyl]oxazoli-dine-2-ones from 5-(S)-acetamidomethyl-3-[4'-(triphenylmethyl)lthio-3'-fluorophenyl]oxazolidine-2-one with chloromethyl thiocyanate (0.041 g, 0.38 mmol) in N-methylpyrrolidine-2-one (1 mL). The synthesis was performed at r.t. for 2 h. The crude product was purified by TLC (eluent: 10% methanol in dichloromethane). Yield 0.022 g (35%). MS (m/z): 324 [M+H]$^+$. $^1$H NMR.

5-(S)-Acetamidomethyl-3-[4'-(3"-methyltetrahydrofuran-2"-one-3"-yl)thio-3'-fluorophenyl]oxazolidine-2-one Prepared according to Method B of the General Procedures for Preparation of 5-(S)-(N-Acylaminomethyl)-3-[4'-(substituted)thio-3'-fluorophenyl]oxazoli-dine-2-ones from 5-(S)-acetamido-methyl-3-[4'-(triphenylmethyl)lthio-3'-fluorophenyl]oxazolidine-2-one with α-bromo-α-methyl-γ-butyrolactone (0.068 g, 0.38 mmol) in N-methylpyrrolidine-2-one (1 mL). The synthesis was performed at r.t. for 2 h. The crude product was purified by TLC (eluent: 10% methanol in dichloromethane). Yield 0.035 g (48%). MS (m/z): 383 [M+H]$^+$. $^1$H NMR.

5-(S)-Acetamidomethyl-3-[4'-(2"-diethylamino)ethylthio-3'-fluorophenyl]-oxazolidine-2-one Prepared according to Method B of the General Procedures for Preparation of 5-(S)-(N-Acylaminomethyl)-3-[4'-(substituted)thio-3'-fluorophenyl]oxazolidine-2-ones from 5-(S)-acetamido-methyl-3-[4'-(triphenylmethyl)lthio-3'-fluorophenyl]oxazolidine-2-one with 2-(diethylamino)ethyl chloride hydrochloride (0.065 g, 0.38 mmol) and 4.37 M sodium methoxide (0.174 mL, 0.760 mmol) in N-methylpyrrolidine-2-one (1 mL). The synthesis was performed at r.t for 2 h. The crude product was purified by TLC (eluent: 10% methanol in dichloromethane). Yield 0.011 g (15%). MS (m/z): 383 [M+H]$^+$. $^1$H NMR.

5-(S)-Acetamidomethyl-3-[4'-(2"-hydroxyethyl)sulfinyl-3'-fluorophenyl]oxazolidine-2-one Sodium periodate (0.014 g, 0.065 mmol) in water (0.5 mL) was added to 5-(S)-acetamidomethyl-3-[4'-(2"-hydroxyethyl)thio-3'-fluorophenyl]-oxazo-lidine-2-one (0.020 g, 0.061 mmol) in methanol (1 mL), and the mixture was stirred at r.t overnight. Solvent was removed under vacuum, and the residue dissolved in ethyl acetate (ca. 5 mL). Resulting solution was washed with water, brine, and dried (MgSO$_4$). Solvent was removed under vacuum, and the crude product purified by TLC (eluent: 10% methanol in dichloromethane). Yield 0.018 g (86%). MS (m/z): 345 [M+H]$^+$. $^1$H NMR.

5-(S)-Acetamidomethyl-3-[4'-(2"-hydroxyethyl)sulfonyl-3'-fluorophenyl]-oxazolidine-2-one 30% Hydrogen peroxide (0.023 mL, 0.244 mmol) was added to 5-(S)-acetamidomethyl-3-[4'-(2"-hydroxyethyl)thio-3'-fluorophenyl]oxazoli-dine-2-one (0.020 g, 0.061 mmol) in acetic acid (1 mL), and the mixture was stirred at 60° C. overnight. Solvent was removed under vacuum, and the residue dissolved in ethyl acetate (ca. 5 mL). Resulting solution was washed with water, brine, and dried (MgSO$_4$). Solvent was removed under vacuum, and the crude product purified by TLC (eluent: 10% methanol in dichloromethane). Yield 0.017 g (77%). M.p. 162–163° C. MS (m/z): 361 [M+H]$^+$. $^1$H NMR.

Ester Oxazolidinone Derivatives 5-(S)-(N-Acetylaminomethyl)-3-[4'-(tert-butoxy)carbonyl-3'-fluorophenyl]-oxazolidine-2-one.

Triphenylphosphine (0.521 g, 1.99 mmol) was added portionwise to a solution of 5-(S)-(N-azidomethyl)-3-[4'-(tert-butoxy)carbonyl-3'-fluorophenyl]oxazolidine-2-one (0.607 g, 1.80 mmol) in THF (10 ml), and the mixture was stirred at r.t. for 2 h. Water (0.259 ml, 14.4 mmol) was added, and the mixture heated at 40° C. overnight. Solvent was removed under vacuum. The oily residue was dissolved in a mixture of acetic anhydride (0.849 ml, 9.00 mmol) and pyridine (0. 146 ml, 18.0 mmol) in dichloromethane (10 ml) and stirred for 4 h. Solvent was removed under vacuum, and the crude product was purified by TLC (eluent: 10% methanol in dichloromethane). Yield 0.62 g (98%). MS (m/z): 353 [M+H]$^+$. $^1$H NMR.

5-(S)-N-Acetylaminomethyl)-3-[4-'carboxy-3'-fluorophenyl]-oxazolidine-2-one 5-(S)-(N-Acetylaminomethyl)-3-[4'-(4"-(tert-butoxy)carbonyl-3'-fluorophenyl]oxazolidine-2-one (6.20 g, 17.5 mmol) was dissolved in 20% trifluoroacetic acid in dichloromethane, and the mixture stirred at r.t. overnight. Solvent was removed under vacuum, and the residue triturated with ether to give product as a white solid. Yield 5.20 g (99%). M.p. 252–253° C.; MS: 297 [M+H]$^+$. $^1$H NMR.

General Procedures for Preparation of 5-(S)-(N-Acylaminomethyl)-3-[4'-[alkyl[or (hetero)aryl]oxy]carbonyl-3'-fluorophenyl]-oxazolidine-2-ones Method A. An appropriate 5-(S)-(N-acylaminomethyl)-3-[4'-(4"-(pentafluorophenyl)oxycarbonyl-3'-fluorophenyl] oxazolidine-2-one resin of the type 5 (0.1 mmol; prepared from resin 4 via two step acylation with an appropriate N-acylating reagent, and subsequent Pfp-activation as described above) was mixed with a selected alcohol reagent (1–3 mmol, typically, 1–2 mmol) and 4-dimethylaminopyridine (0.2–1 mmol; typically, 1 mmol) in aprotic solvent (N,N-dimethylformamide, dichloromethane, or dimethylsulfoxide; preferably, N,N-dimethylformamide, 4–6 mL). The mixture was agitated at 20–70° C. for 6–48 h (typically, at r.t. overnight). The resin was filtered, washed liberally with N,N-dimethylformamide, dichloromethane, methanol, dried in vacuo, and cleaved with 60% trifluoroacetic acid in dichloromethane (5 ml, 2 h). Resulting supernatant was evaporated in vacuo, and the crude product purified by HPLC or Method B. An appropriate alkylating reagent (0.35–1.2 mmol; preferably, 1 mmol) was added to 5-(S)-(N-acetamidomethyl)-3-[4'-(pentafluoro-phenyloxy)carbonyl-3'-fluorophenyl]oxazolidine-2-one (0.100 g, 0.34 mmol) and potassium carbonate (0.187 g, 1.35 mmol) in N,N-dimethylformamide (2 mL), and the mixture agitated at 20–80° C. for 6–24 h (typically, at r.t. overnight). Water (ca. 10–15 mL) was added, and the mixture was extracted with ethyl acetate (ca. 3×20 mL). Combined organic solvents were washed with water, brine, and dried (MgSO$_4$). Solvent was evaporated in vacuo, and the crude product purified by HPLC or TLC.

5-(S)-(N-Acetylaminomethyl)-3-[4'-cyclopropylmethoxycarbonyl-3'-fluoro-phenyl]oxazolidine-2-one Prepared according to Method A of the General Procedures for Preparation of 5-(S)-(N-Acylaminomethyl)-3-[4'-[alkyl[or (hetero)aryl]oxy]carbonyl-3'-fluorophenyl] oxazolidine-2-ones from BAL resin 5-(S)-(N-acylaminomethyl)-3-[4'-(pentafluorophenyl)oxycarbonyl-3'-fluo-rophenyl]oxazolidine-2-one (0.1 mmol) and hydroxymethylcyclopropane (0,144 g, 2 mmol) with 4-dimethylaminopyridine (1 mmol) in N,N-imethylformamide (4 mL). Reaction performed at r.t. overnight. Crude cleaved product was purified by TLC (eluent: 10% methanol in dichloromethane). MS (m/z): 350 [M+H]$^+$. Alternatively, the compound was made according to Method B of aforementioned General Procedure from 5-(S)-(N-acetamidomethyl)-3-[4'-carboxy-3'-fluorophenyl]- oxazolidine-2-one (0.100 g, 0.34 mmol) and (bromomethyl) cyclopropane (0.098 mL, 1 mmol). Reaction was performed at 70° C. overnight. Crude product was purified by TLC (eluent: 10% methanol in dichloromethane). Yield 0.100 g (85%). MS (m/z): 350 [M+H]+. $^1$H NMR.

5-(S)-(N-Acetamidomethyl)-3-[4'-methoxycarbonyl-3'-fluorophenyl]oxazolidine-2-one Prepared according to Method B of the General Procedures for Preparation of 5-(S)-(N-Acylaminomethyl)-3-[4'-[alkyl[or (hetero)aryl]oxy]-carbonyl-3'-fluorophenyl] oxazolidine-2-ones from 5-(S)-(N-acetamido-methyl)-3-[4'-carboxy-3'-fluorophenyl]oxazolidine-2-one (0.100 g, 0.34 mmol) and methyl iodide (0.063 mL, 1 mmol). Reaction was performed at r.t overnight. Crude product was purified by TLC (eluent: 10% methanol in dichloromethane). Yield 104 mg(99%). MS (m/z): 311 [M+H]+. $^1$H NMR. 5-(S)-(N-Acetamidomethyl)-3-[4'-isopropoxycarbonyl-3'-fluorophenyl]-oxazolidine-2-one Prepared according to Method B of the General Procedures for Preparation of 5-(S)-N-Acylaminomethyl)-3-[4'-[alkyl[or (hetero)aryl]oxy]-carbonyl-3'-fluorophenyl] oxazolidine-2-ones from 5-(S)-(N-acetamido-methyl)-3-[4'-carboxy-3'-fluorophenyl]oxazolidine-2-one (0.100 g, 0.34 mmol) and 2-bromopropane (0.095 mL, 1 mmol). Reaction was performed at 70° C. overnight. Crude product was purified by TLC (eluent: 10% methanol in dichloromethane). Yield 105 mg (92%). MS (m/z): 339 [M+H]+. $^1$H NMR.

5-(S)-(N-Acetamidomethyl)-3-[4'-ethoxycarbonyl-3'-fluorophenyl]oxazolidine-2-one Prepared according to Method B of the General Procedures for Preparation of 5-(S)-(N-Acylaminomethyl)-3-[4'-[alkyl[or (hetero)aryl]oxy]-carbonyl-3'-fluorophenyl] oxazolidine-2-ones from 5-(S)-(N-acetamido-methyl)-3-[4'-carboxy-3'-fluorophenyl]oxazolidine-2-one (0.100 g, 0.34 mmol) and ethyl iodide (0.081 mL, 1 mmol). Reaction was performed at r.t. overnight. Crude product was purified by TLC (eluent: 10% methanol in dichloromethane). Yield 107 mg (98%). MS (m/z): 325 [M+H]+. $^1$H NMR.

5-(S)-(N-Acetamidomethyl)-3-[4'-[(N-isopropylidene) imino]oxycarbonyl-3'-fluorophenyl]oxazolidine-2-one A mixture of 5-(S)-(N-acetamidomethyl)-3-[4'-carboxy-3'-fluorophenyl]oxazolidine-2-one (0.100 g, 0.34 mmol), 4-(dimethylamino)-pyridine (0.041 g, 0.34 mmol), diisopropylcarbodiimide (0.053 ml, 0.34 mmol) and acetone oxime (0.025 g, 0.34 mmol) in N,N-dimethylformamide (2 ml) was stirred at r.t overnight. The reaction mixture was diluted with water and extracted with ethyl acetate. Organic layers were washed with brine, and dried (MgSO$_4$). Solvent was remove under vacuum, and the residue was purified by TLC (eluent: 10% methanol in dichloromethane). Yield 0.098 g (83%). MS (m/z): 352 [M+H]+. $^1$H NMR.

5-(S)-(N-Acetamidomethyl)-3-[4'(pyridine-3"-yl) methoxycarbonyl-3'-fluoro-phenyl]oxazolidine-2-one A mixture of 5-(S)-(-acetamidomethyl)-3-[4'-carboxy-3'-fluorophenyl]oxazolidine-2-one (0.100 g, 0.34 mmol), 4-dimethylamino)pyridine (0.041 g, 0.34 mmol), diisopropylcarbodiimide (0.053 ml, 0.34 mmol) and 3-pyridylcarbinol (0.033 g, 0.34 mmol) in N,N-dimethylformamide (2 ml) was stirred at r.t. overnight. The reaction mixture was diluted with water and extracted with ethyl acetate. Organic layers were washed with brine, and dried (MgSO$_4$). Solvent was remove under vacuum, and the residue was purified by TLC (eluent: 10% methanol in dichloromethane). Yield 0.094 g (72%). MS (m/z): 388 [M+H]+. $^1$H NMR.

Amide Oxazolidinone Derivatives

General Procedures for Preparation of 5-(S)-(N-Acylaminomethyl)-3-[4'-[(un)substituted amino]carbonyl-3'-fluorophenyl]-oxazolidine-2-ones 7

Method A. An appropriate 5-(S)-(N-acylaminomethyl)-3-[4'-(4"-(pentafluorophenyl)oxycarbonyl-3'-fluorophenyl]-oxazolidine-2-one resin of the type 5 (prepared from BAL resin immobilized 5-(S)-aminomethyl-3-[4'-carboxy-3'-fluorophenyl]-oxazolidine-2-one 4 via two step acylation with an appropriate N-acylating reagent, and subsequent Pfpactivation as described above (0.029 mmol) was agitated with a selected amine compound (0.1–0.2 mmol; preferably 0.116 mmol) in a polar non-protic solvent such as N-methylpyrrolidine-2-one, N,N-dimethylformamide (2–4 ml) for 16–48 h at 25–70° C. (preferably, at 60° C. overnight) containing 10–20% v/v of an organic base (pyridine, 2,6lutidine, or diisopropylethylamine). Optionally, dimethylsulfoxide (0.5–1 mL) was added for less soluble amine reagents. Also optionally, functionalized amines (such as amino acids or amino alcohols) were predissolved with addition of a silylating reagent (such as bis-trimethylsilylacetamide, 0.2–0.6 mmol) prior to addition to the resin, and the reaction was performed under inert gas atmosphere (nitrogen). Resulted resin was filtered and washed liberally with N-methylpyrrolidine-2-one, MeOH, dichloromethane, and dried under vacuum. The dry resin was cleaved in 60% trifluoroacetic acid in dichloromethane (2 ml) for 2 h at room temperature. The resin was filtered, the filtrate evaporated under vacuum, and crude product purified by preparative TLC (MeOH-dichloromethane) or reverse phase HPLC.

Method B. 60% Trifluoroacetic acid in dichloromethane (5 mL) was added to 5-(S)-azidomethyl-3-[4'-tert-butoxycarbonyl-3'-fluorophenyl]oxazolidine-2-one (0.336 g, 1 mmol), and the solution kept at r.t. for 1 h. Solvents were removed in vacuo to afford 5-(S)-azidomethyl-3-[4'-carboxy-3'-fluorophenyl-]oxazolidine-2-one dried (0.280 g, 99%). N-Trimethylsilyl-N,N-diethylamine (0.23 mL, 1.2 mmol) was added to above product in dry dichloromethane (3 mL) under nitrogen atmosphere, and the solution stirred for 15 min. Solvents and excess reagent were removed in vacuo, and residue dissolved in dichloromethane (4 mL). The solution was cooled to ca. 0° C., and oxalyl chloride (1.5 mmol, 0.13 mL) was added dropwise, followed by catalytic N,N-dimethylformamide (ca. 0.01 mL). The mixture was allowed to warm up to r.t., and stirred at r.t. for another 2 h. Solvents were removed in vacuo, and the resulting 5-(S)-azidomethyl-3-[4'-chlorocarbonyl-3'-fluorophenyl]-oxazolidine-2-one redissolved in dry aprotic solvent (preferably, tetrahydrofuran, pyridine, or acetonitrile, 3–10 mL). Resulted solution (0.8 mL, ca. 0.2 mmol) was added to an appropriate amine reagent (1 mmol) in aprotic solvent (preferably, acetonitrile, or pyridine, 1–5 mL) optionally containing an organic base (preferably, pyridine, 0.5–2 mL). The mixture was stirred at r.t. for 1–5 h. Solvent was removed in vacuo, and resulting 5-(S)-azidomethyl-3-[4'-(substituted)aminocarbonyl-3'-fluorophenyl]-oxazolidine-2-one was typically washed with water, and dried in vacuo. Triphenylphosphine (0.262 g, 1.0 mmol) in tetrahydrofuran (10 mL) was added to above azide intermediate, and the mixture stirred at 45–55° C. ° C. for 2 h. Water (0.5 mL) was added, and the mixture stirred overnight at 50–60° C. Solvents were removed in vacuo, and resulting crude amine intermediates typically washed with excess diethyl ether. Aprotic solvent was added (preferably, tetrahydrofuran, 5–15 mL) was added, followed by pyridine (0.25–0.5 mL) and acetic anhydride (0.2–0.5 mL), and the mixture stirred at r.t. for 0.5–2 h (typically, 1 h). Solvents were removed in vacuo, and resulting product typically washed with excess diethyl ether and dried in vacuo.

Method C. N,N-Diisopropyl-N-ethylamine (0.34 mL, 2 mmol) was added to 5-(S)-acetamidomethyl-3-[4'-carboxy-3'-fluorophenyl]oxazolidine-2-one (0.296 g, 1 mmol) and a coupling reagents, [preferably, O-(7-azabenzotriazole-1-yl)-N,N,N',N'-tetramethyluronium hexafluorophosphate (HATU)] in a polar aprotic solvent such as N,N-dimethylformamide (3 mL) and tetrahydrofuran (2 mL), and the solution was kept at r.t. for 20 min. An appropriate amine (1 mmol) was added, followed by an organic base (preferably, N,N-diisopropyl-N-ethylamine, 0.17 mL, 1 mmol), and the mixture stirred at 20–60° C. for 1–24 h (typically, at r.t. for 1–2 h). Additional base (typically, 1 mmol) was added when amine salts were employed. Optionally, catalytic 4-dimethylaminopyridine (0.05–0.2 mmol) was added for acylation of less reactive amines. Volatile organic solvents were removed in vacuo. The product was typically isolated by precipitation with excess of water (5–60 mL), or by extraction from aqueous solutions with ethyl acetate (20–40 mL). In the latter case, organic layers were washed with saturated aqueous sodium bicarbonate, water, 3% aqueous citric acid, water, brine, and dried ($MgSO_4$). Organic solvent was removed in vacuo, and the product further purified by washing with excess of diethyl ether, or by crystallization from an appropriate solvent (typically, methanol or ethanol).

Method D. N-Ethyl-N'-(3diethylaminopropyl) carbodiimide (0.92 g, 4.8 mmol) was added to 5-(S)-acetamidomethyl-3-[4-carboxy-3'-fluorophenyl]oxazolidine-2-one (1.18 g, 4.0 mmol) and pentafluorophenol (0.81 g, 4.4 mmol) in N,N-dimethylfomamide (50 mL) and the solution stirred at r.t. for 24 h. Most of solvent was removed in vacuo, the residue dissolved in acetonitrile (ca. 40 mL), and this solution added dropwise with stirring into 3% aqueous citric acid (ca. 150 mL). Precipitated 5-(S)-acetamidomethyl-3-[4'-(pentafluorophenyl)oxycarbonyl-3'-fluorophenyl]oxazolidine-2-one was filtered off, washed with water, and dried in vacuo (yield 1.30 g, 70%; M.p. 172–173° C.; Rt 5.2 min). The resulting ester (1 mmol) was dissolved in a polar solvent (preferably, tetrahydrofuran or acetonitrile 10 mL), and an appropriate amine (1–5 mmol) added. The mixture was stirred at r.t. for 1–10 h (typically, 1–2 h). Solvent and excess reagent were removed in vacuo, and the product purified by chromatography or crystallization from an appropriate solvent 5-(S)-Acetamidomethyl-3-[4'-(6"-chloropyridine-3"-yl)aminocarbonyl-3'-fluorophenyl]oxazolidine-2-one Method A. Prepared according to Method A of the General Procedures for Preparation of 5-(S)-(N-Acylaminomethyl)-3-[4'-(4"-(un)substituted amino)carbonyl-3'-fluorophenyl]-oxazolidine-2-ones from BAL resin immobilized 5-(S)-acetamidomethyl-3-[4'-(pentafluorophenyl)oxycarbonyl-3'-fluorophenyl]-oxazolidine-2-one and 2-chloro-5-amino-pyridine in 10% pyridine in N-methylpyrrolidine-2-one (70° C., 48 h). MS: 407 [M+H]$^+$. To obtain the hydrochloride form of this compound, above material (41 mg, ca. 0.1 mmol) was dissolved in methanol (10 mL) with 2M HCl in 1,4-dioxane (5 mL). Resulted solution was filtered, solvents removed in vacuo, and the crude salt washed with excess of diethyl ether.

Method B. Prepared according to Method B of the General Procedures for Preparation of 5-(S)-(N-Acylaminomethyl)-3-[4'-(4"-(un)substituted amino)-carbonyl-3'-fluoro-phenyl]-oxazolidine-2-ones by amide coupling of 5-(S)-azidomethyl-3-[4'-chlorocarbonyl-3'-fluorophenyl]oxazolidine-2-one and 2-chloro-5-aminopyridine in pyridine (3 mL, r.t., 1 h). Solvent was removed in vacuo, and resulting 5-(S)-azidomethyl-3-[4'-(6"-chloropyridine-3"-yl)aminocarbonyl-3'-fluorophenyl] oxazolidine-2-one was washed with water (5×3 mL mL), and dried in vacuo. Triphenylphosphine (0.262 g, 1.0 mmol) in tetrahydrofuran,(10 mL) was added to above azide intermediate, and the mixture stirred at 45° C. for 2 h. Water (0.5 mL) was added, and the mixture stirred overnight at 50° C. Solvents were removed in vacuo, and resulting crude amine intermediate washed with excess diethyl ether. Tetrahydrofuran (15 mL) was added, followed by pyridine (0.25 mL) and acetic anhydride (0.2 mL), and the mixture stirred at r.t for 1 h. Solvents were removed in vacuo, and resulting product washed with excess diethyl ether. MS: 407 [M+H]$^+$. $^1$H NMR.

5-(S)-Acetamidomethyl-3-[4'-(thiazole-2"-yl)aminocarbonyl-3'-fluorophenyl]-oxazolidine-2-one Method A. Prepared according to Method A of the General Procedures for Preparation of 5-(S)-N-Acylaminomethyl)-3-[4'-(4"-(un)substituted amino) carbonyl-3'-fluorophenyl]-oxazolidine-2-ones from BAL resin immobilized 5-(S)-acetamidomethyl-3-[4'-(pentafluorophenyl)oxycarbonyl-3'-fluorophenyl] oxazolidine-2-one and 2-aminothiazole in 10% pyridine in N-methylpyrrolidine-2-one (r.t., 24 h). MS: 379 [M+H]$^+$. $R_t$ 3.8 min. To obtain the hydrochloride form of this compound, above material (38 mg, ca. 0.1 mmol) was dissolved in methanol (10 mL) with 2M HCl in 1,4-dioxane (5 mL), filtered, solvents removed in vacuo, and the residue washed with excess of diethyl ether.

Method B. Prepared according to Method C of the General Procedures for Preparation of 5-(S)-N-Acylaminomethyl)-3-[4'-(4"(un)substituted amino)-carbonyl-3'-fluorophenyl]-oxazolidine-2-ones from 5-(S)-acetamidomethyl-3-[4'-carboxy-3'-fluorophenyl] oxazolidine-2-one and 2-aminothiazole (0.10 g, 1 mmol). The synthesis was performed at r.t. overnight. Tetrahydrofuran was removed in vacuo, and the residue added to water (60 mL). Resulted suspension was kept at r.t. for 1 h, filtered, and the product washed with excess water and dried in vacuo.

5-(S)-Acetamidomethyl-3-[4'-(4,5-dimethylthiazole-2"-yl)aminocarbonyl-3'-fluorophenyl]-oxazolidine-2-one Method A. Prepared according to Method A of the General Procedures for Preparation of 5-(S)-(N-Acylaminomethyl)-3-[4'-(4"-(un)substituted amino) carbonyl-3'-fluorophenyl]-oxazolidine-2-ones from BAL resin immobilized 5-(S)-acetamidomethyl-3-[4'-pentafluorophenyl)oxycarbonyl-3'-fluorophenyl]-oxazolidine-2-one and 2-amino-4,5-dimethylthiazole in 10% pyridine in N-methylpyrrolidine-2-one (r.t., 24 h). MS: 407 [M+H]$^+$. Rt 4.1 min. $^1$H NMR.

Method B. Prepared according to Method C of the General Procedures for Preparation of 5-(S)-(N-Acylaminomethyl)-3-[4'-(4"-(un)substituted amino) carbonyl-3'-fluorophenyl]-oxazolidine-2-ones from 5-(S)-acetamidomethyl-3-[4'-carboxy-3'-fluorophenyl] oxazolidine-2-one and 2-amino4,5-dimethyl-thiazole. The synthesis was performed at r.t for 3 h. MS: 407 [M+H]$^+$. Rt 4.1 min. $^1$H NMR.

5-(S)-Acetamidomethyl-3-[4'-(pyrimidine-4"-yl)aminocarbonyl-3'-fluorophe-nyl]-oxazolidine-2-one Method A. Prepared according to Method A of the the General Procedurse for Preparation of 5-(S)-(N-Acylaminomethyl)-3-[4'-(4"-(un)substituted amino)

carbonyl-3'-fluorophenyl]-oxazolidine-2-ones from BAL resin immobilized 5-(S)-acenidomethyl-3-[4'-(pentafluorophenyl)oxycarbonyl-3'-fluorophenyl]-oxazolidine-2-one and 4-aminopyrimidine in 10% pyridine in N-methylpyrrolidine-2-one (70° C., 48 h). MS: 374 [M+H]$^+$. Rt 3.4 min. $^1$H NMR.

Method B. Prepared according to Method C of the General Procedures for Preparation of 5-(S)-(N-Acylaminomethyl)-3-[4'-(4"-(un)substituted amino)-carbonyl-3'-fluorophenyl]-oxazolidine-2-ones from 5-(S)-acetamidomethyl-3-[4'-carboxy-3'-fluorophenyl] oxazolidine-2-one and 4-aminopyrimidine. The synthesis was performed at r.t. for 24 h. Water (15 mL) was, and the mixture kept at r.t for 3 days to allow for product crystallization. MS: 374 [M+H]$^+$. Rt 3.4 min. $^1$H NMR.

5-(S)-Acetamidomethyl-3-[4'-(thiazole-2"-yl) aminocarbonyl-3'-fluorophenyl]-oxazolidine-2-one Method A. Prepared according to the General Procedure for preparation of 5-(S)-(N-acylaminomethyl)-3-[4'-(4"-(un) substituted amino)carbonyl-3'-fluoro-phenyl]oxazolidine-2-ones from BAL resin immobilized 5-(S)-acetamidomethyl-3-[4'-(pentafluorophenyl)oxycarbonyl-3'-fluorophenyl]oxazolidine-2-one and 5-chloro-2-aminothiazole in 10% pyridine in N-methylpyrrolidine-2-one (70° C., 48 h). MS: 413 [M+H]$^+$. $^1$H NMR.

Method B. Prepared according to Method B of the General Procedures for Preparation of 5-(S)-(N-Acylaminomethyl)-3-[4'-(4"-(un)substituted amino)-carbonyl-3'-fluoro-phenyl]-oxazolidine-2-ones by amide coupling of 5-(S)-azidomethyl-3-[4'-chlorocarbonyl-3'-fluorophenyl]oxazolidine-2-one and 5-chloro-2-aminothiazole hydrochloride in tetrahydrofuran (ca. 4 mL) and acetonitrile (2.5 mL) with pyridine (0.5 mL). The mixture was stirred for 2 h at r.t., and methanol (ca. 7 mL) was added. Resulted precipitate of 5-(S)-azidomethyl-3-[4'-(thiazole-2"-yl)aminocarbonyl-3'-fluorophenyl]-oxazolidine-2-one was filtered, washed with methanol (8 mL), diethyl ether, and dried in vacuo. Triphenylphosphine (0.31 g, 1.2 mmol) in N-methylpyrrolidine-2-one (1.25 mL) and tetrahydrofuran (1.25 mL) was added to above azide intermediate, and the mixture stirred at r.t. for 2 h. Water (0.1 mL) was added, and the mixture stirred overnight at 50° C. Solvents were removed in vacuo, and resulting crude amine intermediate washed with excess diethyl ether. Tetrahydrofuran (8 mL) was added, followed by pyridine (0.5 mL) and acetic anhydride (0.5 mL), and the mixture stirred at r.t. for 30 min. Solvents were removed in vacuo, and resulting product washed with excess diethyl ether, water (2×3 mL), diethyl ether, and dried in vacuo. MS: 413 [M+H]$^+$. $^1$H NMR.

5-(S)-(Methylthio)acetamidomethyl-3-[4'-(6"chloropyridine-3"-yl)amino-carbonyl-3'-fluorophenyl]-oxazolidine-2-one Prepared according to Method A of the General Procedures for Preparation of 5-(S)-N-Acylaminomethyl)-3-[4'-(4"-(un)substituted amino)carbonyl-3'-fluorophen-yl] oxazolidine-2-ones from BAL resin immobilized 5-(S)-(methylthio)acetamidomethyl-3-[4'-(pentafluorophenyl)-oxycarbonyl-3'-fluorophenyl]-oxazolidine-2-one and 2-chloro-5-aminopyridine. MS: 453 [M+H]$^+$. To obtain the hydrochloride form of this compound, above material (45 mg, ca. 0.1 mmol) was dissolved in methanol (10 mL) with 2M HCl in 1,4-dioxane (5 mL), filtered, solvents removed in vacua, and the residue washed with excess of diethyl ether.

5-(S)-Acetamidomethyl-3-[4'-(benzothiazole-2"-yl) aminocarbonyl1–3 ,-fluorophenyl]-oxazolidine-2-one Prepared according to Method C of the General Procedures for Preparation of 5-(S)-(N-Acylaminomethyl)-3-[4'-(4"-(un)substituted amino)carbonyl-3'-fluorophenyl] oxazolidine-2-ones from 5-(S)-acetamidomethyl-3-[4'-carboxy-3'-fluorophenyl]oxazolidine-2-one and 2-aminobenzothiazole. The synthesis was performed at rt. over 3 h. MS: 429 [M+H]$^+$. Rt 4.6 min. $^1$H NMR.

5-(S)-Acetamidomethyl-3-[4'-(6"-methoxybenzothiazole-2"-yl)aminocarbonyl-3'-fluorophenyl]-oxazolidine-2-one Prepared according to Method C of the General Procedures for Preparation of 5-(S)-(N-Acylaminomethyl)-3-[4'-(4"-(un)substituted amino)carbonyl-3'-fluorophenyl] oxazolidine-2-ones from 5-(S)-acetamidomethyl-3-[4'-carboxy-3'-fluorophenyl]oxazolidine-2-one and 6-methoxy-2-aminobenzothiazole. The synthesis was performed at r.t. over 3 h. MS: 459 [M+H]$^+$. Rt 4.7 min. $^1$H NMR. 5-(S)-Acetamidomethyl-3-[4'-(6"-methoxybenzothiazole-2"-yl) aminocarbonyl-3'-fluorophenyl]-oxazolidine-2-one Prepared according to Method C of the General Procedures for Preparation of 5-(S)-(N-Acylaminomethyl)-3-[4'-(4"-(un)substituted amino)-carbonyl-3'-fluorophenyl]-oxazolidine-2-ones from 5-(S)-acetamidomethyl-3-[4'-carboxy-3'-fluorophenyl]oxazolidine-2-one and 5-methylthio-3-aminopyridine. The synthesis was performed at r.t. overnight. MS: 419 [M+H]$^+$. Rt 3.8 min. $^1$H NMR.

5-(S)-Acetamidomethyl-3-[4'-(4"-amino-5"-phenylthiazole-2"-yl)aminocarbo-nyl-3'-fluorophenyl]-oxazolidine-2-one Prepared according to Method C of the General Procedures for Preparation of 5-(S)-(N-Acylaminomethyl)-3-[4'-(4"-(un)substituted amino)carbonyl-3'-fluorophen-yl] oxazolidine-2-ones from 5-(S)-acetamidomethyl-3-[4'-carboxy-3'-fluorophenyl]oxazolidine-2-one and 2,4-diamino-5-phenylthiazole hydrobromide. The synthesis was performed at r.t. overnight. MS: 470 [M+H]$^+$. Rt 4.5 min. $^1$H NMR.

5-(S)-Acetamidomethyl-3-[4'-(5"-ethylthio-1,3,4-thiadiazole-2"-yl)aminocarbo-nyl-3'-fluorophenyl] oxazolidine-2-one Prepared according to Method C of the General Procedures for Preparation of 5-(S)-(N-Acylaminomethyl)-3-[4'-(4"-(un)substituted amino)carbonyl-3'-fluorophen-yl] oxazolidine-2-ones from 5-(S)-acetamidomethyl-3-[4'-carboxy-3-fluorophenyl]oxazolidine-2-one and 5-ethylthio-2-amino-1,3,4-thiadiazole. MS: 440 [M+H]$^+$. R$_t$ 4.4 min. $^1$H NMR.

5-(S)-Acetamidomethyl-3-[4'-(1,3,4-thiadiazole-2"-yl) aminocarbo-nyl-3'-fluorophenyl]oxazolidine-2-one Prepared according to Method C of the General Procedures for Preparation of 5-(S)-(N-Acylaminomethyl)-3-[4'-(4"-(un)substituted amino)carbonyl-3'-fluorophen-yl] oxazolidine-2-ones from 5-(S)-acetamidomethyl-3-[4'-carboxy-3'-fluorophenyl]oxazolidine-2-one and 2-amino-1,3,4-thiadiazole. MS: 380 [M+H]$^+$. R$_t$ 3.6 min. $^1$H NMR.

5-(S)-Acetamidomethyl-3-[4'-(imidazole-2"-yl) aminocarbonyl-3'-fluorophen-yl]oxazolidine-2-one Prepared according to Method A of the General Procedures for Preparation of 5-(S)-(N-Acylaminomethyl)-3-[4'-(4"-(un)substituted amino)carbonyl-3'-fluorophenyl] oxazolidine-2-ones from BAL resin immobilized 5-(S)-(methylthio)acetamidomethyl-3-[4'-(pentafluorophenyl) oxycarbonyl-3'-fluorophenyl]oxazolidine-2-one (0.400 g, ca 0.1 mmol) and 2-aminoimidazole sulfate (0.234 g, 2 mmol). The amine reagent was pre-dissolved in a mixture of 10% pyridine in N-methylpyrrolidine-2-one (4 mL), bis-(trimethylsilyl)acetamide (0.5 mL), and 1,8-diazabicyclo [5.4.0]undec-7-ene (0.15 mL, 1 mmol) at 70° C. over 2 h.

Coupling with the resin reagent was performed at r.t. over 48 h. The crude product after cleavage from resin was purified by reverse-phase HPLC. MS: 362 [M+H]+. $^1$H NMR.

5-(S)-Acetamidomethyl-3-[4'-(1,3,4-triazole-2"-yl) aminocarbonyl-3'-fluorophe-nyl]oxazolidine-2-one Prepared according to Method A of the General Procedures for Preparation of 5-(S)-(N-Acylaminomethyl)-3-[4'-(4"-(un)substituted amino)carbonyl-3'-fluorophenyl] oxazolidine-2-ones from BAL resin immobilized 5-(S)-(methylthio)acetamidomethyl-3-[4'-(pentafluorophenyl) oxycarbonyl-3'-fluorophenyl]oxazolidine-2-one (0.400 g, ca. 0.1 mmol) and 2-amino-1,3,4-triazole (0.168 g, 2 mmol). The amine reagent was predissolved in a mixture of 10% pyridine in N-methylpyrrolidine-2-one (4 mL), bistrimethylsilyl)acetamide (0.5 mL) at 70° C. over 2 h. Coupling with the resin reagent was performed at 60° C. over 48 h The crude product after cleavage from resin was purified by reverse phase HPLC. MS: 363 [M+H]+. R$_t$ 3.1 min. $^1$H NMR.

5-(S)-Acetamidomethyl-3-[4'-pyridine-3"-yl-1"-oxide) aminocarbonyl-3'-flu-orphenyl]-oxazolidine-2-one 30% Aqueous hydrogen peroxide (0.05 mL) was added to 5-(S)-acetamidomethyl-3-[4'-(3"-pyridylamino)carbonyl-3'-fluoro-phenyl]-oxazolidine-2-one (7 mg, ca. 0.02 mmol) and methylrhenium trioxide (MTO, 0.9 mg) in N-methylpyrrolidine-2-one (0.15 mL). The mixture was stirred for 30 min at r.t., and solvents removed in vacuo (0.1 Torr, r.t.). The crude product was washed with methanol (0.5 mL) and diethyl ether. MS: 389 [M+H]+. R$_t$ 3.3 min. $^1$H NMR.

5-(S)-Acetamidomethyl-3-[4'-hydroxyaminocarbonyl-3'-fluorophenyl]-oxazolidine-2-one Prepared according to Method D of the General Procedures for Preparation of 5-(S)-(N-Acylaminomethyl)-3-[4'-(4"-(un)substituted amino)carbonyl-3'-fluorophenyl] oxazolidine-2-ones from 5-(S)-acetamidomethyl-3-[4'-(pentafluorophenyl)oxycarbonyl-3'-fluorophenyl]-oxazolidine-2-one (0.046 g, 0.1 mmol) and O-trimethylsilylhydroxylamine (0.052 mL, ca. 0.5 mmol) in tetrahydrofuran (1 mL). The synthesis was performed for 2 h at r.t. Diethyl ether (4 mL) was added, the precipitated product washed with diethyl ether, tetrahydrofuran (2×0.5 mL), excess ether, and dried in vacuo. MS: 312 [M+H]+. R$_t$ 2.8 min. $^1$H NMR.

5-(S)-Acetamidomethyl-3-[4'-methylaminocarbonyl-3'-fluorophenyl]-oxazo-lidine-2-one Prepared according to Method D of the General Procedures for Preparation of 5-(S)-(N-Acylaminomethyl)-3-[4'-(4"-(un)substituted amino)carbonyl-3'-fluorophenyl] oxazolidine-2-ones from 5-(S)-acetamido-methyl-3-[4'-(pentafluorophenyl)oxycarbonyl-3'-fluorophenyl]-oxazolidine-2-one (0.046 g, 0.1 mmol) and 2 M methylamine in tetrahydrofuran (1 mL, 2 mmol). The synthesis was performed at r.t for 45 min. Diethyl ether (4 mL) was added, the precipitated product washed with diethyl ether, tetrahydrofuran (2×0.5 mL), excess ether, and dried in vacuo. MS: 310 [M+H]+. R$_t$ 3.2 min. $^1$H NMR.

5-(S)-trans-[4"-Methoxyimino)cinnamoyl]methyl-3-[4'-aminocarbonyl-3'-flu-orophenyl]oxazolidine-2-one Prepared according to Method A of the General Procedures for Preparation of 5-(S)-(N-Acylaminomethyl)-3-[4'-(4"-(un)substituted amino)carbonyl-3'-fluorophenyl] oxazolidine-2-ones from BAL resin immobilized 5-(S)-[trans-(4"-methoxyimino)cinnamoyl)methyl-3-[4'-(pentafluorophenyl)oxycarbonyl-3'-fluorophenyl] oxazolidine-2-one (0.400 g, ca 0.1 mmol) and 2 M ammonia in 1,4-dioxane (5 mL, ca. 10 mmol). The synthesis was performed at r.t. overnight. The crude product after cleavage from resin was purified by reverse phase HPLC. MS: 441 [M+H]+. $^1$H NMR.

General Procedure for Preparation of 5-(S)-Amidomethyl-3-[4'-[(un)substituted 1",3",5"-triazine-2"-yl] amino-3'-fluorophenyl]oxazolidine-2-one An appropriate BAL resin immobilized 5-(S)-acylaminomethyl-3-[4'-(9"-fluorenylmethoxycarbonyl) amino-3'-fluorophenyl]oxazolidine-2-one (0.06–0.1 mmol) was deprotected by agitation with 20% piperidine in DMF (4 mL) for 45 min. Resulted aniline resin was washed liberally with N,N-dimethylformamide, dichloromethane, methanol, and dried in vacuo. A solution of an appropriate halogen-substituted triazine reagent (preferably, a chlorotriazine derivative, 1–3 mmol) and organic base (preferably N,N-diisopropyl-N-ethylamine or 2,6-di-t-butylpyridine, 3–6 mmol) in aprotic solvent (preferably, N-methylpyrrolidine-2-one, dichloromethane, 1,4-dioxane, or acetonitrile) was added, and the mixture agitated at 0–80° C. for 12–36 h (typically, at 0–40° C. overnight). Resulted aniline resin was washed liberally with N,N-dimethylformamide, dichloromethane, methanol and dried in vacuo. When the triazine oxazolidinone contained more than one halogen substituent, the reaction was optionally repeated using amine, thiol, or alcohol reagents as described above (40–80° C., 12–36 h). Washed and dry resin was cleaved with 60% trifluoroacetic acid in dichloromethane (5 ml, 2 h). Resulted supernatant was evaporated in vacuo, and the crude product purified by HPLC or TLC.

5-(S)-Acetamidomethyl-3-[4'-(4"-chloro-6"-1",2",3"-triazine-2"-yl)amino-3'-fluorophenyl]oxazolidine-2-one BAL resin immobilized 5-(S)-acetamidomethyl-3-[4'-(9"-fluorenylmethoxycarbonyl)amino-3'-fluorophen-yl] oxazolidine-2-one (0.06 mmol) was deprotected by agitation with 20% piperidine in DMF (4 mL) for 45 min. Resulted aniline resin was washed liberally with N,N-dimethylformamide, dichloromethane, methanol, and dried in vacuo. A solution of cyanuric trichloride (0.194 g, 1.0 mmol) and 2,6-di-t-butylpyridine (0.36 mL, 1.5 mmol) in dichloromethane (4 mL) was added, and the mixture agitated at r.t. for 24 h. Resulted aniline resin was washed liberally with N,N-dimethylformamide, dichloromethane, methanol, and dried in vacuo. 0.5 M Ammonia in 1,4-dioxane (5 mL, 2.5 mmol) was added, and the mixture agitated at r.t. for 24 h. The resin was washed liberally with N,N-dimethylformamide, dichloromethane, methanol, dried in vacuo, and cleaved with 60% trifluoroacetic acid in dichloromethane (5 ml, 2 h). Resulting supernatant was evaporated In vacuo, and the crude product purified by preparative TLC (eluent methanol-dichloromethane 1:10). MS: 396 [M+H]+. R$_t$ 3.6 min. $^1$H NMR.

5-(S)-Acetamidomethyl-3-[4'-(4",6"-dimethoxy-1",3",5"-triazine-2"-yl)amino-3'-fluoro-phenyl]oxazolidine-2-one Prepared according to the General Procedure for Preparation of 5-(S)-Amidomethyl-3-[4'-[(un)substituted triazinyl]-3'-fluorophenyl]oxazolidine-2-one from BAL resin immobilized 5-(S)-acetamidomethyl-3-[4-(9"-fluorenylmethoxycarbonyl)amino-3'-fluorophe-nyl] oxazolidine-2-one (0.06 mmol) and 2-chloro-4,6-dimethoxytriazine (0.275 g, 1.5 mmol). Reaction of the immobilized aniline and the triazine reagent was repeated twice in a mixture of N-methylpyrrolidine-2-one and dichloromethane (1:1, 4 mL) at r.t. overnight. The crude cleaved product was purified by preparative TLC (eluent methanol-dichloromethane 1:10). MS: 407 [M+H]+. $^1$H NMR.

Acylamino Oxazolidinone Derivatives

General Procedure for Preparation of 5-(S)-(N-Acylaminomethyl)-3-[4'-acylamino-3'-fluorophenyl] oxazolidine-2-ones An appropriate BAL resin immobilized 5-(S)-acetamidomethyl-3-[4'-(9"-fluorenylmethoxycarbonyl)amino-3'-fluorophen-yl]oxazolidine-2-one (0.1 mmol) was deprotected by agitation with 20% piperidine in DMF (4 mL) for 45 min. Resulting aniline resin was washed liberally with N,N-dimethylformamide, dichloromethane, methanol, and dried in vacuo. Separately, N,N-diisopropyl-N-ethylamine (3–6 mmol; typically, 3 mmol) was added to selected carboxylic acid (1–2 mmol; typically, 1 mmol) and a coupling reagent [preferably, O-(7-azabenzotriazole-1-yl)-N,N,N',N'-tetramethyluronium hexafluorophosphate or diisopro-pylcarbodiimide; 3–6 mmol; typically, 3 mmol) in a polar aprotic solvent such as N,N-dimethylformamide (7–10 mL, and the mixture agitated at r.t. for 20–30 min. Resulted solution of the pre-activated acid reagent was added to above aniline resin, and the mixture agitated at 20–60° C. for 6–24 h (typically, at r.t. overnight). The resin was washed liberally with N,N-dimethylformamide, dichloromethane, methanol, dried in vacuo, and cleaved with 60% trifluoroacetic acid in dichloromethane (5 ml, 2 h). Resulting supernatant was evaporated in vacuo, and the crude product purified by HPLC or TLC.

5-(S)-(N-Acetamidomethyl)-3-[4'-acetamido-3'-fluorophenyl]oxazolidine-2-ones

Prepared according to the General Procedure for Preparation of 5-(S)-N-Acylaminomethyl)-3-[4'-acylamino-3'-fluorophenyl]oxazolidine-2-ones from BAL resin immobilized 5-(S)-acetamidomethyl-3-[4'-(9"-fluorenylmethoxycarbonyl)amino-3'-fluorophenyl]oxazolidine-2-one (0.1 mmol). The intermediate aniline was acylated with the mixture of acetic anhydride-pyridine-dichloromethane (1:1.5:3, 2 mL). Crude cleaved product was purified by TLC (eluent: 10% methanol in dichloromethane). Yield 0.014 g (46%). MS: 310 [M+H]$^+$. $^1$H NMR.

5-(S)-N-Acetamidomethyl)-3-[4'-(2",4"-thiazole-5"-yl)carbonylamino-3'-fluorophenyl]oxazolidine-2-ones Prepared according to the General Procedure for Preparation of 5-(S)-(N-Acylaminomethyl)-3-[4'-acylamino-3'-fluorophenyl]oxazolidine-2-ones from BAL resin immobilized 5-(S)-acetamidomethyl-3-[4'-(9"-fluorenylmethoxycarbonyl)amino-3'-fluorophen-yl]oxazolidine-2-one (0.1 mmol). Acylation was performed with 2,4-dimethylthiazole-5-carboxylic acid (0.157 g, 1 mmol) pre-activated with diisopropylcarbodiimide (0.086 mL, 0.55 mmol) and pyridine (0.081 mL, 1 mmol) in a mixture of N,N-dimethylformamide-dichloromethane 4:1 (2 mL) at r.t. overnight. Crude cleaved product was purified by TLC (eluent: 10% methanol in dichloromethane). Yield 0.028 g (68%). MS: 407 [M+H]$^+$. $^1$H NMR.

5-(S)-(N-Acetamidomethyl)-3-[4'-(4-pyridine-3"-yl)carbonylamino-3'-fluoro-phenyl]oxazolidine-2-ones Prepared according to the General Procedure for Preparation of 5-(S)-(N-Acylaminomethyl)-3-[4'-acylamino-3'-fluorophenyl]oxazolidine-2-ones from BAL resin inmobilized 5-(S)-acetamidomethyl-3-[4'-(9"-fluorenylmethoxycarbonyl)amino-3'-fluorophen-yl]oxazolidine-2-one (0.02 mmol). Acylation was performed with nicotinic acid (0.049 g, 0.40 mmol) pre-activated with O-(7-azabenzotriazole-1-yl)-N,N,N',N'-tetramethyluronium hexafluorophosphate (0.160 g, 0.20 mmol) and N,N-diisopropyl-N-ethylamine (0.21 mL, 1.20 mmol) in N,N-diethylformamide (1 mL) at r.t. overnight. Crude cleaved product was purified by TLC (eluent: 10% methanol in dichloromethane). Yield 0.023 g (62%). MS: 373 [M+H]$^+$. $^1$H NMR.

Sulfonamido Oxazolidinone Derivatives

General Procedure for Preparation of 5-(S)-(N-Acylaminomethyl)-3-[4'-sulfonamido-3'-fluorophenyl]oxazolidine-2-ones An appropriate BAL resin immobilized 5-(S)-acylaminomethyl-3-[4'-(9"-fluorenylmethoxycarbonyl)amino-3'-fluorophenyl]oxazolidine-2-one (0.1 mmol) was deprotected by agitation with 20% piperidine in DMF (4 mL) for 45 min. Resulted aniline resin was washed liberally with N,N-dimethylformamide, dichloromethane, methanol, and dried in vacuo. The resin was suspended in 20% pyridine in dichloromethane (2 mL), and a solution of selected sulfonyl chloride reagent (1–2 mmol; preferably, 1.25 mmol) in dichloromethane was added. The mixture was agitated at 20–40° C. for 12–36 h (typically, at r.t. overnight). Resin was filtered, washed with methanol, and suspended in 0.1M lithium hydroxide monohydrate in methanol (4 mL). The mixture was agitated at r.t. for 30–90 min (typically, for 90 min). The resin was filtered, washed liberally with N,N-dimethylformamide, dichloromethane, methanol, dried in vacuo, and cleaved with 60% trifluoroacetic acid in dichloromethane (5 ml, 2 h). Resulted supernatant was evaporated in vacuo, and the crude product purified by HPLC or TLC.

5-(S)-(N-Acylaminomethyl)-3-[4'-methylsulfonamido-3'-fluorophenyl]-oxazolidine-2-ones Prepared according to the General Procedure for Preparation of 5-(S)-(N-Acylaminomethyl)-3-[4'-sulfonamido-3'-fluorophenyl]oxazolidine-2-ones from 5-(S)-acylaminomethyl-3-[4'-(9"-fluorenylmethoxycarbonyl)amino-3'-fluorophenyl]oxazolidine-2-one (0.1 mmol) and methanesulfonyl chloride (0.2 mL, 1.25 mmol). The crude cleaved product was purified by TLC (eluent: 10% methanol in dichloromethane). Yield 0.022 g (65%). MS (m/z): 346 [M+H]$^+$. $^1$H NMR.

5-(S)-(N-Acylaminomethyl)-3-[4'-(benzo-2",1",3"-thiadiazole-4"-yl)sulfonamido-3'-fluorophenyl]oxazolidine-2-ones Prepared according to the General Procedure for Preparation of 5-(S)-(N-Acylaminomethyl)-3-[4'-sulfonamido-3'-fluorophenyl]oxazolidine-2-ones from 5-(S)-acylaminomethyl-3-[4'-(9"-fluorenylmethoxycarbonyl)amino-3'-fluorophenyl]oxazolidine-2-one (0.1 mmol) and benzo-2,1,3-thiadiazole-4-sulfonyl chloride (0.295 g, 1.25 mmol). The crude cleaved product was purified by TLC (eluent: 10% methanol in dichloromethane). Yield 0.024 g (52%). MS (m/z): 466 [M+H]$^+$.

5-(S)-(N-Acetamidomethyl)-3-[4'-(4",5"-bromothiophene-2"-yl)sulfonamido-do-3'-fluorophenyl]oxazolidine-2-one.

Prepared according to the General Procedure for Preparation of 5-(S)-(N-Acylaminomethyl)-3-[4'-sulfonamido-3'-fluorophenyl]oxazolidine-2-ones from from BAL resin immobilized 5-(S)-acylaminomethyl-3-[4'-(9"-fluorenylmethoxycarbonyl)amino-3'-fluorophen-yl]oxazolidine-2-one (0.1 mmol) and 2,3-dibromothiophene-5-sulfonyl chloride (0.43 g, 1.25 mmol). The crude cleaved product was purified by TLC (eluent: 10% methanol in dichloromethane). Yield 0.044 g (77%). $^1$H NMR. MS (m/z): 572 [M+H]$^+$.

5-(S)-(N-Acetamidomethyl)-3-[4'-(6"-chloroimidazo[2,1-b]thiazole-5"-yl)sulfonamido-3'-fluorophenyl]oxazolidine-2-one.

Prepared according to the General Procedure for Preparation of 5-(S)-(N-Acylaminomethyl)-3-[4'-sulfonamido-3'-fluorophenyl]oxazolidine-2-ones from from BAL resin immobilized 5-(S)-acylamino-methyl-3-[4'-(9"- fluorenylmethoxycarbonyl)amino-3'-fluorophenyl] oxazolidi-ne-2-one (0.1 mmol) and 6-chloro-imidazo[2,1-b]thiazole-5-sulfonyl chloride (0.32 g, 1.25 mmol). The crude cleaved product was purified by TLC (eluent: 10% methanol in dichloromethane). Yield 0.019 g (39%). $^1$H NMR. MS (m/z): 572 [M+H]$^+$.

5-(S)-(N-Acetamidomethyl)-3-[4'-(2"-acetamido-4"-methylthiazole-5"-yl)-sulfonamido-3'-fluorophenyl] oxazolidine-2-one.

Prepared according to the General Procedure for Preparation of 5-(S)-(N-Acylaminomethyl)-3-[4'-sulfonamido-3'-fluorophenyl]oxazolidine-2-ones from from BAL resin immobilized 5-(S)-acylamino-methyl-3-[4-(9"-fluorenylmethoxycarbonyl)-amino-3'-fluorophenyl] oxazolidine-2-one (0.1 mmol) and 2-acetamidomethyl-5-thiazolesulphonyl chloride (0.32 g, 1.25 mmol). The crude cleaved product was purified by TLC (eluent: 10% methanol in dichloromethane). Yield 0.025 g (52%). $^1$H NMR. MS (m/z): 486 [M+H]$^+$.

5-(S)-(N-Acetamidomethyl)-3-[4'-(N-methyl) methylsulfonamido-3'-fluorophenyl]-oxazolidine-2-one BAL resin immobilized 5-(S)-(N-acetamidomethyl)-3-[4'-methylsulfonamido-3'-fluorophenyl]oxazolidine-2-one was prepared from from BAL resin immobilized 5-(S)-acylaminomethyl-3-[4'-(9"-fluorenylmethoxycarbonyl) amino-3'-fluorophe-nyl]oxazolidine-2-one (0.1 mmol) and methanesulfonyl chloride (0.2 mL, 1.25 mmol) as described above in the synthesis of 5-(S)-(N-acetamidomethyl)-3-[4'-methylsulfonamido-3'-fluorophenyl]oxazolidine-2-one. N-Methylpyrrolidine-2-one (2 ml) was added, followed by methyl iodide (0.16 ml, 2.5 mmol) and 1,8-diazabicyclo[5.4.0]undec-7-ene (0.37 ml, 2.5 mmol). The mixture was agitated overnight at r.t. The resin was filtered, washed thoroughly with dichloromethane and methanol, and dried under vacuum. Oroduct was cleaved with 60% trifluoroacetic acid in dichloromethane (5 mL, 2 h), solvent removed under vacuum, and the crude product purified by TLC (eluent: 10% methanol in dichloromethane). Yield 0.017 g (48%). $^1$H NMR. MS (m/z): 360 M+H]$^+$.

Procedures for Preparation of 3-(Heteroaryl)oxazolidine-2-one Derivatives.

5-(S)-Azidomethyloxazolidine-2-one 5-(R)-Chloromethyloxazolidine-2-one (prepared according to [Danielmeier et al. Efficient Pathways to (R)- and (S)-hydroxymethyl-2-oxazolidinone and some derivatives. Tetrahedron: Asymmetry. 1995, vol. 6, pp. 1181–1190] (5 mmol) is reacted with sodium azide (7–10 mmol) in acetone (ca. 40–50 mL) at r.t for ca, 24 h (until the reaction is completed). Solids are filtered off, and supernatant evaporated under vacuum to afford the product which is immediately used for the next step. Optionally, the synthesis is performed in dry N,N-dimethylformamide under inert atmosphere with sodium azide (5–10 mmol) or tetrabutylammonium azide (5–10 mmol), and the resulting solution of the crude 5-(S)-azidomethyloxazolidine-2-one is employed for the next step without solvent removal.

5-(S)-Azidomethyl-3-(heteroaryl)oxazolidine2-ones and Application Thereof for Preparation of 3-(Heteroaryl) oxazolidine-2-ones An appropriate heteroarylchloride or heteroarylbromide (e.g. pyridyl, pyrimidyl, thienyl, thiazolyl, or thiadiazolyl halide; 5 mmol) is added to the solution of 5-(S)-azidomethyloxazolidine-2-one (ca. 5 mmol) in dry N,N-dimethylformamide (ca. 30–50 mL) at 0–20° C. (typically, at 10–15° C.), followed by addition of a strong base (typically, sodium hydride, 5–15 mmol). The mixture is stirred at 20–120° C. for 2–24 h (typically, for 6 h at r.t.). Excess base is carefully quenched with acetic acid (to pH ca. 5–7), and most of the solvent is removed under vacuum. Water is added, and the mixture extracted with ethyl acetate. Combined organic layers are washed with water, 3% aq. citric acid, water, and the crude product purified by crystallization from appropriate solvents or by silica gel chromatography. Resulted 5-(S)-azidomethyl-3-(hetero-aryl) oxazolidine-2-ones are immobilized on BAL resin just as described above for the synthesis of BAL resin immobilized 5-(S)-aminomethyl-3-[4'-tert-butoxycarbonyl-3'-fluorophenyl]oxazolidine-2-one, and the polymeric reagents thus obtained are used for synthesis of 3-(heteroaryl) oxazolidine-2-ones analogously to described above procedures for the synthesis of respective 3-(fluorophenyl) oxazolidinones.

5-(S)-Azidomethyl-3-[5'-methoxycarbonyl-6'-trifluoromethylpyrimidine-2'-yl]oxazolidine-2-one The compound is prepared according to above protocol for the synthesis of 5-(S)-azidomethyl-3-heteroaryloxazolidine-2-ones from 2-chloro-5-methoxycarbonyl-6-trifluoromethylpyrimidine (1 mmol) and 5-(S)-azidomethyloxazolidine-2-one (1.2 mmol) in N,N-dimethylformamide (5 mL). The reaction is performed with 60% sodium hydride in oil (3 mmol) at 15–20° C. for ca. 2 h. The crude product is purified by silica gel chromatography.

5-(S)-Azidomethyl-3-[5'-carboxy-6'-trifluoromethylpyrimidine-2'-yl]oxazoli-dine-2-one 0.2 M Lithium or sodium hydroxide in a mixture of tetrahydrofuran-water (ca. 10 mL, 2 mmol) is added to 5-(S)-azidomethyl-3-[5'-methoxycarbonyl-6'-trifluoromethylpyrimidine-2'-yl]oxazolidine-2-one (1 mmol), and the mixture stirred at r.t. until the reaction is completed (by TLC analysis). Tetrahydrofuran is removed under vacuum, 3% aq. citric acid is added (to pH ca. 24), and the acid product is extracted with ethyl acetate. Organic layers are washed with water, brine, and dried (MgSO$_4$). Solvent removed under vacuum and the crude product is purified by silica gel chromatography.

BAL Resin Immobilized 5-(S)-Aminomethyl-3-[5'-carboxy-6'-trifluoromethylpyrimidine-2'-yl]oxazolidine-2-one and Its Application Its Preparation of 3-(Pyrimidyl)oxazolidine-2-ones.

Triphenylphosphine (3 mmol) is added to a mixture of BAL aldehyde resin (0.3 mmol) and 5-(S)-azidomethyl-3-[5'-hydroxy-6'-trifluoromethylpyrimidine-2'-yl]oxazolidine-2-one (3 mmol) in tetrahydrofuran (10 mL) with bis (trimethylsilyl)acetamide (ca. 6 mmol) under nitrogen at r.t. The mixture is agitated at room temperature for 2 h and then at 75° C. for 16 h. The mixture is cooled to room temperature, and 1 M sodium cyanoborohydride in THF (6 mL, 6 mmol) is added in one portion. The reaction mixture is agitated for 6–8 h, resulted amine resin filtered, washed liberally with methanol and dichloromethane, and dried under vacuum. BAL resin immmobilized 5-(S)-aminomethyl-3-[5'-carboxy-6'-trifluoromethylpyrimidine-2'-yl]oxazolidine-2-one thus obtained is further used for synthesis of 3-(pyrimidyl)oxazolidine-2-ones just as described above for the synthesis of respective 3(fluorophenyl)oxazolidinones from BAL resin immobilized 5-(S)-aminomethyl-3-[4'-carboxy-3'-fluorophenyl]-oxazolidine-2-one.

3-(Pyridine-2-yl)oxazolidinone Derivatives t-Butyl 6-chloronicotinate.

Thionyl chloride (25 mL) was added to 6-chloronicotinic acid (5.00 g, 0.0317 mol) containing 1 drop of N,N-dimethylformamide, and the mixture heated under reflux for 2 h. The solution was evaporated under vacuum, and residue thoroughly dried under vacuum. The acid chloride thus obtained was dissolved in tetrahydrofuran (50 mL), and 1 M lithium t-butoxide in tetrahydrofuran (66.6 mL, 0.0666 mol) added dropwise at r.t. The mixture was stirred overnight, diluted with water (100 mL) and extracted with ethyl acetate. The extract was washed with sat. aqueous $NaHCO_3$, brine and dried ($MgSO_4$). Solvent was removed under vacuum to afford the pure ester as an off white solid.

Yield 6.23 g (92%). $^1$H NMR MS (m/z): 214 [M+H]$^+$.

3-(t-Butoxycarbonyl)-6-[(R)propane-1,2-diol-3-yl] aminopyridine

A mixture of t-butyl 6chloronicotinate (4.69 g, 0.0220 mol) and (R)-3-amino-1,2-propanediol (5.00 g, 0.0549 mol) in isopropanol (20 ml) was heated at 100° C. overnight. Solvent was removed under vacuum, and the residue taken up in ethyl acetate, washed with water, brine, dried ($MgSO_4$), and evaporated to give nearly pure product as a yellow oil. Yield 5.90 g (99%). $^1$H NMR. MS: 269 [M+H]$^+$.

5-(R)-Hydroxymethyl-3-[3"-(t-butoxycarbonyl) pyridine6"-yl]oxazolidine-2-one

Triethylamine (0.0518 mL, 0.558 mmol) was added to a solution of 3-(t-butoxy-carbonyl)-6-[(R)-propane-1,2-diol-3-yl]aminopyridine (0.100 g, 0.372 mmol) in dichloromethane (3 mL). The mixture was cooled in an ice bath, and 20% phosgene in toluene (0.236 mL, 0.446 mmol) was added dropwise with stirring. The reaction was allowed to warm to r.t. and stirred for at r.t. for 2 h. Water (3 mL) was added, and the organic layer separated, washed with brine and dried ($MgSO_4$). Evaporation under vacuum afforded a white solid residue which was purified by flash column chromatography (eluent:ethyl acetate-hexanes 1:1). Yield 0.093 g (85%). $^1$HMR. (m/z): 295 [M+H]$^+$.

5-(S)-Azidomethyl-3-[3"-t-butoxycarbonyl)pyridine-6"-yl]oxazolidine-2-one

Methanesulfonyl chloride (1.38 mL, 0.0179 mol) was added dropwise with stirring to a solution of 5-(R)-hydroxymethyl-3-[3'-(t-butoxycarbonyl)pyridine-6"-yl] oxazolidine-2-one (5.00 g, 0.0170 mol) and triethylamine (3.55 mL, 0.0255 mol) in dichloromethane (50 mL) at 0° C. The reaction mixture was allowed to warm to r.t. and then poured into water. The organic layer was separated, washed with water, sat. aq. $NaHCO_3$, brine, and dried ($MgSO_4$). Solvent was removed under vacuum to afford the mesylate intermediate. The intermediate thus obtained was heated with sodium azide (5.53 g, 0.085 mol) in N,N-dimethylformamide (ca. 40 mL) at 65° C. for 12 h. The reaction mixture was diluted with water (ca. 100 mL) and extracted with ethyl acetate. Organic layers was washed with water and brine, and dried ($MgSO_4$). The solvent was removed under vacuum and the residue purified by column chromatography (ethyl acetate-hexanes) to afford the pure product. Rt 5.0 min. $^1$H NMR. MS (m/z): 320 [M+H]+.

5-(S)-(N-Acylaminomethyl)-3-[3"-[(un)substituted amino]carbonylpyridine-6"-yl]oxazolidine-2-ones 5-(S)-Azidomethyl-3-[3'-(t-butoxycarbonyl)pyridine-6"-yl]oxazolidine-2-one is immobilized on BAL-type resin with triphenylphosphine and soodium cyanoborohydride as described above for preparation of BAL resin immobilized 5-(S)-aminomethyl-3-[4'-tert-butoxycarbonyl-3'-fluorophenyl]-oxazolidine-2-one. The polymeric reagent thus obtained is deprotected as described for the preparation of BAL resin immobilized 5-(S)-aminomethyl-3-[4'-carboxy-3'-fluorophenyl]oxazolidine-2-one, and resulting BAL resin immobilized 5-(S)-(N-acylaminomethyl)-3-(3"-carboxypyridine-6"-yl)oxazolidine-2-one employed for the synthesis of 5-(S)-(N-acylaminomethyl)-3-[3"-[(un)substituted amino]carbonylpyridine-6"-yl]-oxazolidine-2-ones analogously to the Method A of the General Procedures for Preparation of 5-(S)-(N-Acylaminomethyl)-3-[4'-[(un)substituted amino]-carbonyl-3'-fluorophenyl]oxazolidine-2-ones 7.

BAL Resin Immobilized 5-(S)-(N-Acylaminomethyl)-3-[3"-(9'''-fluorenylmethoxycarbonyl)amino]pyridine-6"-yl] oxazolidine-2-ones and Application Thereof for Preparation of 3-(Pyridyl)oxazolidinones The compound prepared from BAL resin immobilized 5-(S)-(N-acylaminomethyl)-3-(3"-carboxypyridine-6"-yl) oxazolidine-2-on as described above in the procedure for preparation of BAL resin immobilized 5-(S)-acetamidomethyl-3-[4'-(9"-fluorenylmethoxycarbonyl) amino-3'-fluorophenyl]oxazolidine-2-one. The polymeric reagent thus obtained is further employed, e.g., for synthesis of respective 3"-acylated and 3"-sulfonylated 3-(pyridyl) oxazolidinones just as described above in the General Procedures for Preparation of 5-(S)-(N-Acylaminomethyl)-3-[4'-acylamino-3'-fluorophenyl]-oxazolidine-2-ones 5-(S)-(N-Acylaminomethyl)-3-[4'-sulfonamido-3'-fluoro-phenyl] oxazolidine-2-ones [except that resulting products incorporate 3-(pyridyl)oxazolidinone group instead of 3-(fluorophenyl)oxazolidinone group].

Preparation of immobilized epoxide (12a). To PNP resin (23a) (0.5 g, 0.77 mmol/g loading) at room temperature was added allylamine (125 μL, 1.67 mmol) in 2 mL of DMF. The resin was shaken overnight and then filtered. It was sequentially washed with DMF and DCM. After being dried in vacuo, the olefin resin (24a, 100 mg) was treated with mCPBA (80%, 72 mg, 0.355 mmol) in DCM for 16 hrs. The reaction mixture was filtered, and the resin was washed with DCM. Epoxide resin 12a was provided upon drying in vacuo. See FIG. 25.

General method for the reaction of immobilized epoxide 5 with an amine. To epoxide resin 12a at room temperature was added lithium triflate (LiOTf, 5 equivalents) and the amine (1 M in ACN, 10 equivalents). The mixture was shaken at room temperature for 15 hours, providing resin bound amino alcohol. The resin was filtered and sequentially washed with ACN and DMF. Treatment of the resin with TFA in DCM cleaved the amino alcohol. The reaction mixture was filtered and the resin washed with DCM. Concentration of the filtrate in vacuo provided the free amino alcohol.

Amino Alcohol Library. To an array of individual reaction chambers each containing particles or beads of epoxide resin 12a (25 mg) in ACN was added lithium triflate and an amine unit (0.5 mmol). The amine units of Table 2 were used. The array was shaken at room temperature for 15 hours, filtered and sequentially washed with ACN and DMF. The amino alcohol resin was cleaved upon treatment with TFA. The resin was filtered and washed with DCM. A plurality of amino alcohols was provided upon concentration of the filtrate array in vacuo.

General method for the preparation of oxazolidinones. To the resin bound amino alcohol 8a in DMF at room temperature was added N-methylmorpholine (NMM, 10 equivalents) and carbonyldiimidazole (CDI, 5 equivalents). The resin was shaken for 10 hrs, filtered and sequentially washed with DMF and DCM. Treatment of the resin with TFA in DCM for 0.5 hr cleaved the oxazolidinone. The resin was filtered and washed with DCM. The filtrate was concentrated in vacuo to yield an oxazolidinone amine residue 16a. Semi-preparative HPLC provided pure oxazolidinone amine.

Acetylation of Oxazolidinone Amine. To the crude oxazolidinone amine residue 16a in DCM at room temperature was added pyridine (30 equivalents) and acetic anhydride (20 equivalents). The solution was stirred for 2 hrs and concentrated in vacua. The oxazolidinone acetamide residue was purified by HPLC to provide pure oxazolidinone acetamide.

Oxazolidinone Library. To an array of individual reaction chambers each containing particles or beads of epoxide resin 12a (25 mg) in CAN was added lithium triflate and an amine unit (0.5 mmol). The amine units of Table 2 were used. The array was shaken at room temperature for 15 hours, filtered and sequentially washed with CAN and DMF. To the array of amino alcohol resin was added NMM (10 equivalents) and CDI (5 equivalents). The array was shaken at room temperature for 10 hours, filtered and sequentially washed with DMF and DCM. The oxazolidinone resin was cleaved upon treatment with TFA. The resin was filtered and washed with DCM. The filtrate array was concentrated in vacuo and dissolved in DCM, and treated with pyridine (20 equivalents) and acetic anhydride (10 equivalents) for 30 min. A plurality of oxazolidinones was provided upon concentration of the solution array in vacuo.

Preparation of N-[(3-phenyl-2-oxo-5-oxazolidinyl)methyl]acetamide (22a)

To epoxide resin 12a (100 mg) in ACN at room temperature was added LiOTf (50 mg, 0.32 mmol) followed by aniline (61 μL, 0.66 mmol). After 16 hrs, the mixture was filtered and the resin sequentially washed with ACN and DMF. The resin (50 mg) in DMF (0.5 mL) was treated with CDI (27 mg, 0.17 mmol) and NMM (50 μL) to provide resin bound oxazolidinone 20a. The mixture was allowed to stand for 2 hours, after which the resin was filtered and sequentially washed with DMF and DCM. The resin was treated with TFA (90% in DCM, 1 mL) for 1 h, filtered and washed with DCM. The filtrate was concentrated in vacuo to provide a residue (21a). The residue was treated for 1 h at 0° C. with triethylamine (18 μL, 0.13 mmol) and acetyl chloride (10 μL, 0.13 mmol). In vacuo concentration of the reaction mixture provided crude product, which was purified by semi-preparative HPLC to give oxazolidinone 22a (3.6 mg).

Direct Preparation of Oxazolidinone 20a.

To a solution of N-phenyl O-benzyl carbamate (152 mg, 0.67 mmol) in THF (2 mL) at −78° C. was added n-butyl lithium (1.5 M, 0.6 mL, 0.9 mmol). After stirring for 10 min, epoxide resin 12a (100 mg) was added to the reaction mixture. The mixture was allowed to warm to room temperature and stirred overnight. Saturated ammonium chloride solution was added to the reaction mixture. The resin was filtered and sequentially washed with water, DMF and DCM. A portion of the resin was treated with TFA (90% in DCM, 1 mL) to cleave the oxazolidinone, which was isolated upon in vacuo concentration.

Preparation of N-[(3-(4bromophenyl)-2-oxo-5-oxazolidinyl)methyl]-acetamide.

To epoxide resin 12a (300 mg) in ACN (2 mL) at room temperature was added LiOTf (219 mg, 1.41 mmol) followed by 4-bromoaniline (0.5 g, 2.9 mmol). The reaction mixture allowed to stand overnight. The resin was then filtered, washed sequentially with ACN, DMF and DCM and dried in vacuo. The resin (230 mg) was suspended in DMF (2 mL) at room temperature and treated with CDI (125 mg, 0.77 mmol) and NMM (84 μL, 0.77 mmol). After shaking overnight, the resin was filtered and sequentially washed with DMF and DCM. To a portion of the resin (20 mg) was added TFA (50%/ in DCM, 1 mL) at room temperature and the resulting mixture was stirred for 30 min. The resin was filtered and washed with DCM. The filtrate was concentrated in vacuo to provide a residue. Acetic anhydride (0.1 mL) and pyridine (0.1 mL) were added to the residue in DCM (2 mL). The mixture was concentrated and purified by semi-preparative HPLC to give N-[(3-(4-bromophenyl)-2-oxo-5-oxazolidinyl)methyl]-acetamide (2 mg, 41% theoretical yield). $^1$H NMR.

Preparation of N-[[3-(3-fluoro-4-morpholinylphenyl)-2-oxo-5-oxazolidinyl]-methyl]acetamide (28a).

To epoxide resin 5a (100 mg) in ACN (1.0 mL) at room temperature was added LiOTf (78 mg, 0.5 mmol) followed by 3-fluoro-4-morpholinylaniline (197 mg, 1.0 mmol). The reaction mixture was allowed to stir overnight. The resin was then filtered, sequentially washed with ACN, DMF and DCM and dried in vacuo. A portion of the resin (25a) was suspended in DMF (0.8 mL) and treated with CDI (60 mg, 0.38 mmol) and NMM (100 μL, 0.91 mmol). After shaking overnight, the resin was filtered and washed sequentially with DMF and DCM. To a portion of the resin (26a, 48 mg) was added TFA (90% in DCM, 1 mL) and the resulting mixture was allowed to stand for 1 h. The resin was filtered and washed with DCM. The filtrate was concentrated in vacuo to provide a residue. Acetyl chloride (12 μL, 0.17 mmol) and triethylamine (37 μL, 0.268 mmol) were added to the residue in DCM (2 mL) at 0° C. The mixture was concentrated and purified by semi-preparative HPLC to give N-[[(3-(3-fluoro-4-morpholinylphenyl)-2-oxo-5-oxazolidinyl]methyl]-acetamide 28a (1.8 mg, 15% theoretical yield). $^1$H NMR.

Preparation of N-[[3-(4-fluoro-2-morpholinylphenyl)-2-oxo-5-oxazolidinyl]methyl]-acetamide. To epoxide resin 12a (50 mg) in methanol (0.5 mL) was added 4-fluoro-2-morpholinylaniline (50 mg, 0.255 mmol). The reaction mixture was heated to 60° C. overnight and then allowed to cool to room temperature. The resin was filtered, sequentially washed with methanol and DCM and dried in vacuo. To the resin in DMF (0.5 mL) was added CDI (25 mg, 0.15 mmol) and NMM (50 μL, 0.45 mmol). The reaction mixture was shaken for 4 hrs. The mixture was filtered, and the resin was sequentially washed with DMF and DCM. A portion of the resin (19 mg) was treated with TFA (90% in DCM, 1 mL) for 1 h. The reaction mixture was filtered, and the resin was washed with DCM. The filtrate was concentrated to provide a residue. The residue was dissolved in DCM (2 mL) and treated with pyridine (100 μL) and acetic anhydride (100 μL) at room temperature for 1 h. The mixture was concentrated in vacuo and purified by semi-preparative HPLC to give N-[[3-(4-fluoro-2-morpholinylphenyl)-2-oxo-5-oxazolidinyl]methyl]acetamide (1.8 mg, 36% theoretical yield). $^1$H NMR.

Attachment of Amine 32a to a solid support. To dry Peg HS HCl resin (30 g, Perseptive Inc.) was added DIEA (30% in DCM, 150 mL). The mixture was stirred at room temperature for 30 min. The resin was filtered, sequentially washed with DCM, methanol and DCM and dried in vacuo. To 30 g. (18 mmol) of the resin in DMF (80 mL) were added Bal Linker 30a (8.04 g, 1.7 eq., Perseptive Inc.), HATU (11.3 g, 1.6 eq.) and DIEA (18 mL, 3.5 eq.). The reaction mixture was allowed to stand overnight at room temperature. The mixture was filtered and the resin was sequentially washed with DMF, MeOH, DCM and TMOF. To the resin was added amine 32a (18.2 g, 3 eq.) in 100 mL of TMOF. The mixture was stirred for 1 h, after which 50 mL of a NaBH$_3$(CN)-THF solution (1 M) was added. The reaction mixture was stirred for 30 min., filtered and sequentially washed with methanol and DCM. In vacuo concentration of the filtrate afforded amine resin 33a. Cleavage of a portion of the resin with TFA provided a 70% theoretical loading yield (0.6 mmol/g) of amine 32a. $^1$H NMR.

Preparation of amides derived from amine 33a. To amine resin 33a (25 mg) in DMF (1 mL) at room temperature was added a solution of carboxylic acid (0.5 mmol) and diisopropylcarbodiimide (0.25 mmol). After 16 hrs, the reaction mixture was filtered, and the resin 36a was sequentially washed with DMF and DCM. The resin was treated with TFA (90% in DCM) to provide the free amide 37a, which was obtained upon filtration and in vacuo concentration. HPLC and MS analysis of the amide residue showed that it was of greater than 80% purity.

Preparation of Sulfonamides Derived from Amine 33a.

To amine resin 33a (25 mg) was added a solution of sulfonyl chloride (0.5 mmol) in DCM at room temperature. After standing for 16 hrs, the reaction mixture was filtered, and the resin was sequentially washed with DMF and DCM. The resin was treated with TFA (90% in DCM) to provide the free sulfonamide 35a, which was obtained upon filtration and in vacuo concentration. HPLC and MS analysis of the amide residue showed that it was of greater than 80% purity.

Preparation of Ureas Derived from Amine 33a.

To amine resin 33a (25 mg) was added a solution of isocyanate (0.5 mmol) in DCM at room temperature. After standing for 16 hrs, the reaction mixture was filtered, and the resin was sequentially washed with DMF and DCM. The resin was treated with TFA (90% in DCM) to provide the free urea 39a, which was obtained upon filtration and in vacuo concentration. HPLC and MS analysis of the amide residue showed that it was of greater than 80% purity.

Preparation of Phenylsulfide Derivatives from Amine 33a.

To amine resin 33a was added a solution of bromoacetic acid (3 eq.) and DIC (1.5 eq.) in DMF at room temperature. After 16 hrs, the reaction mixture was filtered to provide the bromoacetyl derivative 40a. The resin was sequentially washed with DMF and DCM and dried in vacuo. To the resin (50 mg) in DMF was added potassium carbonate (50 mg) and thiophenol (0.5 mmol). The mixture was shaken overnight, filtered and sequentially washed with DMF, water, DMF and DCM. The resin was treated with TFA (90% in DCM) to afford the sulfide (5.0 mg, 40% theoretical yield).

Method of Wittig Reaction from Acetyl Bromide 40a.

To the bromoacetyl resin (40, 50 mg) in DMF (1 mL) was added triphenylphosphine (10 equivalents). After 16 hrs at room temperature, the resin was washed with DMF, and treated with potassium carbonate (20 equivalents) and benzaldehyde (10 equivalents) for 16 hrs at room temperature. The resin was washed with DMF, water, DMF and DCM, and cleaved with TFA (50% in DCM) to give (S)-N-[[3-(3-fluoro-4-morpholinylphenyl)-2-oxo-5-oxazolidinyl]methyl] cinnamamide (44): $^1$H NMR (300 MHz) 7.62 (d, J=15.6 Hz, 1H), 7.54–7.33 (m, 6H), 7.09 (d, J=8.8 Hz, 1H), 6.94 (t, J=9.2 Hz, 1H,), 6.53 (d, J=15.6 Hz, 1H,), 4.87–4.82 (m, 1H), 4.08 (t, J=9.0 Hz, 1H), 3.86 (t, J=4.2 Hz, 4H), 3.84–3.63 (m, 3H), 3.05 (t, J=4.2 Hz, 4H); MS (m/z) 426 (M$^+$+1).

Arylsulfide Library.

To an array of individual reaction chambers each containing particles or beads of bromoacetyl resin 40a in DMF is added potassium carbonate and a thiol unit at room temperature. The thiol units designated in Table 1 are used. The array is shaken for 10 hrs, filtered and sequentially washed with DMF, water, DMF and DCM. The thio alcohol resin is cleaved upon treatment with TFA. The resin is filtered and washed with DCM. A plurality of sulfides is provided upon concentration of the filtrate array in vacuo.

Preparation of an Amide Library Derived from Amine 33a.

To an array of individual reaction chambers each containing particles or beads of amine resin 33a in DMF was added a solution of a carboxylic acid unit and diisopropylcarbodiimide. The carboxylic acid units designated in Table 4 were used. The array was shaken at room temperature for 16 hrs, filtered and sequentially washed with DMF and DCM. The amide resin was cleaved upon treatment with TFA. The resin was filtered and washed with DCM. A plurality of amides was provided upon concentration of the filtrate array in vacuo.

Preparation of a Sulfonamide Library Derived from Amine 33a.

To an array of individual reaction chambers each containing particles or beads of amine resin 33 in DCM was added a solution of a sulfonyl chloride unit. The sulfonyl chloride units designated in Table 3 were used. The array was allowed to stand for 16 hrs. It was then filtered and sequentially washed with DMF and DCM. The sulfonamide resin was cleaved upon treatment with TFA. The resin was filtered and washed with DCM. A plurality of sulfonamides was provided upon concentration of the filtrate array in vacuo.

Preparation of a Urea Library Derived from Amine 33*a*.

A To an array of individual reaction chambers each containing particles or beads of amine resin 33*a* in DCM was added a solution of an isocyanate unit. The isocyanates of Table 3 were used. The array was allowed to stand for 16 hrs. It was then filtered and sequentially washed with DMF and DCM. The urea resin was cleaved upon treatment with TFA. The resin was filtered and washed with DCM. A plurality of ureas was provided upon concentration of the filtrate array in vacuo.

Preparation of an Amide Library Using the Amine Units in FIG. 30

To an array of individual reaction chambers each containing particles or beads of aldehyde functionalized resin 31a is added an amine subunit in TMOF. The subunits listed in FIG. 30 are used. The mixture is stirred for 1 h, after which a NaBH$_3$(CN)-THF solution is added. The reaction is stirred for 30 min., filtered and sequentially washed with methanol and DCM. In vacuo concentration of the filtrate affords the respective amine resins. The respective amine resin is placed in an array of individual reaction chambers. To the individual reaction chambers is added a solution of a carboxylic acid unit and diisopropylcarbodiimide. The carboxylic acid units designated in Table 4 are used. The array is shaken at room temperature for 16 hrs, filtered and sequentially washed with DMF and DCM. The amide resin is cleaved upon treatment with TFA. The resin is filtered and washed with DCM. A plurality of amides is provided upon concentration of the filtrate array in vacua.

Preparation of an Amide Library Using the Amine Units in FIGS. 29, 30, and 31

To epoxide resin 7a (X=NH) in DMF is added a solution of a carboxylic acid unit and diisopropylcarbodiimide. The carboxylic acid units designated in Table 4 are used. After 3 hours, the resin is filtered, sequentially washed with DMF and DCM, and dried in vacuo. The respective resin is placed in an array of individual reaction chambers. To the resin in CAN in the individual reaction chambers is added LiOTf followed by an amine unit. The amine units shown in FIGS. 29, 30, and 31 are used. The array is shaken at room temperature for 15 hours, filtered and sequentially washed with CAN and DMF. To the array of amino alcohol resins is added NMM (10 equivalents) and CDI (5 equivalents). The array is shaken at room temperature for 10 hours, filtered and sequentially washed with DMF and DCM. The oxazolidinone resin is cleaved upon treatment with TFA. The resin is filtered and washed with DCM. A plurality of oxazolidinones is provided upon concentration of the solution array in vacuo. (The amines of FIGS. 29, 30, and 31 can be made according to procedures described in the following publications: U.S. Pat. No. 4,948,801; U.S. Pat. No. 4,705,799; U.S. Pat. No. 5,164,510; U.S. Pat. No. 4,975,538; U.S. Pat. No. 5,225,565; U.S. Pat. No. 5,182,403; U.S. Pat. No. 5,247,090; U.S. Pat. No. 5,231,188; U.S. Pat. No. 4,461,773; EP 0 785 201 A1; WO 97/19089; DE 196 01 265 A1; WO 97/27188; EP 0 789 026 A1; DE 196 01 264 A1; DE 196 04 223 A1; WO 97/30995; WO 97/09328; Van Delft et al. (1997) *Synthesis* 450–454; Wang et al. (1989) *Tetrahedron* 45:1323–1326; and Denis et al. (1994) Bioorg. & Med. Chem. Lett. 4:1925–1930; which are hereby incorporated by reference.)

Assay Protocol for β-Lactamase Inhibition. The lactamase (20–120 ng/mL) was incubated with a potential inhibitor with 1% DMSO in 50 mM potassium phosphate buffer, pH 7.0, with 0.005% Brij-35 for 30 min at room temperature. 100 µM of nitrocefin was then added to the reaction mixture and the hydrolysis of the nitrocefin was monitored by measuring the absorption increase at 490 nm. Inhibition of the potential compounds was calculated by comparing the rate of absorption increase with the control sample which containing the identical mixture except inhibitors. The $IC_{50}$, was obtained by fitting the inhibition data into a standard 2-parameter $IC_{50}$ equation with a non-linear least-square fitting program (DeltaGraph).

Assay Protocol for Antimicrobial Activity. Minimum inhibitory concentrations (MICs) were determined using the microdilution method in 96-well format plates. Compounds were suspended in DMSO at 5 or 10 mg/ml and stored at 4° C. until used. They were diluted in Mueller-Hinton Broth (MHB) or Trypticase Soy Broth (TSB) and used for MIC determination. The range of concentrations tested was 64–0.0625 µl final concentration using a two-fold dilution system.

The inoculum was prepared from cells grown on Trypticase Soy Agar (TSA) and incubated overnight at 35° C., 5 to 10 colonies were used to inoculate MHB or TSB broths, and the culture was incubated overnight at 35° C. The overnight culture was diluted 1:10, incubated for one hour at 35° C., diluted to the appropriate inoculum size and applied to the wells containing broth and test compound. Inoculum sizes were $1 \times 10^5$ to $5 \times 10^5$ CFU/ml. Strains used included *P. aeruginosa* VPAE1001, *E. faecium* VVEFA1001, *E. faecium* VanA VEFA1002, *S. aureus* VSAU1003, *S. aureus* MRSA VSAU1004, *E. coil* VEC05, and *E. coli* (arc-) VEC05.

Plates were incubated at 35° C. for 48 hours and MIC were recorded after 18 hours of incubation, for bacteria, and 48 for yeasts. MIC was defined as the lowest concentration of compound that does not produce visible growth after incubation.

Antimicrobial Activity for Representative Compounds in Animals

In vivo data was obtained for representative compounds i, ii, and iii to demonstrate the practical utility of the oxazolidinone compounds for treatment of a bacterial infection in animals.

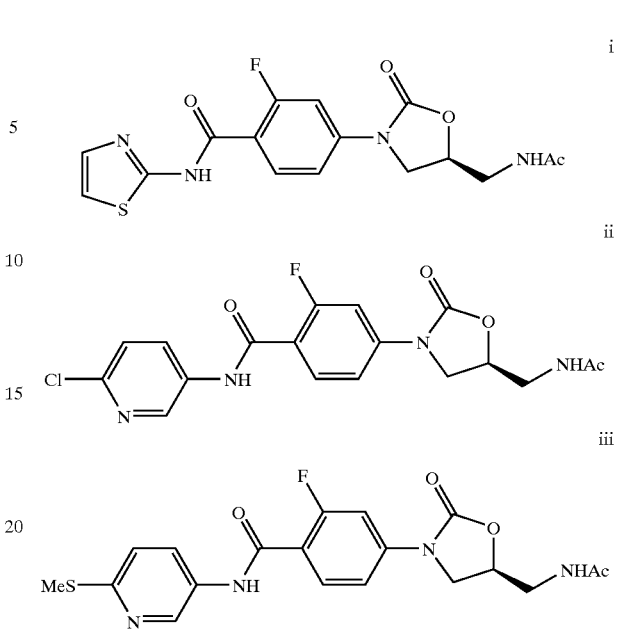

CDI female mice (Charles River Laboratories) weighing 18–22 grams were injected intraperitoneally with 0.2 ml of a suspension containing $3*10^7$ cfu of *S. aureus* (Smith strain) in 7% hog gastric mucosa (mucin). The mice were treated, either intravenously (i.v.) or orally (p.o.), 1 h and 5 h after infection. Five groups of six mice each were given different dosage levels representing two-fold dilutions of each compound (range of 25 mg/kg–1.56 mg/kg). The compounds were all formulated in 40% aqueous hydroxypropyl-beta-cyclodextrin in PBS and untreated controls were dosed with vehicle alone.

Mortality in each group was monitored daily for 6 days and cumulative mortality was used to determine the 50% protective doses ($PD_{50}$) which were calculated using the method of Reed and Muench [(a) Lorian, V. Antibiotics in laboratory medicine. Baltimore: Williams & Wilkins. 1996, p. 635–636; (b) Reed, L. J.; Muench H. A simple method of estimating fifty percent endpoints. Am. J. Hyg. 1938, 27, pp. 493–497] (Table 1). For animals receiving vehicle alone, there was a 79% mortality rate (19/24) in the p.o. dosing group and an 88% mortality rate (15/17) in the i.v. group; giving a total mortality rate for untreated controls of 83%.

$PD_{50}$ for above compounds was in a range 2.3–7.2 mg/kg for i.v. administration and 7.5–14.9.mg/kg for p.o. administration, with compound iii being the most preferred.

TABLE 1

| Thiols |
|---|
| 2-mercaptobenzothiazole |
| 2-mercapto-4-methylpyridine HCl |
| 2-mercaptothiazoline |
| 2-mercaptopyridine |
| 2-mercapto-(3H)-quinazoline |
| 2-mercapto-1-methyl imidazole |
| 5-(methylthio)-1,3,4-thiodiazole-2-thiol |
| 2-mercapto-6-thien-2-yl-4-(trifluoromethyl)pyridine-3-carbonitrile |
| thiazolo[4,5-b]pyridine-2-thiol |
| 4-(4-methoxyphenyl)pyrimidine-2-thiol |
| 2-mercapto-3-(trifluoromethyl)pyridine |
| 4,6-dimethyl-2-mercaptopyridine-3-carbonitrile |
| 4-trifluoromethylpyrimidine-2-thiol |
| ethyl 3-cyano-2-mercapto-6-methylpyridine-4-carboxylate |

TABLE 1-continued

Thiols 2-mercapto-5-(trifluoromethyl)pyridine
5-chloro-2-mercaptobenzothiazole
4-methyl-4H-1,2,4-triazole-3-thiol
2,4,6-trimethylbenzylmercaptan
2-quinolinethiol
8-quinolinethiol HCl
3-chloro-5-(trifluoromethyl)pyridine-2-thiol
7-trifluoromethyl-4-quindine-thiol
2,4,6,-trichlorobenzenethiol
5-[3-(trifluoromethyl)benzylthio]-1,3,4-thiadiazole-2-thiol
4-(4-chlorophenyl)pyrimidine
thiomalic acid
2,6-dichlorobenzenethiol
4-hydroxythiophenol
5-(4,5-dichloroimidazole)
3-mercaptopropionic acid
3,4-dichlorobenzenethiol
2,6,-dichlorobenzenethiol
2-methoxybenzenethiol
2-bromothiophenol
4-fluorothiophenol
4-bromo-2-(trifluoromethoxy)benzenethiol
3-(trifluoromethyl)benzenethiol
thiolactic acid
3,4-dimethoxybenzenethiol
4-methoxybenezenethiol
2-(trifluoromethyl)benzenethiol
4-(trifluoromethoxy)benzylthiol

TABLE 2

Amines 4-iodoaniline
2-iodoaniline
4-phenoxyaniline
3-trifluoromethylamine
m-anisidine
o-anisidine
2-trifluoromethylaniline
3-chloroaniline
1,4-benzodioxane-6-amine
5-aminoindan
3,4-(methylenedioxy)-aniline
3-phenoxyaniline
4-morpholinoaniline
4-amino-1-benzyl-piperidine
2-Bromoanaline
3-fluoroanaline
4-trifluoromethoxyaniline
4-methylmercaptoaniline
3-bromoaniline
2-fluoroaniline
4-fluoroaniline
2,4-difluoroaniline
3,4-difluoroaniline
2,5-difluoroaniline
1-amino-5,6,7,8,-tetrahydronapthalene
3,5-difluoroaniline
3-fluorobenzylamine
4-fluorobenzylamine
4-aminoacetophenone
4-aminobenzophenone
3-benzyloxyaniline
1-(3-aminopropyl)imidazole
4-(2-aminoethyl)-morpholine
m-phenetidine
3-chloro-4-fluoroaniline
2-bromo-5-(trifluoromethyl)aniline
2-amino-3-benzyloxypyridine
2'-aminoacetophenone
4-aminobenzoic acid
4-aminobiphenyl
3'-aminoacetophenone

TABLE 2-continued

Amines 4-(3'-aminopropyl)morpholine
aminopyrazine
2-aminopyridine
3-aminopyridine
4-aminopyridine
6-aminoquinoline
8-aminoquinoline
4-aminoveratrole
4-bromo-2,6-difluoroaniline
4-bromo-2-fluoroaniline
4-bromo-3-(trifluoromethyl)aniline
4-bromo-3-methylaniline
2-bromo-4-fluoroaniline
2-bromo-4-methylaniline
3-bromo-4-methylaniline
4-butoxyaniline
3-fluoro-4-methylaniline
4-aminoquinaldine
2-chloro-4,6-dimethylaniline
2-chloro-4-aminotoluene
2-chloro-4-fluoroaniline
4-chloroaniline
2,4-dibromo-6-fluoroaniline
2,4-dibromoaniline
2,5-dibromoaniline
2,4-dichloroaniline
2,5-dichloroaniline
3,4-dichloroaniline
3,5-dichloroaniline
2,3-difluoroaniline
N,N-dimethy-1,4-phenylenediamine
5-fluoro-2-methylaniline
2-fluoro-4-iodoaniline
5-amimo-2-methoxpyridine
2-methylmercapto)-aniline
sulfanilamide
sulfisomidine
p-bromoaniline
2-(4-aminophenyl)-6-methylbenzothiazole
4-amino-4'-nitrodiphenyl sulfide
3-aminophenol
4-aminophenol
4'-aminoacetanilide
3-aminobenzyl alcohol
4-aminophenethyl alcohol
2-aminoanthraquinone
6-aminonicotinamide
2-amino--6-fluorobenzothiazole
2-amino-5-(4-nitrophenylsulfone)thiazole
2-amino-4-methoxybenzothiazole
2-amino-4-chlorobenzothiazole
2-amino-5-bromothiazole HBr
2-aminothiazole
2-aminobenzothiazole
2-amino-6-methoxybenzothiazole
2-amino-6-nitrobenzothiazole
2-amino-4-methylbenzothiazole
2-amino-4-(4-chlorophenyl)thiazole
2-amino-5,6-dimethylbenzothiazole
2-amino-6-methylbenzothiazole
2-amino-6-chlorobenzothiazole
2-amino-6-ethoxybenzothiazole
2-amino-5-nitrothiazole
2-amino-5-(ethylthio)-1,3,4-thiadiazole
methyl 3-amino-2-thiophene carboxylate
N-[4-(4-aminobenzyl)phenyl)]-5-norbornene-2,3-dicarboximide
2-amino-4-pheylthiazole HBr
2-amino-3,5-dichloropyridine
2-amino-5-bromo-pyridine
2-amino-4-picoline
5-amino-2-chloropyridine
2-amino-4,6-dimethylpyridine
2-amino-5-chloropyridine
2-amino-2-chloropyridine
2-amino-5-picoline
2-amino-6-picoline
9-aminoacridine

TABLE 2-continued

Amines 5-aminoisoquinoline
3-aminoquinoline
2-amino-4,6-dimethylpyrimidine
1-aminoisoquinoline
5-aminoquinoline
2-amino-4,6-dichloropyrimididine
3-amino-5,6-dimethyl-1,2,4-triazine
2-amino-4-chloro-6-methylpyrimidine
2-amino-4-methylpyrimidine
5-amino-3-methylisothiazole
2-amino-5-bromopyrimidine
2-amino-4,6-dimethoxypyrimidine
2-amino-4-methoxy-6-pyrimidine
4-amino-6-chloro-2-(methylthio)pyrimidine
2-amino-5-chlorobenzoxazole
2-amino-5-trifluoromethyl-1,3,4-thiadizole
3-amino-5-methylisoxazole
4-amino-2,1,3-benzothiadiazole
2-amino-1,3,4-thiadiazole
3-amino-1-phenyl-2-pyrazolin-5-one
6-amino-1,3-dimethyluracil
4-amino-1,2-naphthoquinone hemihydrate
3-amino-1-(2,4,6-trichlorophenyl)-2-pyrazolin-5-one
1-(2-aminophenyl)pyrrole
N-(4-amino-2-methylphenyl)-4-chlorophthalimide
2-amino-3-chloro-5-(trifluotomethyl)pyridine
2-amino-3-picoline
2-amino-4-methyl-5-nitropyridine
2-amino-4-methylthiazole
2-amino-5-ethyl-1,3,4-thiadazole
2-aminopyrimidine
3-aminocrotononitrile
3-amino-1,2,4-trizole
3-aminopyrazole
4-amino-2,3,5,6-tetrafluoropyridine
4-aminopyrimidine
5-amino-1-ethylpyrazole
5-amino-1-phenyl-4-pyrazolecarboxamide
5-amino-3-methylisoxazole
5-aminouracile

TABLE 3

Sulfonyl chlorides and Isocyanates p-toluenesulfonyl chloride
2,4-dichlorobenzenesulfonyl chloride
2-thiophenesulfonyl chloride
styrenesulfonyl chloride
2-methoxycarbonylphenyl isocyanate
4-acetylphenyl isocyanate
cyclohexyl isocyanate
p-tolyl isocyanate

TABLE 4

Carboxylic acids pyruvic acid
p-toluic acid
o-tolylacetic acid
phenylacetic acid
trans-2-pentenoic acid
methylthio acetic acid
4-methoxycinnamic acid
nonanoic acid
3-methoxypropionic acid
4-methoxycyclohexanecarboxylic acid
phenylpropiolic acid
1-naphthylacetic acid
pentafluoropropionic acid
piperonylic acid

TABLE 4-continued

Carboxylic acids

N-(2-furoyl)glycine
propionic acid
2,3,4,5,6-pentafluorophenylacetic acid
4-pentenoic acid
octanoic acid
3-methoxyphenylacetic acid
4-methylcinnamic acid
methacrylic acid
p-(dimethylamino)cinnamic acid
phenylpyruvic acid
nicotinic acid
2-methylcinnamic acid
methoxyacetic acid
phenoxybenzoic acid
phenoxyacetic acid
cyclopropanecarboxylic acid
glycolic acid
trans-3-hexenoic acid
4-(trifluoromethyl)mandelic acid
2-(2-methoxyethoxy)acetic acid
diphenylacetic acid
2-bromo-4,5-dimethoxycinnamic acid
3,4-dihydroxyhydrocinnamic acid
3-methoxycinnamic acid
4-chlorophenoxyacetic acid
4-(4-nitrophenyl)butyric acid
3-(4-chlorobenzoyl)propionic acid
2-(4-hydroxyphenoxy)propionic acid
2-chlorocinnamic acid
2-biphenylcarboxylic acid
2-(4-chlorophenoxy)-2-methylpropionic acid
benzoylpropionic acid
3-(phenylthio)acrylic acid
3,5-di-tert-butyl-4-hydroxycinnamic acid
4-bromobutyric acid
4-bromomandelic acid
decanoic acid
4-hydroxycinnamic acid
2-nitrocinnamic acid
2,3,4-trifluorocinnamic acid
homovanillic acid
3-methoxycyclohexanecarboxylic acid
2-ethoxycinnamic acid
2,5-difluorophenylacetic acid
4-fluorocinnamic acid
2,6-difluorophenylacetic acid
3,3-diphenylpropionic acid
cis-pinonic acid
2-fluorobenzoic acid
cyanoacetic acid
1,2,3,4-tetrahydro-2-naphthoic acid
trans-2-phenyl-1-cyclopropanecarboxylic acid
4-(4-methoxyphenyl)butyric acid
2-formylphenoxyacetic acid
3-(4-fluorobenzoyl)propionic acid
difluoroacetic acid
3-chlorobenzo[b]thiophene-2-carboxylic acid
4-methoxybenzylidenecyanoacetic acid
1-adamantaneacetic acid
1-adamantanecarboxylic acid
1-fluorencarboxylic acid
(2-naphthoxy)acetic acid
1H-benzimidazole-5-carboxylic acid
2-(2,4,5-trichlorophenoxypropionic acid)
3-hydroxycinnamic acid
abietic acid
isoxazole-5-carboxylic acid
(4-chloro-o-tolyloxy)-butyric acid
3-pyridylacetic acid
alpha-methyl-2,4,5-trimethoxycinnamic acid
2-chlorophenylacetic acid
3-fluorophenylacetic acid
(S)-(+)-mandelic acid
2,4-difluorophenylacetic acid
butyric acid
4-methoxyphenylacetic acid
4-ethoxyphenylacetic acid TABLE 4-continued Carboxylic acids trans-2-hexenoic acid
3,4-dihydroxycinnamic acid
2,3-dichlorophenoxyacetic acid
S-benzylthioglycolic acid
3,4-(methylenedioxy)phenylacetic acid
(alpha, alpha,alpha-trifluoro-m-tolyl) acetic acid
3,4-difluorophenylacetic acid
2-furioic acid
4-acetylphenoxyacetic acid
4-(3,4-dimethoxyphenyl)butyric acid
cyclohexanepropionic acid
7-methoxy-2-bezofuran carboxylic acid
2-(triflouromethyl)cinnamic acid
2,4-dinitrophenylacetic acid
2,4-dichlorophenylacetic acid
2-nitrophenylpyruvic acid
iodoacetic acid
acetic acid
4-(2,4-dichlorophenoxy)-butyric acid
3-(3,4,5-trimethoxyphenyl)propionic acid
6-chloro-2H-1-benzopyran-3-carboxylic acid
4-acetamidocinnamic acid
3-hydroxyphenylacetic acid
2-chloro-6-fluorocinnamic acid
3-fluoro-4-hydroxyphenylacetic acid
4-fluorophenylacetic acid
trans-3-fluorocinnamic acid
3-bromocinnamic acid
2-pyridylacetic acid
alpha-fluorocinnamic acid
4-(2-cyclohexenyloxy)benzoic acid
1-naphthoic acid
2-bromophenylacetic acid
4-nitrocinnamic acid
2-propylpentanoic acid
3,4-dihydro-2,2-dimethyl-4-oxo-2h-pyran-6-carboxylic acid
3-(2-methoxyphenyl)propionic acid
2-fluorocinnamic acid
tiglic acid
(4-pyridylthio)acetic acid
4-hydroxyphenylacetic acid
4-bromophenylacetic acid
chloroacetic acid
chromone-2-carboxylic acid
4-bromocinnamic acid
alpha-phenyl-cinnamic acid
benzoylformic acid
dichloroacetic acid
3,5-dimethoxy-4-hydroxycinnamic acid
trans-4-(trifluoromethyl) cinnamic acid
cyclohexylacetic acid
cyclopentylpropionic acid
(−)-mentoxyacetic acid
alpha-fluorophenylacetic acid
3-(3,4-dimethoxyphenyl)propionic acid
3,4-dichlorocinnamic acid
4-fluorophenoxyacetic acid
thiophenoxyacetic acid
3,5-bis(trifluoromethyl)phenylacetic acid
(4-methylphenoxy)acetic acid
6-methylchromone-2-carboxylic acid
(3,4-(dimethoxyphenyl)acetic acid
3-chlorophenylacetic acid
2,3,4,5,6-pentafluorocinnamic acid
3-indolepropionic acid
2-thiopheneacetic acid
6-bromocoumarin-3-carboxylic acid
4-pyridylacetic acid
alpha-methylhydrocinnamic acid
alpha-phenylcinnamic acid
cis-2-methoxycinnamic acid
4-phenylcinnamic acid
4-chloro-o-anisic acid
4-ethoxycinnamic acid
2-phenylpropionic acid
3,4-methylenedioxy)cinnamic acid
1-phenyl-1-cyclopropanecarboxylic acid 3-cyanobenzoic acid
3,4,5-trimethoxyphenylacetic acid
(2-amino-thiazole-4-yl)acetic acid
2,3-dimethoxybenzoic acid
4-chorophenylacetic acid
bis(4-chlorophenoxy)acetic acid
tetrahydro-2-furoic acid
trans-styrylacetic acid
4-chlorocinnamic acid
alpha-methylcinnamic acid
alpha-cyanocinnamic acid
4-methylvaleric acid
4-pyrazolecarboxylic acid
2-fluorophenylacetic acid
3-(1-naphthyl)acrylic acid
3-bromophenylacetic acid
alpha-cyano-3-hydroxycinnamic acid
2-(3-chlorophenoxy)propionic acid
2,5-dimethylcinnamic acid
2,6-dichlorophenylacetic acid
3-phenoxypropionic acid
2,6-dichlorocinnamic acid
(2,5-dimethoxyphenyl)acetic acid
2,3,4-trimethoxycinnamic acid
2,3,4-trimethoxybenzoic acid
2-chlorobenzoic acid
3,4,5-trimethoxycinnamic acid
cyclobutanecarboxylic acid
cyclohexene-1-carboxylic acid
4-nitrophenylacetic acid
benzoylbutyric acid
3,5-dimethoxybenzoic acid
alpha-cyano-4-hydroxycinnamic acid
cyclopentanecarboxylic acid
5-(pyrid-2-yl)thiophene-2-carboxylic acid
bromoacetic acid
trans-4-hydroxy-3-methoxycinnamic acid
4-chloro-2-fluorocinnamic acid
2-octynoic acid
3-(p-tolyl)propionic acid
4-chlorobenzoic acid
2-methoxyphenylacetic acid
4-biphenylcarboxylic acid
2-chloro-4-fluorocinnamic acid
2-norbornameacetic acid
2-naphthylacetic acid
2-methyl-1-cyclohexanecarboxylic acid
(1-naphthoxy)acetic acid
2,5-dimethoxybenzoic acid
cyclopentylacetic acid
ethoxyacetic acid
cyclohexanebutyric acid
2-methylcyclopropane-carboxylic acid
4-methylcyclohexaneacetic acid
4-hydroxymandelic acid monhydrate
4-bromo-2-fluorocinnamic acid
lauric acid
2-bromovaleric acid
2,6-dimethoxybenzoic acid
trans-2,3-dimethoxycinnamic acid
3-(4-hydroxyphenyl)propionic acid
3-(4-methoxybenzoyl)-propionic acid
(alpha, alpha,alpha-tri-fluoro-p-tolyl)acetic acid
hydrocinnamic acid
3,4-difluorocinnamic acid
3,5-bis(trifluoromethyl)benzoic acid
(3,5-dimethoxyphenyl)acetic acid
9-anthracenecarboxylic acid
3-(trifluoromethyl)cinnamic acid
m-tolylacetic acid
4-formylcinnamic acid
3-furic acid
crotonic acid
alpha-acetamidocinnamic acid
alpha-phenylcyclopentaneacetic acid
diphenylacetic acid
4,5-dimethoxy-2-nitrocinnamic acid

TABLE 4-continued

Carboxylic acids 4-(methylthio)phenylacetic acid
3,5-dimethoxycinnamic acid
3-nitrocinnamic acid
5-chlorobenzo[b]thiophene-3-acetic acid
3-methyl-2-phenylvaleric acid
3-(trifluorometoxy)cinnamic acid
4-biphenylacetic acid
3-bromo-4-fluorocinnamic acid
3-(2-hydroxyphenyl)propionic acid
2,4-difluorocinnamic acid
5-methoxy-1-indanone-3-acetic acid
alpha-methoxyphenylacetic acid
2-thiophenecarboxylic acid
3-(4-methoxyphenyl)propionic acid
4-acetoxy-3-methoxycinnamic acid
2-methoxycinnamic acid
3-benzoylbenzoic acid
levulinic acid
3,4-dichlorophenylacetic acid
3-methylindene-2-carboxylic acid
4-phenoxybutyric acid
2-hydroxycinnamic acid
2-ethoxy-1-naphthoic acid
2-chloro-5-nitrocinnamic acid
3,3-dimethylacrytic acid
4-pentynoic acid
4-acetoxycinnamic acid
2-(p-toluoyl)-benzoic acid
3,5-difluorocinnamic acid
2-ethoxybenzoic acid
trans-2-methyl-2-pentenoic acid
cycloheptanecarboxylic acid
tetrahydro-3-furoic acid
3,5-difluorophenylacetic acid
trans-2,6-difluorocinnamic acid
thioctic acid
5-bromo-2-fluorocinnamic acid
11-phenoxyundecanoic acid 2,4-dichlorophenoxyacetic acid
2-(2,4-dichlorophenoxy)-propionic acid
2,2-dimethylbutyric acid
o-tolulic acid
2-bromo(4,5-(methylenedioxy)cinnamic acid
alpha-bromophenylacetic acid
trans-N-(2-furfurylideneacetyl)-glycine 3-chlorobenzoic acid
D-3-phenyllactic acid
2-phenoxybutyric acid
2-(4-chlorophenoxy)propionic acid
2-acetoxycinnamic acid
(R)-(–)-mandelic acid
(+–)-6-methoxy-alpha-methyl-2-naphthaleneacetic acid
(+–)-2-(2-chlorophenoxyy)propionic acid
(+–) 2-phenyoxypropionic acid
1-methyl-1-cyclohexanecarboxylic acid
2,5-dimethoxycinnamic acid
2-(2-aminothiazole-4-yl-2-methoxyiminoacetic acid
2-acetamidoacrylic acid Although the foregoing invention has been described in some detail by way of illustration and example for purposes of clarity and understanding, it will be apparent to those skilled in the art that certain changes and modifications may be practical. Therefore, the description and examples should not be construed as limiting the scope of the invention

What is claimed is:

1. A method of preparing combinatorial libraries of compounds of the formula Ib, comprising the steps of:

a) attaching a plurality of aryl oxazolidinones to a plurality of solid supports;

b) functionalizing the 4-position of the aryl groups of the attached oxazolidinones to produce an $R_1$ substituent; and, optionally, c) removing the oxazolidinones from the solid supports;

wherein compounds of formula Ib have the structure:

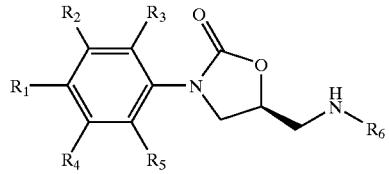

1b wherein $R_2$, $R_3$, $R_4$ and $R_5$ are, independently, hydrogen alkyl, heteroalkyl, heteroaryl or an electron withdrawing group;

$R_6$ is acyl or sulfonyl; and $R_1$ is one of the following functional groups:

$C(O)NR_7R_8$, wherein $R_7$ and $R_8$ are, independently, hydrogen, alkyl, heteroalkyl, aryl or heteroaryl;

$C(O)OR_9$, wherein $R_9$ is hydrogen, alkyl, heteroalkyl, aryl or heteroaryl;

$C(O)R_{10}$, wherein $R_{10}$ is hydrogen, alkyl, heteroalkyl, aryl or heteroaryl;

$SR_{11}$, wherein $R_{11}$ is hydrogen, alkyl, heteroalkyl, aryl or heteroaryl;

$S(O)_2R_{11}$, wherein $R_{11}$ is hydrogen, alkyl, heteroalkyl, aryl or heteroaryl;

$S(O)R_{11}$, wherein $R_{11}$ is hydrogen, alkyl, heteroalkyl, aryl or heteroaryl;

$NR_{12}R_{13}$, wherein $R_{12}$ and $R_{13}$ are, independently, hydrogen, acyl, sulfonyl, alkyl, heteroalkyl, aryl or heteroaryl;

2-oxazolyl, wherein $R_{14}$ is at the 4-position and $R_{15}$ is at the 5-position of the oxazolyl, and wherein $R_{14}$ and $R_{15}$ are, independently, hydrogen, alkyl, heteroalkyl, aryl, heteroaryl or an electron withdrawing group;

2-aminothiazolyl, wherein $R_{16}$ is at the 4-position and $R_{17}$ is at the 5-position of the thiazole, and wherein $R_{16}$ and $R_{17}$, are, independently, hydrogen, alkyl, heteroalkyl, aryl, heteroaryl or an electron withdrawing group;

$CH_2NR_{18}R_{19}$, wherein $R_{18}$ and $R_{19}$ are, independently, hydrogen, alkyl, heteroalkyl, aryl, heteroaryl, acyl or sulfonyl; and wherein the aryl oxazolidinones in step a) comprise the structure

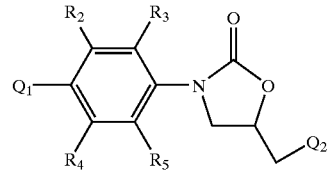

wherein $R_2$, $R_3$, R4 and $R_5$ are defined above;

$Q_1$ is selected from —C(O)O-PG, —S-PG, —CH(OC$_{1-4}$alkyl)$_2$, where PG is a protecting group; and $Q_2$ is $N_3$, wherein the resin includes a carbonyl containing moiety and attaching the plurality of aryl oxazolidinones to the plurality of solid supports in step a comprises converting $Q_2$ to an iminophosphorane or an amine and reacting the iminophosphorane or the amine with the carbonyl moiety of the resin to form an imine.

2. The method of claim 1, wherein $Q_1$ is —C(O)O-PG.

3. The method of claim 2, wherein functionalizing the 4-position of the aryl groups comprises converting the —C(O)O-PG group into a —C(O)NR$_7$R$_8$, —C(O)OR$_9$, —C(O)R$_{10}$, —NR$_{12}$R$_{13}$, 2-oxazolyl, or 2-aminothiazolyl group.

4. The method of claim 1, wherein Q, is —S-PG.

5. The method of claim 4, wherein functionalizing the 4-position of the aryl groups comprises converting the —S-PG group to a —SR$_{11}$, —S(O)R$_{11}$, or —S(O)$_2$R$_{11}$ group.

6. The method of claim 1, wherein Q$_1$ is —CH(OC$_{1-4}$ alkyl)$_2$.

7. The method of claim 6, wherein functionalizing the 4-position of the aryl groups comprises converting the —CH(OC$_{1-4}$alkyl)$_2$ group to a —CH$_2$NR$_{18}$R$_{19}$ group.

* * * * *